US009061057B2

(12) United States Patent
Kularatne et al.

(10) Patent No.: US 9,061,057 B2
(45) Date of Patent: Jun. 23, 2015

(54) SYNTHESIS AND COMPOSITION OF AMINO ACID LINKING GROUPS CONJUGATED TO COMPOUNDS USED FOR THE TARGETED IMAGING OF TUMORS

(71) Applicant: Purdue Research Foundation, West Lafayette, IN (US)

(72) Inventors: Sumith A. Kularatne, West Lafayette, IN (US); Sakkarapalayam M. Mahalingam, West Lafayette, IN (US); Philip S. Low, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 0 days.

(21) Appl. No.: 14/207,130

(22) Filed: Mar. 12, 2014

(65) Prior Publication Data

US 2014/0271476 A1    Sep. 18, 2014

Related U.S. Application Data

(63) Continuation of application No. 14/010,098, filed on Aug. 26, 2013.

(60) Provisional application No. 61/791,921, filed on Mar. 15, 2013.

(51) Int. Cl.
| | | |
|---|---|---|
| A61B 5/00 | (2006.01) |
| A61B 8/00 | (2006.01) |
| A61B 10/00 | (2006.01) |
| A61K 49/00 | (2006.01) |
| G01N 33/569 | (2006.01) |
| G01N 33/566 | (2006.01) |
| G01N 33/50 | (2006.01) |

(52) U.S. Cl.
CPC ...... *A61K 49/0052* (2013.01); *G01N 33/56966* (2013.01); *A61K 49/0032* (2013.01); *G01N 33/566* (2013.01); *G01N 33/5091* (2013.01); *A61K 49/0034* (2013.01)

(58) Field of Classification Search
USPC .......................................... 424/9.6
See application file for complete search history.

(56) References Cited

U.S. PATENT DOCUMENTS

| 4,337,339 A | 6/1982 | Farina et al. |
| 7,547,721 B1 | 6/2009 | Miwa et al. |
| 2012/0003151 A1 | 1/2012 | Low et al. |

OTHER PUBLICATIONS

Milstein et al. (Applied Optics 2005, 44, 2300-2310).*
Moon et al. (Bioconj. Chem. 2003, 14, 539-545).*
PCT, Notification of Transmittal of the International Search Report and the Written Opinion of the International Searching Authority, or the Declaration for International Application No. PCT/US 13/56629, dated Aug. 26, 2013 (17 pages).

* cited by examiner

*Primary Examiner* — Michael G Hartley
*Assistant Examiner* — Melissa Perreira
(74) *Attorney, Agent, or Firm* — McAndrews, Held & Malloy, Ltd.

(57) ABSTRACT

The present disclosure relates to compounds that are useful as near-infrared fluorescence probes, wherein the compounds include i) a pteroyl ligand that binds to a target receptor protein, ii) a dye molecule, and iii) a linker molecule that comprises an amino acid or derivative thereof. The disclosure further describes methods and compositions for making and using the compounds, methods incorporating the compounds, and kits incorporating the compounds.

19 Claims, 64 Drawing Sheets

| Compound # | Linker (X) | Dye (Y) |
|---|---|---|
| 1 | Asp-Arg-Asp-Cys | DyLight680-malimide |
| 2 | Asp-Arg-Asp-Cys | DyLight750- malimide |
| 3 | EDA | IR800CW |

| Compound # | Linker (X) | Dye (Y) |
|---|---|---|
| 3 | EDA | IR800CW |
| 4 | EDA | LS288 |
| 5 | EDA | ZW800 |
| 6 | EDA | Kodak2 |
| 7 | Lys | IR800CW |
| 8 | Lys | LS288 |
| 9 | Lys | ZW800 |
| 10 | Lys | Kodak2 |

FIGURE 6
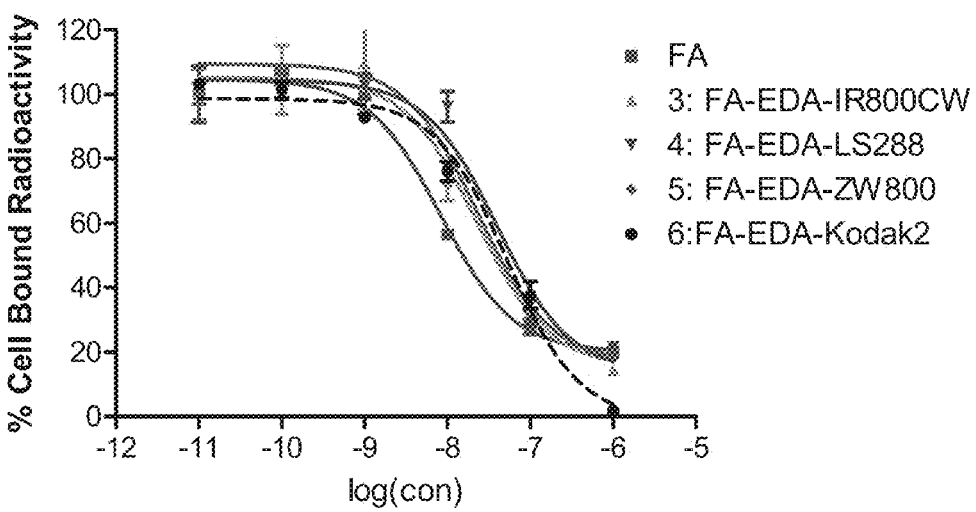
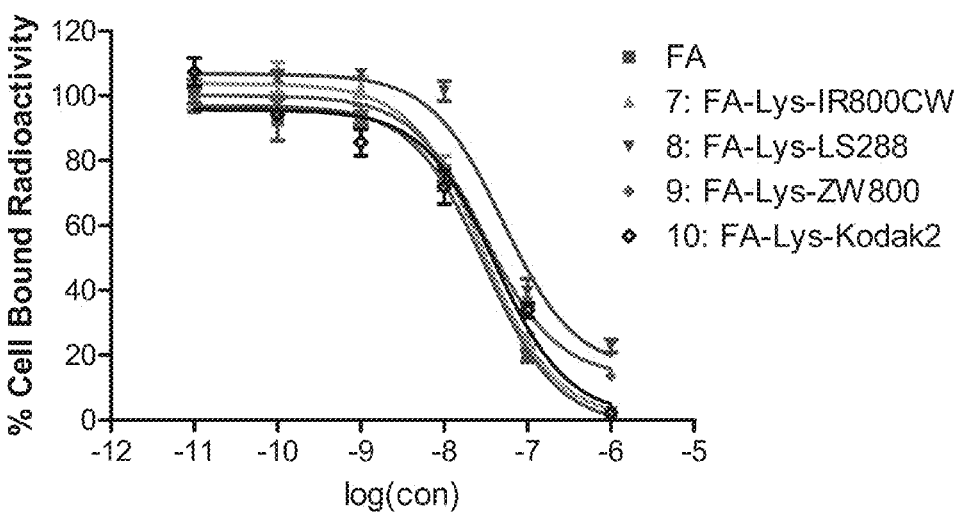
| Linker | LS288 | IR800 | ZW800 | Kodak2 |
|---|---|---|---|---|
| FA-EDA | 30.7 | 19.3 | 23.3 | 30.6 |
| FA-Lys | 50.1 | 22.8 | 30.5 | 39.7 |

FIGURE 7A
(a) 3: FA-EDA-IR800    4: FA-EDA-LS288    5: FA-EDA-ZW800    6: FA-EDA-Kodak 2
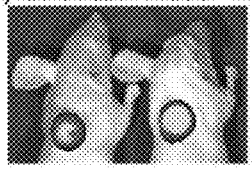 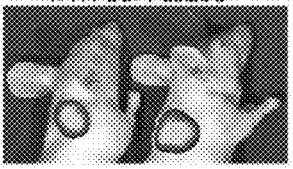 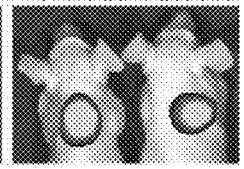 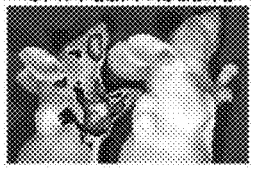
(b) 4:FA-EDA-LS288   3: FA-EDA-IR800   5: FA-EDA-ZW800   6: FA-EDA-Kodak 2
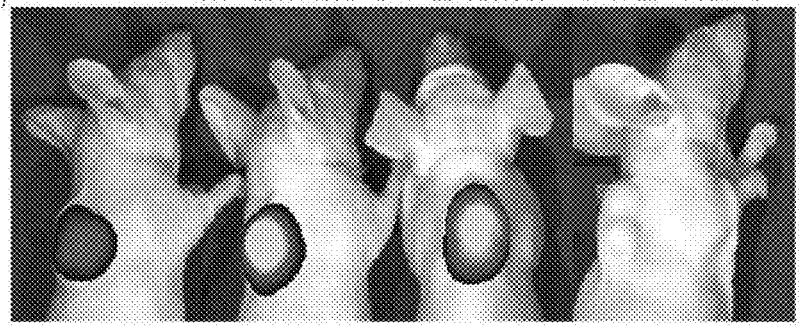
(c) 7: FA-Lys-IR800    8: FA-Lys-LS288    9: FA-Lys-ZW800
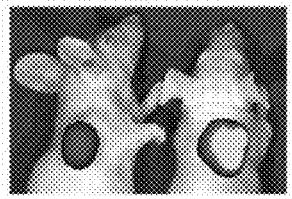 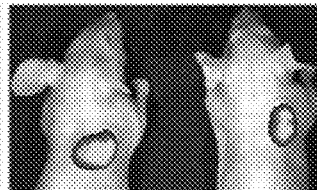 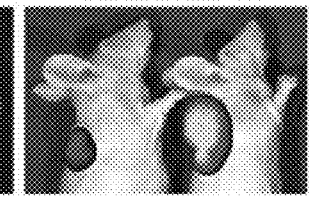

FIGURE 7B
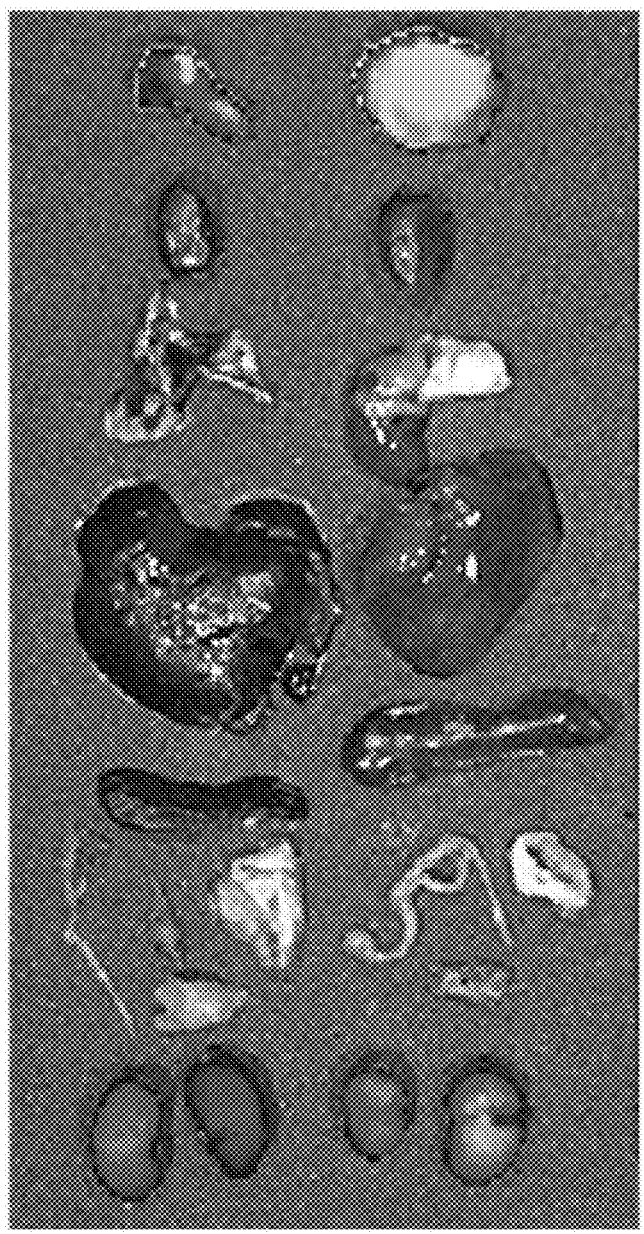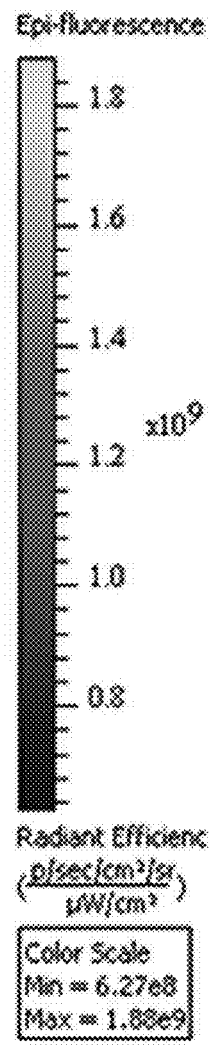

FIGURE 7B - Cont.
FA-EDA-IR800
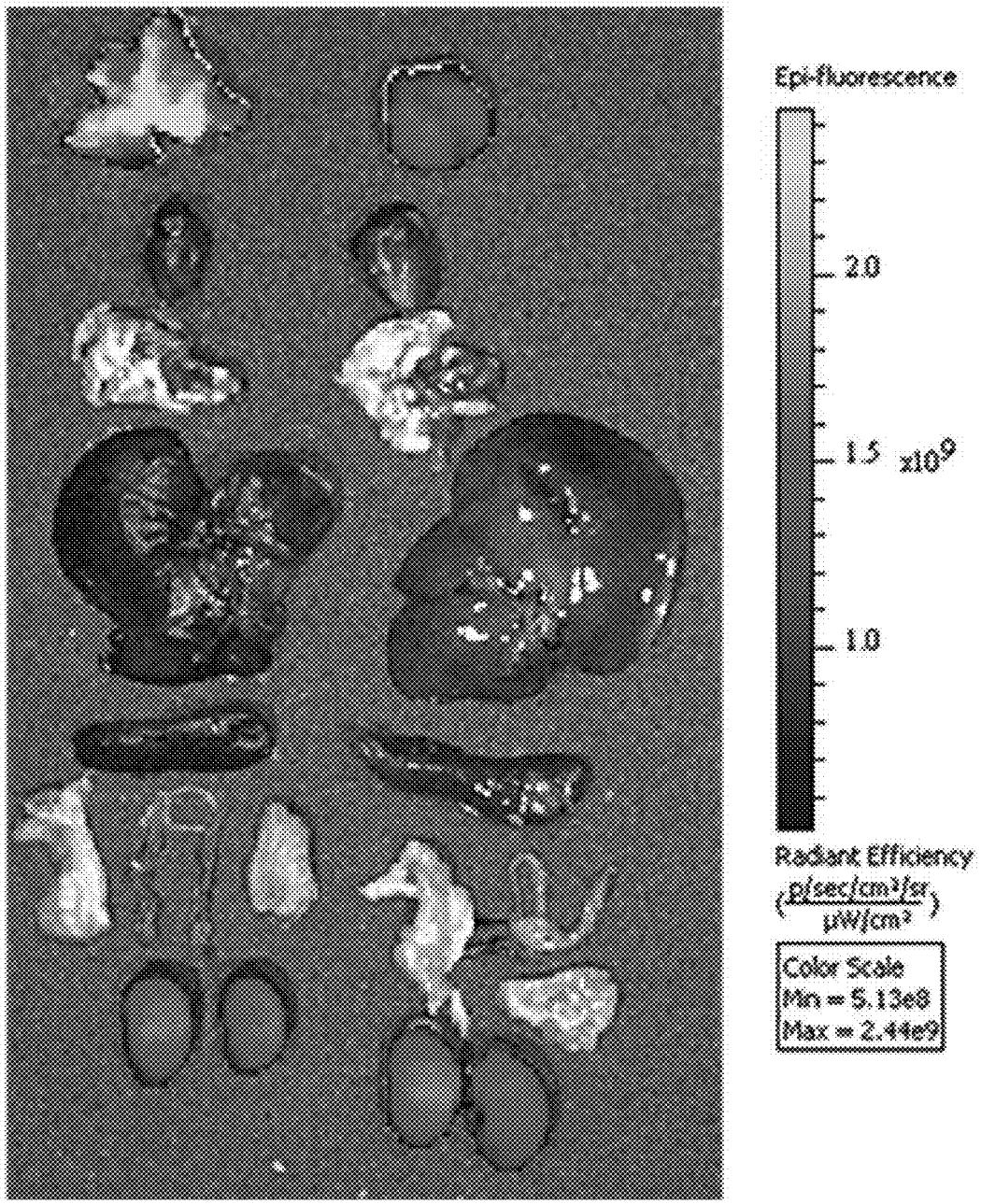

FIGURE 7B - Cont.
FA-EDA-ZW800
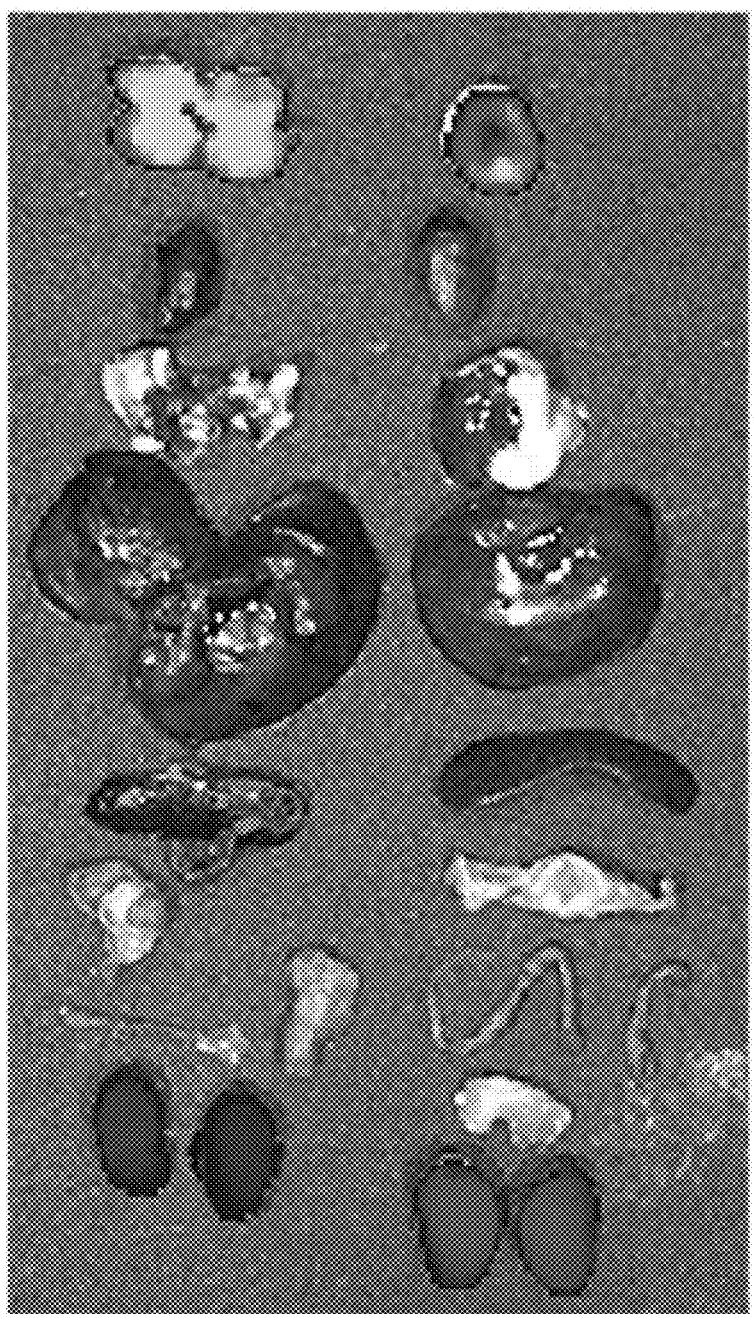
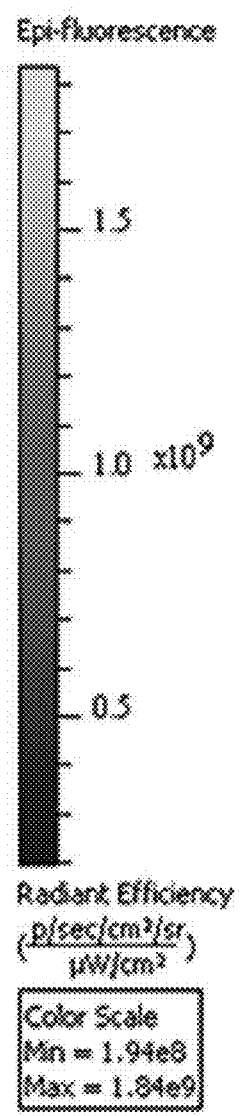

FIGURE 7B - Cont.
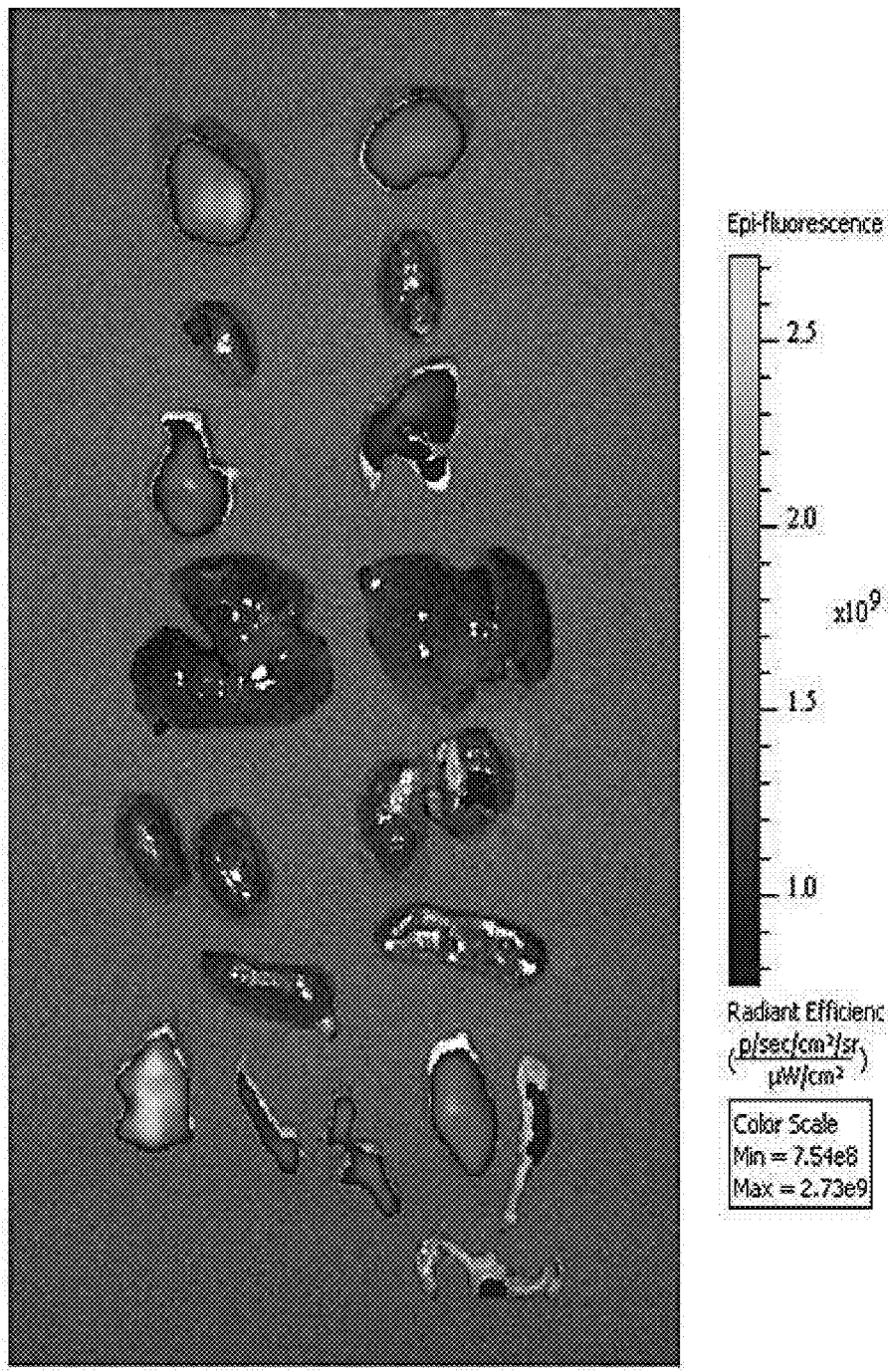

FIGURE 7B - Cont.
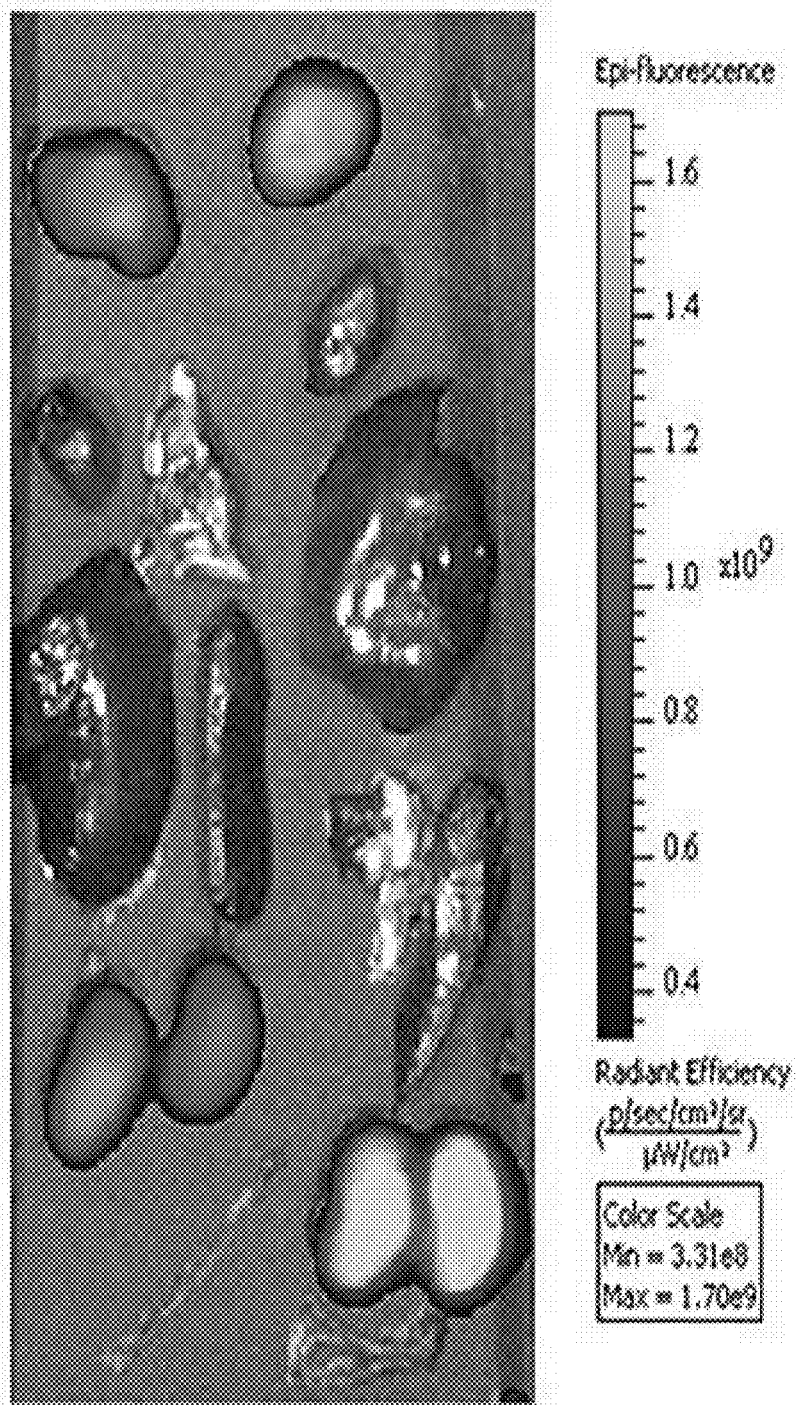

FIGURE 7B - Cont.
FA-Lys-IR800
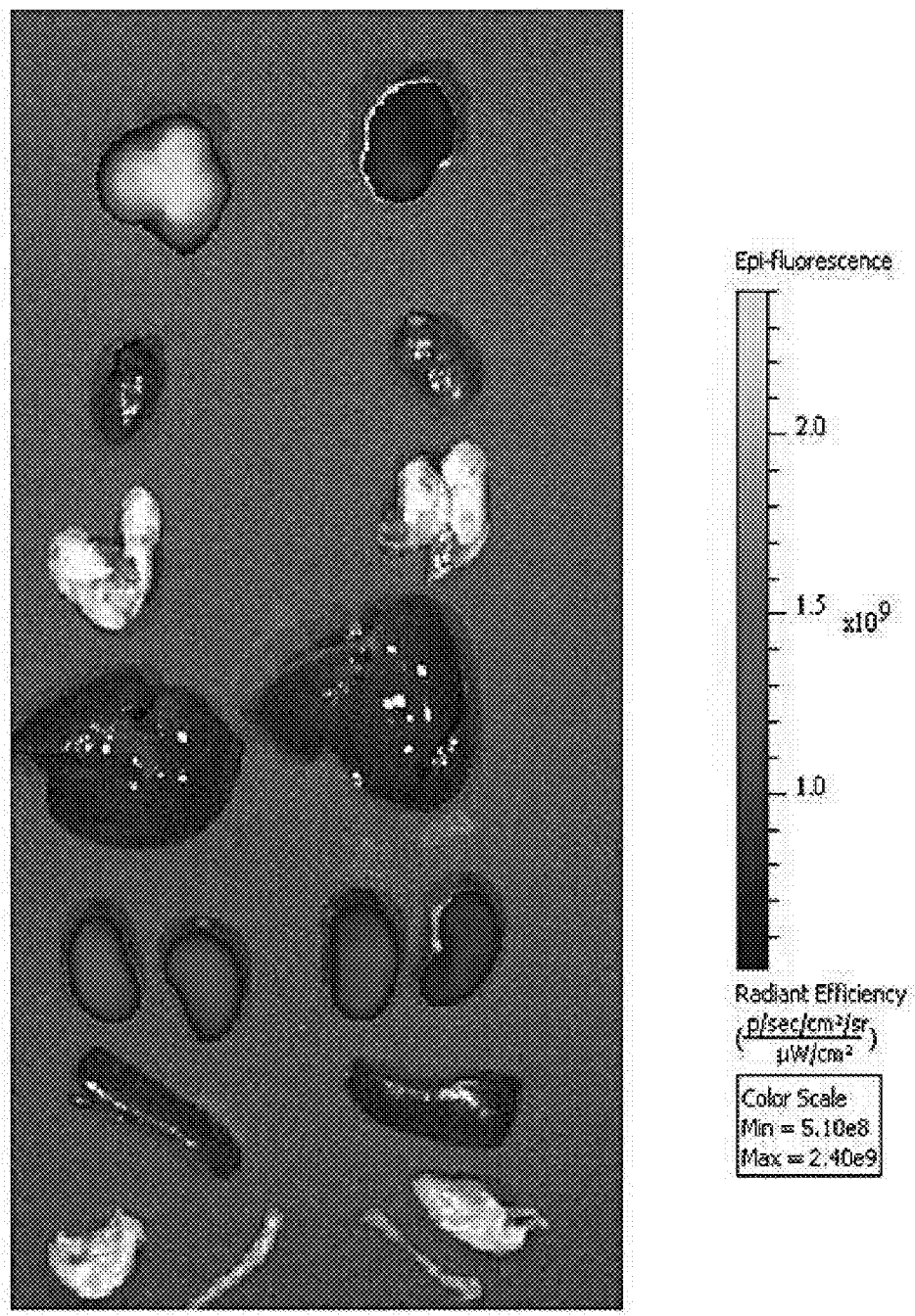

FIGURE 7B - Cont.
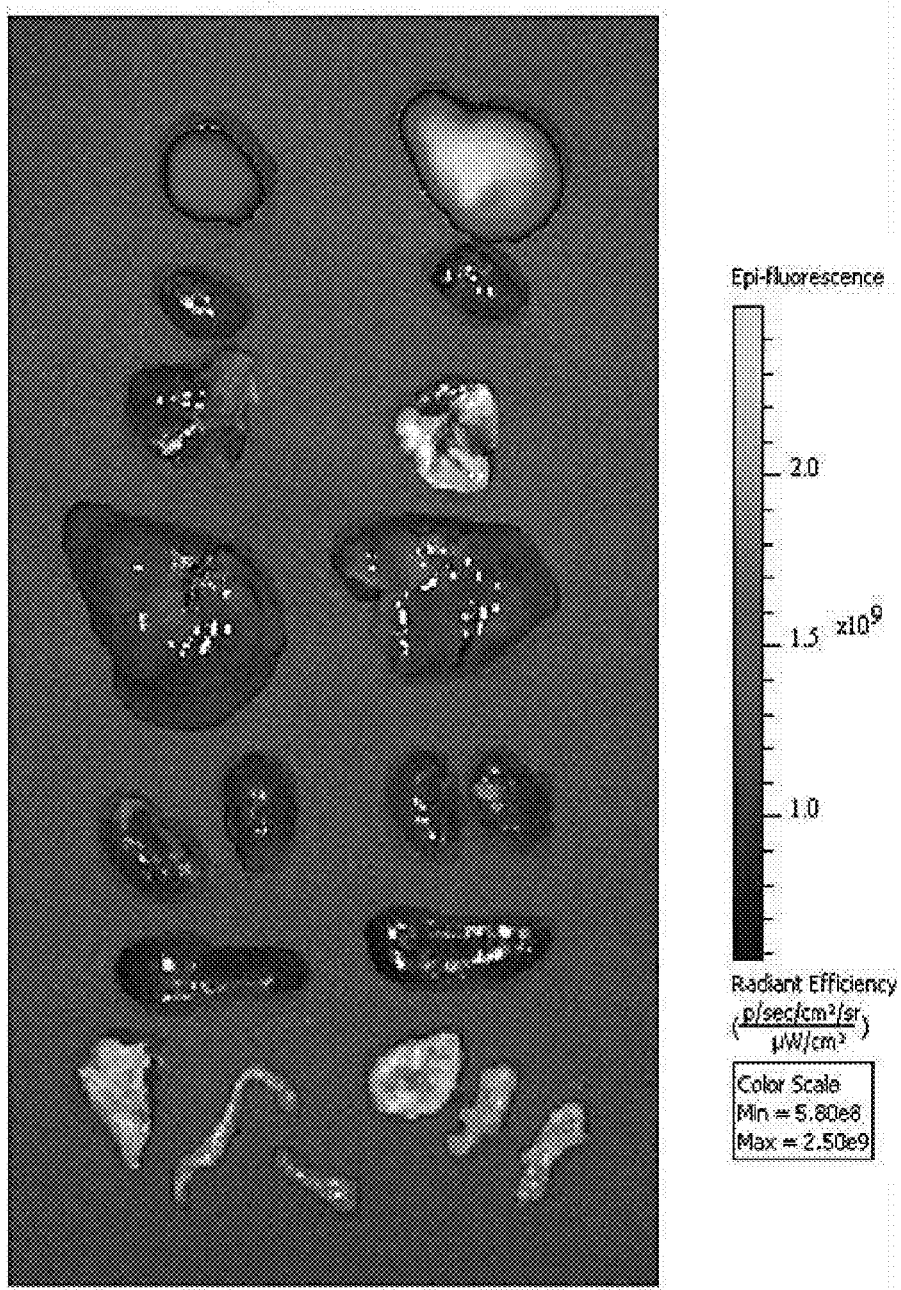

FIGURE 7B - Cont.
Pte-Lys-LS288
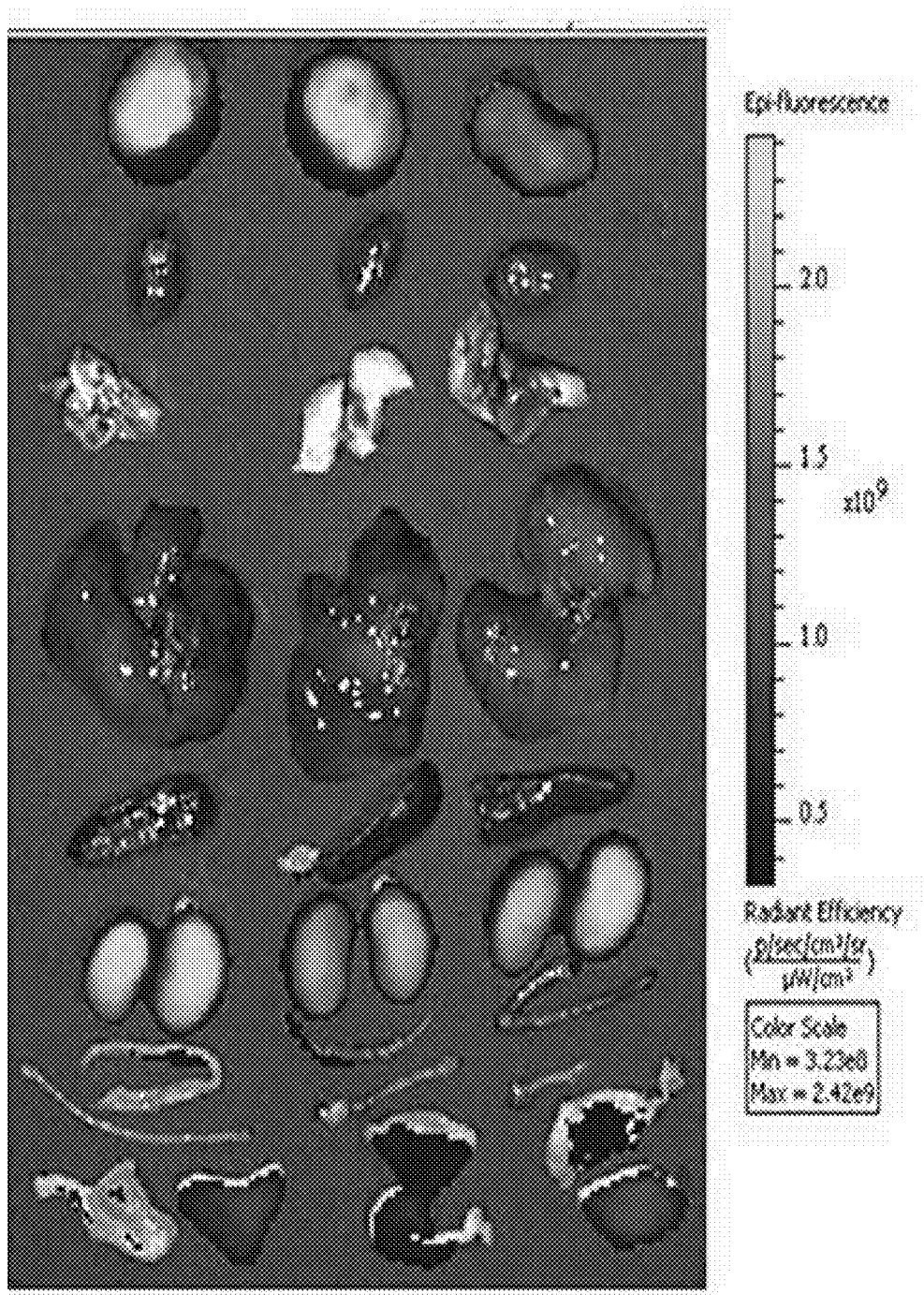

FIGURE 7B - Cont.
Pte-DHDADS-LS288
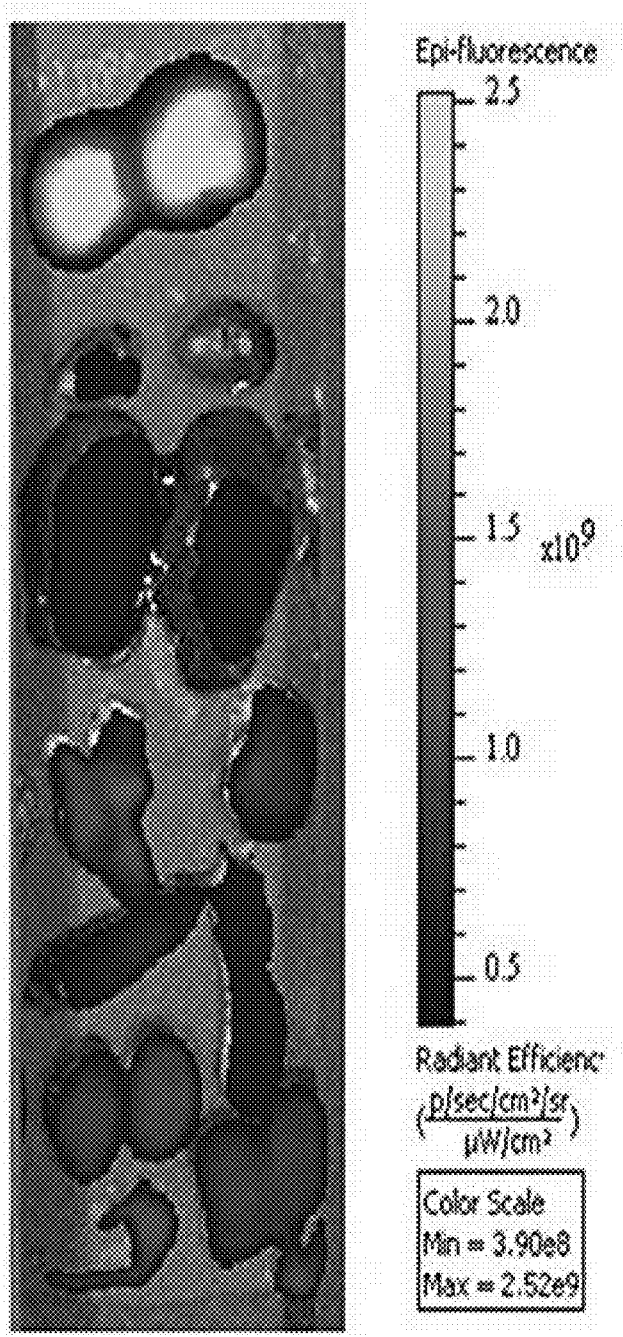

A) Amino acid linkers

| Compound # | Linker (X) | Dye (Y) |
|---|---|---|
| 11 | L-Tyr | S0456 |
| 12 | L-Cys | S0456 |
| 13 | L-Lys | S0456 |
| 14 | L-Ser | S0456 |
| 15 | L-AminoPro | S0456 |
| 16 | D-Tyr | S0456 |
| 17 | D/L-Tyr | S0456 |
| 18 | L-Tyr | S0121 |
| 19 | L-Tyr | Kodak |
| 20 | L-Tyr | S2076 |

M = H, Na and/or K

FIGURE 11
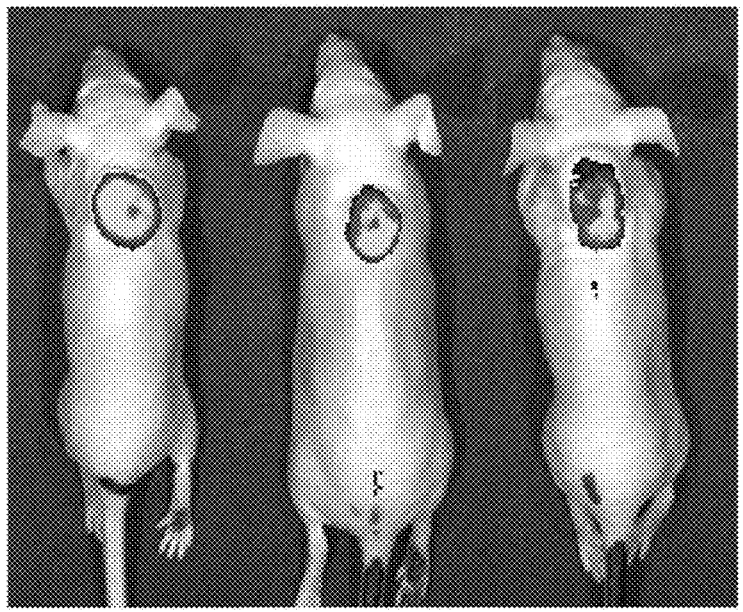
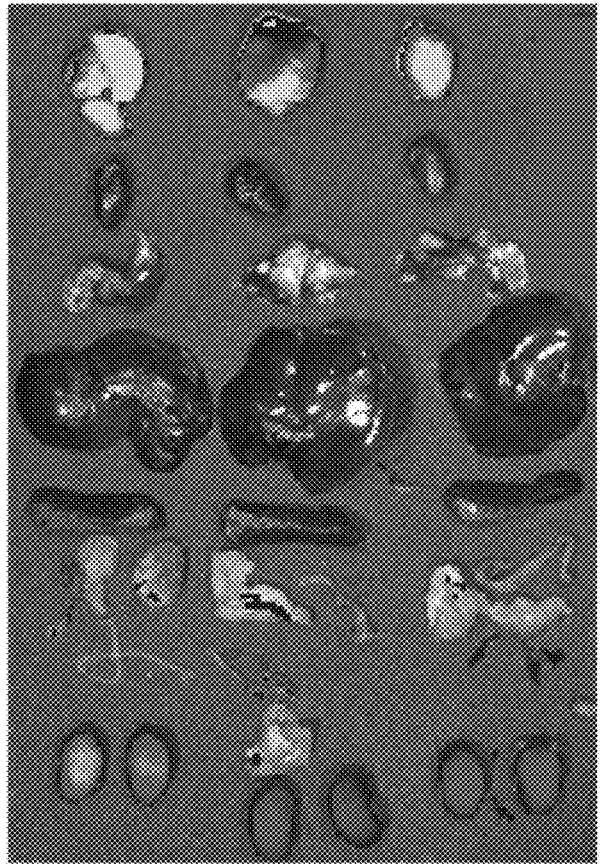

| Test article | Binding affinity | Relative Binding Affinity |
|---|---|---|
| Folic acid | 7.4 | 1 |
| OTL-0038 | 10.4 | 0.7 |
| OTL-0039 | 81.8 | 0.09 |

FIGURE 17

| Dose (nmol) | Results |
|---|---|
| 0.3 | Lower uptake in the tumor and high kidney uptake |
| 1.0, 3.0, and 10.0 | High tumor and kidney uptake |
| 30.0 | High tumor uptake but less kidney uptake |
| 60.0 | High tumor uptake but less kidney uptake. substantial lungs, stomach, small intestine, large intestine uptake |
| 90.0 | High tumor uptake but less kidney uptake. substantial heart, lungs, liver, spleen, stomach, small intestine, large intestine uptake |

0.3 nmol

FIGURE 18 - CONT.
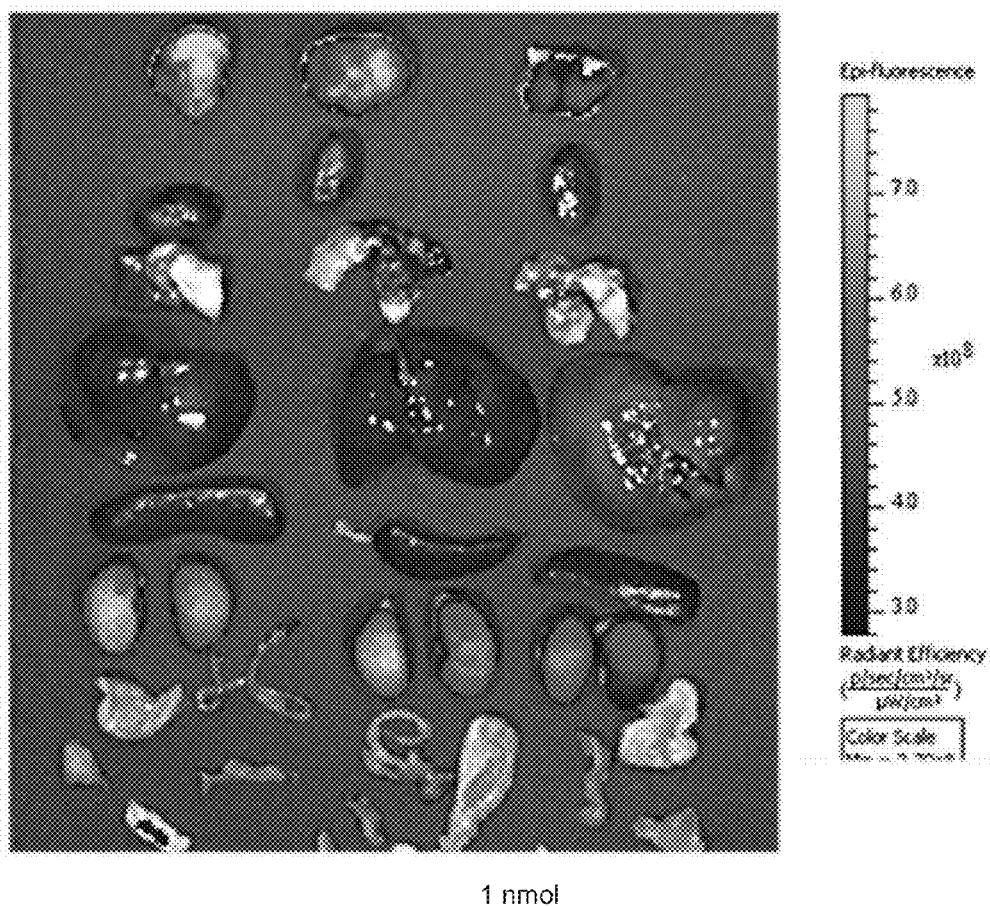
1 nmol

FIGURE 18 - CONT.
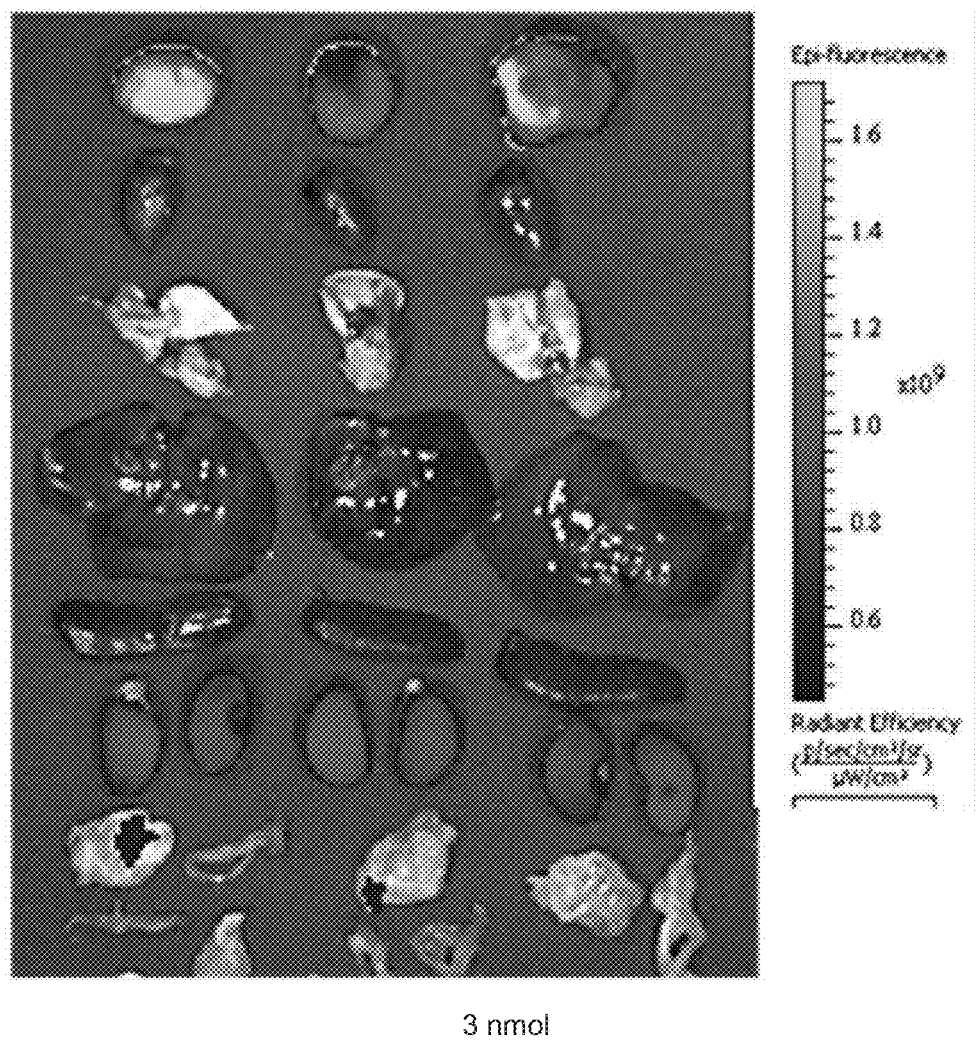
3 nmol

FIGURE 18 - CONT.
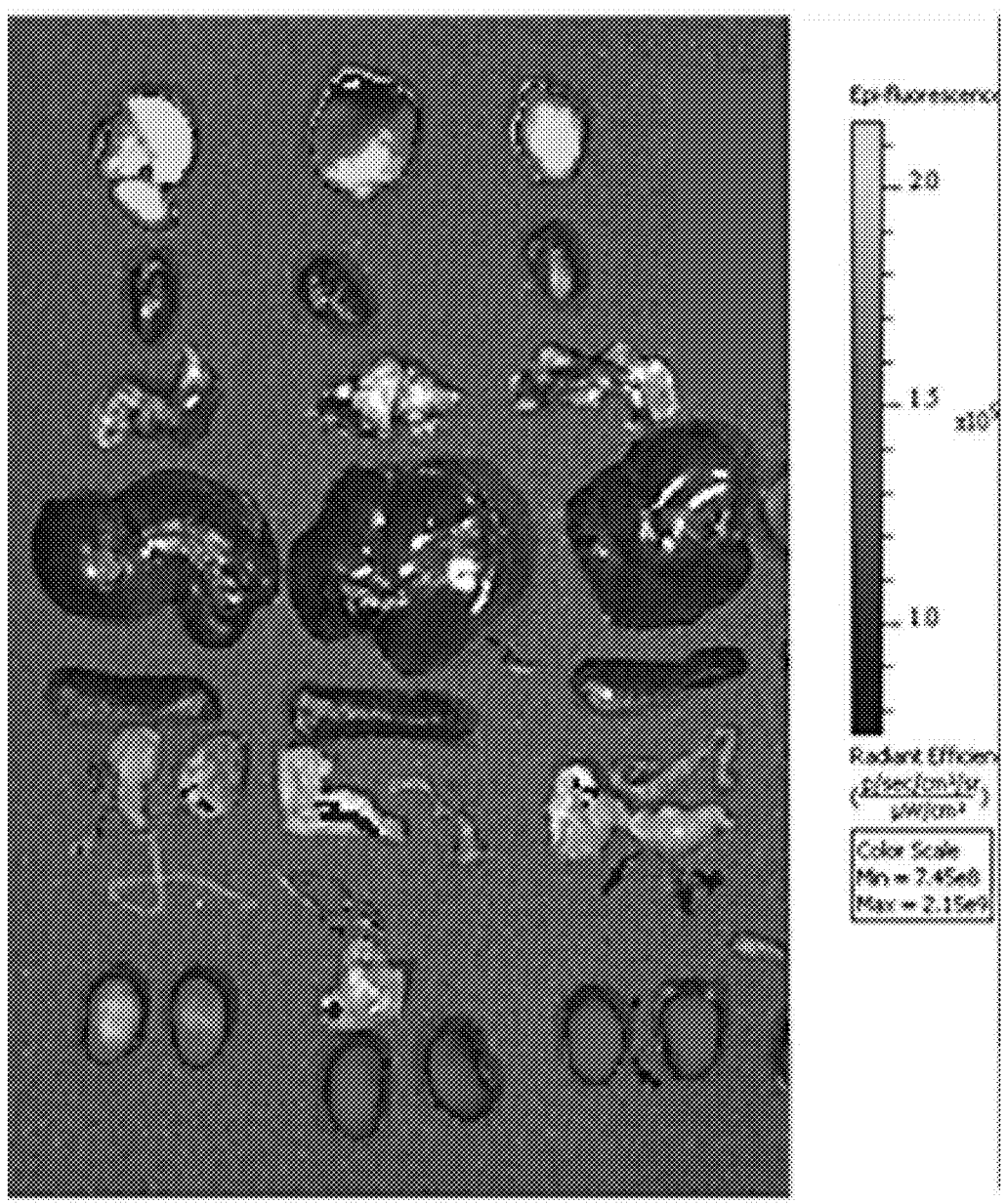
10 nmol

FIGURE 18 - CONT.
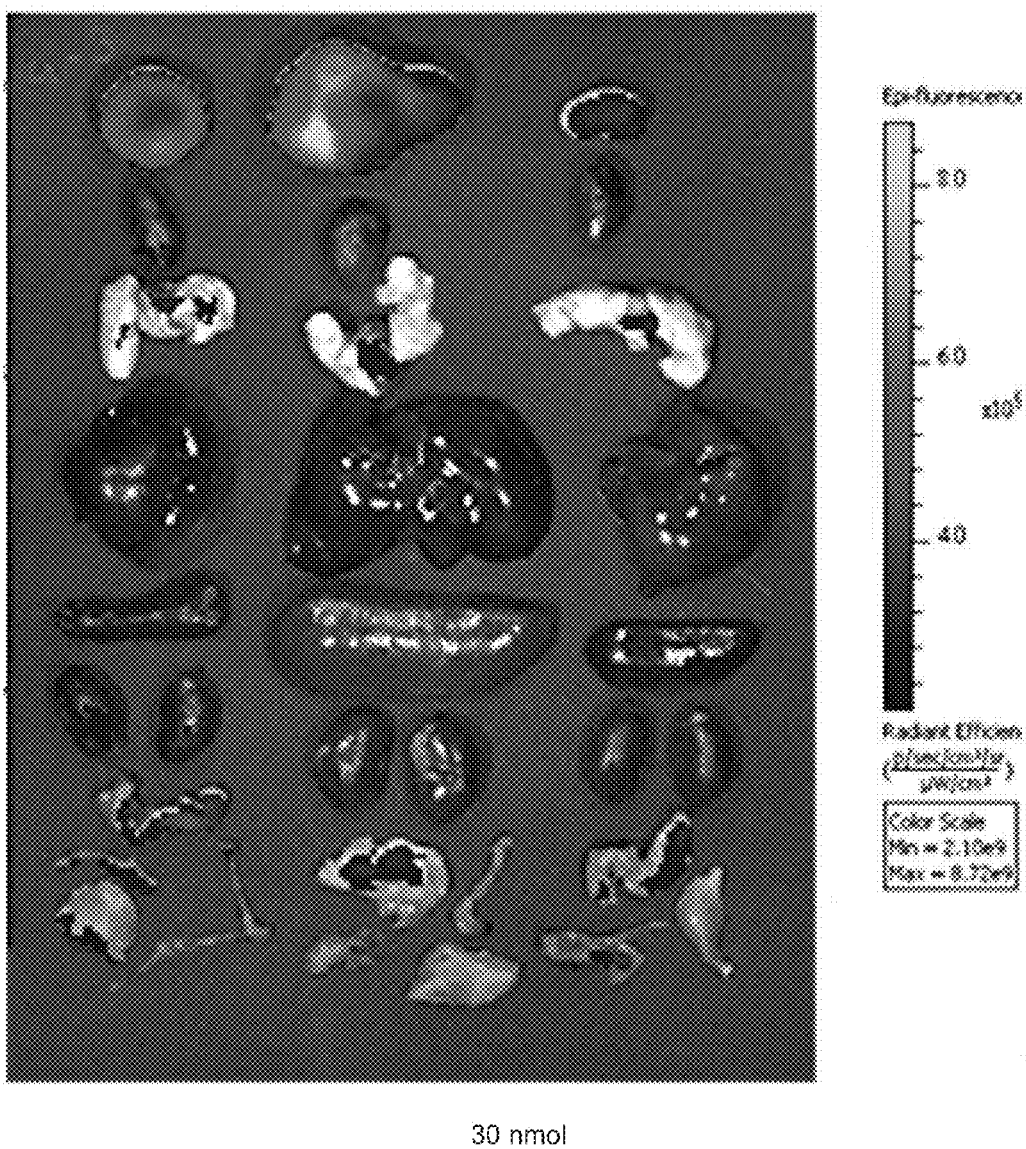
30 nmol

FIGURE 18 - CONT.
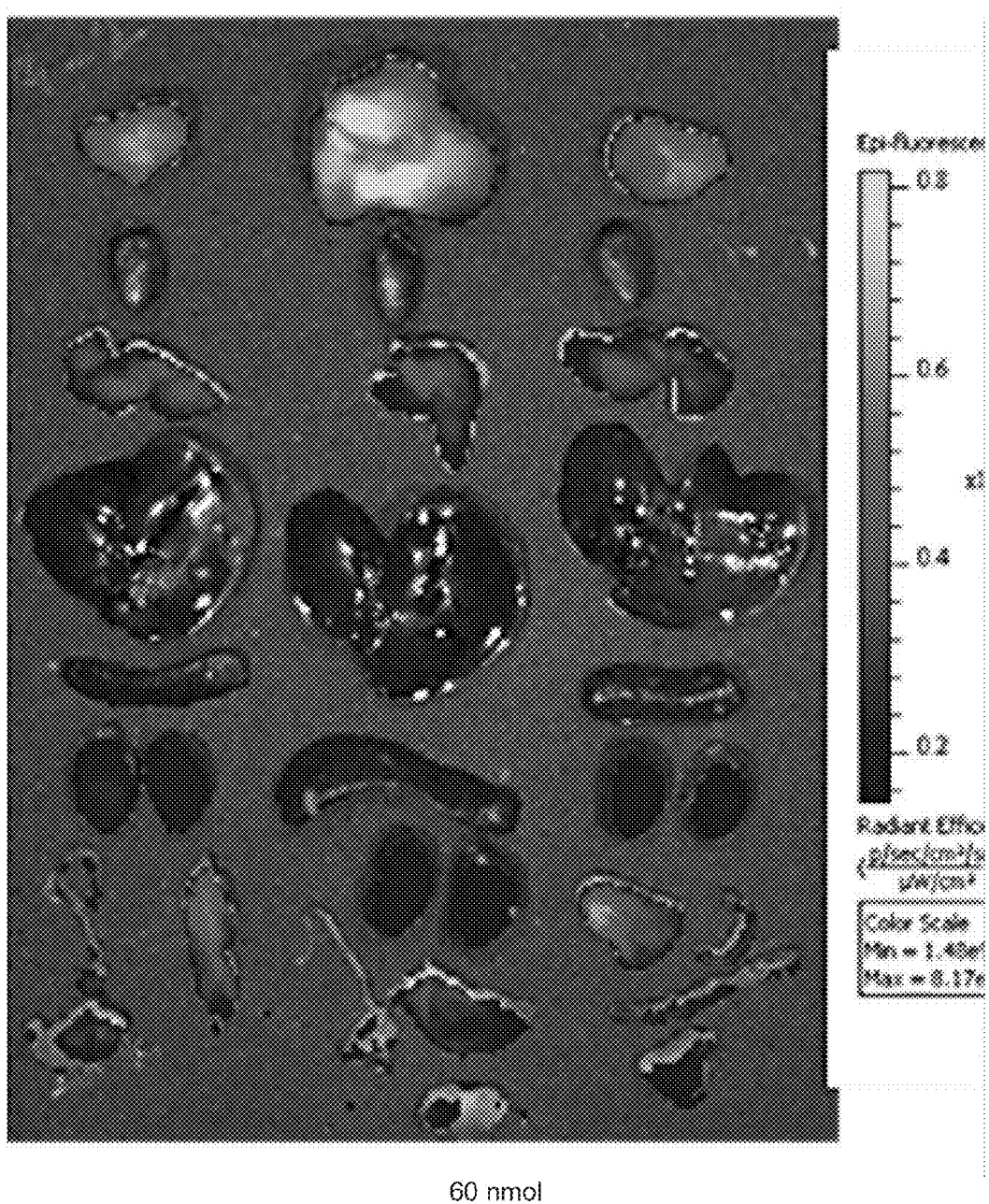
60 nmol

FIGURE 18 - CONT.
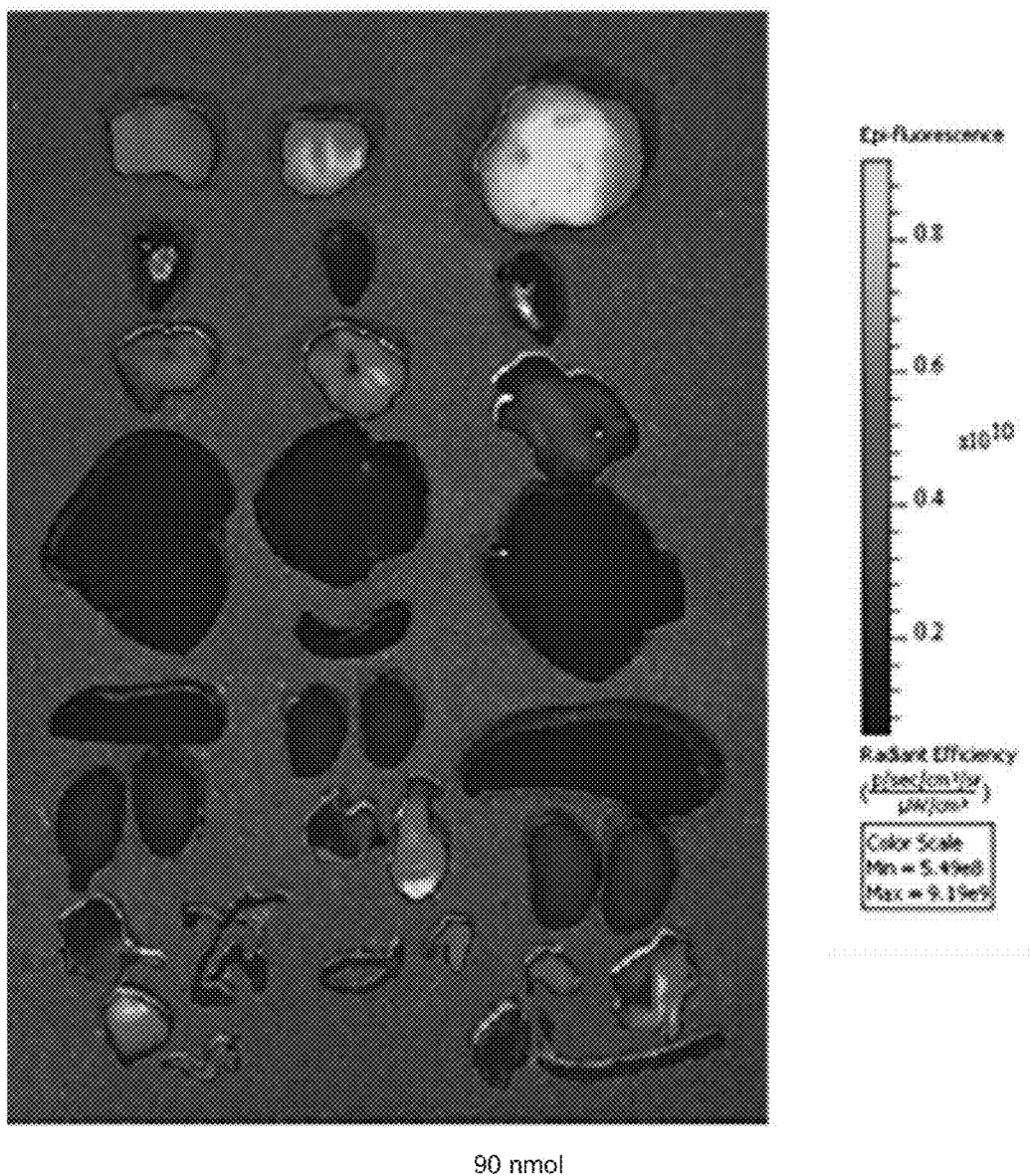
90 nmol

FIGURE 23A - Cont.
OTL-0044

FIGURE 23A - Cont.
OTL-0045
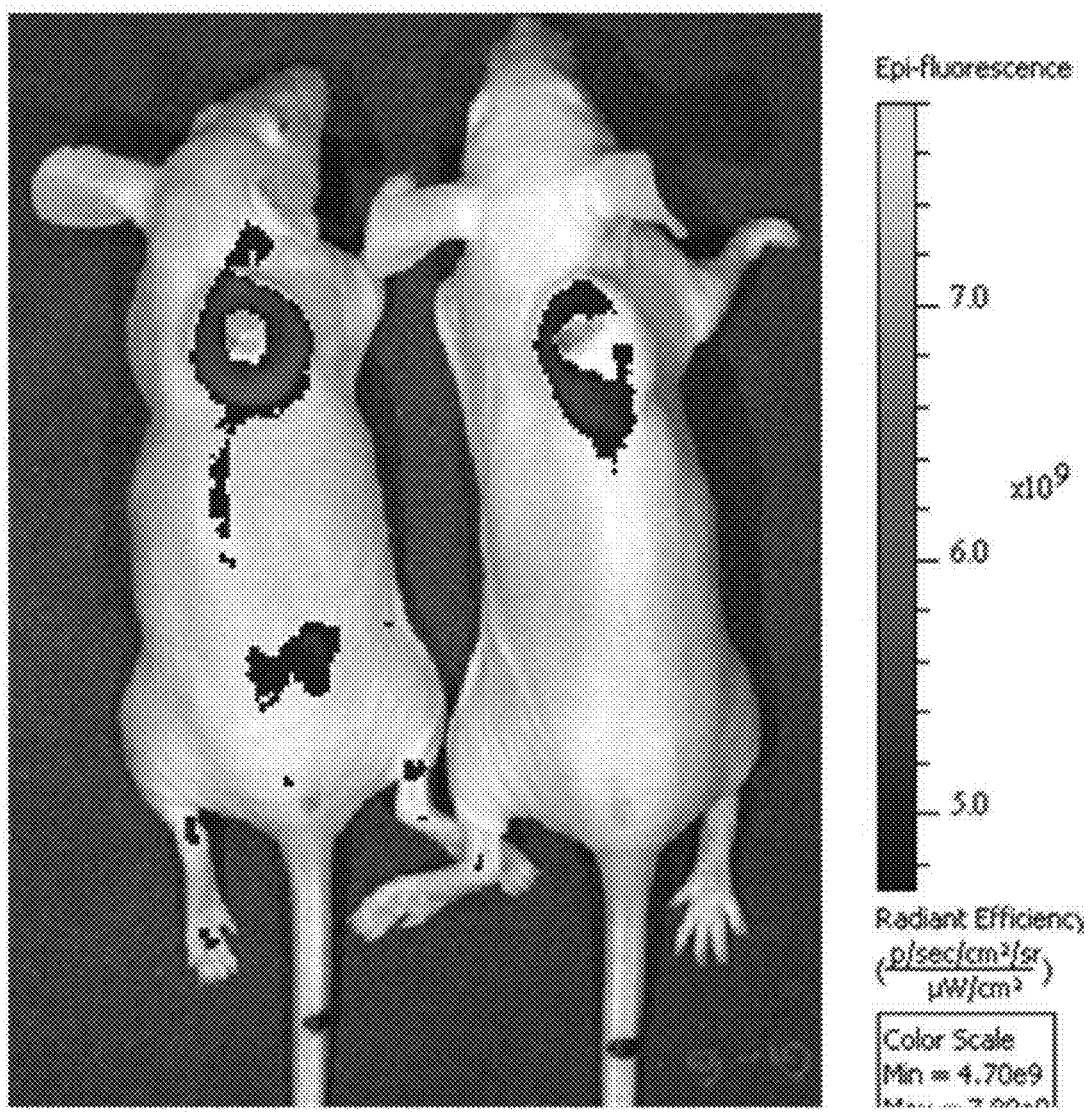

FIGURE 23A - Cont.
OTL-0046
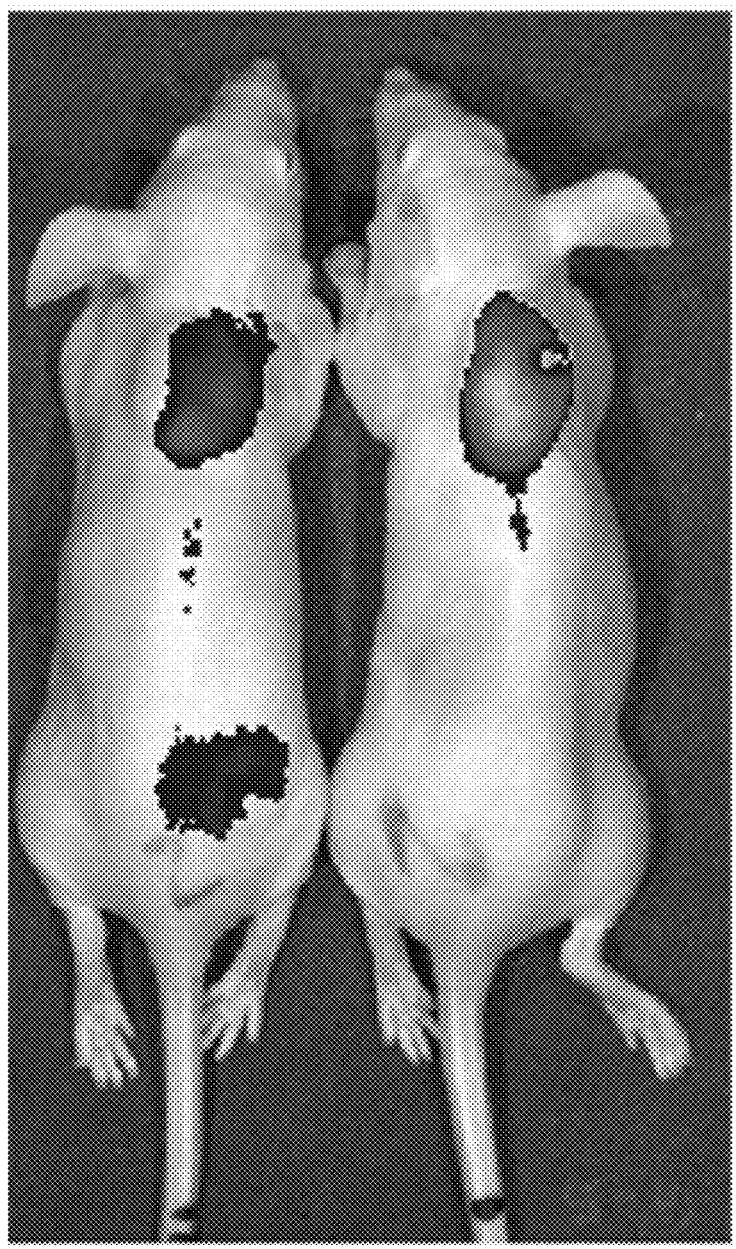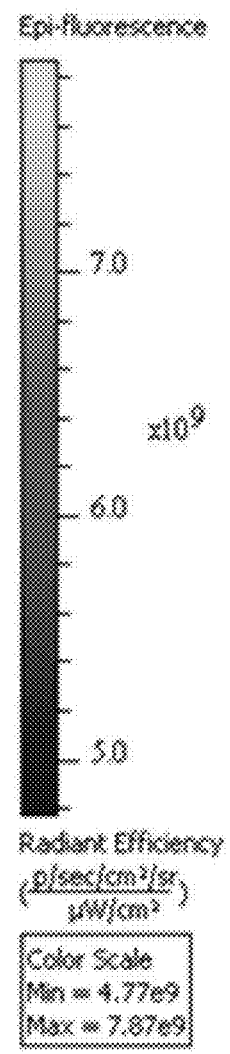

FIGURE 23A - Cont.
OTL-0047
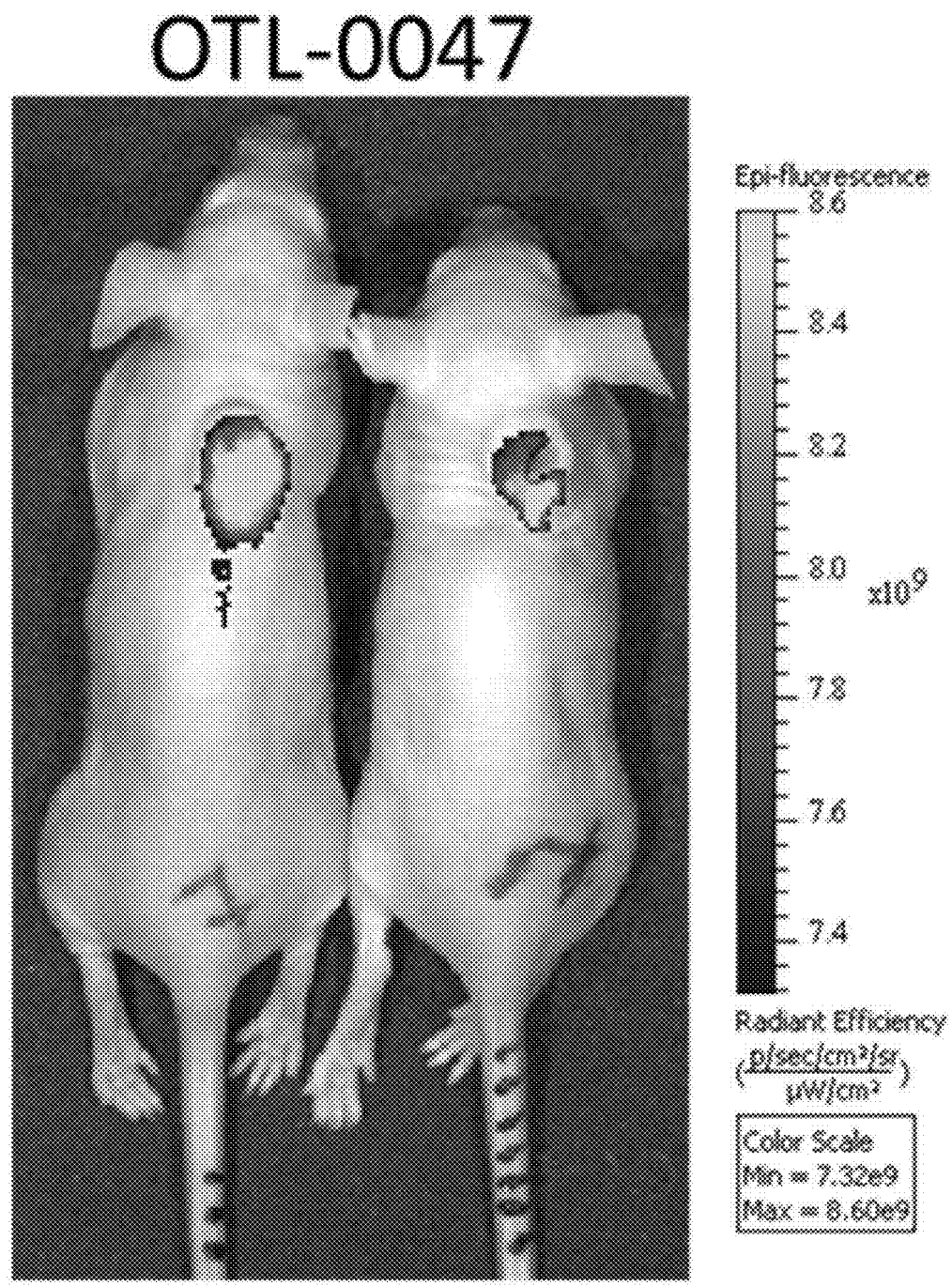

FIGURE 23A - Cont.
OTL-0048

FIGURE 23B - Cont.
OTL-0044
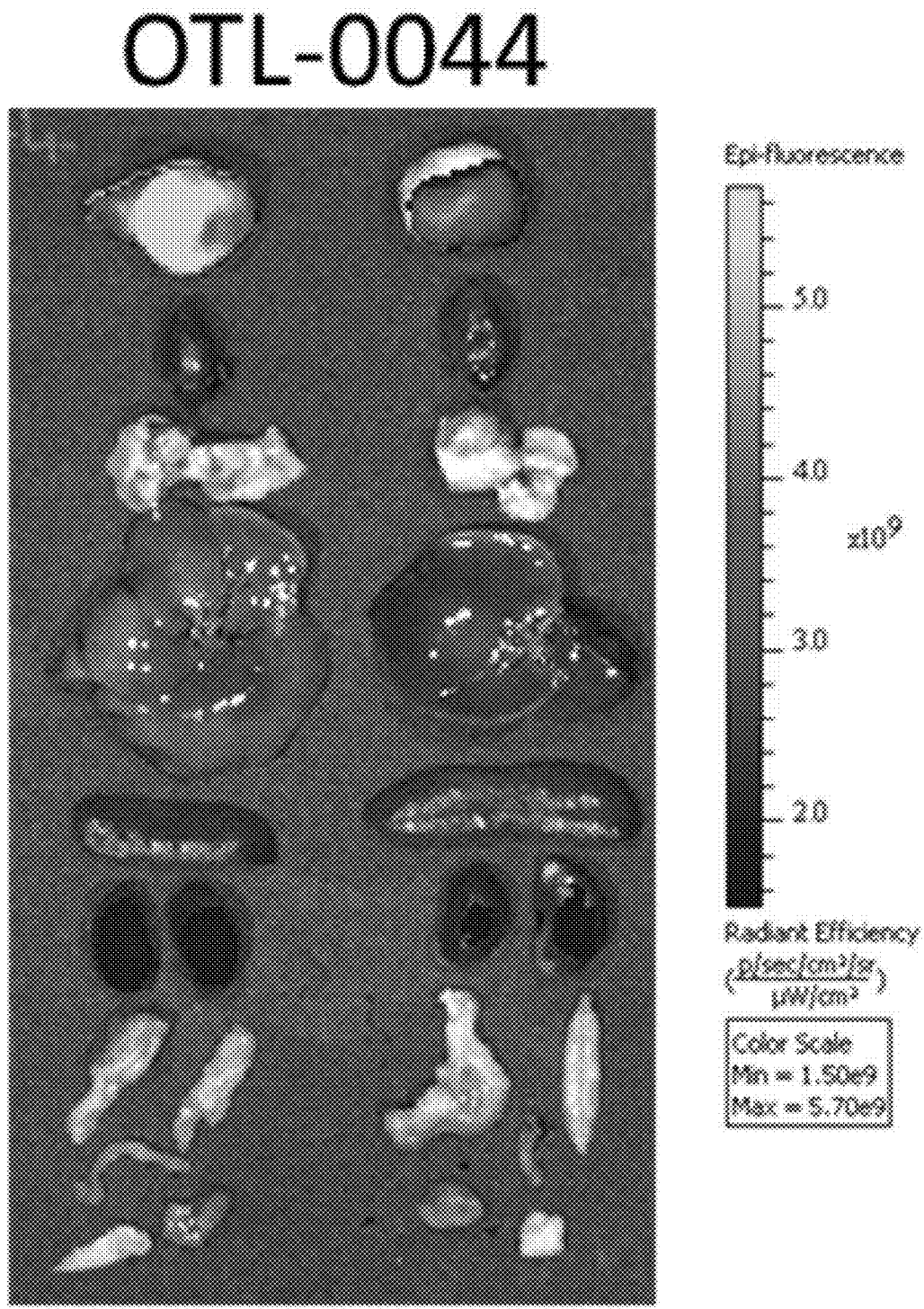

FIGURE 23B - Cont.
OTL-0045
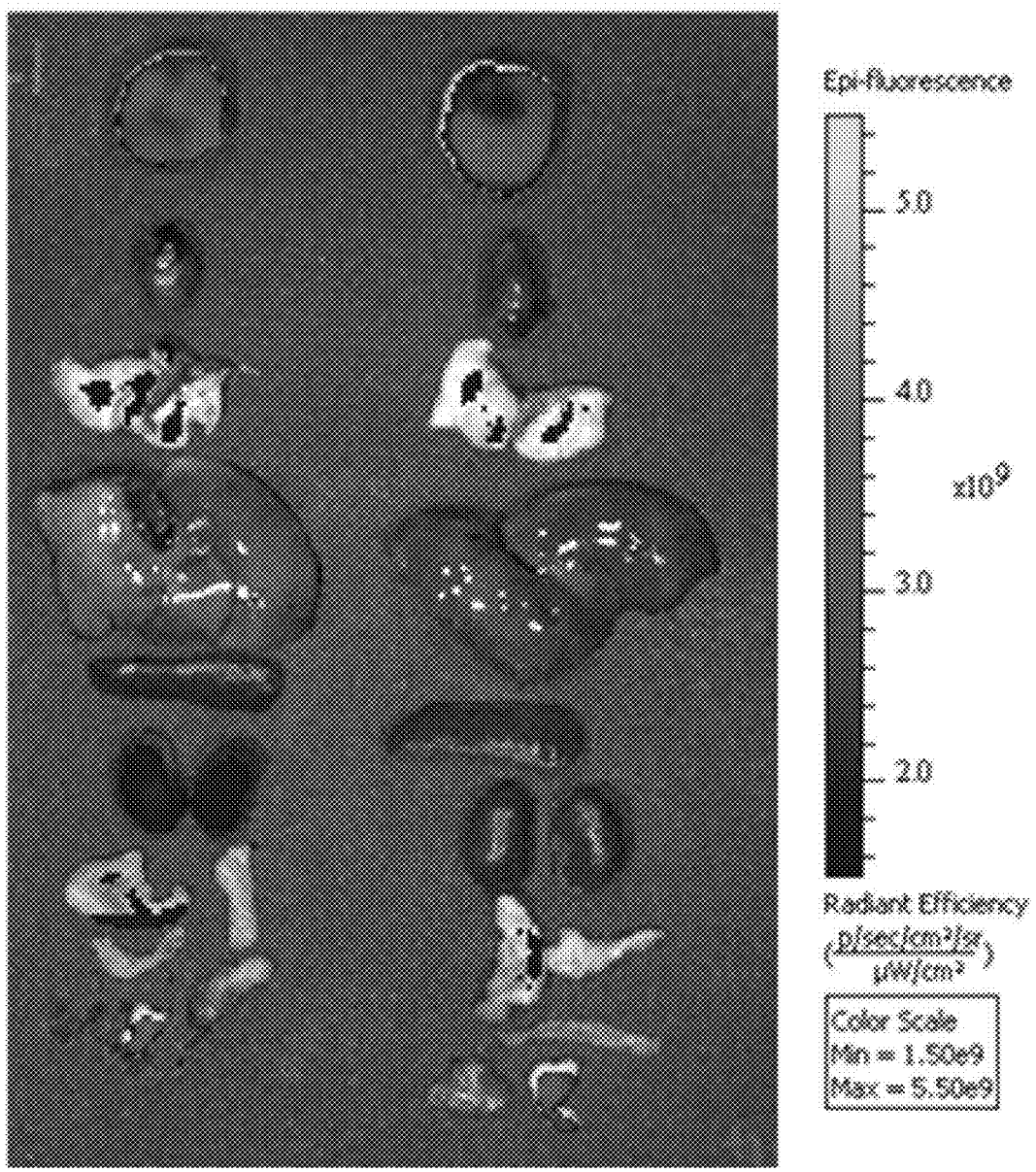

FIGURE 23B - Cont.
OTL-0046
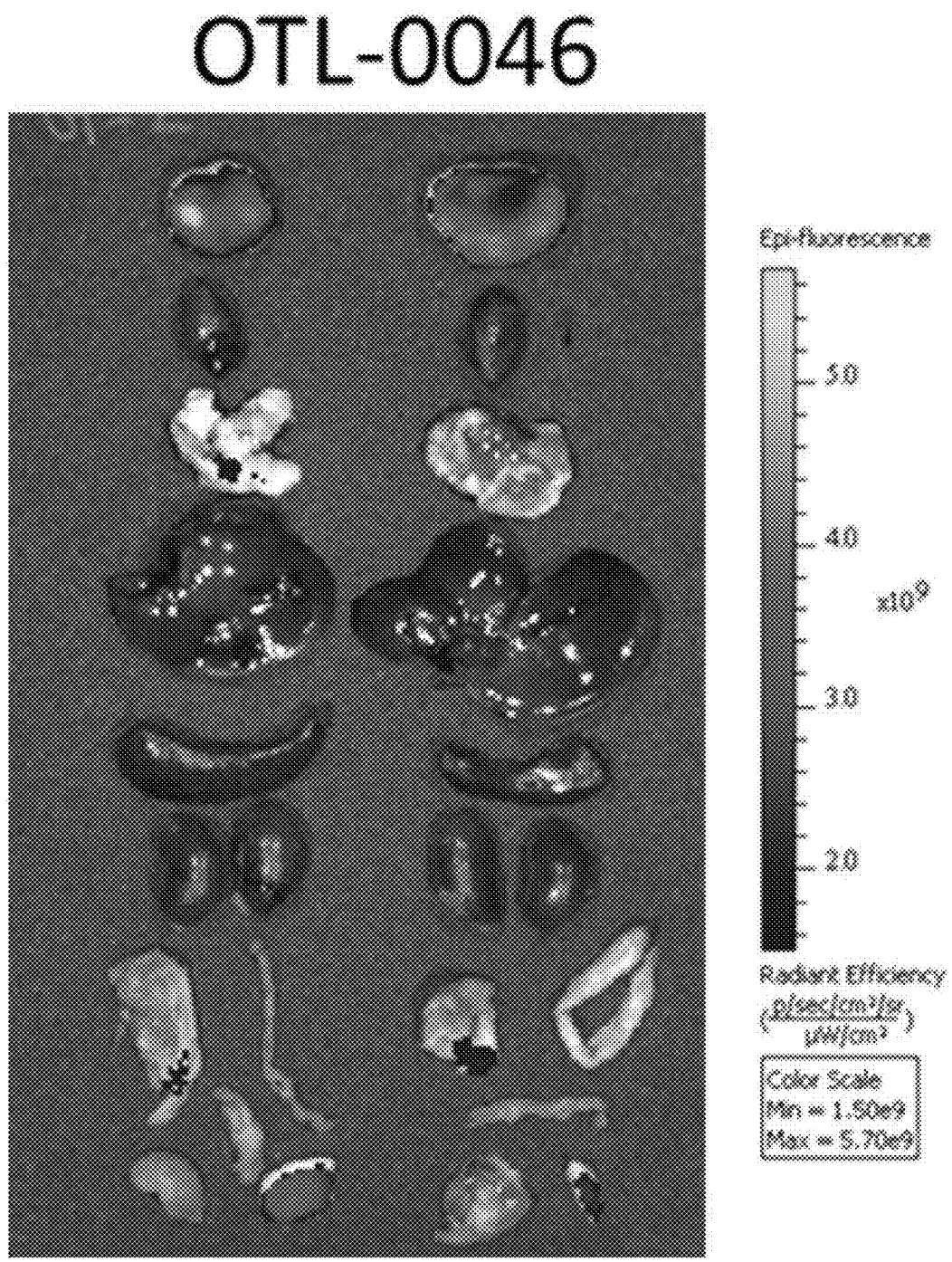

FIGURE 23B - Cont.
OTL-0047
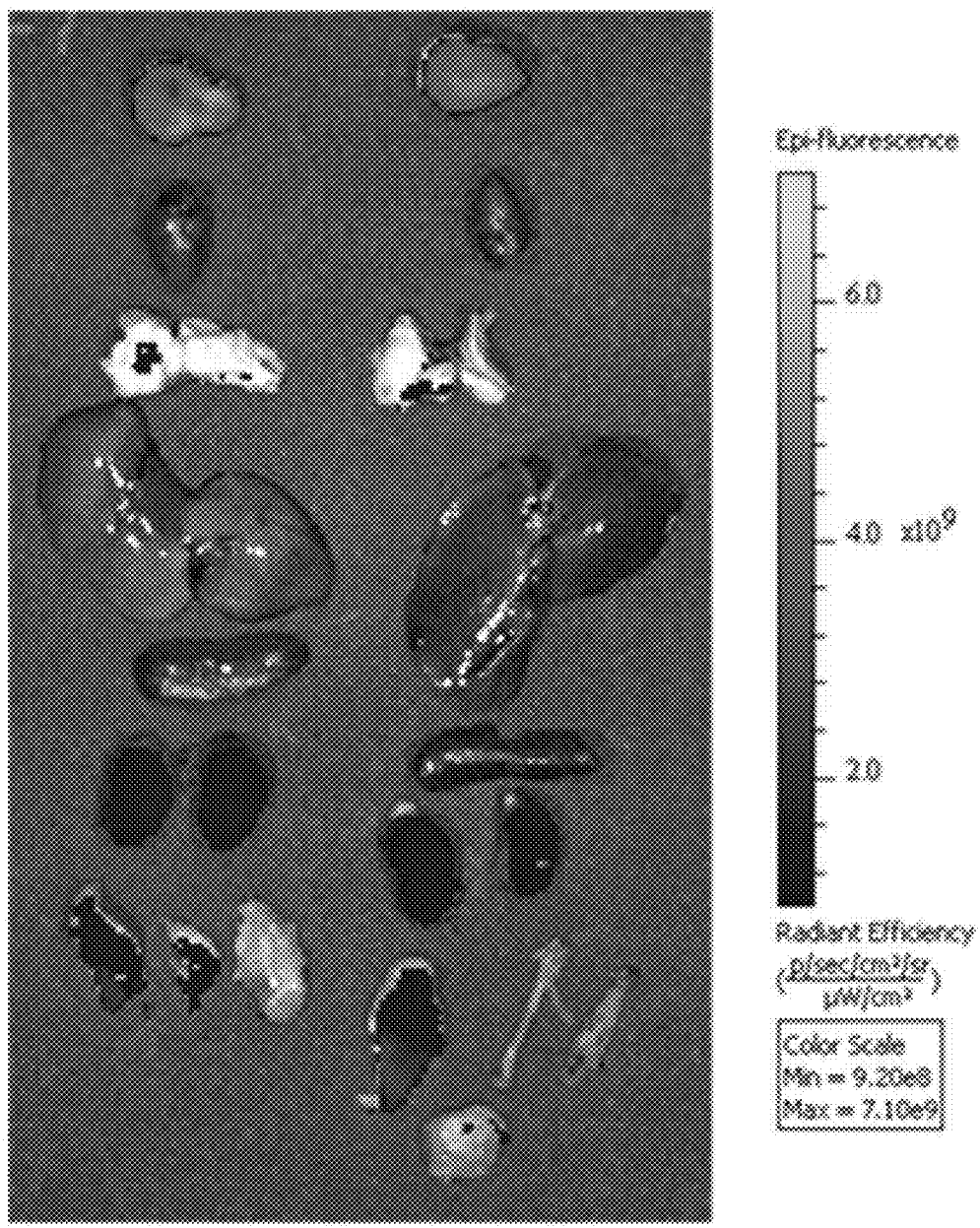

FIGURE 23B - Cont.
OTL-0048
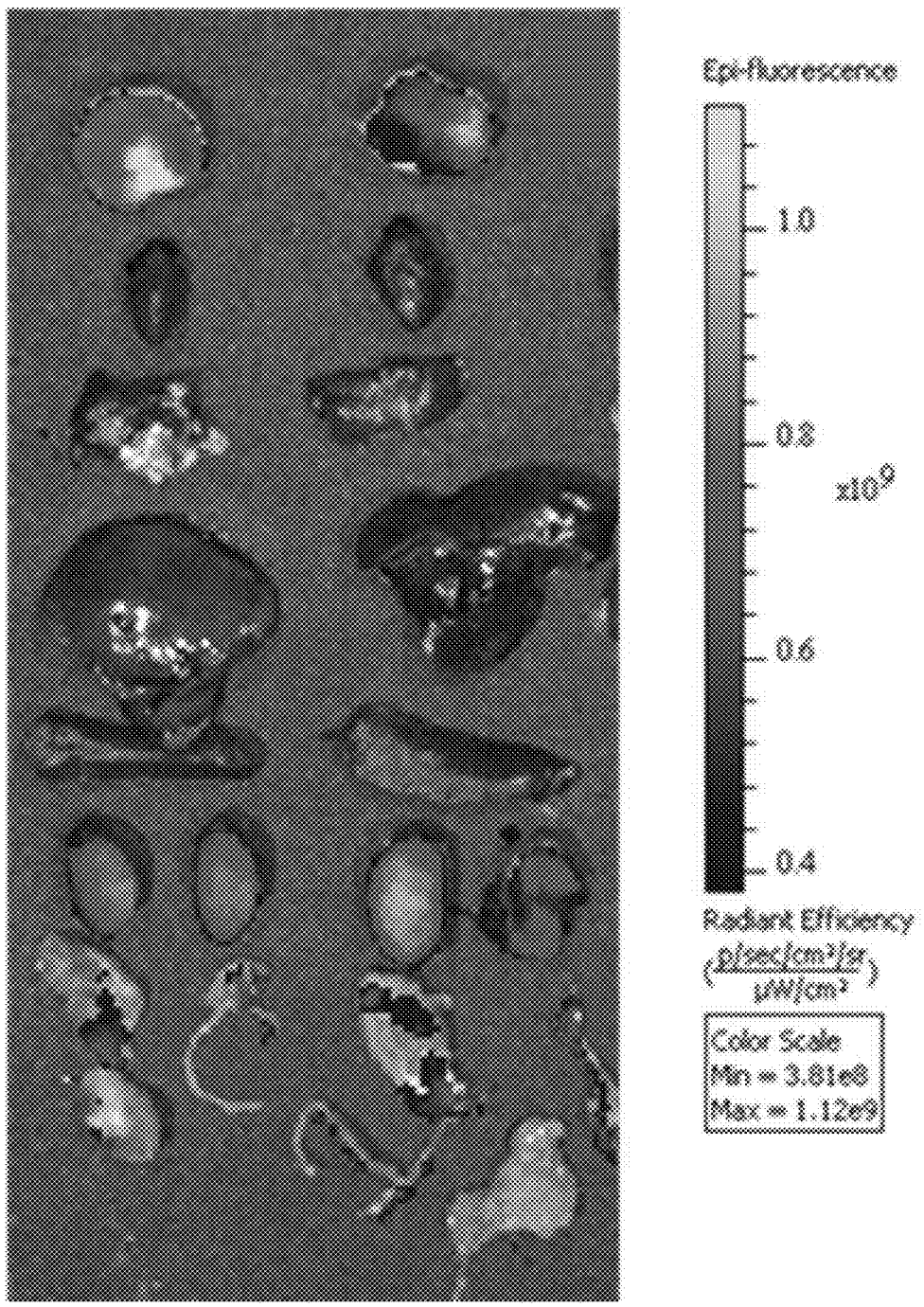

FIGURE 24 - Cont.
Pte-Lys-S0456
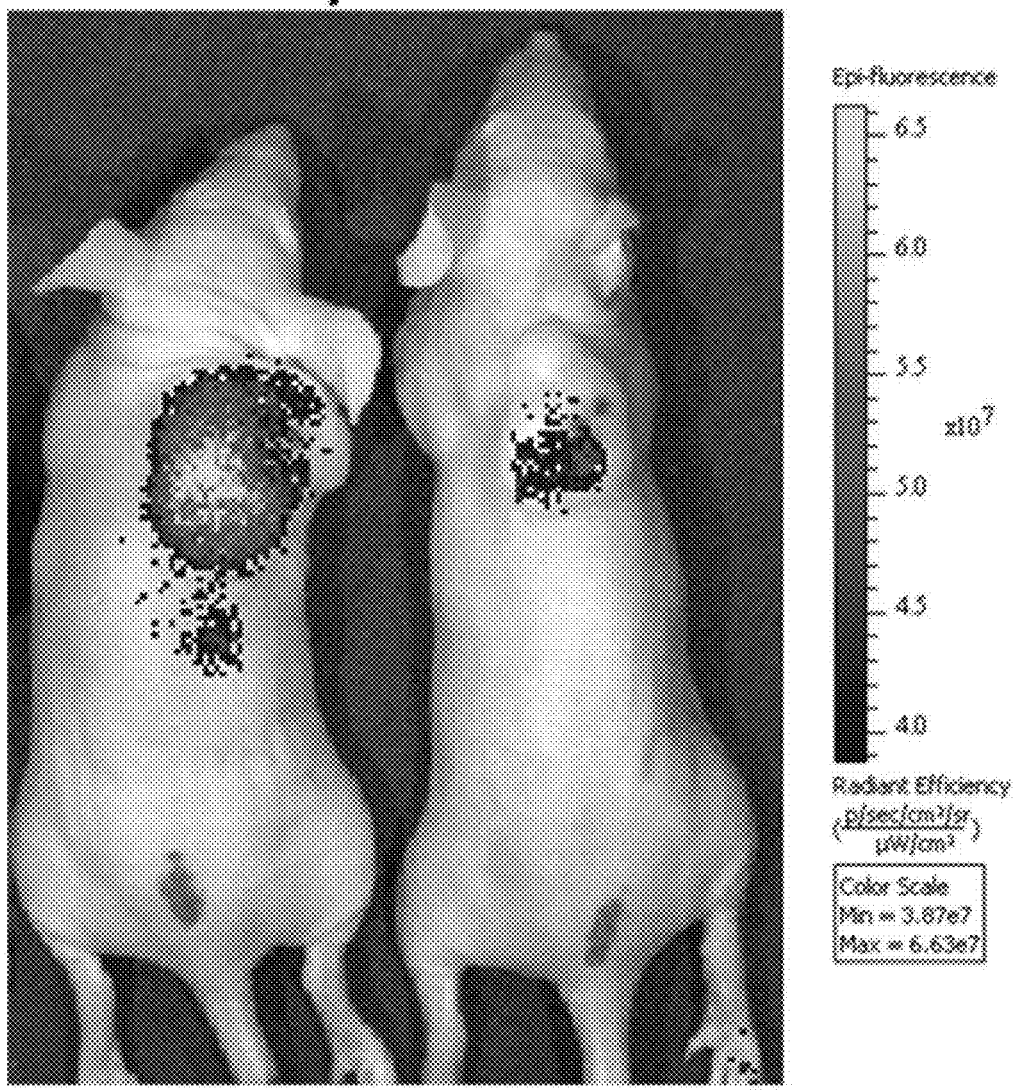

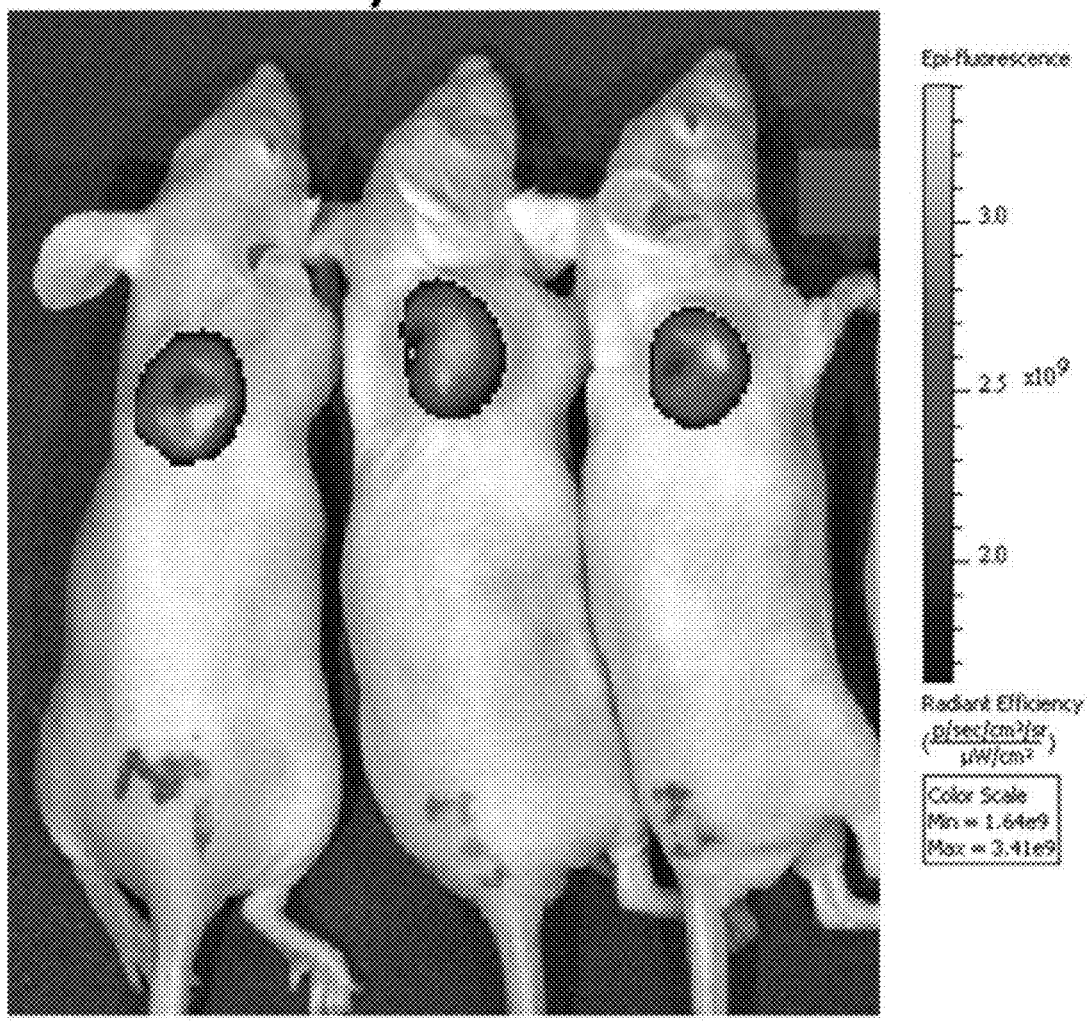
FIGURE 24 - Cont.

FIGURE 25
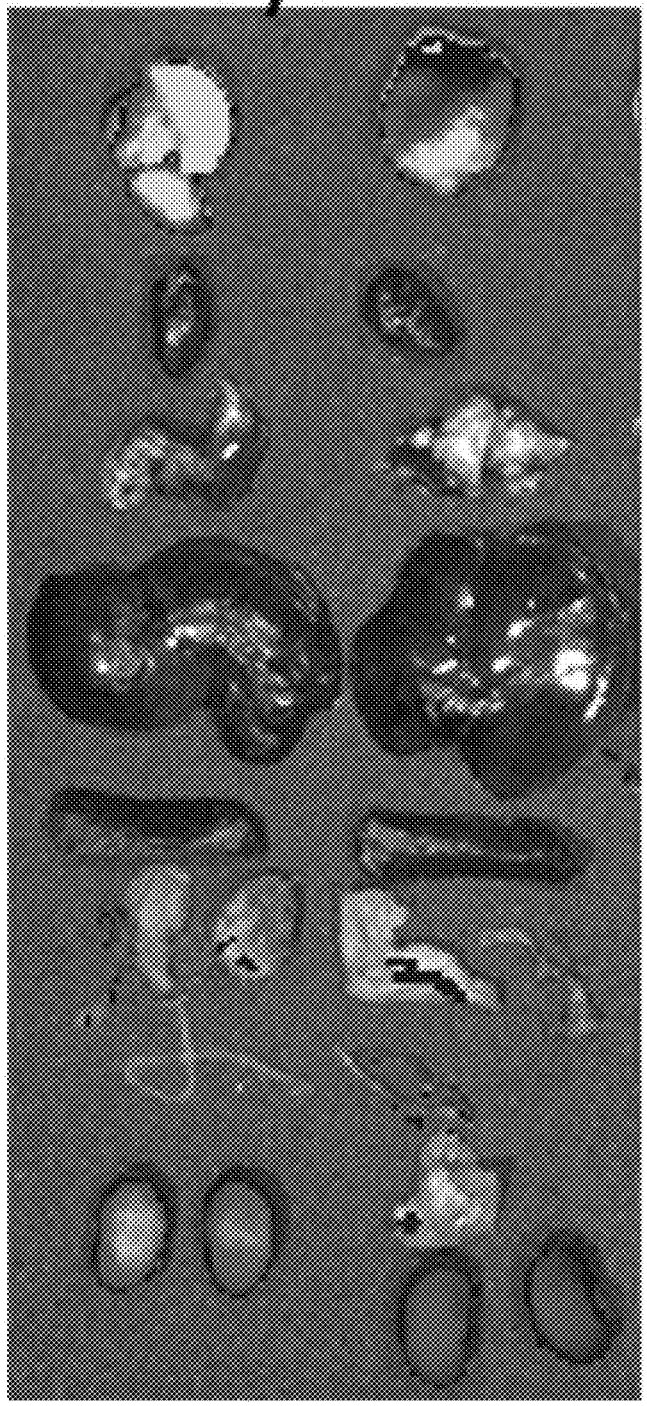
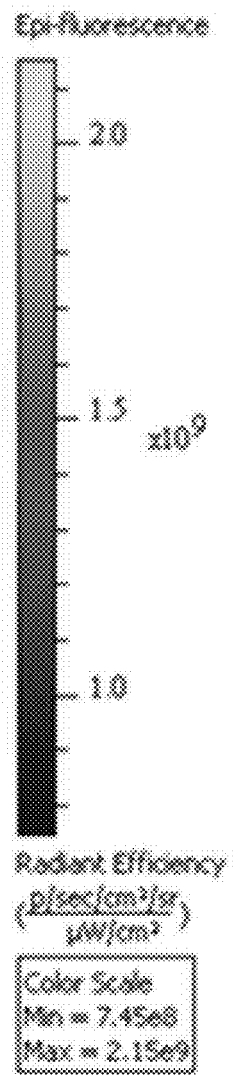

FIGURE 25 - Cont.
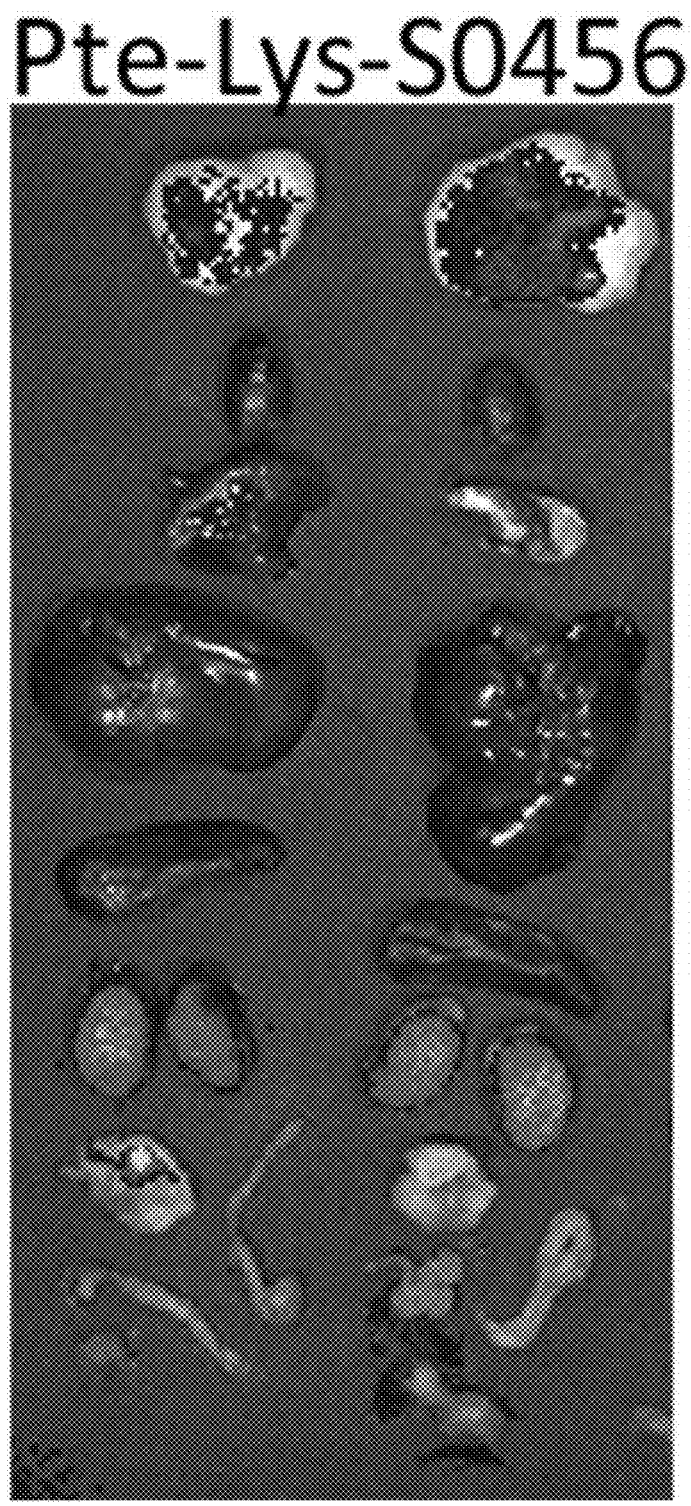

FIGURE 25 - Cont.
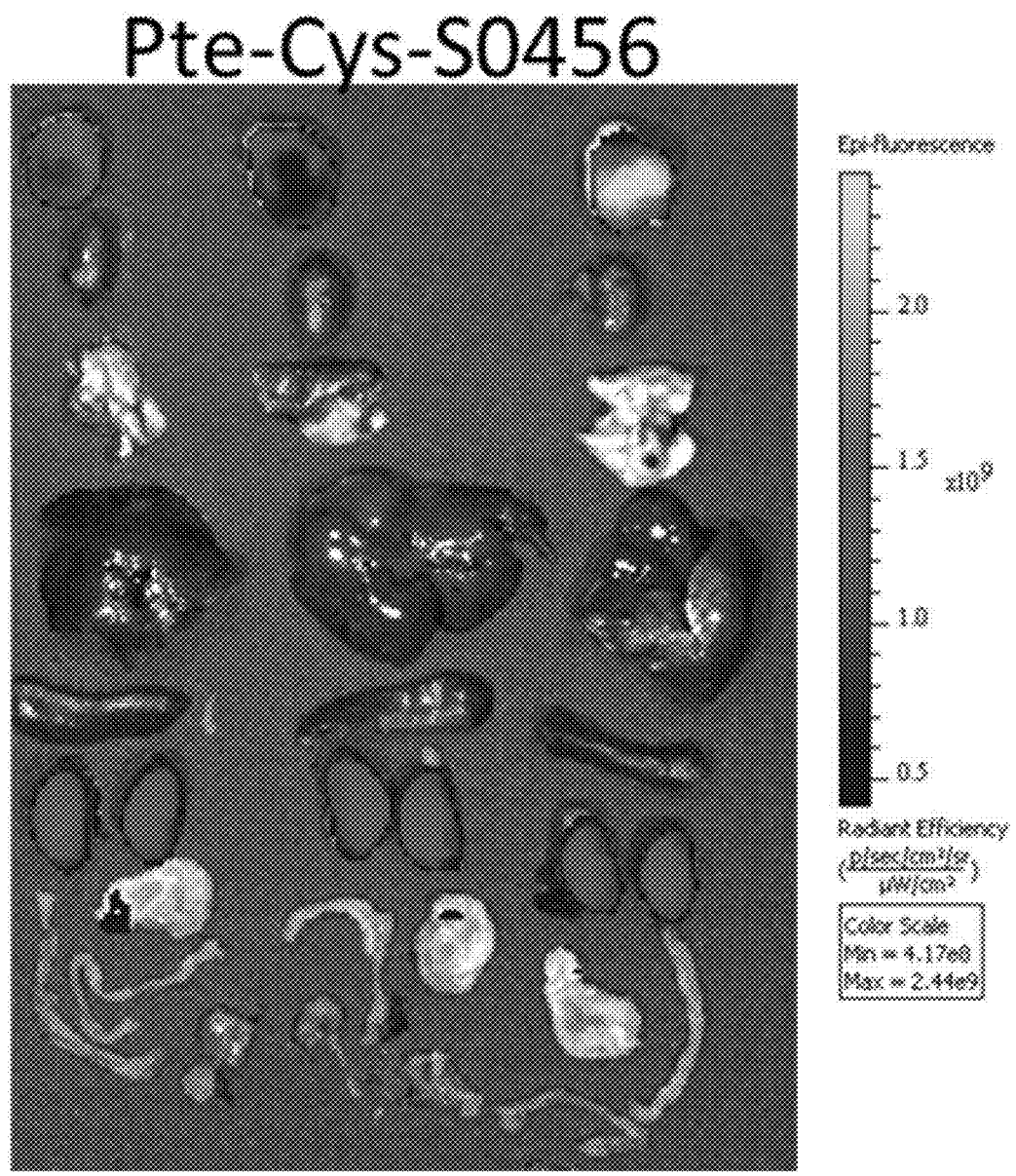

FIGURE 26 - Cont.
OTL-0052
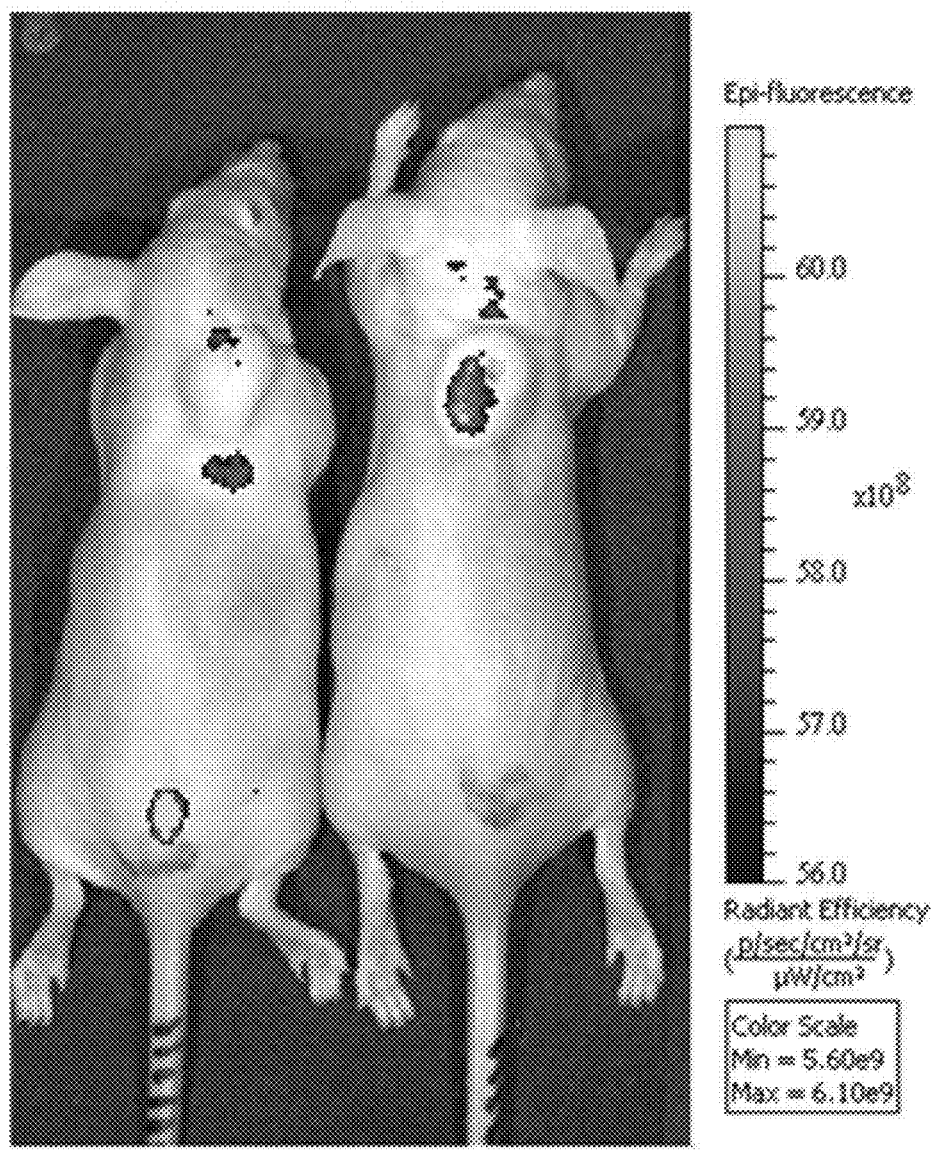

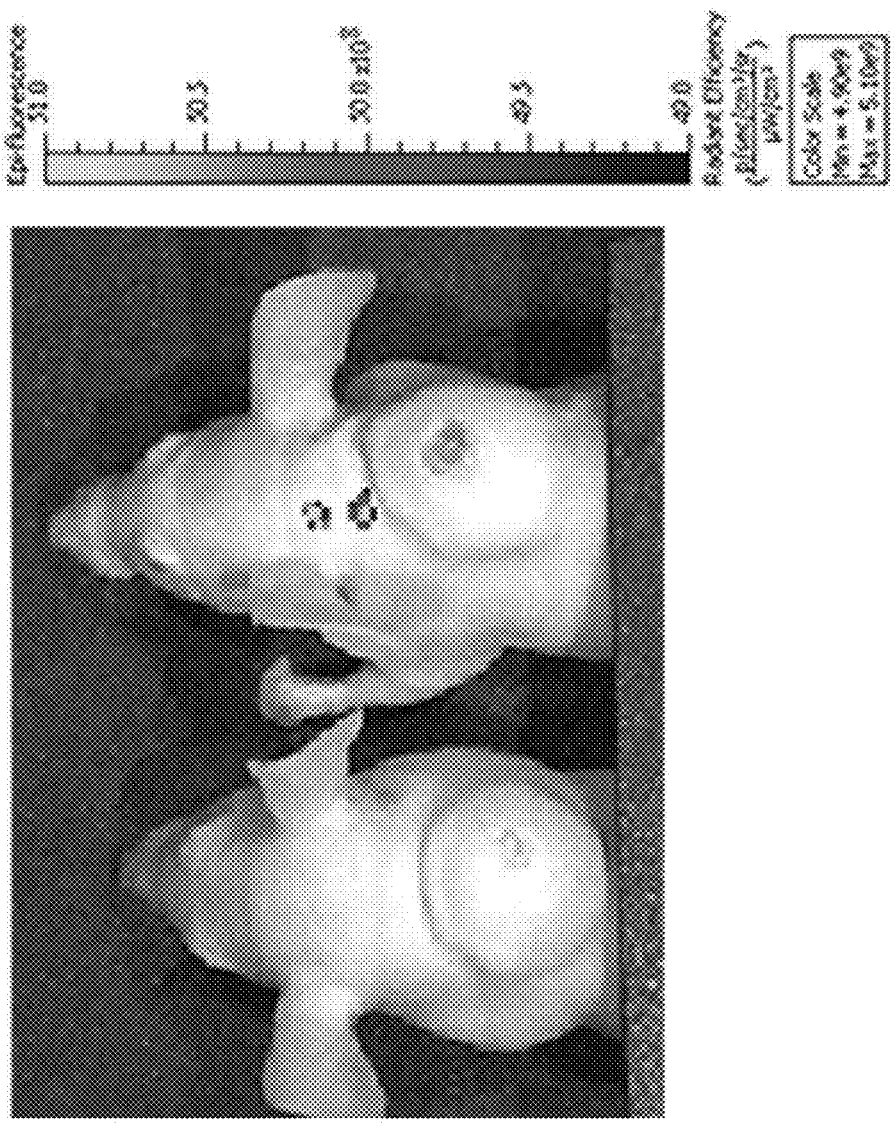
FIGURE 26 - Cont.

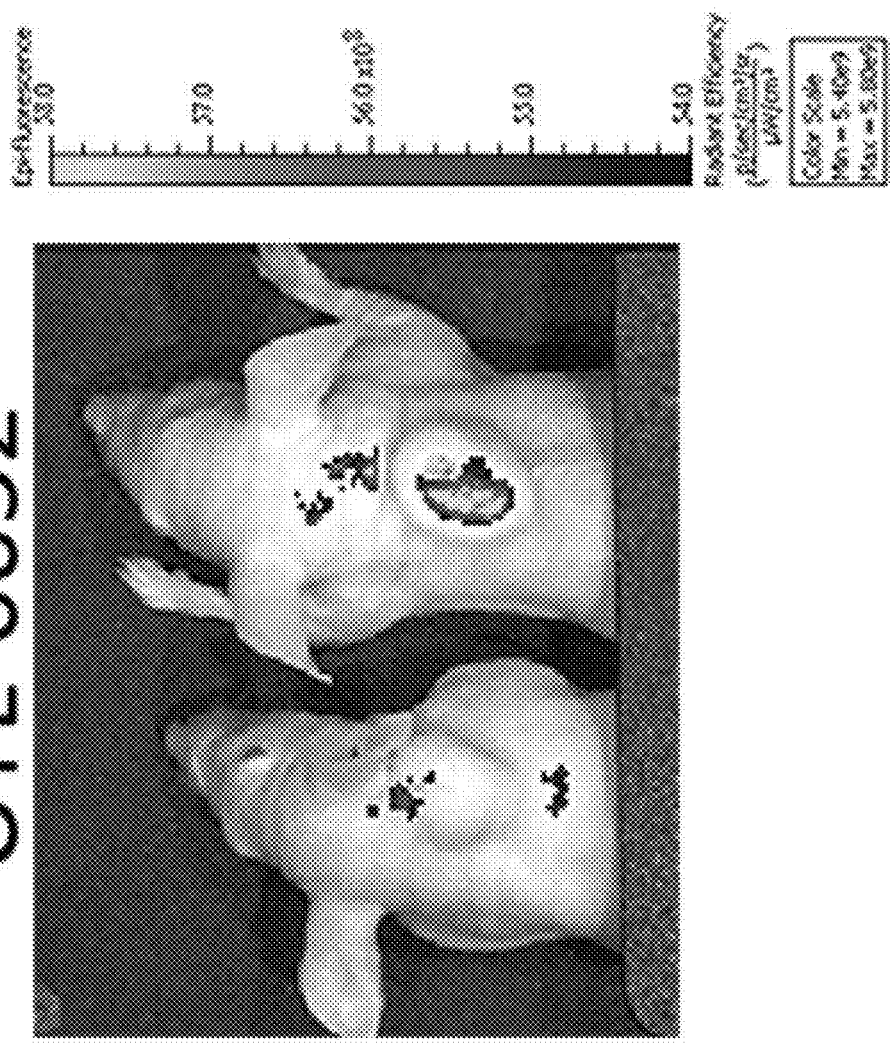
FIGURE 26 - Cont.

FIGURE 27 - Cont.
OTL-0052
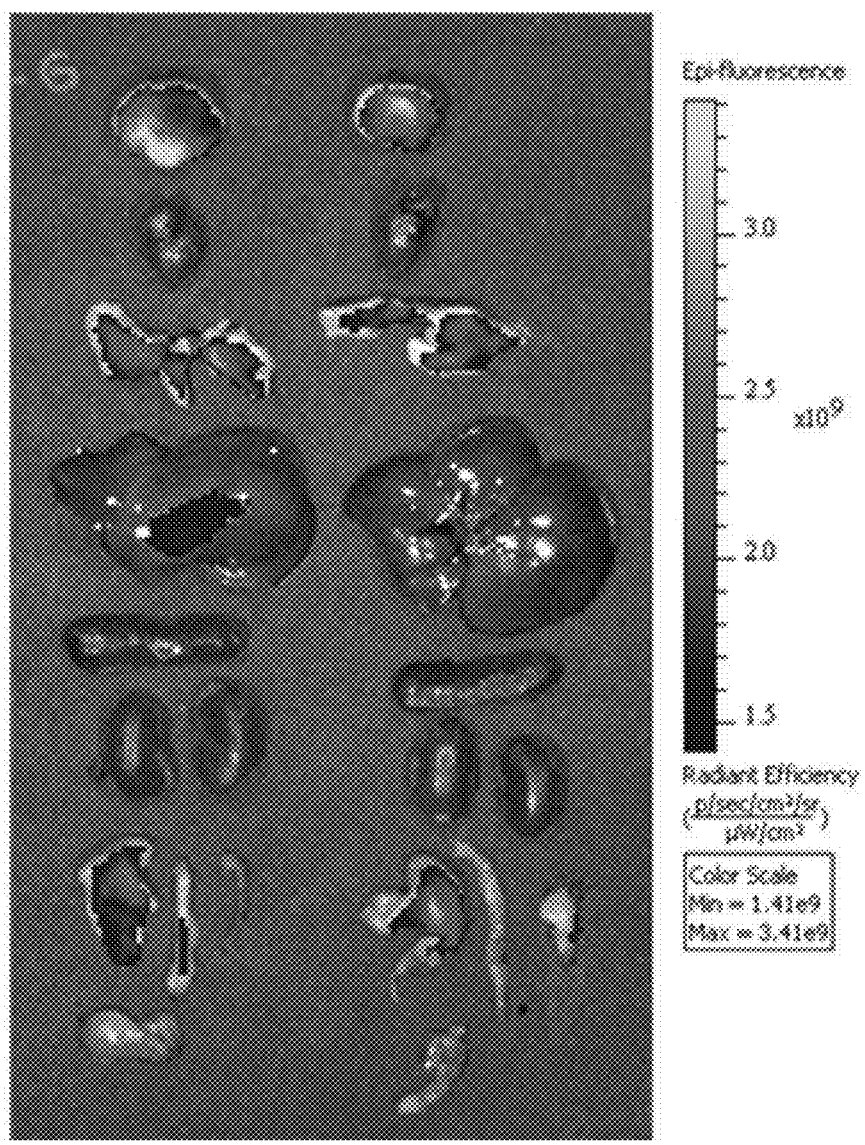

SYNTHESIS AND COMPOSITION OF AMINO ACID LINKING GROUPS CONJUGATED TO COMPOUNDS USED FOR THE TARGETED IMAGING OF TUMORS

RELATED APPLICATIONS

The present patent application is a continuation of U.S. patent application Ser. No. 14/010,098, which was filed on Aug. 26, 2013 and claimed the priority benefit of U.S. Provisional Patent Application Ser. No. 61/791,921, filed Mar. 15, 2013, the content of each of the aforementioned applications is hereby incorporated by reference in its entirety into this disclosure.

FIELD DISCLOSURE

The present disclosure is in the area of diagnostics. This disclosure provides methods of synthesizing and utilizing amino acid linking groups that are conjugated to a compound used for the targeted imaging of tumors. Conjugation of the amino acid linking groups increase specificity and detection of the compound. Methods and compositions for use thereof in diagnostic imaging are contemplated.

BACKGROUND OF THE DISCLOSURE

Surgical removal of malignant disease constitutes one of the most common and effective therapeutic for primary treatment for cancer. Resection of all detectable malignant lesions results in no detectable return of the disease in approximately 50% of all cancer patients[1] and may extend life expectancy or reduce morbidity for patients in whom recurrence of the cancer is seen. Not surprisingly, surgical methods for achieving more quantitative cytoreduction are now receiving greater scrutiny.

Resection of all detectable malignant lesions results in no detectable return of the disease in approximately 50% of all cancer patients and may extend life expectancy or reduce morbidity for patients in whom recurrence of the cancer is seen. Given the importance of total resection of the malignant lesions, it is beneficial to ensure that the malignant lesions are accurately and completely identified. Identification of malignant tissue during surgery is currently accomplished by three methods. First, many tumor masses and nodules can be visually detected based on abnormal color, texture, and/or morphology. Thus, a tumor mass may exhibit variegated color, appear asymmetric with an irregular border, or protrude from the contours of the healthy organ. A malignant mass may also be recognized tactilely due to differences in plasticity, elasticity or solidity from adjacent healthy tissues. Finally, a few cancer foci can be located intraoperatively using fluorescent dyes that flow passively from the primary tumor into draining lymph nodes. In this latter methodology, fluorescent (sentinel) lymph nodes can be visually identified, resected and examined to determine whether cancer cells have metastasized to these lymph nodes.

Despite the recognition of the importance of removal of tumor and the availability of certain identification techniques for visualizing tumor mass, many malignant nodules still escape detection, leading to disease recurrence and often death. Thus, there is a need for improved tumor identification. This motivation has led to introduction of two new approaches for intraoperative visualization of malignant disease. In the first, a quenched fluorescent dye is injected systemically into the tumor-bearing animal, and release of the quenching moiety by a tumor-specific enzyme, pH change, or change in redox potential is exploited to selectively activate fluorescence within the malignant mass. In the second approach, a fluorescent dye is conjugated to a tumor-specific targeting ligand that causes the attached dye to accumulate in cancers that over-express the ligand's receptor. Examples of tumor targeting ligands used for this latter purpose include folic acid, which exhibits specificity for folate receptor (FR) positive cancers of the ovary, kidney, lung, endometrium, breast, and colon, and DUPA, which can deliver attached fluorescent dyes selectively to cells expressing prostate-specific membrane antigen (PSMA), i.e. prostate cancers and the neovasculature of other solid tumors. Beneficially, one folate-targeted fluorescent dye (folate-fluorescein or EC17) has been recently tested intra-operatively in human ovarian cancer patients. In this study, ~5× more malignant lesions were removed with the aid of the tumor-targeted fluorescent dye than without it, and all resected fluorescent lesions were confirmed by pathology to be malignant.

Conventional fluorescent techniques use probes in the visible light spectrum (~400-600 nm), which is not optimal for intra-operative image-guided surgery as it is associated with a relatively high level of nonspecific background light due to collagen in the tissues. Hence the signal to noise ratio from these conventional compounds is low. Moreover, the absorption of visible light by biological chromophores, in particular hemoglobin, limits the penetration depth to a few millimeters. Thus tumors that are buried deeper than a few millimeters in the tissue may remain undetected. Moreover ionization equilibrium of fluorescein (pKa=6.4) leads to pH-dependent absorption and emission over the range of 5 to 9. Therefore, the fluorescence of fluorescein-based dyes is quenched at low pH (below pH 5).

For example, the potential use of EC17 dye for a more widespread use in optical imaging for the characterization and measurement diseased tissue in a clinical setting has been hampered by the major drawback of that the attached dye (fluorescein) emits fluorescence in the visible range. This makes EC17 and related dyes poor for in vivo use in tissues because tissues typically autofluoresce strongly in the visible range, and light penetrates tissue poorly. Moreover, EC17 (folate-ethelenediamine-fluorescein isothiocynate) consists a thiourea linker. It is well known that thiourea compounds have low shelf life due to the instability of the thiourea linkage. Thus, a compound such as EC17 is not optimal for use in optical imaging because of this unstability and the related decomposition of the decomposition of thiourea bridge.

The combination of light absorption by hemoglobin in the visible light spectrum (<600 nm) and water and lipids in the IR range (>900 nm), offers an optical imaging window from approximately 650-900 nm in which the absorption coefficient of tissue is at a minimum. A suitable alternative to dyes that emit light in the visible range would be to develop dyes that can be used in the near infra red (NIR) range because light in the near infrared region induces very little autofluorescence and permeates tissue much more efficiently. Another benefit to near-IR fluorescent technology is that the background from the scattered light from the excitation source is greatly reduced since the scattering intensity is proportional to the inverse fourth power of the wavelength. Low background fluorescence is necessary for highly sensitive detection. Furthermore, the optically transparent window in the near-IR region (650 nm to 900 nm) in biological tissue makes NIR fluorescence a valuable technology for in vivo imaging and subcellular detection applications that require the transmission of light through biological components.

While the use of light in the NIR range for deeper tissue imaging is preferable to light in the visible spectrum, the NIR imaging dyes currently used in the art suffer from a number of challenges and disadvantages such as a susceptibility to photobleach, poor chemical stability, absorbance and emission spectra that fall within the same range as many physiological molecules (resulting in high background signal and autofluorescence). Moreover, most of the NIR dyes are not stable during the synthesis, especially conjugating to a ligand with an amine linker, leading to multiple unwanted side products. Therefore, taking ligand-targeted NIR imaging agent for clinic can be expensive. Thus, current imaging methods that utilize NIR fluorescent probes are not effective in deep tissue imaging (>5 mm from the surface), in quantifying fluorescence signal in mammalian tissues, or in production cost that increase preclinical-to-clinical translational time.

Two promising approaches to fluorescence-guided surgery are currently under intense investigation for use in the clinic. In one method, an activatable NIR fluorescent probe, which is minimally fluorescent in the steady state due to its proximity to an attached quencher, becomes highly fluorescent upon release of the quencher in malignant tissue. One of the most commonly used release mechanisms involves incorporation of a peptide sequence between the dye and the quencher that can be specifically cleaved by a tumor-enriched protease (i.e. cathepsins, caspases and matrix metalloproteinases). A major advantage of this strategy lies in the absence of fluorescence in tissues that lack the activating enzyme, allowing tissues along the excretion pathway (e.g. kidneys, bladder, liver) to remain nonfluorescent unless they fortuitously express the cleaving enzyme. Such tumor-activated NIR dyes can also generate substantial fluorescence in the tumor mass as long as the malignant lesion is enriched in the cleaving protease and the released dye is retained in the tumor. The major disadvantage of this methodology arises from the poor tumor specificities of many of the relevant hydrolases (most of which are also expressed in healthy tissues undergoing natural remodeling or experiencing inflammation). Moreover, the abundance of the desired proteases may vary among tumor masses, leading to slow or no activation of fluorescence in some malignant lesions and rapid development of fluorescence in others.

Thus, there remains a need for a dye substance that can be used to specifically target diseased tissue and has increased stability and brightness for use in vivo for tissue imaging.

BRIEF SUMMARY OF THE DISCLOSURE

This disclosure provides a method for synthesizing amino acid linking groups that are conjugated to a compound used for the targeted imaging of tumors and lymph nodes. In certain embodiments, this disclosure relates to a compound or a salt derivative thereof, that comprises a folate or pteroyl ligand, a linking group, and a fluorescent dye. In certain embodiments, the linking group can be an amino acid, an isomer, a derivative, or a racemic mixture thereof. In other aspects, the fluorescent dye is selected from the group consisting of LS288, IR800, SP054, S0121, KODAK, S2076 and S0456.

In some aspects, this disclosure provides a method of conjugating an amino acid linking group to a fluorescent dye, wherein the amino acid can be tyrosine, serine, theronine, lysine, arginine, asparagine, glutamine, cysteine, selenocysteine, isomers, and the derivatives thereof. In certain embodiments, the amino acid, isomers, or the derivatives thereof, contain an —OH, —NH$_2$, or —SH functional group that upon addition of the fluorescent dye in slight molar excess produces the conjugation of fluorescent group with the amino acid, isomer, or the derivatives thereof. In other embodiments, the amino acid, isomers, or the derivatives thereof, contains an —OH functional group that upon synthesis generates an ether bond with the fluorescent dye that increases the brightness and detection of the compound. In some embodiments, this disclosure relates to the conjugation of the amino acid linking group with the fluorescent dye, wherein the amino acid, isomers, or the derivatives thereof, contains an —SH, —SeH, —PoH, or —TeH functional group that upon synthesis generates a C—S, C—Se, C—Po, or C—Te bond with the fluorescent dye. In some aspects, this disclosure relates to the conjugation of the amino acid linking group to a fluorescent dye that has an absorption and emission maxima between about 500 nm and about 900 nm. In other aspects, the amino acid linking group is conjugated to a fluorescent dye that has an absorption and emission maxima between about 600 nm and about 800 nm.

In additional embodiments, this disclosure provides a method for conjugating the amino acid linking group to a folate ligand, wherein the amino acid linking group is tyrosine, serine, theronine, lysine, arginine, asparagine, glutamine, cysteine, selenocysteine, isomers or the derivatives thereof, and is conjugated to folate through a dipeptide bond. In additional aspects, this disclosure provides a method of conjugating the linking group with a folate ligand, wherein the linking group is tyrosine, serine, theronine, lysine, arginine, asparagine, glutamine, cysteine, selenocysteine, isomers, or the derivatives thereof, and is conjugated to folate through a homo-oligopeptide bond. In other embodiments, this disclosure relates to a method of conjugating a pteroyl ligand to an amino acid linking group, wherein the linking group is tyrosine, serine, theronine, lysine, arginine, asparagine, glutamine, cysteine, selenocysteine, isomers or the derivatives thereof. In certain aspects, the carboxylic acid of the linking group is bound to the alpha carbon of any amino acid, hence increasing the specificity of the compound for targeted receptors. In some embodiments, the amino acid linking group contributes specificity to the compound, wherein the observed binding affinity of the compound to targeted receptors is folate receptor.

In additional aspects, the compound is highly selective for targeting to tumor cells expressing the target receptor.

In other embodiments, this disclosure relates to the use of a compound designated, Pte-Tyr-S0456 (OTL-0038) for image guided surgery, tumor imaging, lymph node imaging, inflammatory diseases, atherosclerosis, infection diseases, forensic applications, mineral applications, dental, gel staining, DNA sequencing, nerve staining, or plastic surgery. In other aspects, the Pte-Tyr-S0456 derivative can be Pte-D-Tyr-S0456, Pte-homoTyr-S0456, Pte-beta-homo-Tyr-S0456, Pte-(NMe)-Tyr-S0456, Pte-Tyr(OMe)—S0456, Pte-Tyr(OBn)-S0456, Pte-NHNH-Tyr-OAc—S0456, salts, or derivatives thereof.

In other aspects, this disclosure provides a method of synthesizing the compound, wherein a protecting group is used to avoid undesired reactivity with groups other than the amino groups that might generate unwanted compounds. The methods provided in this disclosure produce a final compound with a yield of over 98% purity.

In certain aspects, this disclosure relates to a compound used for the targeted imaging of tumors, wherein the compound could be used for research, diagnostic, or therapeutic purposes. In other embodiments, this disclosure provides a composition comprising an imaging compound and a pharmaceutically acceptable carrier, excipient, diluents, or salts.

In other aspects, this disclosure relates to a compound which has a formula selected from the group consisting of:

5
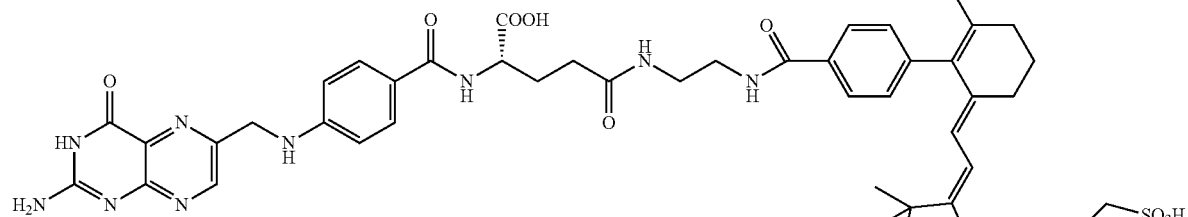
6
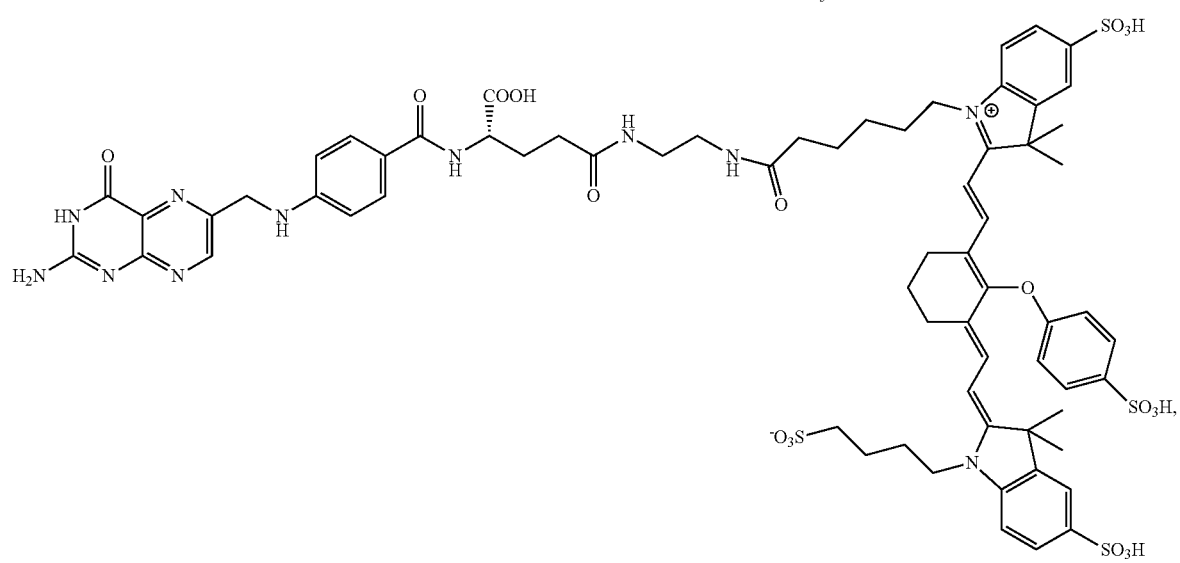
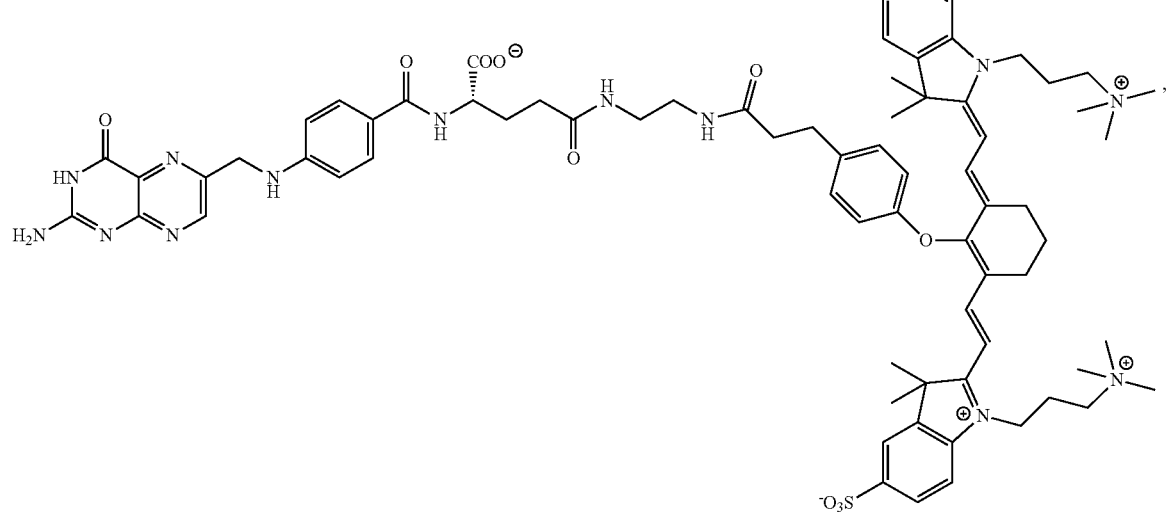

-continued
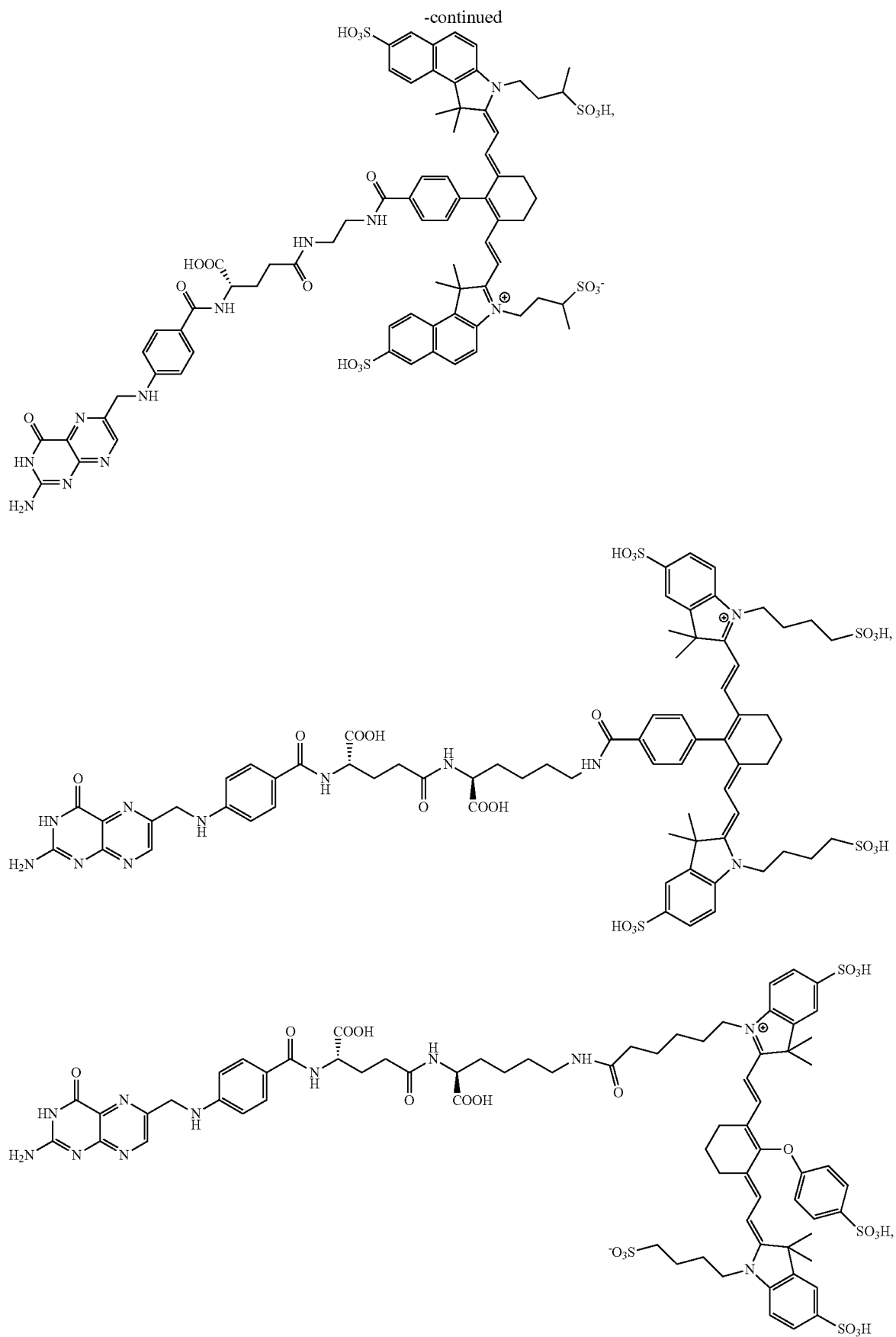

-continued
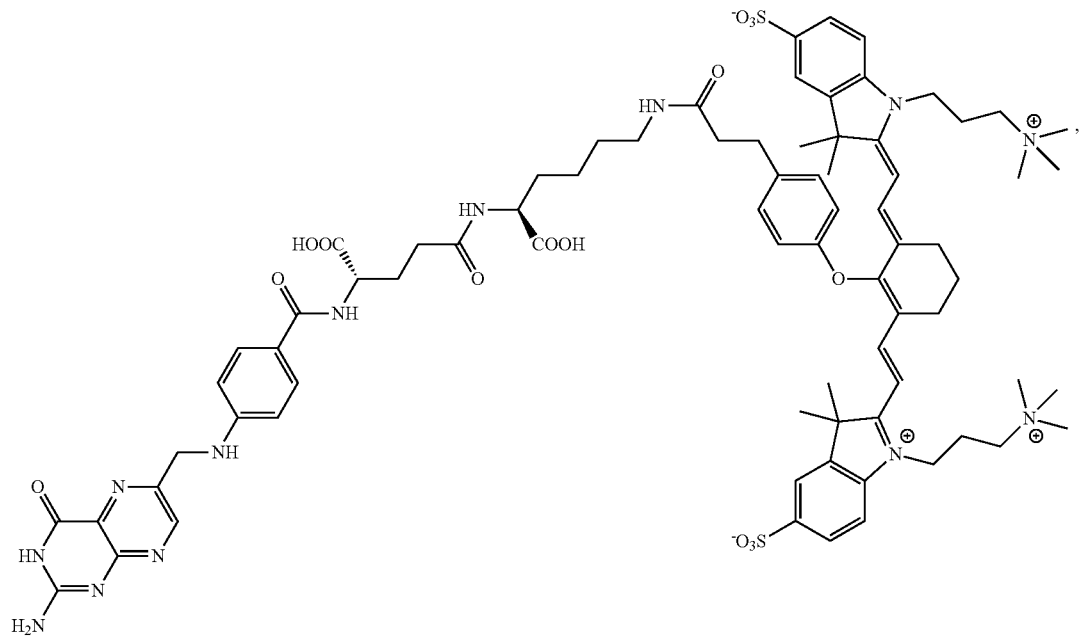
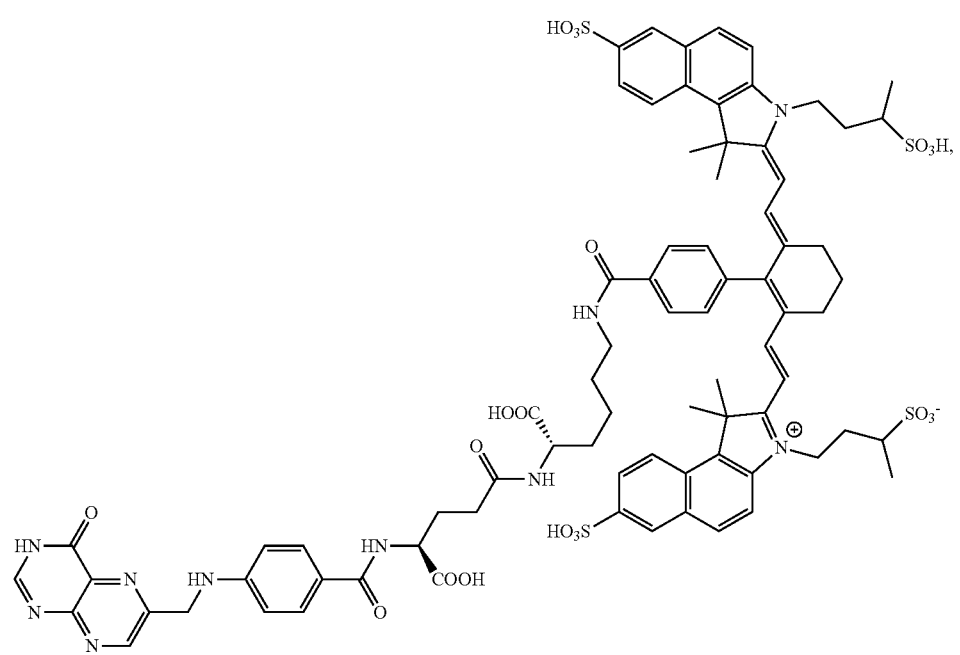

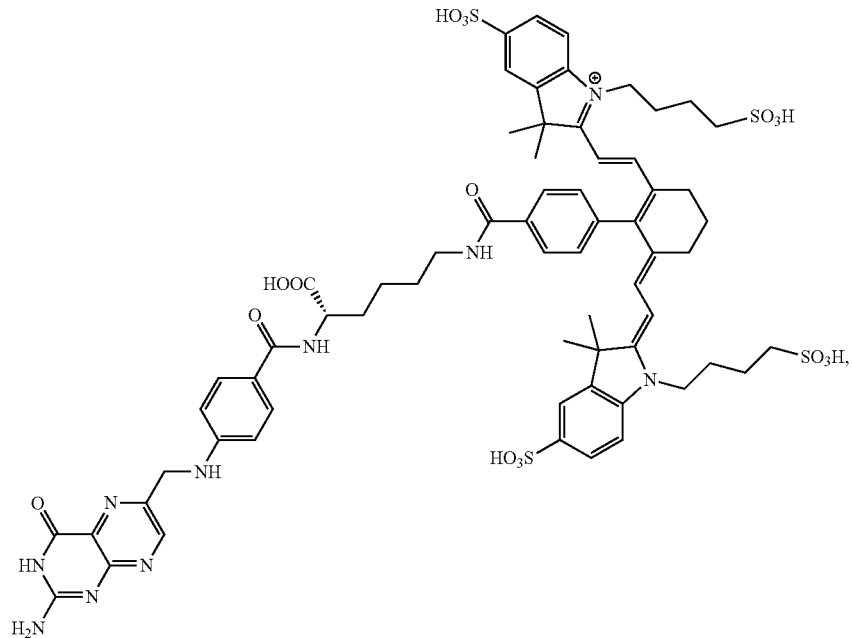
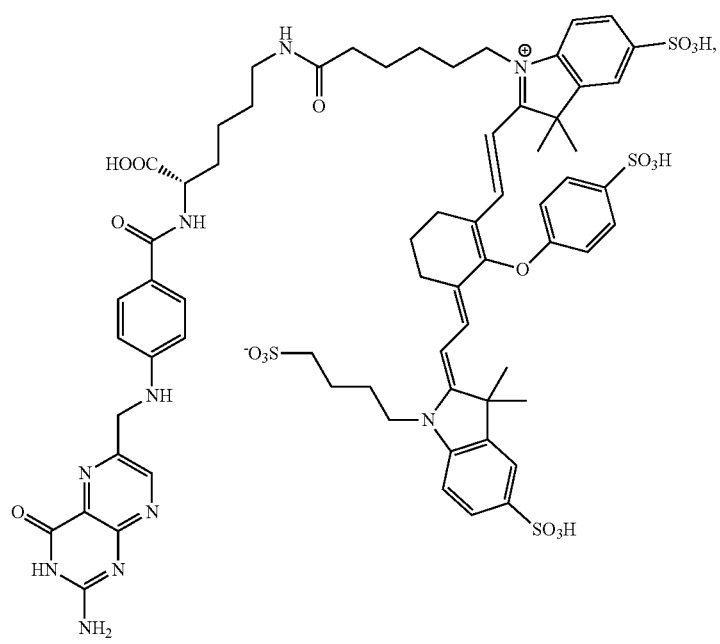

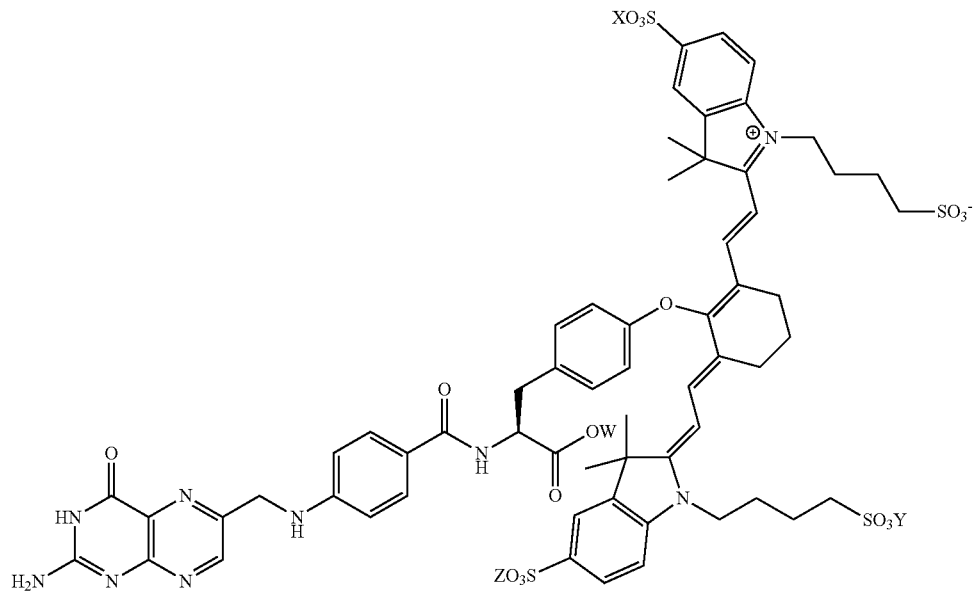
30
wherein W, X, Y, or Z is H, Na, or $NH_4^+$,
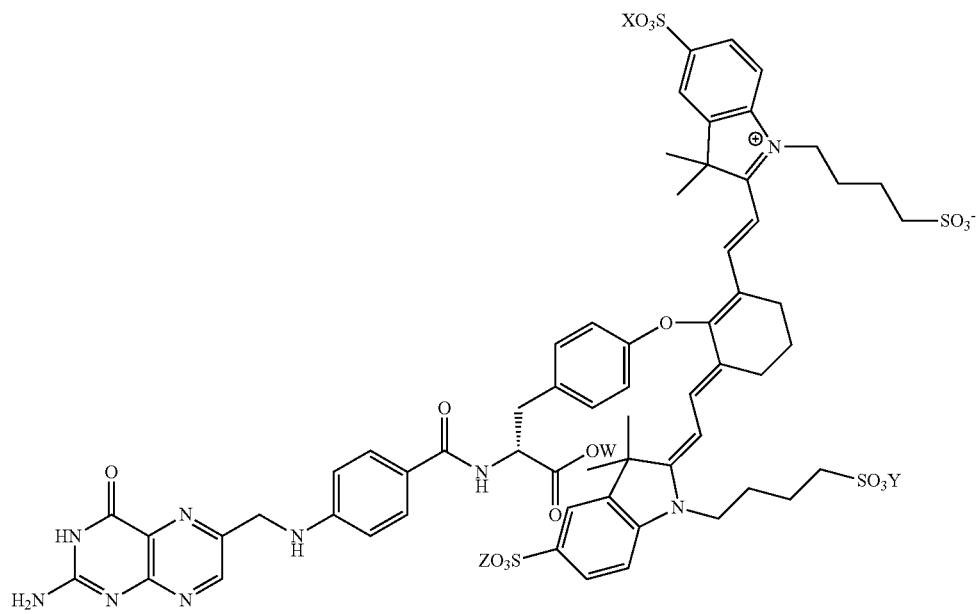
wherein W, X, Y, or Z is H, Na, or $NH_4^+$,

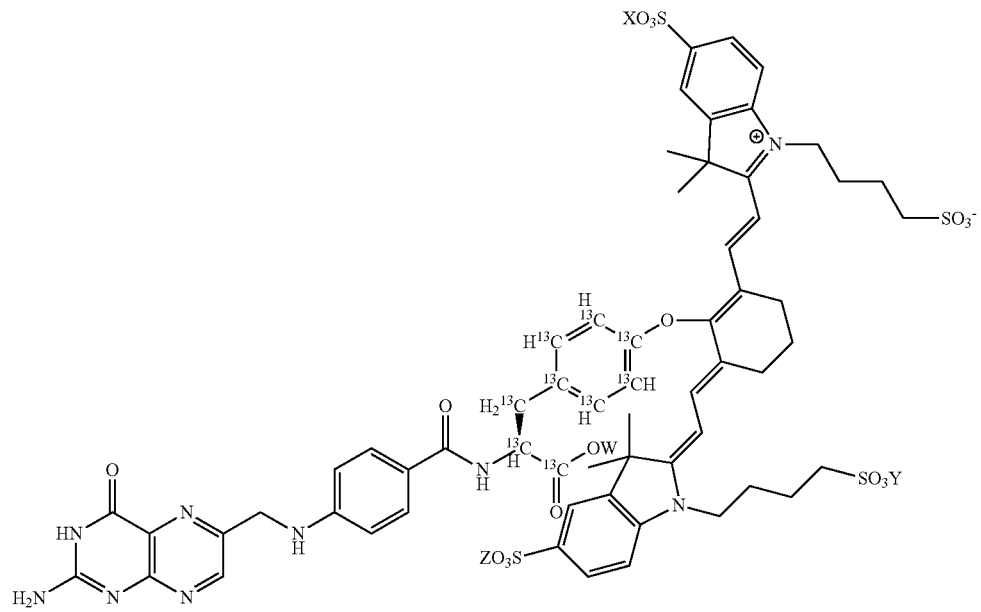
wherein W, X, Y, or Z is H, Na, or $NH_4^+$,
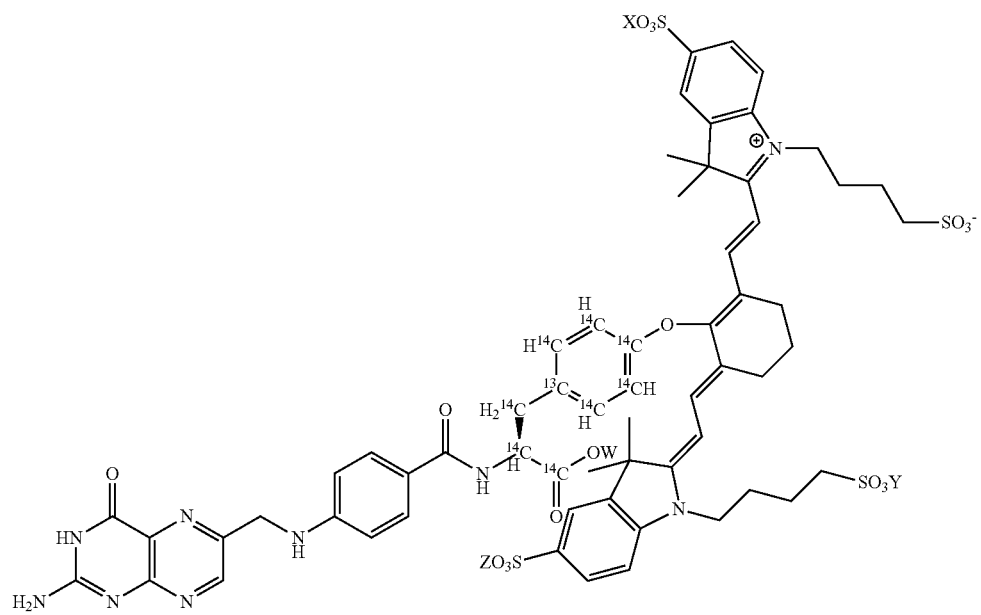
wherein W, X, Y, or Z is H, Na, or $NH_4^+$,

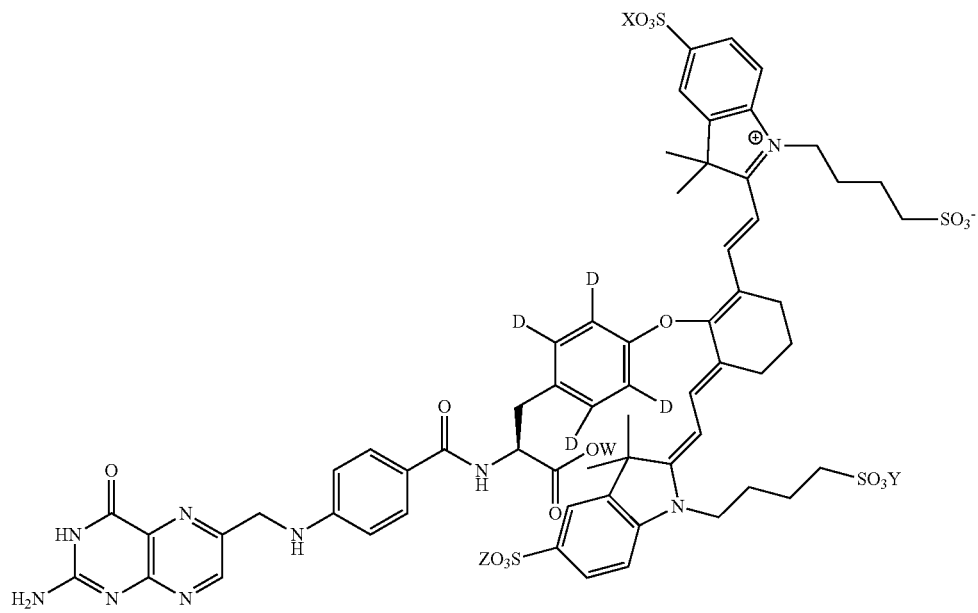
wherein W, X, Y, or Z is H, Na, or $NH_4^+$,
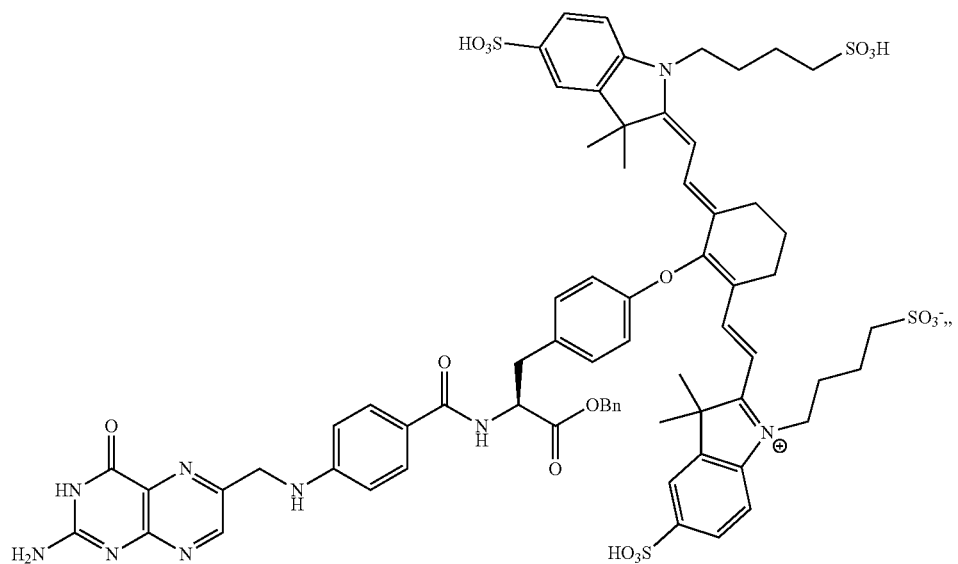

-continued
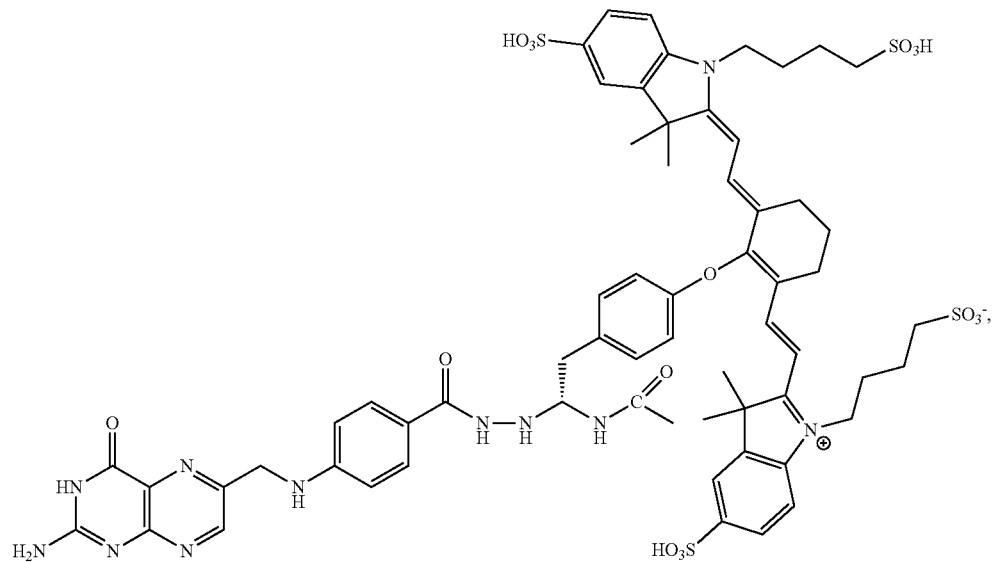
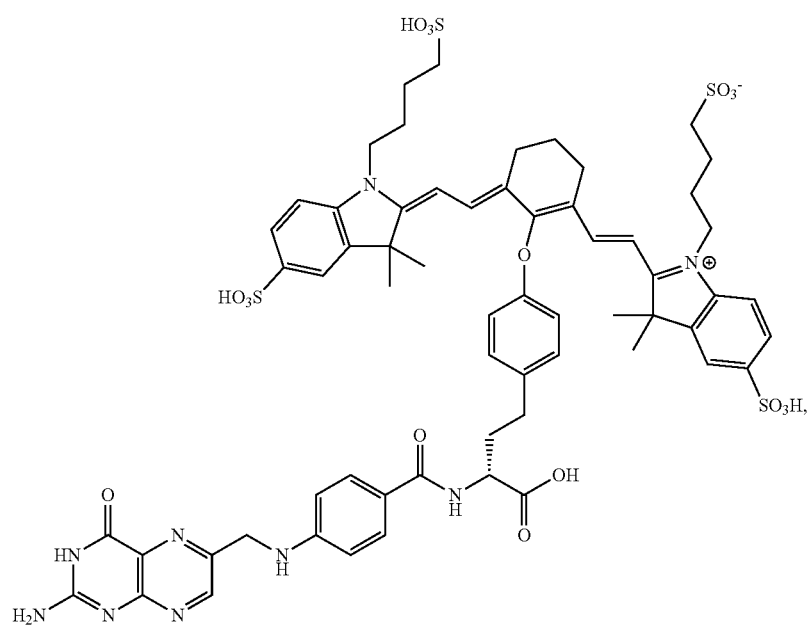

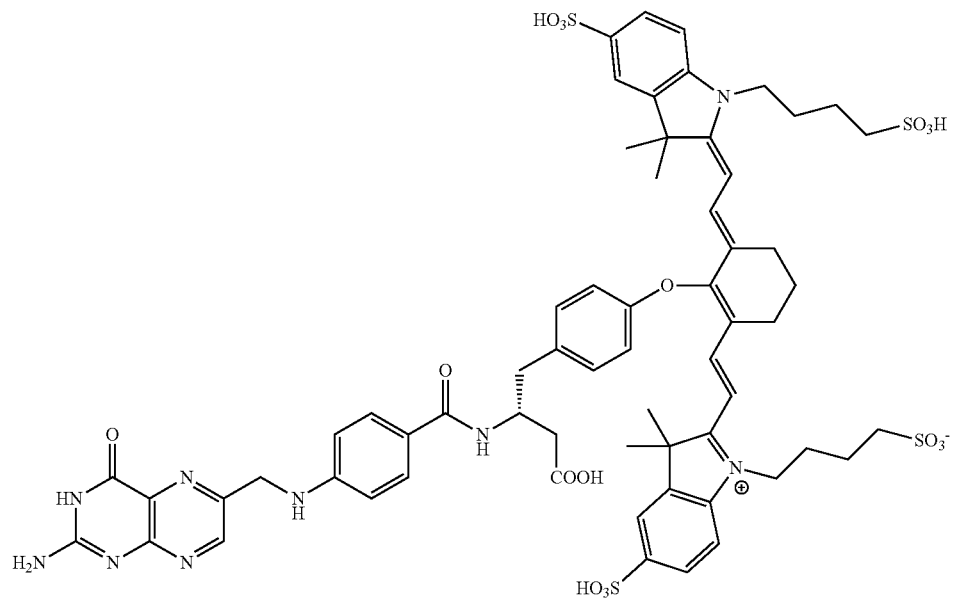
wherein tyrosine is beta homo,
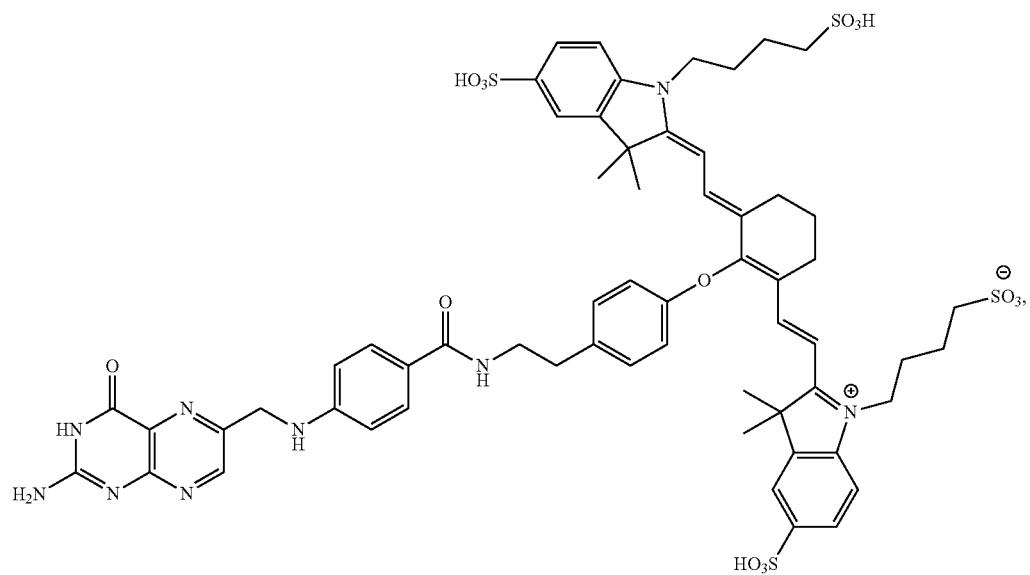

-continued
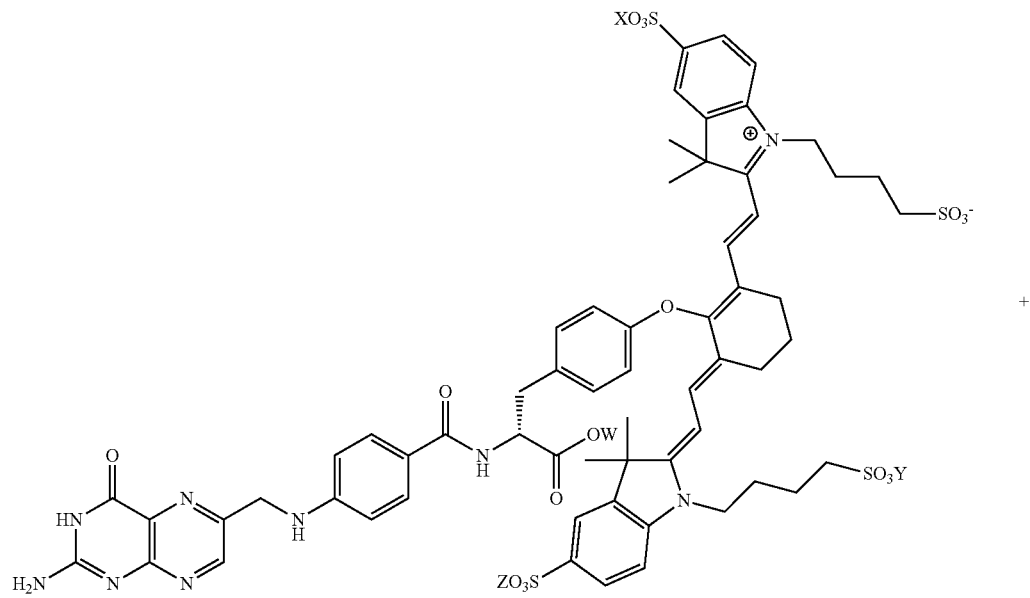
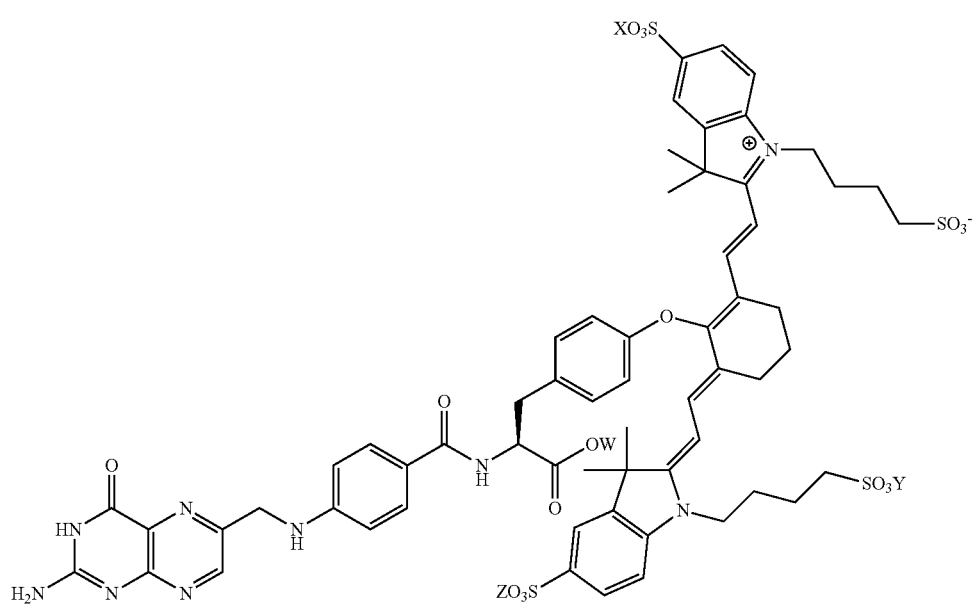
wherein W, X, Y, or Z is H, Na, or $NH_4^+$,

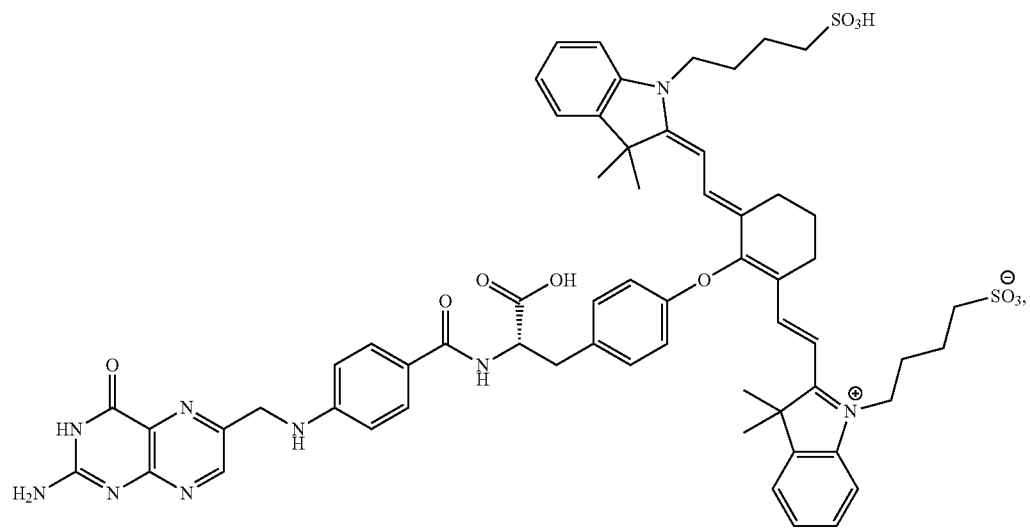
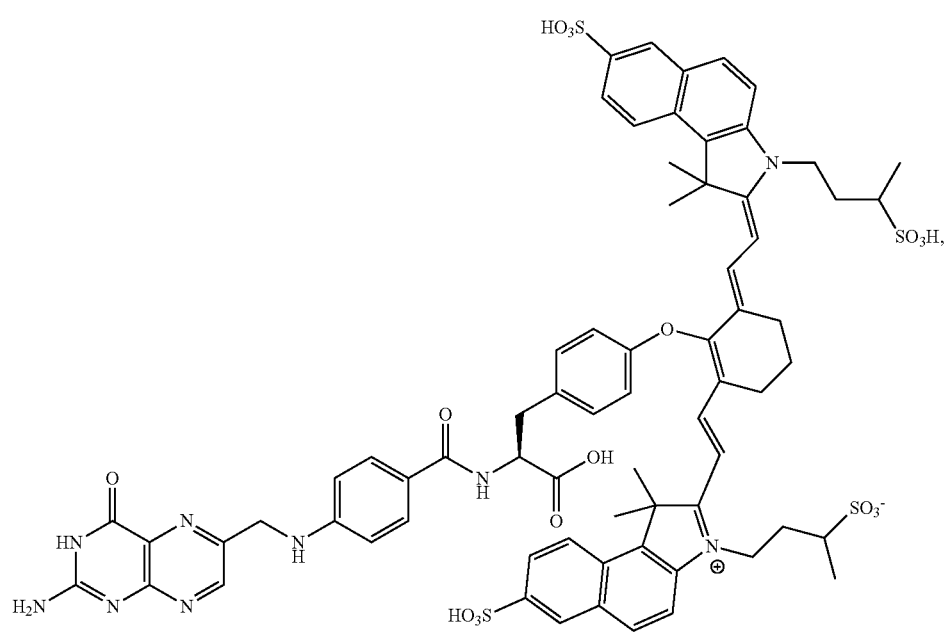

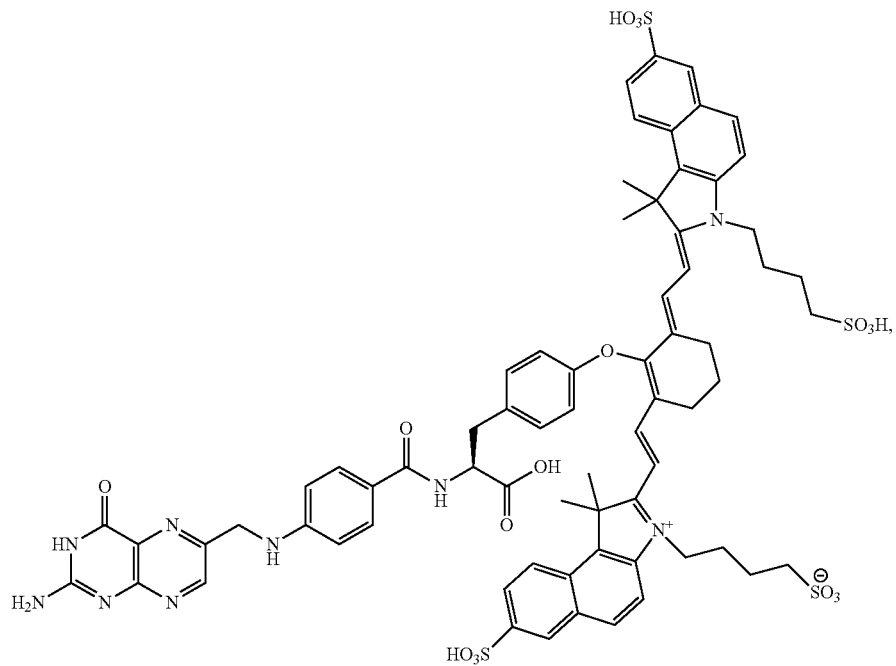
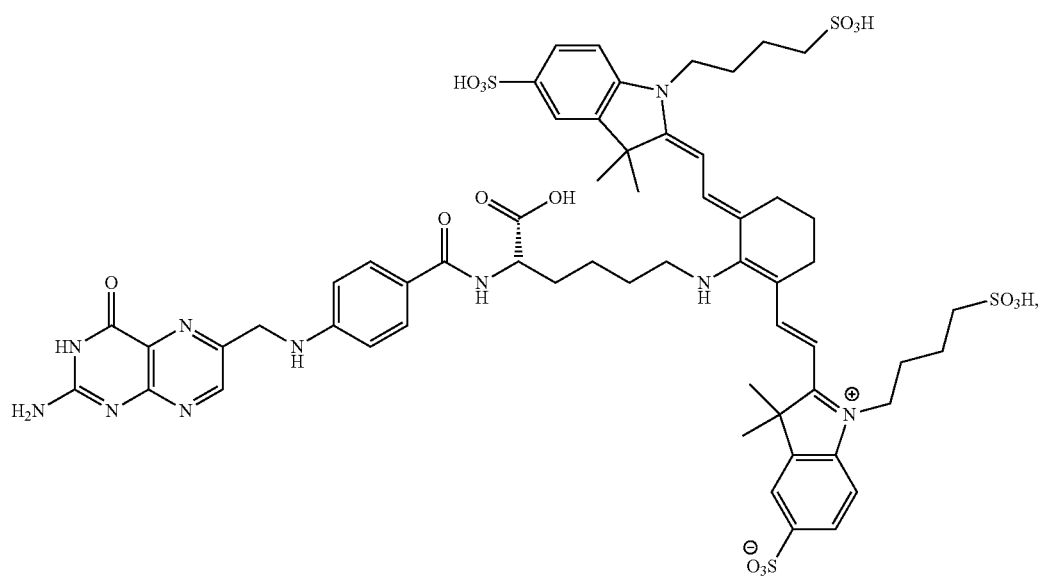

-continued

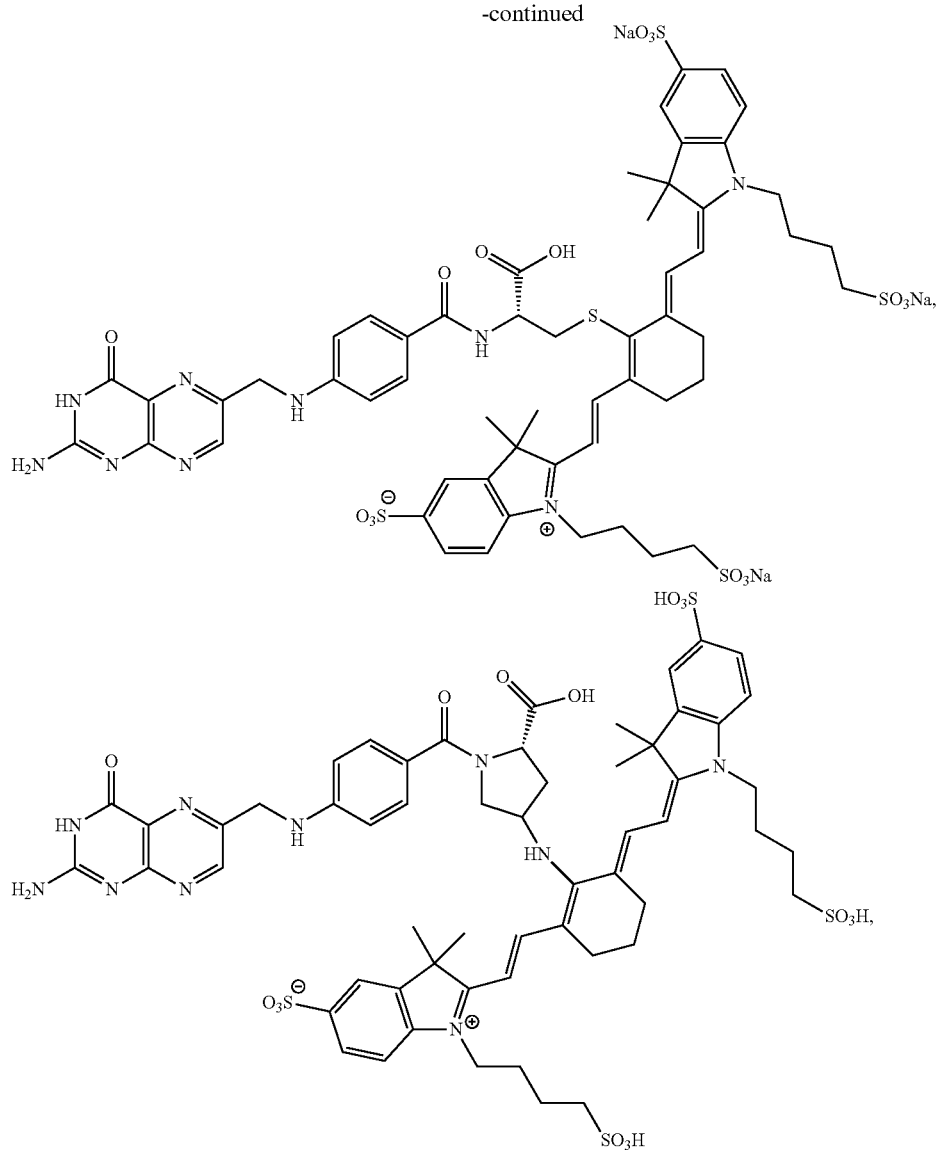

and a pharmaceutically acceptable salt thereof.

BRIEF DESCRIPTION OF SEVERAL VIEWS OF THE DRAWINGS

FIG. 6 shows isotherms of folate-linkers and 2$^{nd}$ generation folate-NIR dye conjugates to cultured cancer cells (competition studies with radiolabeled folic acid. This assay will provide binding affinity and specificity for folate receptor at the same time). Binding curves of A: folate-EDA- and B: folate-Lys-NIR dye conjugates to folate receptor expressing KB cells are shown.

FIG. 7 shows images and ex vivo tissue biodistribution of 2$^{nd}$ generation folate-NIR conjugates. FIG. 7A shows fluorescent images of nude mice with KB tumor xenografts 2 hours following intravenous injection of 10 nmol folate-NIR conjugate. The following portions of FIG. 7A show the following (a) folate-EDA-NIR conjugates administered mouse group were imaged individually, (b) head-to-head comparison of folate-EDA-NIR conjugate administered mice, and (c) folate-Lys-NIR conjugates administered mouse group were imaged individually. FIG. 7B shows ex vivo tissue biodistribution of animals administered with folate-NIR conjugates.

FIG. 11 shows whole body fluorescent images and ex vivo tissue biodistribution of mice injected 10 nmol of Pte-Tyr-50456. Portion A of FIG. 11 shows fluorescent images of nude mice with KB tumor xenografts 2 hours following intravenous injection of 10 nmol folate receptor targeted-NIR conjugates (overlay of Fluorescent and white light images). Portion B of FIG. 11 shows ex vivo tissue biodistribution of conjugates following harvesting tissues previously imaged mice.

FIG. 12 shows head-to-head comparison of Pte-L-Try-50456 (OTL-0038) with $2^{nd}$ generation folate-NIR conjugates.

FIG. 17 depicts a table that summarizes tumor uptake of OTL-0038. Tissue biodistribution was analyzed in mice injected with increasing amounts of OTL-0038, ranging from 0.3-90 nmol. Data analysis of biodistribution was examined 2.5 hours post injection.

FIG. 25 demonstrates tissue biodistribution of OTL-0038 (Pte-Tyr-S0456), OTL-0053 (Pteroyl-Lys-S0456), and OTL-0054 (Pteroyl-Cys-S0456) 2 hours post injection. Excitation: 745 nm. Emission: 830 nm.

DETAILED DESCRIPTION OF THE DISCLOSURE

Figure 1:
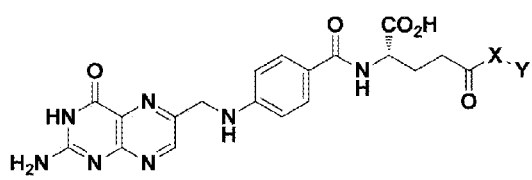
FIG. 1 shows folate receptor-targeted 1$^{st}$ generation folate-NIR dye conjugates.

Surgery is one of the best therapies for all the solid tumors, such as prostate, ovarian, lung, breast, colon, and pancreatic cancer. While surgery is effective in 50% of patients with solid tumors in the US, chemo- and radiotherapy alone are effective in less than 5% of all cancer patients. Over 700,000 patients undergo cancer surgery every year in the US and 40% of surgical patients have a recurrence of locoregional disease within 5 years. Despite major advances in the oncology field over the last decade, there remain significant hurdles to overcome in the field. For example, it remains difficult to achieve complete resection of the primary tumor with negative margins, removal of the lymph nodes harboring metastatic cancer cells and identification of satellite disease. Achieving improvements in these three cases not only improves disease clearance but also guides decisions regarding postoperative chemotherapy and radiation. While non-targeted fluorescent dyes have been shown to passively accumulate in some tumors, the resulting tumor-to-background ratios are often poor and the boundaries between malignant and healthy tissues can be difficult to define. Although ligand targeted fluorescence dyes (e.g., EC17: Folate-EDA-FITC) have been used for imaging a tissue, those dyes have been ineffective as they would not penetrate deep tissue and hence only identified the specific cells on the surface of a tissue rather than deeper within the tissue sample. In addition, it has been shown that the excitation and emission spectra of these previous fluorescence dyes was such that it produced significant background noise such that the targeted tissue was not easily detected. In addition, as discussed in the background above, fluorescein-based dyes have the disadvantages that of low shelf-life stability. EC17 easily decomposes as a result of the instability of the thiourea bridge in that compound. In addition, as EC17 uses fluorescein which has the drawback of a relatively high level of nonspecific background noise from collagen in the tissues surrounding the imaging site. Moreover, the absorption of visible light by biological chromophores, in particular hemoglobin, further limits the usefulness of dyes that incorporate fluorescein. This means that conventional dyes cannot readily detect tumors that may be buried deeper than a few millimeters in the tissue. Furthermore, fluorescence from fluorescein is quenched at low pH (below pH 5)

In order for a dye material to be useful in detecting and guiding surgery or providing other tissue imaging it is important to overcome these drawbacks.

Several criteria were considered in preparation of conjugates including near infrared dyes. Ease of synthesis and chemical stability were primary chemical attributes. Spectral properties, such as absorption and emission spectra and quantum yield, were considered. Several biological properties were evaluated, such as binding affinity in cell studies, whole body animal imaging using mice with tumors, and biodistribution. Specifically for biodistribution several aspects were considered including dead mice after 2 hours per oral distribution, live mice imaging and dose escalation. Finally, safety considerations were taken including Maximum Tolerance Dose (MTD), ImmunoHistoChemical (IHC) analysis, and general clinical pathology analysis.

The present disclosure provides pteroyl conjugates of near infrared dyes that are stable, fluoresce in the infrared range, and penetrate deep within targeted tissue to produce a specific and bright identification of areas of tissue that express folate receptor. More specifically, the pteroyl conjugates are linked to the near infrared dyes through an amino acid linker. Even more specifically, it has been found that where the amino acid linker is tyrosine or a derivative of tyrosine, the intensity of the fluorescence of the dye is maintained or even enhanced.

An amino acid is defined as including an amine functional group linked to a carboxylic acid functional group, and a side-chain specific to each amino acid. An alpha amino acid is any compound of the general formula $R^5CH(NH_2)COOH$ (α-amino acid), wherein $R^5$ is selected from the group consisting of H or any known amino acid side chain.

A beta amino acid is defined as including an amine functional group linked at a beta carbon and a carboxylic acid functional group linked at the alpha carbon. A beta homo amino acid is defined as including an amine functional group linked at a beta carbon, a carboxylic acid functional group linked at the alpha carbon and a side-chain starting at either the alpha carbon or the beta carbon wherein the side-chain is bound to another amino acid.

Naturally occurring amino acids can be divided into the following four groups: (1) acidic amino acids, (2) basic amino acids, (3) neutral polar amino acids, and (4) neutral nonpolar amino acids. Representative amino acids within these various groups include, but are not limited to: (1) acidic (negatively charged) amino acids such as aspartic acid and glutamic acid; (2) basic (positively charged) amino acids such as arginine, histidine, and lysine; (3) neutral polar amino acids such as glycine, serine, threonine, cysteine, tyrosine, asparagine, and glutamine; and (4) neutral nonpolar (hydrophobic) amino acids such as alanine, leucine, isoleucine, valine, proline, phenylalanine, tryptophan, and methionine.

Conserved substitution for an amino acid within a naturally occurring amino acid sequence can be selected from other members of the group to which the naturally occurring amino acid belongs. For example, the aliphatic side chains group of amino acids is glycine, alanine, valine, leucine, and isoleucine. Conserved substitution of naturally occurring amino acid valine includes use of glycine, alanine, leucine, or isoleucine.

The aliphatic-hydroxyl side chain group of amino acids is serine and threonine. The amide-containing side chain group of amino acids is asparagine and glutamine. The aromatic side chain group of amino acids is phenylalanine, tyrosine, and tryptophan. The basic side chain group of amino acids is lysine, arginine, and histidine. The sulfur-containing side chain group of amino acids having is cysteine and methionine. Examples of naturally conservative amino acids substitutions are: valine for leucine, serine for threonine, phenylalanine for tyrosine, lysine for arginine, cysteine for methionine, and asparagine for glutamine.

In preferred embodiments, it is shown herein that such pteroyl conjugates specifically target to tumor cells within a tissue. Moreover, the intensity of the fluorescence in greater than the intensity of previously observed with other near infrared dyes that are targeted with folate for folate receptor positive tumors. This increased intensity allows the targeting and clear identification of smaller areas of biological samples (e.g., smaller tumors) from a tissue being monitored. In addition, the increased intensity of the compounds of the present disclosure provides the added advantage that lower doses/quantities of the dye can be administered and still produces meaningful results. Thus, the compounds of the present disclosure lead to more economical imaging techniques. Moreover, there is an added advantaged that a lower dose of the compounds of the disclosure as compared to conventional imaging compounds minimizes the toxicity and other side effects that are attendant with administration of foreign materials to a body.

Furthermore, identification of small tumors will lead to a more accurate and more effective resection of the primary tumor to produce negative margins, as well as accurate identification and removal of the lymph nodes harboring metastatic cancer cells and identification of satellite disease. Each of these advantages positively correlates with a better clinical outcome for the patient being treated.

In specific experiments, it was found that use of amino acids other than tyrosine as the linker resulted in loss of near infrared fluorescence. For example, see discussion of Scheme I. Specifically note the synthetic pathway lead to undesired by-product 4 as major product that does not have NIR properties However, it is contemplated that in addition to tyrosine and tyrosine derivatives, a pteroyl conjugate of a near infrared dye with cysteine or cysteine derivatives also may be useful. Furthermore, it is contemplated that a direct linkage of the pteroyl or folate moiety to the dye or linkage of the dye to pteroic acid or folic acid through an amine linker also produces a loss of intensity of the fluorescence from the conjugate whereas the presence of the tyrosine or tyrosine derivative as the linking moiety between the pteroyl (targeting moiety) and the near infrared dye (the fluorescing moiety) is beneficial to maintain or enhance the fluorescence of the conjugated compound. Tyrosine-based compounds of the disclosure do not require an extra amine linker to conjugate the S0456 and further because conjugation through the phenol moiety of the tyrosine leads to enhanced fluorescence.

The compounds can be used with fluorescence-mediated molecular tomographic imaging systems, such as those designed to detect near-infrared fluorescence activation in deep tissues. The compounds provide molecular and tissue specificity, yield high fluorescence contrast, brighter fluorescence signal, and reduce background autofluorescence, allowing for improved early detection and molecular target assessment of diseased tissue in vivo (e.g., cancers). The compounds can be used for deep tissue three dimensional imaging, targeted surgery, and methods for quantifying the amount of a target cell type in a biological sample.

Compounds

In an aspect the disclosure relates to compounds comprising the formula: Formula (I):

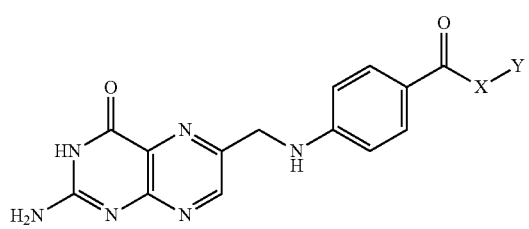

(formula I)

wherein:

X is an amino acid or a derivative thereof, and

Y is a dye that has a fluorescence excitation and emission spectra in the near infra red range, and said compound maintains or enhances the fluorescence of Y.

In some embodiments, the amino acid or amino acid derivative induces a shift in the electronic emission spectrum, the electronic absorption spectrum, or both the electronic emission and absorption spectrum, relative to the electronic spectra of the unmodified dye molecule. Suitably, the shift in the electronic spectrum is a bathochromic shift (i.e., shift to longer wavelength/lower frequency) that helps to improve the detection of the compound in the near infrared (NIR) spectral window and/or reduce the amount of background signal, autofluorescence, interferences from the tissue surrounding the area being visualized. More specifically, this shift in electronic spectrum is particularly observed with NIR dyes that comprise electronegative atoms that are incorporated into the 6-membered ring. Thus, in certain embodiments the amino acid or amino acid (X) derivative comprises an electron-rich moiety such as, for example, oxygen, sulfur, or nitrogen.

Non-limiting examples of such amino acids can include cysteine, methionine, threonine, serine, tyrosine, phenylalanine, tryptophan, histidine, lysine, arginine, aspartic acid, glutamic acid, asparagine, and glutamine, or derivatives thereof.

In embodiments of this aspect, the disclosure provides compounds of Formulas (I)a, (I)b, (I)c, and (I)d:

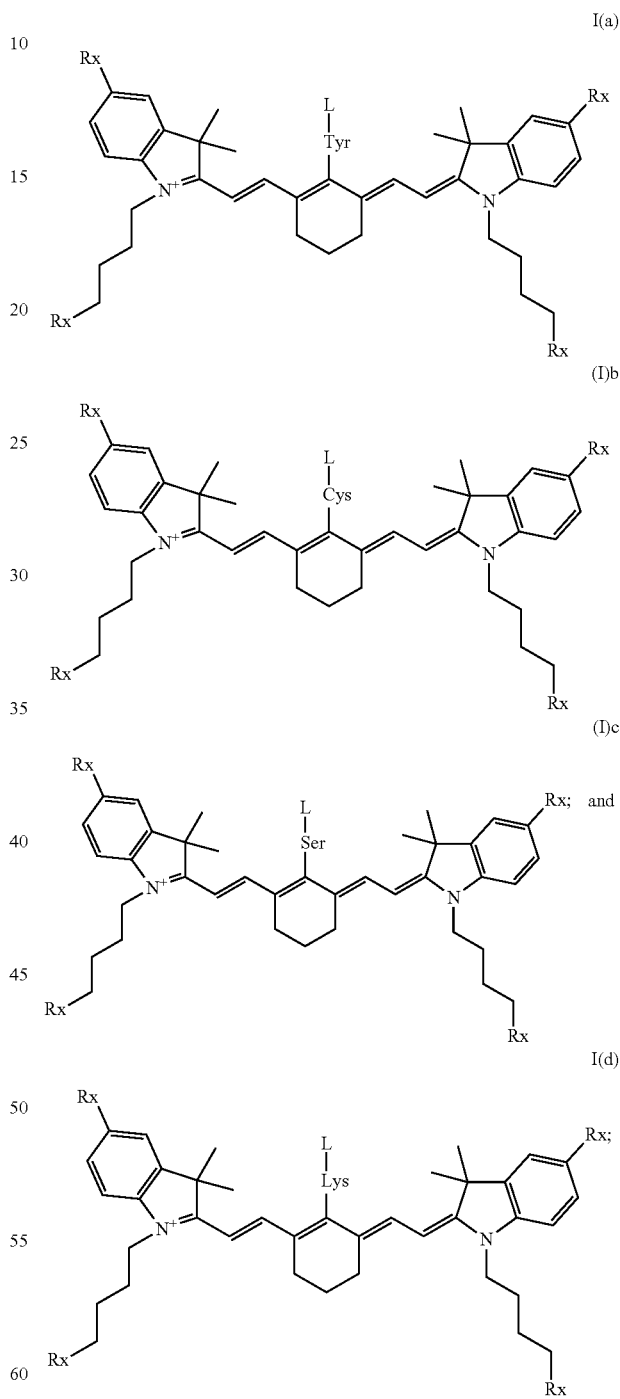

wherein the Tyr, Cys, Ser, and Lys groups indicate a tyrosine, a cysteine, a serine, and a lysine amino acid residue, respectively, or derivatives thereof, and L is preferably a pteroyl or folate and Rx each comprises an independently selected solubilizing group that is optionally absent.

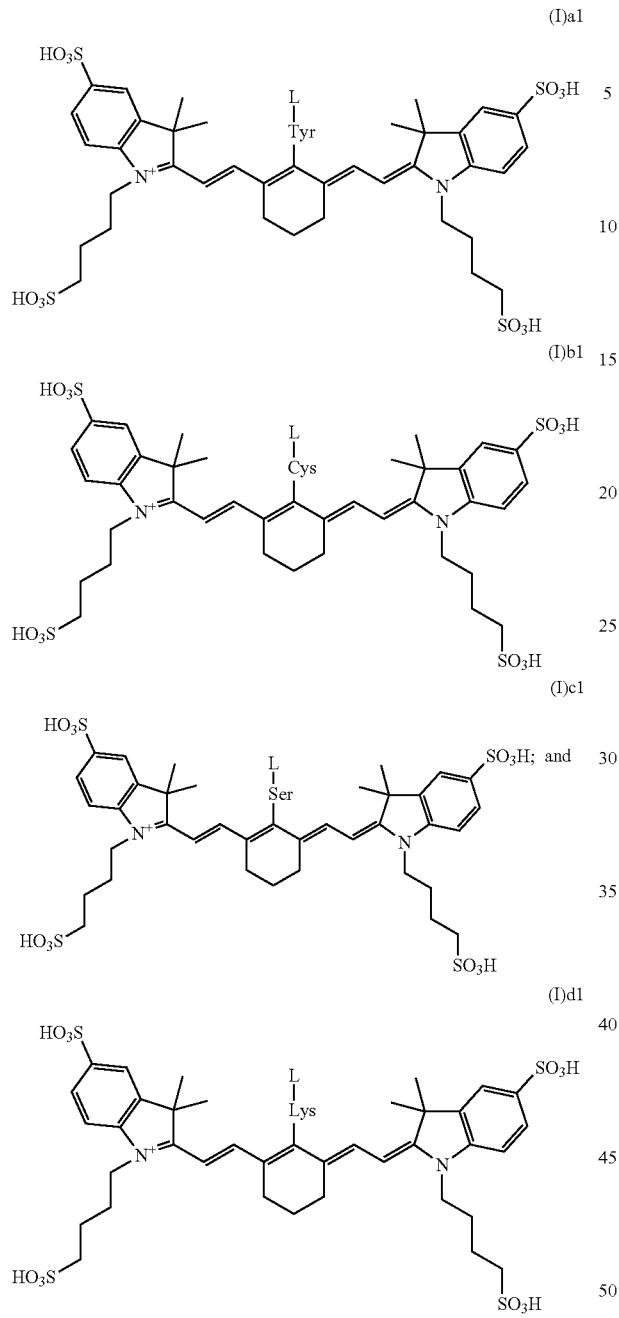

Wherein the Tyr, Cys, Ser, and Lys groups indicate a tyrosine, a cysteine, a serine, and a lysine amino acid residue, respectively, or derivatives thereof, and L is preferably a pteroyl or folate. Preferably, L is pteroyl.

In specific preferred embodiments the disclosure provides a compound of Formula I(a), wherein Tyr is selected from the group consisting of:

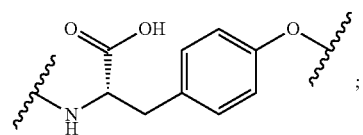

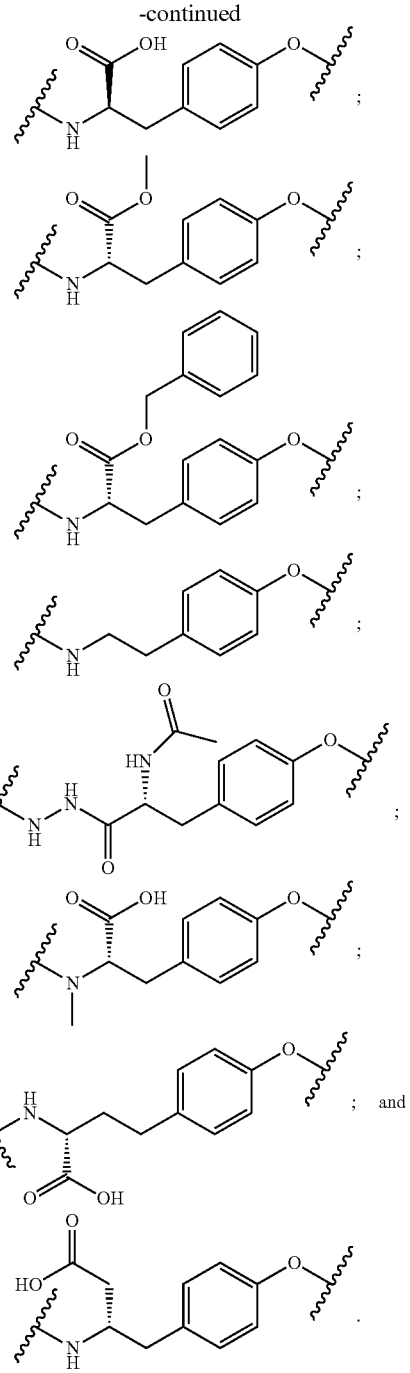

Suitably, the compounds disclosed herein have a maximum light absorption wavelengths in the near infrared region of between about 650 nm and 1000 nm, for example and preferably, at approximately 800 nm.

In specific preferred embodiments, the compounds disclosed herein include a ligand (L) that is effective to target the compound to a particular cell or tissue type and allow for imaging of that targeted cell or tissue. It is preferable the L is either pteroyl moiety or folate moiety and more preferable that L is pteroyl moiety. However, it is contemplated that the skilled person may use some other ligand L to target the compounds to a particular cell surface protein or receptor protein of interest. In specific and preferred embodiments, the ligand comprises pteroyl:

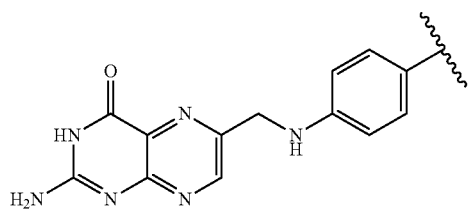 [SMILES: *c1ccc(NCc2cnc3nc(N)[nH]c(=O)c3n2)cc1]

Synthesis of Compounds

The compounds disclosed herein can be made using conventional methods known in the literature. See for example, the dye compounds were synthesized as previously reported.

However, in specific preferred embodiments, the present disclosure provides more efficient synthetic methods for generating the compounds described herein (i.e., Compounds of Formula I). For example, the compounds having formulae I(a)-I(d) can be prepared in accordance to the general schemes outlined in each of Schemes I, II, and III below.

Scheme I, illustrates a synthetic scheme previously used to generate compounds of Formula I where the target ligand comprises folate linked through an amino acid (lysine) to the dye molecule. Briefly, the folate ligand modified by attachment to the amino group of the amino acid is reacted with a bridged ether derivative of the dye under conditions to yield products (3) and (4). However, it is notable that compound 3 is the preferred desirably compound but the synthetic pathway lead to presence of undesired by-product 4 as major product that does not have NIR properties. Moreover, its spectral properties are pH dependant. Thus, this scheme demonstrates the major drawback of ether bridged dyes. In the conventional production of these dyes, 30-60% of the yield is of the desired product and whereas 40-70% of the yield is of the undesired byproduct.

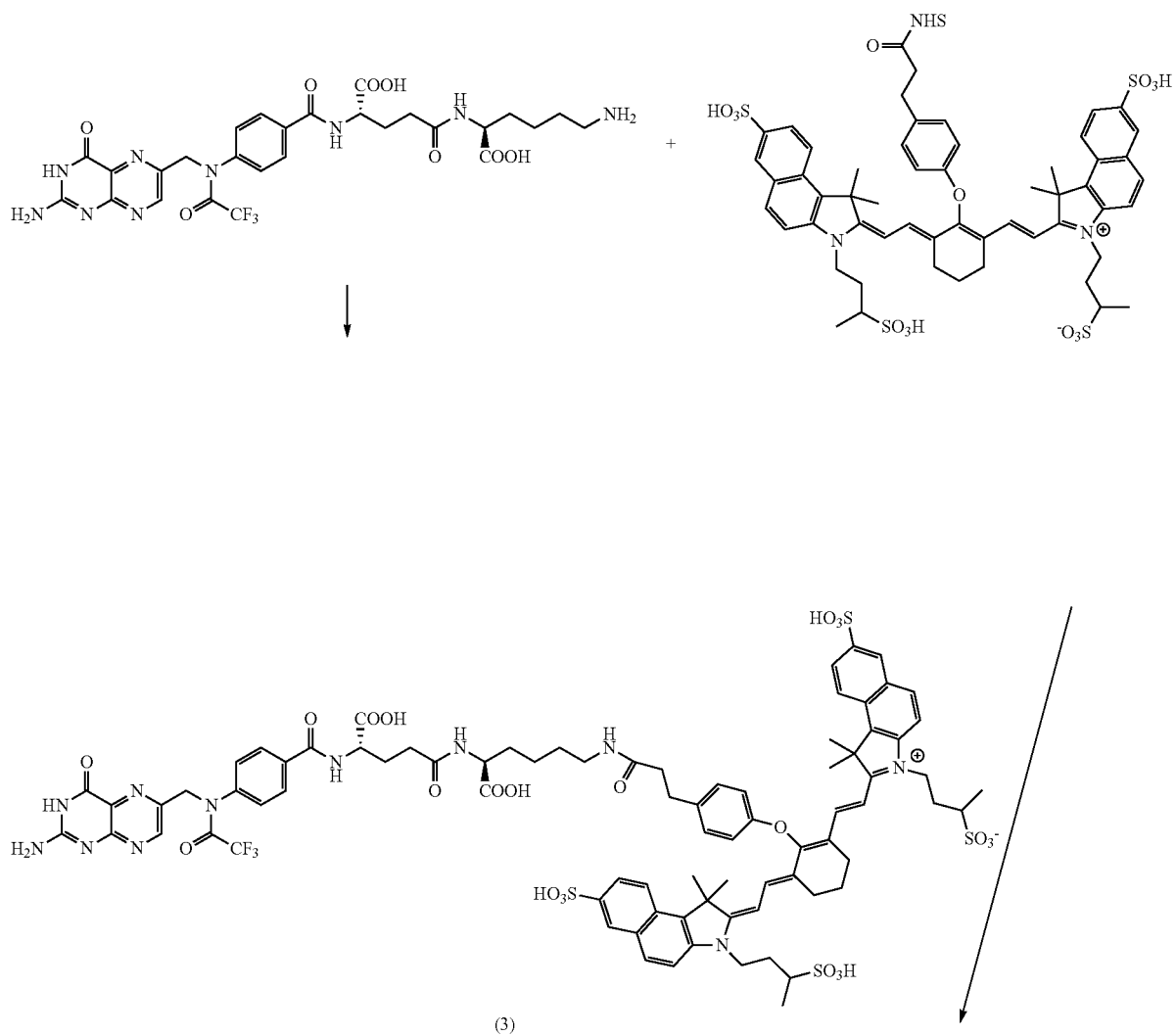

-continued

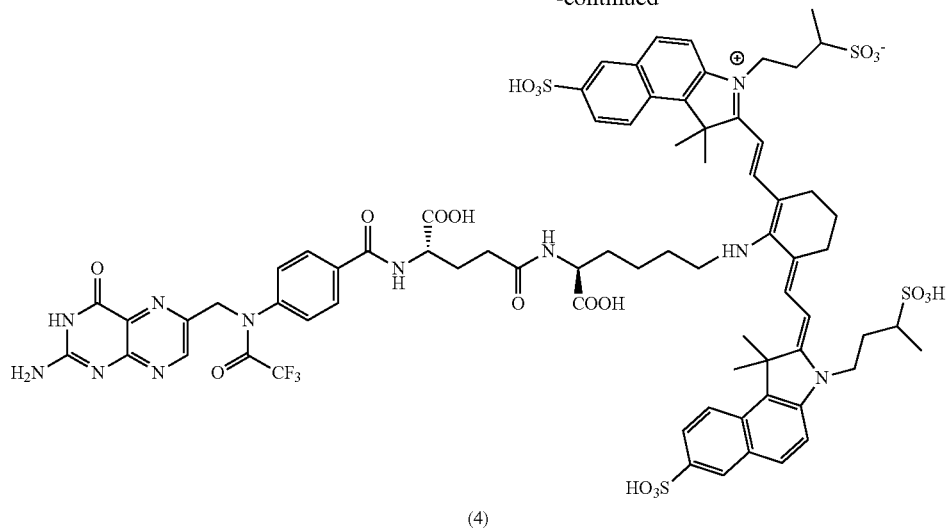

(4)

Scheme II provides a synthetic route that includes only three reaction steps and provides the product compound (5) in high yields (above 98%). Briefly, the targeting ligand (1) (illustrated in Scheme II with a pteroyl group) and an amino acid or amino acid derivative (2) that optionally includes protecting groups to avoid undesired reactivity with groups other than the amino group of the amino acid are mixed in a HATU[(O-(7-azabenzotriazol-1-yl)-N,N,N',N'-tetramethyluronium hexafluorophosphate)]/DIPEA (Diisopropylethylamine)/DMF (dimethylformamide) solvent system and reacted at a room temperature and for a sufficient time (5 minutes) to allow coupling of (2) through the amino functionality to ligand (1) to provide (3). Compound (3) can be advantageously precipitated by adding dilute acid to the reaction mixture. More specifically, Compound 3 was precipitated in 1N HCl (hydrochloric acid) to get final compound over 98% purity, in these embodiments, the costly HPLC or column chromatography steps are avoided. Compound (3) is reacted to remove the protecting groups on the amino acid portion of the compound by reacting the compound at room temperature in TFA (trifluoroacitic acid):water:TIPS (triisopropylsilane) solvent system for provide compound (4). The compound 4 was purified by precipitation with diethyl ether or methyl-t-butyl ether to yield over 98% purity without HPLC (High performance liquid chromatography) or column chromatography. Compound (4) is reacted in a basic aqueous system (e.g., NaOH, sodium hydroxide) in order to remove the protecting group functionalities and is subsequently reacted, in slight molar excess, with the dye (S0456) in water for a time of 15 minutes and at a temperature of 80-100° C. that allows for coupling between the dye and (4), to yield final compound (5). Compound 5 was precipitated with acetone to give over 98% pure Pte-Tyr-S0456. When NaOH is used the sodium salt of Pte-Tyr-S0456 is produced.

Scheme II:

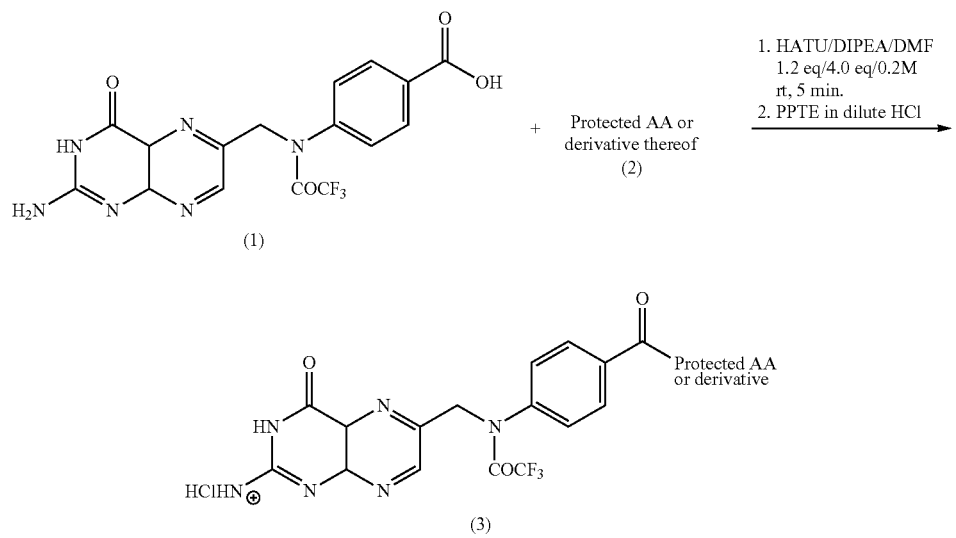

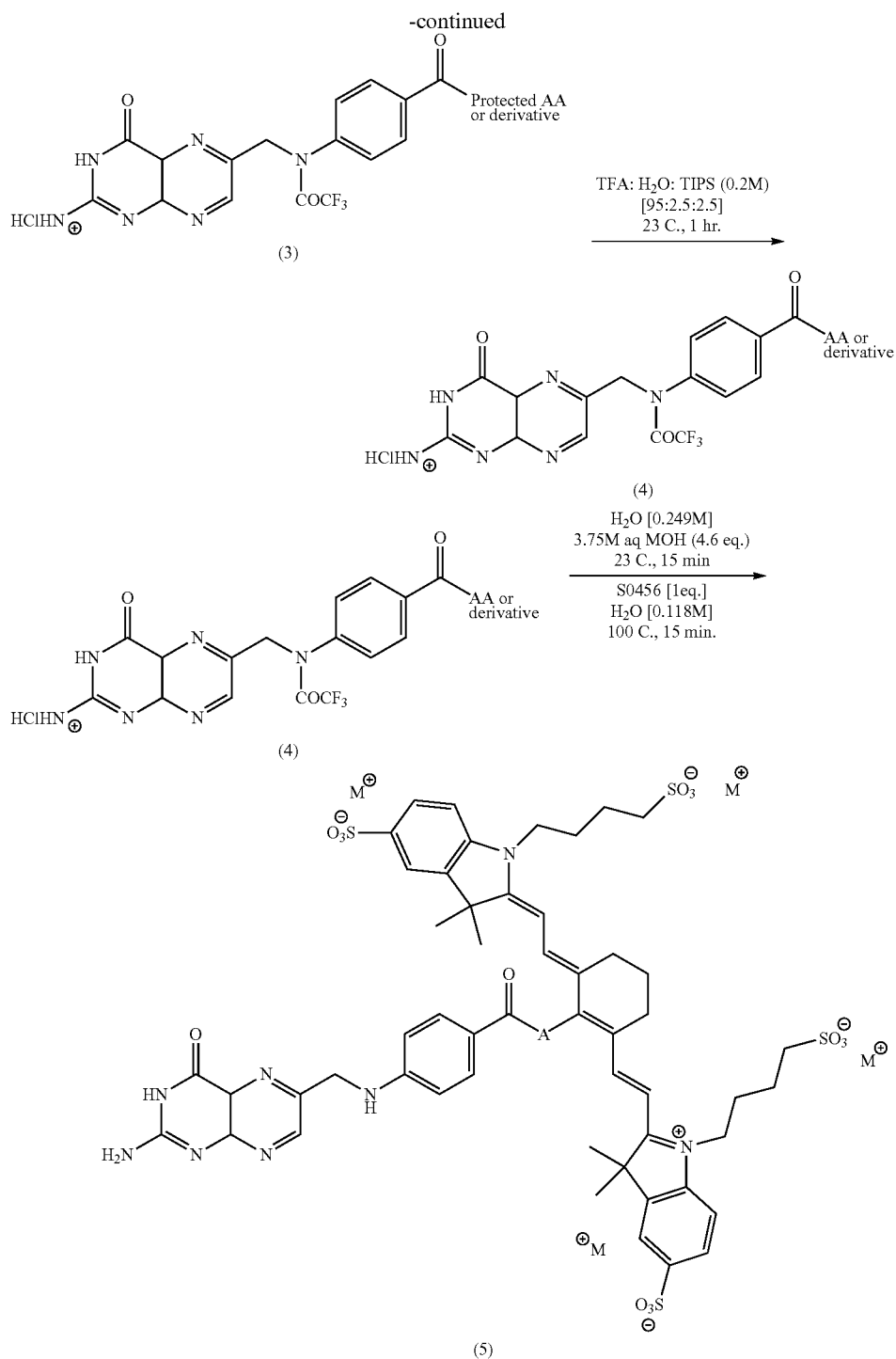

Scheme III provides an alternative solid phase synthetic route to produce the compounds disclosed herein and provide similar yields as described in Scheme II. Briefly, an amino acid bound to a substrate (1) (illustrated in Scheme III below as protected tyrosine attached to a resin bead) is reacted to remove the Fmoc (Fluorenylmethyloxycarbonyl) protecting group in 20% piperidine in DMF, and is subsequently reacted with the targeting ligand (again illustrated by pteroyl below) in HATU/DIPEA/DMF for a time and at a temperature sufficient to allow coupling of the ligand to the amine functional group of the amino acid to provide (2). Compound (2) is reacted to remove the substrate and any protecting groups on the amino acid in a series of reactions in a TFA:Water:TIPS solvent system to provide (3). Following a similar final step as described in Scheme II, compound (3) is reacted in a basic aqueous system in order to remove the protecting group functionalities and is subsequently reacted, in slight molar excess, with the dye (S0456) in water for a time and at a temperature that allows for coupling between the dye and (3), to yield final compound (4).

Scheme III:
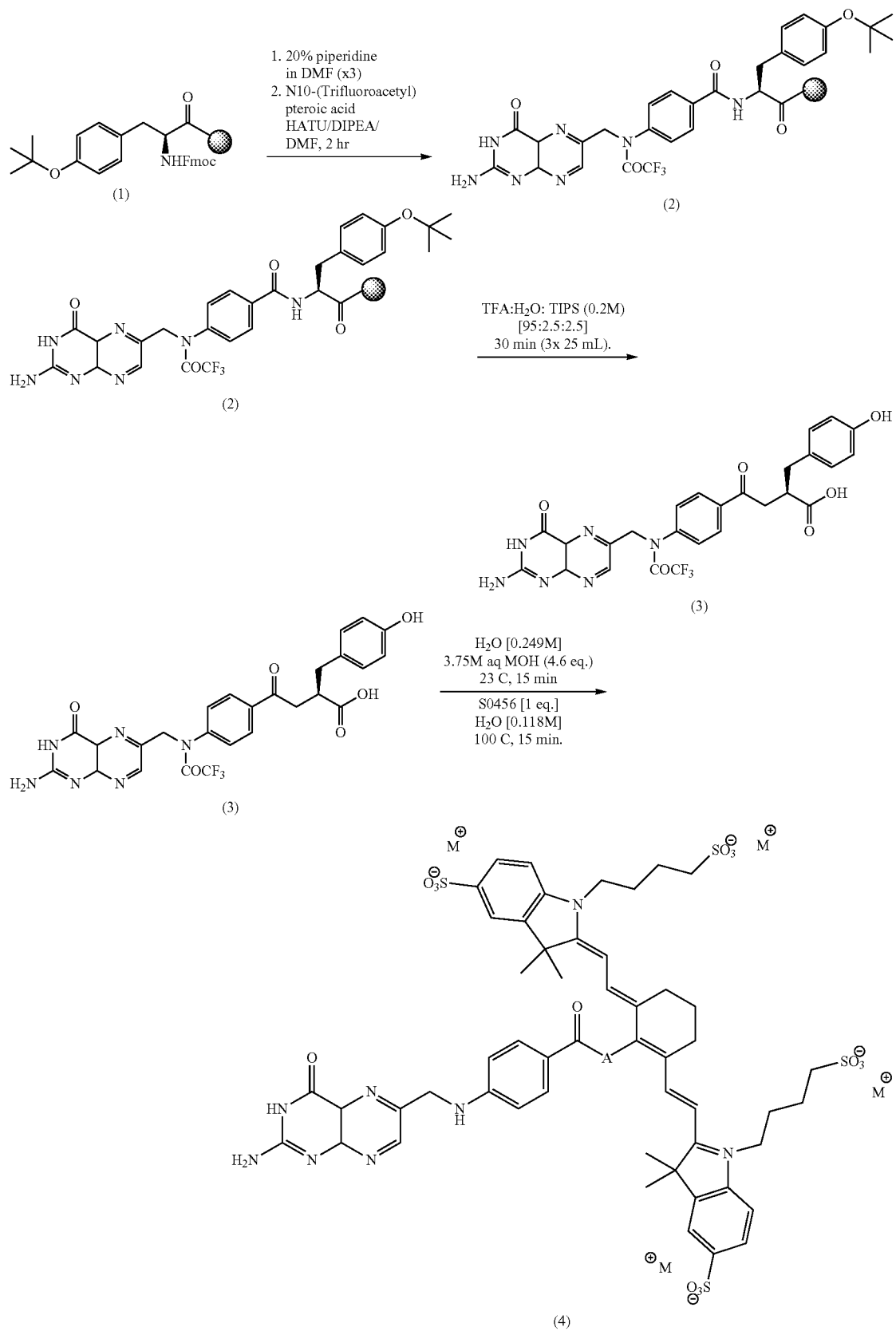

The above schemes merely illustrate several non-limiting synthetic approaches by which the compounds disclosed herein may be prepared. It will be appreciated that one of skill in the art will be able to identify and incorporate modifications to the above schemes that would provide other compounds having the physical properties that are within the scope of the disclosure. For example, while the above Schemes illustrates folate and pteroyl groups as the targeting ligands of the compounds disclosed herein, one of skill will appreciate that other targeting ligands can be readily incorporated into the synthetic scheme and generate alternative compounds of the Formula I. As another example, a one of skill will appreciate that the absorption/emission wavelengths of the dye portion of the compounds can be modulated by adjusting the length of the polymethine chain and selecting the appropriate aryl or heteroaryl groups (e.g., indole vs. benzoindole) as well as linking amino acid groups. In a further example, one of skill in the art will recognize that the extinction coefficient and fluorescence intensity of the dye can be varied by adjusting the rigidity of the polymethine chain (e.g., by introducing a ring system into the polymethine chain such as cyclohexene, cyclobutanone, among others) as is generally known in the art. Accordingly, one of skill in the art will be able to modify the synthesis by selecting the appropriate reagents to make any of the compounds disclosed herein and optionally being able to vary particular physical properties of the compounds.

Methods of Use

As noted herein above, there is a need for near infrared dye compounds that specifically target to regions within a tissue. This is so that the compounds may be used in imaging techniques and to assist in the diagnosis and therapeutic intervention of disease. As discussed in detail above, the compounds provided herein are useful as dyes and imaging agents in the NIR region of the light spectrum. As such, the compounds have broad applicability to any number of imaging, diagnostic, and targeted therapeutic methods.

In specific embodiments, the present disclosure relates to methods that incorporate at least one of the compounds disclosed herein (e.g., of Formula I, I(a), I(b), I(c), and/or I(d)). can be used to specifically and sensitively identify tumors within a tissue. More specifically, the identified tumors may then be therapeutically resected through surgical methods. In this manner, the compounds of the present disclosure may be useful in fluorescence guided surgical resection of tumors, lymph nodes, and the like. Alternatively, the compounds of the present disclosure may readily be used in whole body imaging in which the compound is administered to a subject and the localization of the fluorescence facilitates identification of a tumor site.

In this manner, the compounds of the present disclosure can be used for the in vivo identification of diseased tissue in a subject in need thereof. The disclosure method includes irradiating an in vivo body part of the subject containing diseased tissue with light having at least one excitation wavelength in the near infrared range from about 600 nm to about 1000 nm. Fluorescence emanating from a compound of the present disclosure administered to the subject and which has specifically bound to and/or been taken up by the diseased tissue in the body part, in response to the at least one excitation wavelength is directly viewed to determine the location and/or surface area of the diseased tissue in the subject.

Light having a wavelength range from 600 nm and 850 nm lies within the near infrared range of the spectrum, in contrast to visible light, which lies within the range from about 401 nm to 500 nm. Therefore, the excitation light used in practice of the disclosure diagnostic methods will contain at least one wavelength of light to illuminates the tissue at the infrared wavelength to excite the compounds in order that the fluorescence obtained from the area having uptake of the compounds of the present disclosure is clearly visible and distinct from the auto-fluorescence of the surrounding tissue. The excitation light may be monochromatic or polychromatic. In this manner, the compounds of the present disclosure are advantageous as they eliminate the need for use of filtering mechanisms that would be used to obtain a desired diagnostic image if the fluorescent probe is one that fluoresces at wavelengths below 600 nm. In this manner, the compounds of the present disclosure avoid obscured diagnostic images that are produced as a result of excitation light of wavelengths that would be reflected from healthy tissue and cause loss of resolution of the fluorescent image.

Operating rooms for surgical procedures can be equipped with an overhead light that produces wavelengths of light in the optical emitting spectrum useful in practice of disclosure diagnostic methods, such as a lamps that produce light in the appropriate wavelength. Such a light can be utilized in the practice of the disclosure diagnostic methods merely by turning out the other lights in the operating room (to eliminate extraneous light that would be visibly reflected from tissue in the body part under investigation) and shining the excitation light of near infrared wavelength into the body cavity or surgically created opening so that the fluorescent image received directly by the eye of the observer (e.g., the surgeon) is predominantly the fluorescent image emanating from the fluorophore(s) in the field of vision. Light emanating from a source in the 600 nm and 850 nm range, preferably 750 nm-850 nm range would be used in accomplishing the goal of direct visualization by the observer so that light reflecting from the body part, other than that from the fluorescing moiet(ies), is minimized or eliminated.

Accordingly, in disclosure diagnostic methods, the diseased tissue (and bound or taken-up targeting construct) is "exposed" to the excitation light (e.g, by surgically created opening or endoscopic delivery of the light to an interior location. The disclosure disclosed method is particularly suited to in vivo detection of diseased tissue located at an interior site in the subject, such as within a natural body cavity or a surgically created opening, where the diseased tissue is "in plain view" (i.e., exposed to the human eye) to facilitate a procedure of biopsy or surgical excision of the area that has been highlighted by uptake of the compounds of the present disclosure. As the precise location and/or surface area of the tumor tissue are readily determined by the uptake of the compounds of the present disclosure, the methods employing the compounds of the present disclosure provide a valuable guide to the surgeon, who needs to "see" in real time the exact outlines, size, etc. of the mass to be resected as the surgery proceeds.

Thus, in specific embodiments, the present disclosure entails optical imaging of a biological tissue that expresses a folate receptor by contacting the tissue with a composition comprising compounds of the present disclosure (e.g., compounds of Formula I) and allowing time for the compound in the composition to distribute within the tissue and interact with the site of folate receptor. After a sufficient time for such interaction has passed, the tissue is illuminated with an excitation light to cause the compound in the composition to fluoresce. The fluorescence is then detected as and where such fluorescence is observed is an area that contains the folate receptor.

In like manner, the compounds of the present disclosure are used to identify a target cell type in a biological sample by contacting the biological sample with such compounds for a time and under conditions that allow for binding of the compound to at least one cell of the target cell type. The bound compound is then optically detected such that presence of fluorescence of the near infrared wavelength emanating from the bound, targeted compound of the present disclosure indicated that the target cell type is present in the biological sample. This method thus provides an image of the targeted cell type in the tissue being assessed. Most preferably, the targeted cell type is a tumor cell or a lymph node to which a tumor cell has spread.

These methods advantageously provide an improved method of performing image guided surgery on a subject as the administration of a composition comprising the compound of the disclosure under conditions and for a time sufficient for said compound to accumulate at a given surgical site will assist a surgeon in visualizing the tissue to be removed. Preferably the tissue is a tumor tissue and illuminating the compound that has been taken up by the tissue facilitates visualization of the tumor by the near infrared fluorescence of the compound using infrared light. With the aid of the visualization facilitated by the targeting of the compound of the disclosure to the tumors site, surgical resection of the areas that fluoresce upon excitation by infrared light allows an improved and accurate removal of even small tumors.

It should be understood that in any of the surgical methods of the disclosure the compounds of the present disclosure may be administered before the surgical incision takes place or even after the surgical cavity and site of the tumor has been revealed by the surgery.

If the putative diseased site is a natural body cavity or surgically produced interior site, an endoscopic device can be optionally used to deliver the excitation light to the site, to receive fluorescence emanating from the site within a body cavity, and to aid in formation of a direct image of the fluorescence from the diseased tissue. For example, a lens in the endoscopic device can be used to focus the detected fluorescence as an aid in formation of the image. As used herein, such endoscope-delivered fluorescence is said to be "directly viewed" by the practitioner and the tissue to which the targeting construct binds or in which it is taken up must be "in plain view" to the endoscope since the light used in the disclosure diagnostic procedure will not contain wavelengths of light that penetrate tissue, such as wavelengths in the near infrared range. Alternatively, the excitation light may be directed by any convenient means into a body cavity or surgical opening containing a targeting construct administered as described herein and the fluorescent image so produced can be directly visualized by the eye of the observer without aid from an endoscope. With or without aid from any type of endoscopic device, the fluorescent image produced by the disclosure method is such that it can be viewed without aid of an image processing device, such as a CCD camera, TV monitor, photon collecting device, and the like.

It is contemplated that the diagnostic or imaging methods of the present disclosure allow the surgeon/practitioner to contemporaneously see/view/visualize diseased or abnormal tissue through a surgical opening to facilitate a procedure of biopsy or surgical excision. As the location and/or surface area of the diseased tissue are readily determined by the diagnostic procedure of the disclosure employing the compounds described herein, the disclosure method is a valuable guide to the surgeon, who needs to know the exact outlines, size, etc. of the mass, for example, for resection as the surgery proceeds. In particular, it is noted that the compounds of the disclosure fluorescence in the near infrared range to a greater intensity than those previously described. As such, advantageously, it is contemplated that less of the compound will be needed to achieve diagnostic imaging. In addition, the compounds of the present disclosure penetrate deep into the tumor and hence the disclosure advantageously allows a greater accuracy that the tumor has been removed.

The present disclosure provides methods for utilizing a diagnostic procedure during surgery in a subject in need thereof by administering to the subject a composition comprising a compound of the present disclosure and irradiating an in vivo body part of the subject containing diseased tissue with light having at least one excitation wavelength in the range from about 600 nm to about 850 nm, directly viewing fluorescence emanating from a targeting construct administered to the subject that has specifically bound to and/or been taken up by the diseased tissue in the body part, wherein the targeting construct fluoresces in response to the at least one excitation wavelength, determining the location and/or surface area of the diseased tissue in the subject, and removing at least a portion of the tumor tissue.

In yet another embodiment, the present disclosure provides methods for in vivo diagnosis of tumor tissue in a subject in need thereof. In this embodiment, the disclosure method comprises contacting samples of tumor cells obtained from the subject in vitro with a plurality of detectably labeled compounds, each of which binds to or is selectively taken up by a distinct tumor type, determining which of the compounds is bound to or taken up by the sample tumor cells, administering a diagnostically effective amount of at least one biologically compatible fluorescing targeting construct containing a compound of the present disclosure that has been determined to bind to and/or be taken up by the sample tumor cells and a fluorophore responsive to at least one wavelength of light in the range from about 600 nm to about 850 nm, and diagnosing the location and/or surface area of the tumor tissue in the in vivo body part by directly viewing fluorescence emanating from the targeting construct bound or taken up in the tumor tissue upon irradiation thereof with light providing the at least one excitation wavelength for the fluorescent targeting construct.

In some embodiments, a single type of fluorescent moiety is relied upon for generating fluorescence emanating from the irradiated body part (i.e., from the fluorescent targeting construct that binds to or is taken up by diseased tissue) and subjecting the targeting construct with a source of light from the near infrared spectrum.

In other embodiments, it is contemplated that a plurality. (i.e., two, three, four, or more) targeting constructs are used to obtain a diagnostic image. Such additional targeting constructs may be additional compounds of the present disclosure distinct from the first such compound. Alternatively, the additional targeting constructs may comprise the dyes described herein but with the pteroyl moiety being replaced by a ligand for another receptor other than folate receptor. In still other embodiments, the additional targeting moieties may be other fluorescing targeting constructs (e.g., antibodies, or biologically active fragments thereof, having attached fluorophores) that bind to other receptors or antigens on the tumor or tissue (e.g., a site of atherosclerosis, infection, cardiovascular diseases, neurodegenerative diseases, immunologic diseases, autoimmune diseases, respiratory diseases, metabolic diseases, inherited diseases, infectious diseases, bone diseases, and environmental diseases or the like) to be imaged. Any additional targeting moiety that specifically targets the tumor or specific site on the tissue may be used provided that it is specific for the site to be monitored. The purpose of the additional fluorescing targeting construct is to increase the intensity of fluorescence at the site to be monitored thereby thereby aiding in detection of diseased or abnormal tissue in the body part. For example, a given tumor may have numerous markers and in addition to the compounds of the present disclosure a cocktail of fluorescent moieties is provided which are specific for that given tumor such that the signal emanating from the tumor is generated by more than one compound or fluorescent moiety that has targeted and become localized to the tumor site of interest.

In practice, the skilled person would administer a compound of the present disclosure either alone or as part of a cocktail of targeting detectable moieties and allow these compounds and targeting moieties to bind to and/or be taken up by any targeting tissue that may be present at the site under investigation and then provide a supply of the light source. Typically, the compounds of the present disclosure and any additional targeting moieties will be administered prior to surgery for a time and in compositions that allow the fluorescent compounds of the present disclosure as well as any additional fluorescent constructs to be taken up by the target tissue.

Those of skill in the art will be able to devise combinations of successively administered fluorescing targeting constructs, each of which specifically binds to the target site. It is preferable that all of the fluorescing targeting constructs used in such cocktails to identify the target tissue comprise fluorophores that fluoresce within the same wavelength band or at the same wave length as does the compound of the present disclosure (e.g. a fluorescing sensitive to near infrared wavelength of light in the compounds of the present disclosure) to minimize the number of different light sources that need to be employed to excite simultaneous fluorescence from all of the different targeting constructs used in practice of the disclosure method. However, it is contemplated that the additional targeting moieties other than the compounds of the present disclosure may fluorescence in response to the irradiating light at a different color (i.e., has a different wavelength) than that from the florescent compounds of the present disclosure. The difference in the colors of the fluorescence emanating from the compounds of the present disclosure and those of the additional targeting compounds may aid the observer in determining the location and size of the diseased tissue. In some examples, it may be desirable to include fluorophores in targeting constructs targeted to target normal tissue and the compounds of the present disclosure to target diseased tissue such that the contrast between the diseased tissue and normal tissue is further enhanced to further aid the observer in determining the location and size of the target tissue. The use of such additional fluorophores and targeting agents in addition to the compounds of the present disclosure provides the advantage that any natural fluorescence emanating from normal tissue is obscured by the fluorescence emanating from fluorophore(s) in supplemental targeting constructs targeted to the normal tissue in the body part. The greater the difference in color between the fluorescence emanating from normal and target tissue, the easier it is for the observer to visualize the outlines and size of the target tissue. For instance, targeting a fluorescing targeting construct comprising a fluorophore producing infrared light from the compounds of the present disclosure to the target tissue (i.e., abnormal tissue) and a fluorophore producing green light to healthy tissue aids the observer in distinguishing the target tissue from the normal tissue. Those of skill in the art can readily select a combination of fluorophores that present a distinct visual color contrast.

The spectrum of light used in the practice of the disclosure method is selected to contain at least one wavelength that corresponds to the predominate excitation wavelength of the targeting construct, or of a biologically compatible fluorescing moiety contained within the targeting construct. Generally the excitation light used in practice of the disclosure method comprises at least one excitation wavelength of light in the near infrared wavelength range from about 600 nm to about 850 nm However, when a combination of targeting ligands that fluoresce at different wavelengths is used in practice of the disclosure, the spectrum of the excitation light must be broad enough to provide at least one excitation wavelength for each of the fluorophores used. For example, it is particularly beneficial when fluorophores of different colors are selected to distinguish normal from diseased tissue, that the excitation spectrum of the light(s) include excitation wavelengths for the fluorophores targeted to normal and target tissue.

As noted herein the compounds of the present disclosure are specifically targeted to the folate receptor by way of pteroyl or folate ligand being part of the compounds of the present disclosure. In embodiments where an additional targeting moiety is used, the targeting construct of such an additional targeting moiety is selected to bind to and/or be taken up specifically by the target tissue of interest, for example to an antigen or other surface feature contained on or within a cell that characterizes a disease or abnormal state in the target tissue. As in other diagnostic assays, it is desirable for the targeting construct to bind to or be taken up by the target tissue selectively or to an antigen associated with the disease or abnormal state; however, targeting constructs containing ligand moieties that also bind to or are taken up by healthy tissue or cell structures can be used in the practice of the disclosure method so long as the concentration of the antigen in the target tissue or the affinity of the targeting construct for the target tissue is sufficiently greater than for healthy tissue in the field of vision so that a fluorescent image representing the target tissue can be clearly visualized as distinct from any fluorescence coming from healthy tissue or structures in the field of vision.

For example, colon cancer is often characterized by the presence of carcinoembryonic antigen (CEA), yet this antigen is also associated with certain tissues in healthy individuals. However, the concentration of CEA in cancerous colon tissue is often greater than is found in healthy tissue, so an anti-CEA antibody could be used as a ligand moiety in the practice of the disclosure. In another example, deoxyglucose is taken up and utilized by healthy tissue to varying degrees, yet its metabolism in healthy tissues, except for certain known organs, such as the heart, is substantially lower than in tumor. The known pattern of deoxyglucose consumption in the body can therefore be used to aid in determination of those areas wherein unexpectedly high uptake of deoxyglucose signals the presence of tumor cells.

The disease or abnormal state detected by the disclosure method can be any type characterized by the presence of a known target tissue for which a specific binding ligand is known. For example, various heart conditions are characterized by production of necrotic or ischemic tissue or production of artherosclerotic tissue for which specific binding ligands are known. As another illustrative example, breast cancer is characterized by the production of cancerous tissue identified by monoclonal antibodies to CA15-3, CA19-9, CEA, or HER2/neu. It is contemplated that the target tissue may be characterized by cells that produce either a surface antigen for which a binding ligand is known, or an intracellular marker (i.e. antigen), since many targeting constructs penetrate the cell membrane. Representative disease states that can be identified using the disclosure method include such various conditions as different types of tumors, bacterial, fungal and viral infections, and the like. As used herein "abnormal" tissue includes precancerous conditions, necrotic or ischemic tissue, and tissue associated with connective tissue diseases, and auto-immune disorders, and the like. Further, examples of the types of target tissue suitable for diagnosis or examination using the disclosure method include cardiac, breast, ovarian, uterine, lung, endothelial, vascular, gastrointestinal, colorectal, prostatic tissue, endocrine tissue, and the like, as well as combinations of any two or more thereof.

Simply by way of example, antigens for some common malignancies and the body locations in which they are commonly found are known to those of skill in the art, and targeting ligands, such as antibodies or for these antigens or indeed ligands where the antigens are receptors are known in the art. For example, CEA (carcinoembryoinc antigen) is commonly found in tumors from the colon, breast and lung; PSA (prostate specific antigen, or sometimes referred to as prostate specific membrane antigen (PSMA)) is specific for prostate cancer; CA-125 is commonly found in tumors of ovarian cancer origin, CA 15-3, CA19-9, MUC-1, Estrogen receptor, progesterone receptor and HER2/neu are commonly found in breast cancer tumors, alpha-feto protein is found in both testicular cancer and hepatic cancer tumors, beta-human chorionic gonadotropin is found testicular cancer and choriocarcinoma, both estrogen receptor and progesterone receptor also are found in uterine cancer tumors and epidermal growth factor receptor is commonly found in tumors from bladder cancer. Other tumor specific ligands and markers are well known to those of skill in the art. In preferred embodiments, the present disclosure employs folate or pteroyl moieties for targeting the folate receptor and PMSA target moieties for targeting the dyes to prostate cancer cells.

It is contemplated that any of these commonly known markers of tumors can be targeted either using the dyes described herein (by switching out the pteroyl moiety for a moiety that specifically targets these markers) or alternatively, these markers can be targeted in addition and in combination with the folate receptor that is being targeted using the compounds of the present disclosure. As discussed previously, it may be particularly advantageous to have targeting moieties to several different markers on a given tumor to serve as a diagnostic cocktail in which several markers are targeted to more brightly and clearly visualize the tumor.

In addition to chemical compounds, the targeting moieties in such cocktails may include a protein or polypeptide, such as an antibody, or biologically active fragment thereof, preferably a monoclonal antibody. The supplemental fluorescing targeting construct(s) used in practice of the disclosure method may also be or comprise polyclonal or monoclonal antibodies tagged with a fluorophore. The term "antibody" as used in this disclosure includes intact molecules as well as functional fragments thereof, such as Fab, F(ab')2, and Fv that are capable of binding the epitopic determinant. Methods of making these fragments are known in the art. (See for example, Harlow & Lane, Antibodies: A Laboratory Manual, Cold Spring Harbor Laboratory, New York, 1988, incorporated herein by reference). As used in this disclosure, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

In addition to antibodies, the cocktails may comprise compounds in which the ligand moiety attached to the fluorescent targeting construct is selected from among the many biologically compatible compounds that bind with specificity to receptors and/or are preferentially taken up by tumor cells, and can be used as the ligand moiety in the disclosure targeting constructs. Compounds that are preferentially "taken up" by tumor cells may enter the cells through surface or nuclear receptors (e.g., hormone receptors), pores, hydrophilic "windows" in the cell lipid bilayer, and the like.

Illustrative of this class of compounds to target tumors are somatostatin, somatostatin receptor-binding peptides, deoxyglucose, methionine, and the like. Particularly useful somatostatin receptor-binding peptides are a long-acting, octapeptide analog of somatostatin, known as octreotide (D-phenylalanyl-L-cysteinyl-L-phenylalanyl-D-tryptophyl-L-lysyl-L-threonyl-N-[2-hydroxy-1-(hydroxymethyl)propyl]-L-cysteinamide cyclic (2→7)-disulfide), lanreotide, an oral formulation of octreotide, P829, P587, and the like. Somatostatin-binding peptides are disclosed in U.S. Pat. No. 5,871,711, and methods for linking such peptides covalently to a radioisotope through their carboxyl terminal amino acid under reducing conditions are disclosed in U.S. Pat. No. 5,843,401, which are both incorporated herein by reference in their entireties. One of skill in the art can readily adapt such teachings for the preparation of fluorescence-sensitive somatostatin receptor-binding peptides by substituting the fluorescing moieties of this disclosure in the place of a radioisotope.

Somatostatin and somatostatin receptor-binding peptides are particularly effective for use as the tumor-targeting ligand moiety in the targeting construct when the disease state is a neuroendocrine or endocrine tumor. Examples of neuroendocrine tumors that can be diagnosed using the disclosure method include adenomas (GH-producing and TSH-producing), islet cell tumors, carcinoids, undifferentiated neuroendocrine carcinomas, small cell and non small cell lung cancer, neuroendocrine and/or intermediate cell carcinomas, neuroendocrine tumors of ovary, cervix, endometrium, breast, kidney, larynx, paranasal sinuses, and salivary glands, meningiomas, well differentiated glia-derived tumors, pheochromocytomas, neuroblastomas, ganglioneuro(blasto)mas, paragangliomas, papillary, follicular and medullary carcinomas in thyroid cells, Merkel cell carcinomas, and melanomas, as well as granulomas and lymphomas. These tumor cells are known to have somatostatin receptors and can be targeted using somatostatin or somatostatin receptor binding peptides as the tumor-targeting ligand in the disclosure fluorescent targeting construct.

Vasointestinal peptide (VIP), which is used in VIP receptor scintigraphy (I. Virgolini, Eur J. Clin. Invest. 27(10):793-800, 1997, is also useful in the disclosure method for diagnosis of small primary adenocarcinomas, liver metastases and certain endocrine tumors of the gastrointestinal tract.

Another molecule illustrative of the tumor-targeting ligands that are preferentially taken up by tumors is deoxyglucose, which is known to be preferentially taken up in a variety of different types of tumors. Illustrative of the types of tumors that can be detected using deoxyglucose as the tumor-targeting ligand include melanoma, colorectal and pancreatic tumors, lymphoma (both HD and NHL), head and neck tumors, myeloma, cancers of ovary, cancer, breast, and brain (high grade and pituitary adenomas), sarcomas (grade dependent), hepatoma, testicular cancer, thyroid (grade dependent) small cell lung cancer, bladder and uterine cancer, and the like.

Yet other tumor-targeting compounds that can be used in cocktails of the present disclosure include 1-amino-cyclobutane-1-carboxylic acid and L-methionine. L-methionine is an essential amino acid that is necessary for protein synthesis. It is known that malignant cells have altered methionine metabolism and require an external source of methionine.

Additional examples of biologically compatible tumor-targeting compounds that bind with specificity to tumor receptors and/or are preferentially taken up by tumor cells include mammalian hormones, particularly sex hormones, neurotransmitters, and compounds expressed by tumor cells to communicate with each other that are preferentially taken up by tumor cells, such as novel secreted protein constructs arising from chromosomal aberrations, such as transfers or inversions within the clone.

Hormones, including sex hormones, cell growth hormones, cytokines, endocrine hormones, erythropoietin, and the like also serve well as tumor targeting moieties. As is known in the art, a number of tumor types express receptors for hormones, for example, estrogen, progesterone, androgens, such as testosterone, and the like. Such hormones are preferentially taken up by tumor cells, for example, via specific receptors.

The targeting constructs and supplemental targeting constructs used in practice of the disclosure method can be administered by any route known to those of skill in the art, such as topically, intraarticularly, intracisternally, intraocularly, intraventricularly, intrathecally, intravenously, intramuscularly, intraperitoneally, intradermally, intratracheally, intracavitarily, and the like, as well as by any combination of any two or more thereof.

The most suitable route for administration will vary depending upon the disease state to be treated, or the location of the suspected condition or tumor to be diagnosed. For example, for treatment of inflammatory conditions and various tumors, local administration, including administration by injection directly into the body part to be irradiated by the excitation light (e.g., intracavitarily) provides the advantage that the targeting construct (e.g., fluorescently tagged antibodies) can be administered in a high concentration without risk of the complications that may accompany systemic administration thereof.

The compounds of the present disclosure as well as any additional targeting constructs used in diagnostic cocktails comprising the compounds of the present disclosure are administered in a "effective amount" for diagnosis. An effective amount is the quantity of a targeting construct necessary to aid in direct visualization of any target tissue located in the body part under investigation in a subject. A "subject" as the term is used herein is contemplated to include any mammal, such as a domesticated pet, farm animal, or zoo animal, but preferably is a human. Amounts effective for diagnostic use will, of course, depend on the size and location of the body part to be investigated, the affinity of the targeting construct for the target tissue, the type of target tissue, as well as the route of administration. Local administration of the targeting construct will typically require a smaller dosage than any mode of systemic administration, although the local concentration of the targeting construct may, in some cases, be higher following local administration than can be achieved with safety upon systemic administration.

Since individual subjects may present a wide variation in severity of symptoms and each targeting construct has its unique diagnostic characteristics, including, affinity of the targeting construct for the target, rate of clearance of the targeting construct by bodily processes, the properties of the fluorophore contained therein, and the like, the skilled practitioner will weigh the factors and vary the dosages accordingly.

The compounds of the present disclosure as well as cocktails comprising these compounds can be formulated as a sterile injectable suspension according to known methods using suitable dispersing or wetting agents and suspending agents. The sterile injectable preparation may also be a sterile injectable solution or suspension in a non-toxic parenterally-acceptable diluent or solvent, for example, as a solution in 1-4, butanediol. Sterile, fixed oils are conventionally employed as a solvent or suspending medium. For this purpose any bland fixed oil may be employed, including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate, or the like. Buffers, preservatives, antioxidants, and the like, can be incorporated as required, or, alternatively, can comprise the formulation.

It will be apparent to those skilled in the art that various changes may be made in the disclosure without departing from the spirit and scope thereof, and therefore, the disclosure encompasses embodiments in addition to those specifically disclosed in the specification, but only as indicated in the appended claims.

The examples that follow are merely provided for the purpose of illustrating particular embodiments of the disclosure and are not intended to be limiting to the scope of the appended claims. As discussed herein, particular features of the disclosed compounds and methods can be modified in various ways that are not necessary to the operability or advantages they provide. For example, the compounds can incorporate a variety of amino acids and amino acid derivatives as well as targeting ligands depending on the particular use for which the compound will be employed. One of skill in the art will appreciate that such modifications are encompassed within the scope of the appended claims.

EXAMPLES

Example 1

Development of Tumor-Targeted Near Infrared Dyes for Fluorescence Guided Surgery Complete surgical resection of malignant disease is the only reliable method for intervention in cancer. Unfortunately, quantitative tumor resection is often limited by a surgeon's ability to locate all malignant disease and distinguish it from healthy tissue. Fluorescence guided surgery has emerged as a tool to aid surgeons in the identification and removal of malignant lesions. While non-targeted fluorescent dyes have been shown to passively accumulate in some tumors, the resulting tumor-to-background ratios are often poor and the boundaries between malignant and healthy tissues can be difficult to define. To circumvent these problems, the present disclosure shows development of high affinity tumor targeting ligands that bind to receptors that are overexpressed on cancer cells and deliver attached molecules selectively into these cells.

In the present example, use of two tumor-specific targeting ligands (i.e. folic acid that targets the folate receptor (FR) to deliver near infrared (NIR) fluorescent dyes specifically to FR-expressing cancers, thereby rendering only the malignant cells highly fluorescent. The present Example shows that all FR-targeted NIR dyes examined bind cultured cancer cells in the low nanomolar range. Moreover, upon intravenous injection into tumor-bearing mice with metastatic disease, these same ligand-NIR dye conjugates render receptor-expressing tumor tissues fluorescent, enabling their facile resection with minimal contamination from healthy tissues.

1A: Materials and Methods

The results shown in the present example were obtained using specific materials and methods described herein. It is contemplated that the skilled person may be able to modify these methods, reaction conditions, and test conditions and still produce results that demonstrate the efficacy of the FR-targeted NIR dyes of the present disclosure.

a. Synthesis and Characterization of Folate-NIR Conjugates.

Figure 5:
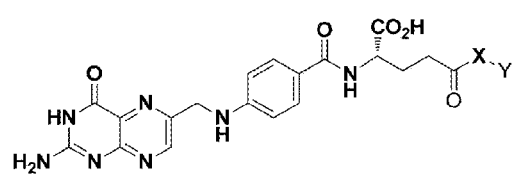
FIG. 5 shows receptor-targeted 2$^{nd}$ generation folate-NIR dye conjugates
Figure 8:
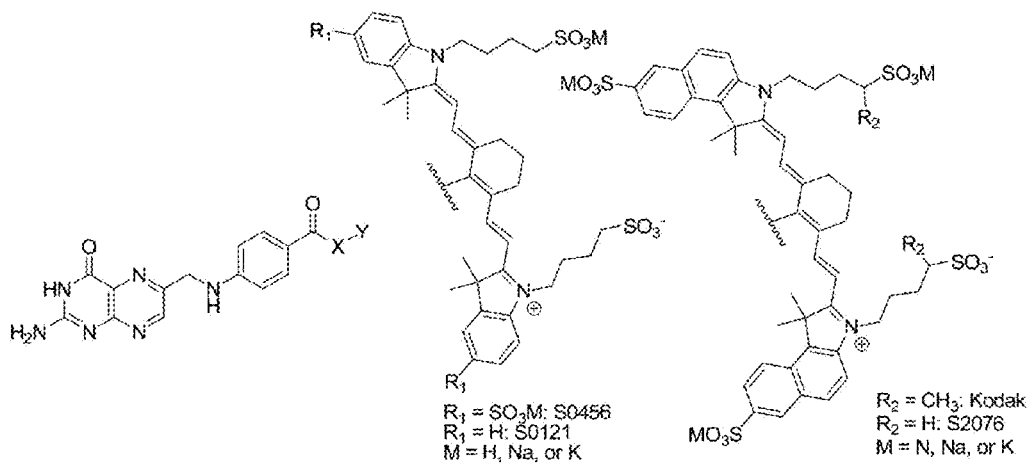
FIG. 8 shows folate receptor-targeted $3^{rd}$ generation NIR dye conjugates
Figure 9:
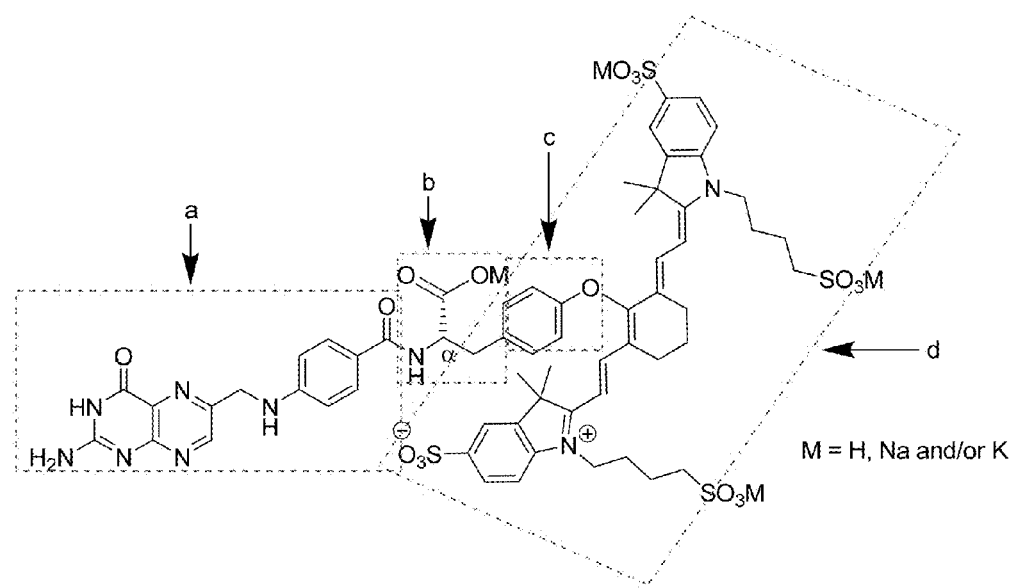
FIG. 9 depicts the rationale of Pte-L-Tyr-S0456 NIR dye conjugate. It shows the structure of Pteroyl-Tyr-S0456 (OTL-0038) with four beneficial functionalities. a=pteroic acid as a targeting molecule; b=α-carboxylic acid from tyrosine for tumor specificity and improve binding affinity for folate receptor; c=phenolic moiety from tyrosine to enhance (bright) fluorescence intensity; d=near-IR fluorescent probe. Therefore, tyrosine acts as part of ligand, linker, and near-IR dye. In other word, tyrosine is a linker that improves the binding affinity and specificity of ligand (pteroic acid). It also enhances the brightness of the NIR dye.

All ligands and linkers were synthesized as previously reported in literature. After purification, folate-targeting ligands were conjugated to selected NIR dyes as shown in FIGS. 1, 5, and 8. Dye conjugates were purified using reverse phase preparative HPLC [Waters, xTerra C18 10 µm; 19×250 mm; λ=280 nm; solvent gradient: 0 to 30% or 80% B in 30 min run, A=10 mM NH$_4$OAc buffer in water (pH=7.0), B=Acetonitrile (ACN)]. Purified compounds were analyzed using LC-MS (ESI) mass spectrometry (Waters, X-Bridge C18 5 µm; 3.0×15 mm).

b. Culture of Folate Receptor Expressing Cells Lines.

L1210A cells were obtained from Dr. Manohar Ratnam and KB cells were obtained from American Type Culture Collection (ATCC; Rockville, Md.). Cells were cultured in folate deficient 1640 RPMI medium supplemented with 10% heat inactivated fetal bovine serum (HIFBS), 1% L-glutamine, and 1% penicillin streptomycin (Invitrogen, Carlsbad, Calif.). All cell lines were cultured in 5% carbon dioxide, 95% air-humidified atmosphere at 37° C.

c. Analysis of Binding Affinity and Specificity of Folate-NIR Dye Conjugates by Fluorometery.

KB (200,000 cells/well in 500 µL) were seeded into 24-well plates and allowed to form monolayers over 48 h. Spent medium in each well was replaced with fresh medium (0.5 mL) containing increasing concentrations of folate-NIR dye conjugate in the presence or absence of 100-fold excess competing ligand; i.e. folic acid. After incubating for 1 hour at 37° C., cells were rinsed with fresh medium (3×0.5 mL), dissolved in 1% aqueous SDS (0.600 mL), and assayed for fluorescence by transfer to a quartz cuvette and analysis of fluorescence emission intensity at each dye's excitation and emission maximum using a Agilent Technologies Cary Eclipse fluorescence spectrophotometer. The conjugate's dissociation constant ($K_d$) was calculated by plotting fluorescence emission units versus the concentration of targeted near infrared dye added using GraphPad Prism 4.03.

d. In Vivo Mouse Models of Metastasis.

All animal procedures were carried out with the approval of the Purdue Animal Care and Use Committee. For studies involving FR-expressing tumors, 5-6 week old female DBA/2 mice were purchased from Harlan Laboratories (Indianapolis, Ind.) and placed on folate deficient diet for two weeks prior to and during each study. Tumor metastases were induced by injecting 1×10$^6$ L1210A (FR expressing) cells into the left ventricle of the heart using a 30 gauge needle. Tumors were allowed to develop for 4 weeks, after which the animals were injected intravenously with 10 nmols of the desired FR-targeted NIR dye dissolved in 100 µl saline. After 4 hours, animals were sacrificed by $CO_2$ asphyxiation and imaged as described below.

e. Fluorescent Imaging of Mice with Metastatic Disease.

Animal imaging experiments were performed using a Caliper Ivis Lumina II Imaging Station with Living Image 4.0 software. Settings for imaging Alexa Fluor 647 and DyLight 680 conjugates: lamp level: high; excitation: 605; emission: Cy5.5; epi illumination; binning: (M) 4; FOV=7.5; f-stop=4; acquisition time=1 s. Settings for imaging DyLight 750 and IR800CW conjugates: lamp level: high; excitation: 745; emission: ICG; epi illumination; binning: (M) 4, FOV=12.5; f-stop=4; acquisition time=1 s.

f. H&E Staining of Normal and Diseased Tissues.

After imaging, organs were dissected and stored in 5 ml formalin and submitted to the Purdue Histology & Phenotyping Laboratory for H&E staining. In brief, tissue samples were processed using a Sakura Tissue-Tek VIP 6, sectioned using a Thermo Finesse ME microtome and stained with H&E reagent using a Shandon Vari-Stain 24-2 autostainer. H&E stained slides were then imaged using an Olympus BH-2 research microscope with an Olympus DP70 camera.

B. Results a. Synthesis of Tumor-Targeted NIR Dyes.

For selective tumor targeting, the inventors conjugated commercially available NIR dyes to folate. Most folate-NIR dye conjugates were synthesized at high yield and subsequently purified using HPLC to homogeneity.

b. Binding Affinity and Specificity of Targeted NIR Dyes.

Figure 2:
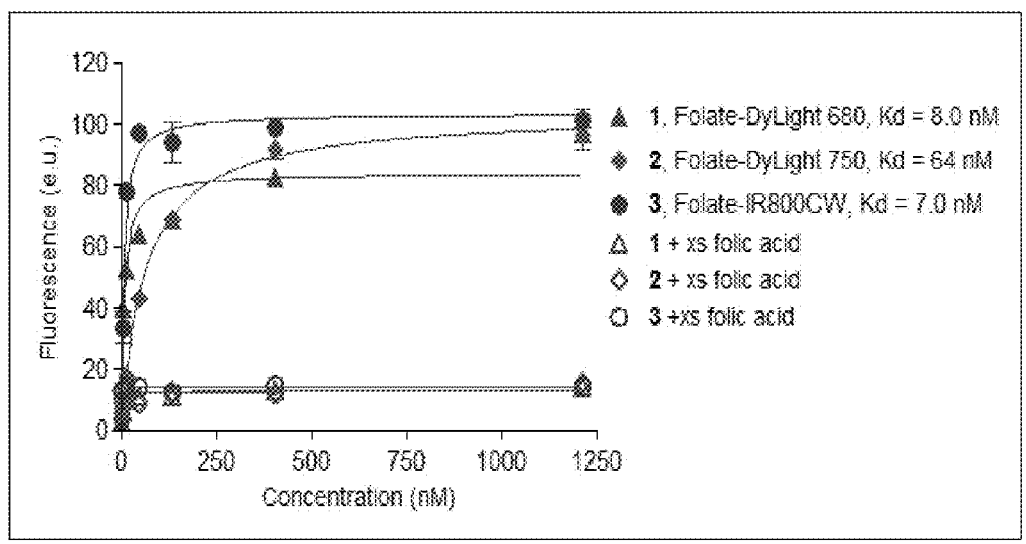
FIG. 2 shows binding isotherms of 1$^{st}$ generation folate-NIR conjugates and binding curves of folate-NIR dye conjugates to folate receptor expressing KB cells. The targeted conjugates are DyLight 680 (triangles), Alexa Fluor 750 (diamonds), and IR800CW (circles).

Because the cargo attached to a ligand can often interfere with ligand binding, it was beneficial to test the binding affinities of the folate-NIR dye conjugates to FR expressing cancer cells. Binding affinities of all conjugates were found to be in the low nanomolar range (FIG. 2), with some variation depending on the attached dye, suggesting that the linked cargo only mildly influences ligand binding. The specificity of folate-NIR dye conjugates for their receptors was also determined in vitro by adding excess folic acid. As seen in FIG. 2, binding was nearly quantitatively inhibited by co-incubation with 100-fold molar excess of folic acid.

c. Imaging of Tumor-Targeted NIR Dyes In Vivo.

Prior to evaluation of the tumor specificities of the tumor-targeted dyes in vivo, it was beneficial to compare the intensities of the selected dyes upon excitation through tissue. For this purpose, 1 mL of phosphate buffered saline containing 100 nM each of dye (Alexa Fluor 647, DyLight 680, DyLight 750, IR800CW) was placed in an Eppendorf tube, which in turn was positioned under a 1 cm thick section of fresh porcine muscle, and the resulting tissues were imaged under the same conditions in both a Kodak Image Station and IVIS Lumina Imager, only the optimal excitation and emission wavelengths were always selected for each dye in each instrument. IR800CW produced the brightest fluorescent signal, with DyLight 750 yielding a signal of intermediate intensity, and Alexa Fluor 647 and DyLight 680 displaying the weakest fluorescence.

Figure 3:
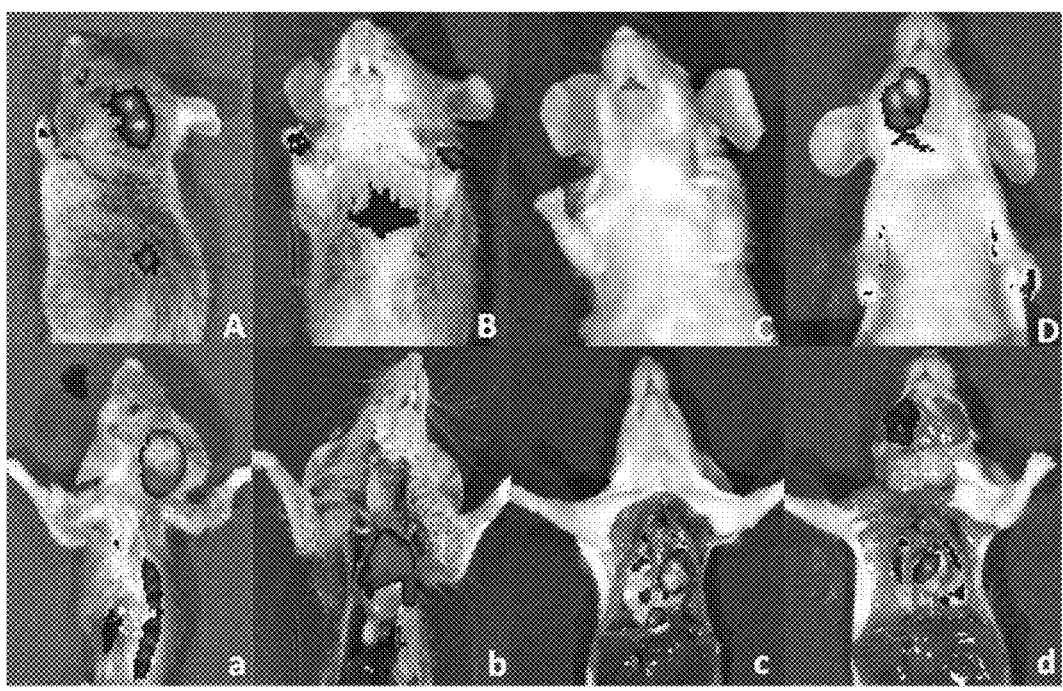
FIG. 3 shows images of mice with metastatic disease (experimental model) 4 hours following intravenous injection of 1$^{st}$ generation folate-NIR dye conjugates. Fluorescent and white light image overlays of intact (A-D) and surgically opened (a-d) tumor-bearing mice are shown. Athymic nude mice with FR-expressing metastatic L1210A tumors were injected intravenously with 10 nmol folate-DyLight 680 (A/a) or folate-DyLight 750 (B/b) and imaged 4 hours later.

In order to compare the abilities of the above folate-NIR dye conjugates to detect metastatic tumor nodules in vivo, a murine model of tumor metastasis was developed that involved intracardiac injection of $10^6$ L1210A cells (FR expressing cells) followed by normal husbandry of the mice for 4 weeks to allow nascent tumors to grow. Tumor-bearing mice were then treated with 10 nmol of selected folate-NIR dye conjugate via tail vein injection, and mice were euthanized 4 hours later for fluorescence imaging. As seen in FIG. 3, tumor loci could be readily distinguished, yielding strong contrast between fluorescent cancer nodules and adjacent healthy tissues. In some cases, fluorescent tumors could even be seen in images of intact mice (FIG. 3, top panels), however, due to differences in tumor size, location, and depth, it was not possible to unequivocally establish which NIR dye yielded the best images in intact animals.

Figure 4:
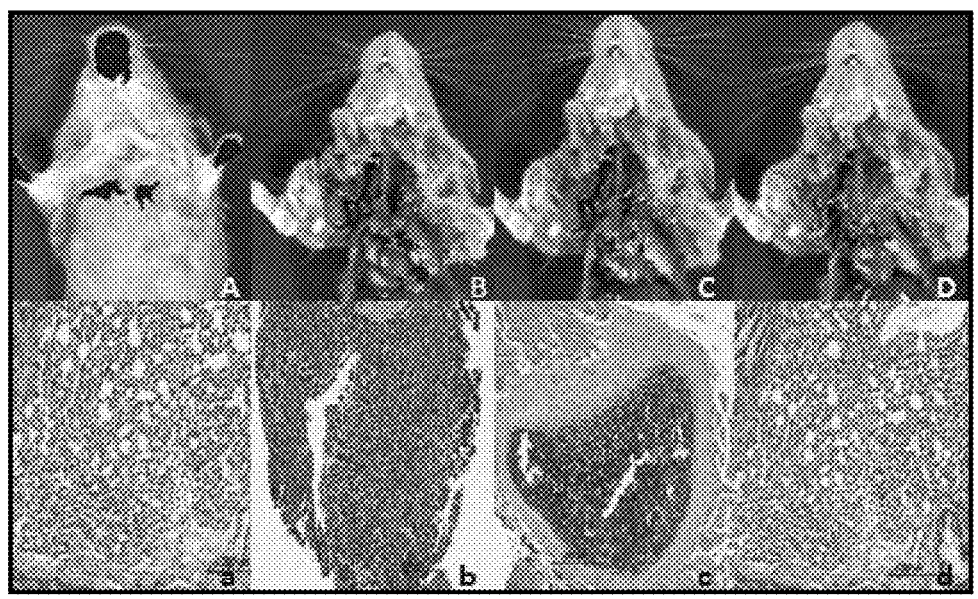
FIG. 4 shows H&E analysis of tissue resected during sequential tumor debulking surgery. A-D show fluorescent and white light image overlays of L1210A metastatic tumor-bearing mice 4 hours following tail vein injection with 10 nmol folate-IR800CW. The portions of FIG. 4 show the following: A shows a whole body image, B shows an opened chest cavity, C shows the opened chest cavity after removal of primary tumor, D shows the opened chest cavity after removal of all secondary nodules. The portions of FIG. 4 show the following: a-d show H&E staining of the following (a) healthy control lung, (b) primary tumor, (c) secondary tumor nodule, and (d) residual tissue.

Finally, in order to mimic a live surgical setting, resection of fluorescent tumor tissue was performed in stages, with the largest masses being removed first, and smaller malignant loci being excised after more prominent fluorescent masses had been cleared (FIG. 4). Beneficially, removal of the primary masses often revealed secondary metastases that were not visible prior to the initial rounds of surgery and would have likely been missed without the aid of the tumor-specific fluorescence. Following these multiple rounds of resection, when all visible fluorescence had been removed, excised tissues were submitted for histological analysis, and these studies revealed that all fluorescent nodules were indeed malignant. Beneficially, random sampling of the remaining tissues demonstrated that nonfluorescent regions were non-malignant (FIG. 4d), suggesting an apparent quantitative removal of cancerous lesions with the aid of the tumor-targeted fluorescent dyes.

C. Discussion

A second approach to fluorescence-guided surgery involves conjugation of an NIR dye to a tumor-specific targeting ligand that binds avidly to cancer cells and clears quantitatively from most healthy tissues. Advantages of this approach include: i) the rapid rate of tumor visualization, owing to the fact that tumor uptake and normal tissue clearance of the dye can occur within minutes of intravenous injection, ii) the stability of tumor contrast, arising from the fact that the ligand-dye conjugates are commonly internalized by the cancer cells via receptor-mediated endocytosis, iii) the specificity of the fluorescence whenever the targeted receptor is either absent, weakly expressed, or inaccessible in normal tissues, and iv) the absence of "bleeding" of fluorescence from malignant into nonmalignant tissues, due to high affinity retention of the ligand-dye conjugate on its receptor, creating highly defined boundaries that clearly demark the cancer. A disadvantage of the strategy derives from the fact that the ligand-targeted dye is always fluorescent, even during excretion, preventing imaging of kidney and bladder tumors until excretion of the dye is complete.

One surprising result from these studies was the smaller size of malignant lesions that could be readily detected in vivo. Thus, more detailed analyses of several sites with punctuate metastatic disease revealed that cancer cell clusters as small as 50 µm could be visualized with use of higher resolution optics. Because clusters of even a few cells can eventually lead to recurrence of the cancer, the ability to detect and remove even the smallest metastatic lesions could eventually lead to reduced patient mortality, assuming an appropriate camera can be designed.

While most applications of fluorescence-guided surgery likely remain to be discovered, some uses of the technology can already be envisioned. First, more malignant lesions will potentially be identified and resected due to better visualization of tumor masses. Second, in cases where maximal preservation of normal tissues is essential (i.e. cancers of the brain, breast, pancreas, head and neck, etc.), careful shaving of fluorescent lesions until no fluorescence remains might enable more efficient conservation of healthy tissue. Third, pre-operative staging of cancer patients might eventually be possible via laparoscopic interrogation of proximal lymph nodes for fluorescent lesions, obviating the need for surgery when significant metastases are clearly observed and eliminating the requirement for subsequent surgical sampling of sentinel lymph nodes when only a single tumor mass is detected.

In conclusion, the present Example demonstrates that tumor-targeted NIR dyes have the potential to reshape standard surgical procedures by improving visualization of malignant tissues, leading more complete and precise diseased tissue removal and improved patient outcome.

Example 2

Design and Synthesis of the Optimal Folate Conjugated Near-Infrared Probe with High Targeting Affinity and Sensitivity for Fluorescence Guided Cancer Surgery Even with the sophisticated tools for tumor identification, many malignant nodules still escape detection, leading to disease recurrence and often death. Motivated by a need for improved tumor identification, two new approaches for intra-operative visualization of malignant disease have been introduced. In the first, a quenched fluorescent dye is injected systemically into the tumor-bearing animal, and release of the quenching moiety by a tumor-specific enzyme, pH change, or change in redox potential is exploited to selectively activate fluorescence within the malignant mass. In the second, a fluorescent dye is conjugated to a tumor-specific targeting ligand that causes the attached dye to accumulate in cancers that over-express the ligand's receptor. Examples of tumor targeting ligands used for this latter purpose include folic acid, which exhibits specificity for folate receptor (FR) positive cancers of the ovary, kidney, lung, endometrium, breast, and colon. Beneficially, a folate-targeted fluorescent dye (folate-fluorescein or EC17) has been recently tested intra-operatively in human ovarian cancer patients. In that study, ~5× more malignant lesions were removed with the aid of the tumor-targeted fluorescent dye than without it, and all resected fluorescent lesions were confirmed by pathology to be malignant.

Unfortunately, a major deficiency with the above clinical study derived from the fact that the attached dye (fluorescein) emits fluorescence in the visible range, i.e. where autofluorescence is strong and light penetrates tissue poorly. Because light in the near infrared (NIR) region induces little autofluorescence and permeates tissue much more efficiently, the inventors postulated that a more complete tumor resection would be possible if an NIR dye were used to guide the surgery. Although there are a limited number of commercially available NIR fluorophores and largely based on the cyanine chemical structure with specific modifications by each manufacturer (FIG. 6). Fortunately, each of the fluorophore series come as reactive fluorophores that can be readily conjugated to the protein or ligand of interest for specific in vivo targeting through conjugation chemistry. Most of the commercially available experimental NIR fluorophores are available as N-hydroxysuccinimide (NHS) esters which can be used for fluorophore conjugation at N-terminal amine. To evaluate and identify the best folate conjugated NIR probe for image guided cancer surgery, the inventors have conjugated the photostable NHS ester NIR dyes (compounds a-c below) with N-terminal amine functionalized folates (Fol-EDA and Fol-Lys) yielded the expected NIR probes (1a-c and 2a-c) along with the major elimination side products (1e-g and 2e-g). In order to get the enhanced yield the more stable NIR dye LS288 NHS ester (d) was utilized and isolated the folate conjugated NIR dyes 1d and 2d with good yields. The optical properties and photostability of the synthesized folate-NIR probes 1a-d and 2a-d were characterized.

-continued

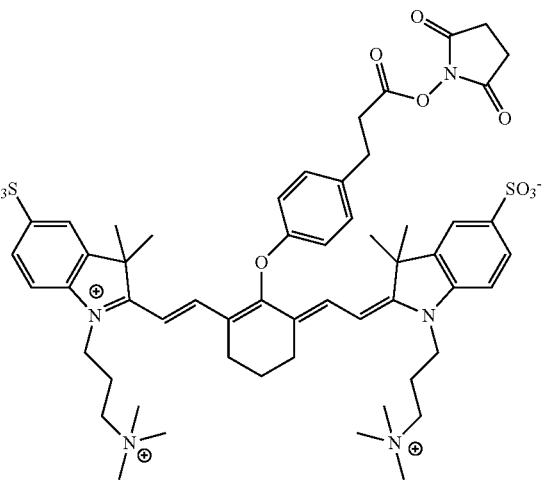

ZW800-NHS ester

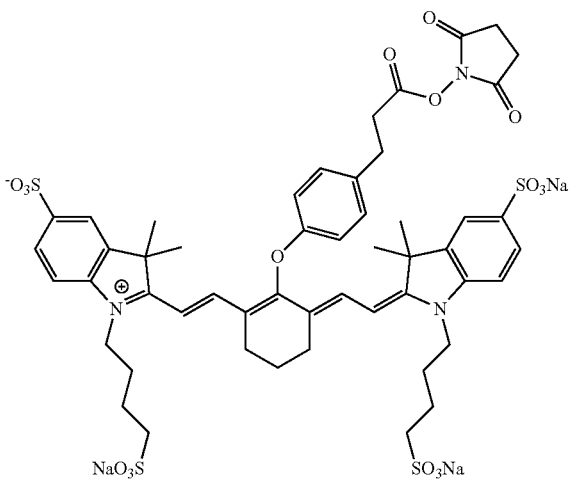

LMNIR2-NHS ester

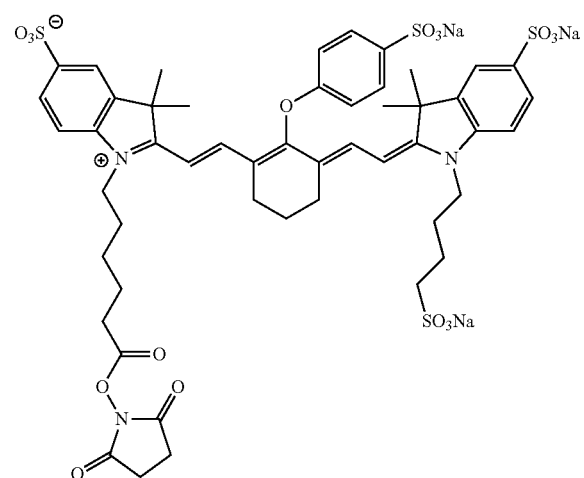

IR800CW-NHS ester

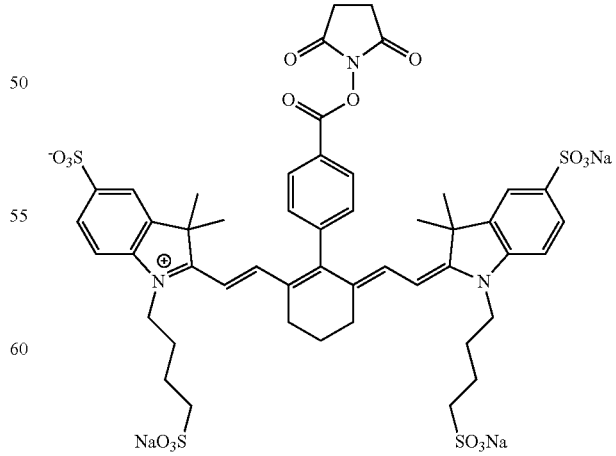

LS288-NHS ester

The fluorescence excitation and emission spectra of all folate-NIR probes 1a-d and 2a-d (500 L; 5 M in PBS) at same concentration showed almost similar intensity. The cytotoxicity and folate receptor affinity of the probe were investigated by in vitro cell experiments and the tumor-targeting capability was in vivo investigated in five groups of nude mice bearing FR+ KB tumor xenograft also biodistribution were examined by using the Lumina II near-infrared fluorescence imaging system. Unfortunately, the biodistribution shown synthetically favorable high yielding folate-NIR probes of FIG. 6 compound 1d and FIG. 7 compound 2d had two fold less brightness of the fluorescence intensity on tumor compare with other folate-NIR probes of FIG. 6 compounds 1a-c and FIG. 7 compounds 2a-c.

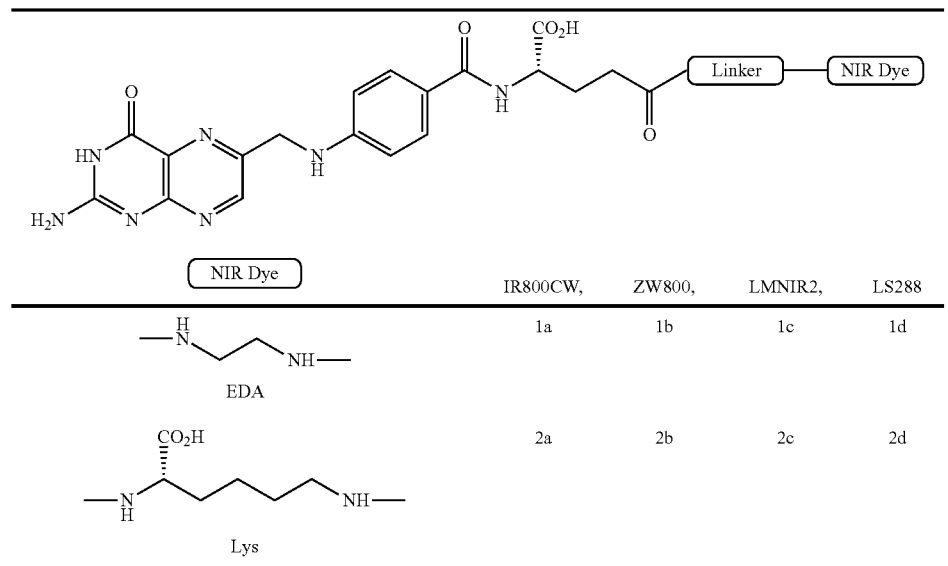

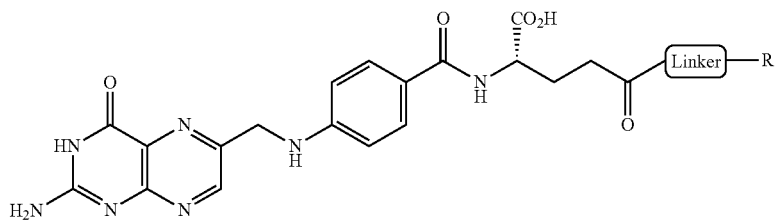

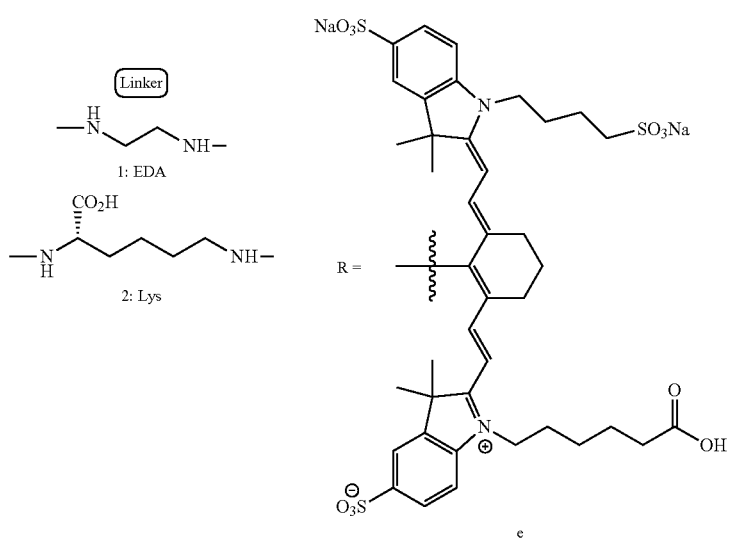

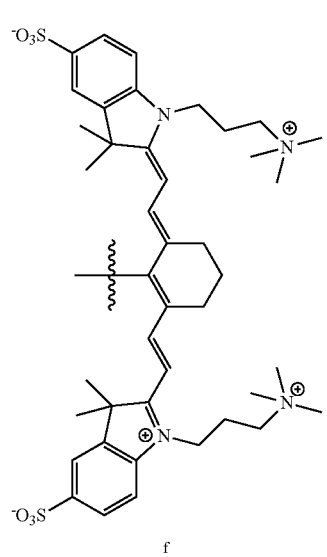

f

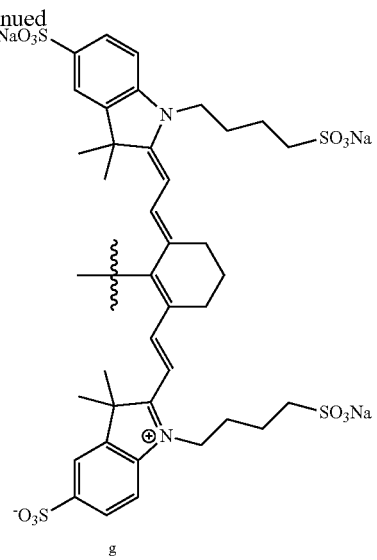

g

In view of the structure the beneficial variation was the substitution ($S_{NR1}$) at the central vinylogous cyclohexe carbon ($C(sp^2)$) by phenol moiety in NIR dyes a-c and phenyl moiety in NIR dye d also with their corresponding final folate-NIR probes. These above reasons have motivated the inventors to develop a new modified folate-NIR probe with photostable, selective, sensitive and high fluorescent intensity at physiological pH.

For solving the problem, the overall strategy was to choose S0456 as a commercially available precursor NIR fluorophore should contains four $SO_3H$ groups for solubility and rigid cyclohexenyl ring in the middle of fluorophore for photostability and vinylogous cyclohexe chloride ($C(sp^2)Cl$) to connect phenolic oxygen which will be beneficial for high sensitivity and bright fluorescence for in vivo tumor imaging. Moreover, the structural requirements for folate receptor ligands with folate binding pocket have been investigated to improve the binding affinity and selectivity of the ligands to the receptor. The crystal structure of folate receptor has not been established and there is an argument that pteroic acid, a fragment of folic acid lacking the distal glutamyl residue is good enough for binding to the high affinity folate receptor. To determine whether the -carboxylic acid in glutamyl residue is beneficial for binding with folate receptor the inventors synthesized various amino acid and non-amino acid pteroyl conjugates and its NIR probes. Next, the inventors compared all these new modified folate-NIR probes for in vitro binding affinity with folate receptor positive cancel cells and in vivo imaging with folate receptor positive KB tumor. Interestingly, the inventors did not observe much variation in binding affinity but there was a remarkable change in tumor specificity and fluorescence intensity. The study was consistent with all folate-NIR conjugates and suggested -carboxylic acid in glutamyl residue is beneficial for specific tumor targeting, uptake and the substitution of phenolic oxygen on the central vinylogous cyclohexe carbon ($C(sp^2)$) in NIR dye will be beneficial for high fluorescence intensity of the tumor tissue. Therefore, it is urgent to develop a simpler and more straightforward strategy to obtain optimal new modified folate-NIR fluorescent probe for image guided cancer surgery. The inventors designed and synthesized a sensitive, photostable and tumor selective new modified folate-NIR fluorescent probe (Pteroyl-Tyr-S0456; FIG. 6) with high fluorescence intensity for a clinical application.

In the present Example, the inventors designed a folate receptor-targeted near-infrared fluorescence probe (Pteroyl_Tyr_S0456) with strengthened fluorescence intensity and photostability. The high targeting capability for folate receptor-overexpressed tumors with bright fluorescence intensity was demonstrated. This new Pteroyl_Tyr_S0456 conjugation improved the dynamics of the probe in mice subjects and enhanced the targeting capability and sensitivity to FR overexpressed tumors. Results in this Example demonstrate that this new NIR probe possesses great potential in the diagnosis of early stage tumors.

Example 3

Comparative Analysis of OTL-0001 (FA-EDA-LS288), OTL-0002 (FA-EDA-IR800), OTL-0003 (FA-EDA-ZW800), and OTL-0004 (FA-EDA-Kodak2)

Material and Methods:

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude mice (5 weeks old, 18-20 g) were purchased from Harlan (IN) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 h light-dark cycle for the duration of the study. Mice were identified individually by ear punch. All animal procedures were approved by Purdue Animal Care and Use Committee. Animal care and studies were performed according to national and international guidelines for the humane treatment of animals.

Whole Body Imaging:

Seven-week-old female nu/nu mice were inoculated subcutaneously with KB cells ($1.0 \times 10^6$/mouse in folate free RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm$^3$ in volume, animals (2 mice/group) were intravenously injected with 10 nmol of test article (FA-EDA-LS288, FA-EDA-IR800, FA-EDA-ZW800 and FA-EDA-Kodak2) in phosphate buffered saline (100 µL). After 2 h, animals were euthanized by $CO_2$ asphyxiation. Whole body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: 830 nm; epi illumination; binning: 4 (M), FOV=12.5; f-stop=2; acquisition time=1 s.

Tissue Biodistribution:

Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:—lamp level: medium; excitation: 745 nm; emission: 830 nm; epi illumination; binning: 4 (M), FOV=12.5; f-stop=2; acquisition time=1 s.

Results:

Whole body imaging: As seen in the FIG. 7a, FA-EDA-LS288, FA-EDA-IR800, and FA-EDA-ZW800 accumulated predominantly in the folate receptor positive tumors, with no substantial fluorescence activity in the other tissues. However, FA-EDA-Kodak2 did not accumulated in the tumors. Moreover, direct comparison demonstrated that tumor fluorescence intensity FA-EDA-IR800 injected mice were brighter (higher fluorescence intensity) than the mice treated with the other folate-conjugated near IR dyes (FIG. 7b).

Conclusion:

The brightness and specificity of the conjugates listed from best to worst are as follows: FA-EDA-IR800, FA-EDA-ZW800, FA-EDA-LS288, FA-EDA-Kodak2. The conjugates containing IR800 and ZW800 showed the highest tumor-accumulated fluorescence while the conjugate containing Kodak showed very low specificity for the tumor. The low fluorescence seen in the Kodak conjugate may be due to the fact that the dye excites at 800 nm. The IVIS image system does not have a filter to excite at 800 nm, so the low fluorescence in the tumors may be due to using a poor excitation wavelength.

Example 4

Whole body Imaging and Biodistribution of Folate Receptor-Targeted Near Infrared dyes Material and Methods:

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude mice (5 weeks old, 18-20 g) were purchased from Harlan (Indianapolis, Ind.) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 h light-dark cycle for the duration of the study. Mice were identified individually by ear punch. All animal procedures were approved by Purdue Animal Care and Use Committee. Animal care and studies were performed according to national and international guidelines for the humane treatment of animals.

Whole Body Imaging:

Seven-week-old female nu/nu mice were inoculated subcutaneously with KB cells ($1.0 \times 10^6$/mouse in folate free RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm$^3$ in volume, animals (2-3 mice/group) were intravenously injected with 10 nmol of test article in phosphate buffered saline (100 µL). After 2 hours, animals were euthanized by $CO_2$ asphyxiation. Whole body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: ICG (830 nm); epi illumination; binning: 4 (M), FOV=12.5; f-stop=2; acquisition time=1 s.

Tissue Biodistribution:

Following whole body imaging, animals were dissected and selected tissues (heart, lung, liver, spleen, kidneys, stomach, small intestine, large intestine, muscle, skin, and tumor) were analyzed for fluorescence activity using IVIS imager as before. Settings for imaging:—lamp level: medium; excitation: 745 nm; emission:ICG (830 nm); epi illumination; binning: 4 (M), FOV=12.5; f-stop=2; acquisition time=1 s.

Results:

Whole Body Imaging:

As seen in the FIG. 1, FA-EDA-LS288, FA-EDA-IR800, and FA-EDA-ZW800 accumulated predominantly in the folate receptor positive tumors, with no substantial fluorescence activity in the other tissues. Moreover, direct comparison demonstrated that tumor fluorescence intensity FA-EDA-IR800 injected mice were brighter (higher) than the mice treated with the other folate-conjugated near IR dyes (FIG. 2).

Tissue Biodistribution:

Analysis of tissue biodistribution was performed on animals under the same conditions by euthanizing each mouse, removing their organs and imaging them using an IVIS imager. As seen in the FIG. 2, the highest fluorescence intensity was observed in FR-positive tumors and the kidneys. The kidney uptake was anticipated since the apical membrane of the proximal tubule of the kidney has been known to express high levels of folate receptor. Moreover, it's possible that the probes are excreted through the kidneys due to their low molecular weights and half-life (most of the folate conjugates have <30 min half-life).

Conclusion:

The brightness and specificity of the conjugates listed from best to worst are as follows: FA-EDA-IR800, FA-EDA-ZW800, FA-EDA-LS288, FA-EDA-Kodak2. The conjugates containing IR800 and ZW800 showed the highest tumor-accumulated fluorescence while the conjugate containing Kodak showed very low specificity for the tumor and low fluorescence compared to the others.

A. Materials and Methods

The results shown in the present example were obtained using specific materials and methods described herein. It is contemplated that the skilled person may be able to modify these methods, reaction conditions, and test conditions and still produce results that demonstrate the efficacy of the FR-targeted NIR dyes of the present disclosure.

a. Synthesis and Characterization of Folate-NIR Conjugates.

Synthesis and characterization of folate NIR conjugates was performed substantially as described in Example 1.

b. Relative Binding Affinity of Folate-NIR Conjugates (4) to FR.

KB cells that overexpress FR-a were seeded in 24-well (100,000 cells/well) Falcon plates and allowed to form monolayers over a period of 24 h. Spent medium in each well was replaced with 10 nM [$^3$H]-folate in the presence of increasing concentration (0.1 nM-1 µM) of the test article or folic acid in fresh medium (0.5 mL). After incubating for 1 hour at 37° C., cells were rinsed with PBS (2×0.5 mL) and 1 M trichloroacetic acid (1×0.5 mL) to remove any unbound radioactive materials. After adding 1% sodium dodecylsulfate in PBS (0.5 mL), cells were transferred into individual scintillation vials containing Ecolume scintillation cocktail (3.0 mL) and counted in a liquid scintillation analyzer. The relative binding affinities were calculated using a plot of cell bound radioactivity versus the concentration of the test article using Graph Pad Prism 4.

c. In Vivo Mouse Models of Subcutaneous Tumor Xenografts.

Five-week-old female nu/nu mice were inoculated subcutaneously with KB cells (1.0×10$^6$/mouse in RPMI medium) on their shoulders. Growth of the tumors was measured in two perpendicular directions every 2 days using a caliper (body weights were monitored on the same schedule), and the volumes of the tumors were calculated as 0.5×L×W2 (L) longest axis and W) axis perpendicular to L in millimeters). Once tumors reached between 400 and 500 mm$^3$ in volume, animals were treated with folate receptor-targeted NIR dye conjugate (10 nmol) in phosphate buffered saline (100 µL). After 2 h, animals were sacrificed by $CO_2$ asphyxiation and imaged as described below.

d. Fluorescent Imaging of Mice with FR$^+$ KB Tumor.

Animal imaging experiments were performed using a Caliper Ivis Lumina II Imaging Station with Living Image 4.0 software. Settings for imaging Alexa Fluor 647 and DyLight 680 conjugates: lamp level: high; excitation: 605; emission: Cy5.5; epi illumination; binning: (M) 4; FOV=7.5; f-stop=4; acquisition time=1 s. Settings for imaging DyLight 750 and IR800CW conjugates: lamp level: high; excitation: 745; emission: ICG; epi illumination; binning: (M) 4, FOV=12.5; f-stop=4; acquisition time=1 s.

B. Results a. Synthesis of Tumor-Targeted NIR Dyes.

Figure 10A:
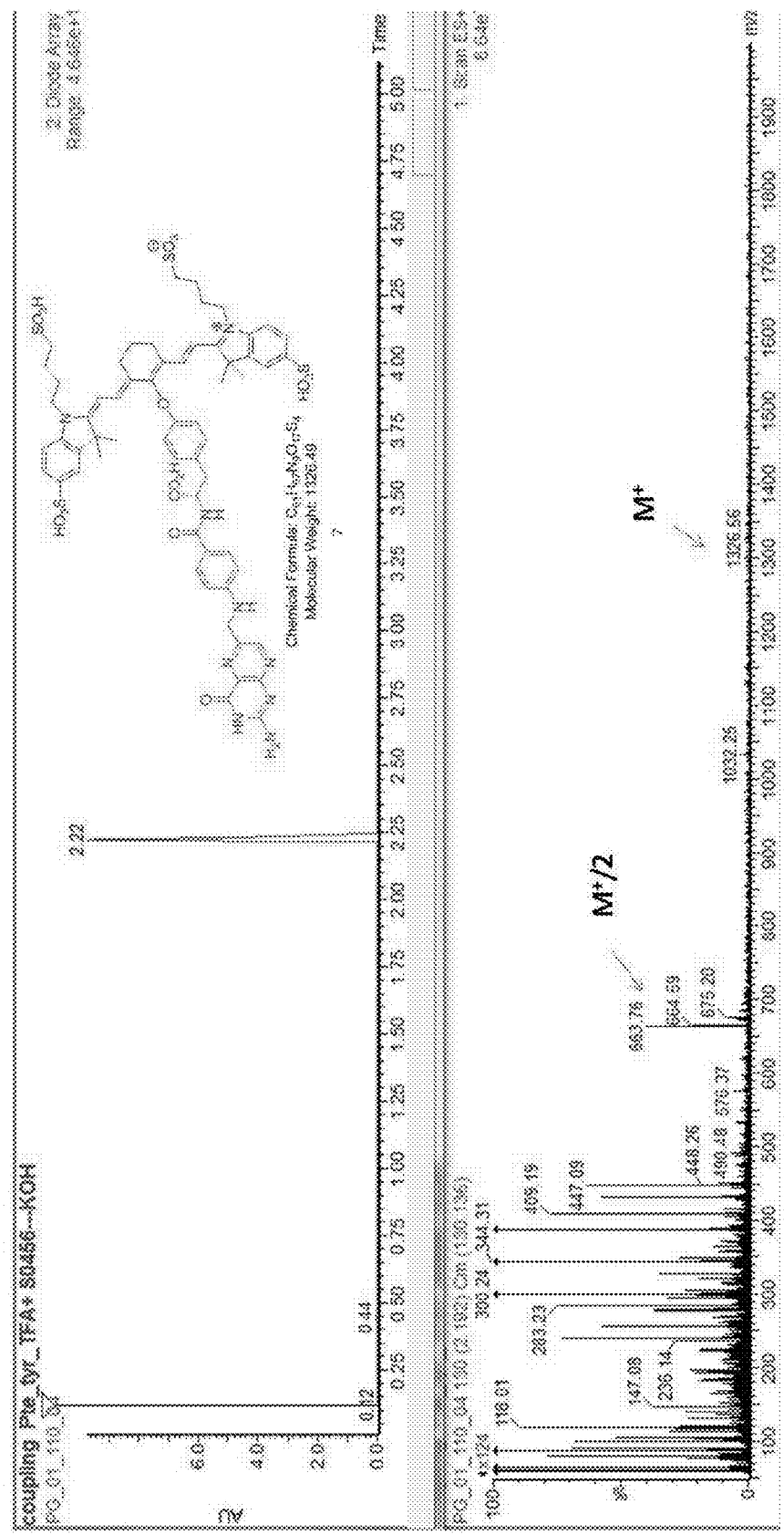
FIGS. 10A and 10B show the monitoring of reaction progress of (A) Pte-Tyr-50456 (OTL-0038) and (B) folate-EDA-IR800CW by LC/MS respectively. Pte-Tyr-S0456 gave 99% pure desired product with over 98% yield whereas folate-EDA-IR800CW furnished multiple byproducts with 30-40% of desired product.
Figure 10B:
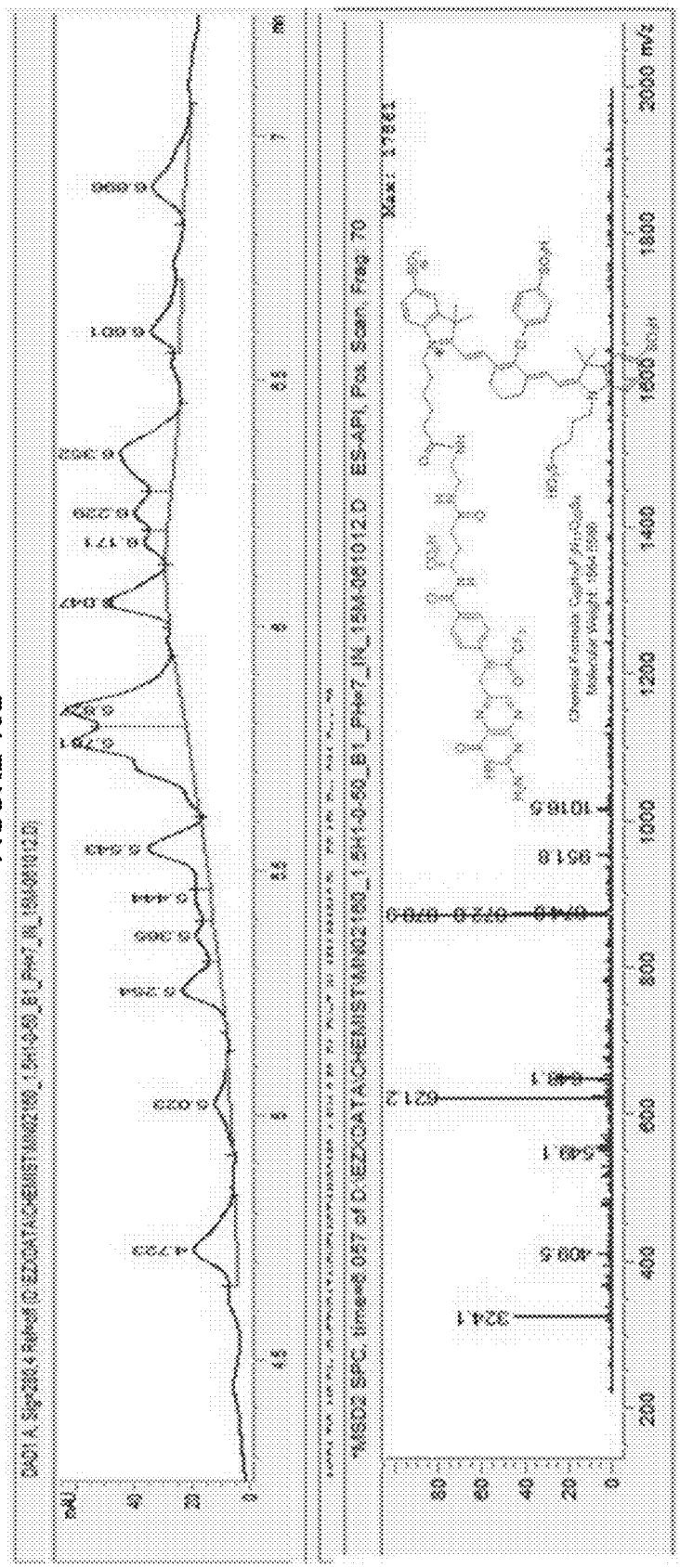

For selective tumor targeting, the inventors conjugated commercially available NIR dyes to either folate or pteroate via amide bond formation using NHS activated dye or Williamson ether synthesis reaction using chloro-derivative of NIR dye. Pte-aminoacid-NIR, especially tyrosine, were synthesized in very high yield (>98%) without any HPLC or special purification technique (by precipitation) with very high purity (>98%). The amino acids refereeing here are tyrosine and its analogues, cystine, serine, lysine, etc. The NIR dyes that we used are S0456, Kodak, S0121, and S2076 (not limited to). Synthesis of ether bridged NIR conjugates of folates such as folate-IR800CW (3) and folate-ZW800 (5), however, resulted in production of prominent side products (FIG. 10B) that needed especial purification techniques such as HPLC thereby leading to higher production cost and increasing time length for preclinical to clinic translation. This will not only effect for advancement of surgical oncology but also patients who are waiting for new therapeutic agents. Moreover, higher production cost may indirectly effect for patients and their insurance providers due to increasing cost of the drug. Importantly, Pte-Tyr-50456 reaction did not yield any undesired by product and reaction was completed within 15 min with high yield and high purity (FIG. 10A).

b. Binding Affinity and Specificity of Folate Receptor-Targeted NIR Dyes.

The affinity and specificity of folate- and pteroate-NIR conjugates were first evaluated using cancer (KB) cells that overexpressed folate receptor. The competition studies with tritiated folic acid (radiolabeled folic acid) demonstrated that folate- or pteroate-NIR conjugates not only binding to folate receptor with high affinity (low nanomolar values) but also with high specificity (FIG. 6). The competition studies with tritiated folic acid (radiolabeled folic acid) demonstrated that Pte-Tyr-S0456 binds folate receptor with high affinity and specificity suggesting that conjugation of bulky S0456 moiety via phenolic oxygen did not compromise the binding of Pte-Tyr to flote receptor.

c. Imaging of Tumor-Targeted NIR Dyes In Vivo.

In order to compare the abilities of the above folate-NIR dye conjugates to detect tumors, a xenograft model was developed that involved implantation of KB cells subcutaneously (FR expressing cells) followed by normal husbandry of the mice for 4 weeks to allow nascent tumors to grow. Tumor-bearing mice were then treated with 10 nmol of selected folate-NIR dye conjugate via tail vein injection, and mice were euthanized 2 hours later for fluorescence imaging. As seen in FIG. 7A tumor loci could be readily distinguished, yielding strong contrast between fluorescent cancer nodules and adjacent healthy tissues. Most importantly, intact fluorescent tumors were even seen in images of intact mice without opening or harvesting the tumor (FIG. 7A). Head-to-head whole body fluorescence imaging study for 2$^{nd}$ generation folate receptor targeted NIR agents indicated that folate-IR800CW (3) was competitive (in terms of fluorescent brightness) to all the other dyes (FIG. 7A, 2$^{nd}$ raw). However, unfortunately, folate-IR800CW (3) was not stable during the synthesis leading to form over 60% of undesired byproducts. As mentioned before, this will cause for finding especial purification techniques indicating path for higher production cost, higher waiting period for clinical translation, and surgeons and patients will not have access to the drug.

Figure 12A:
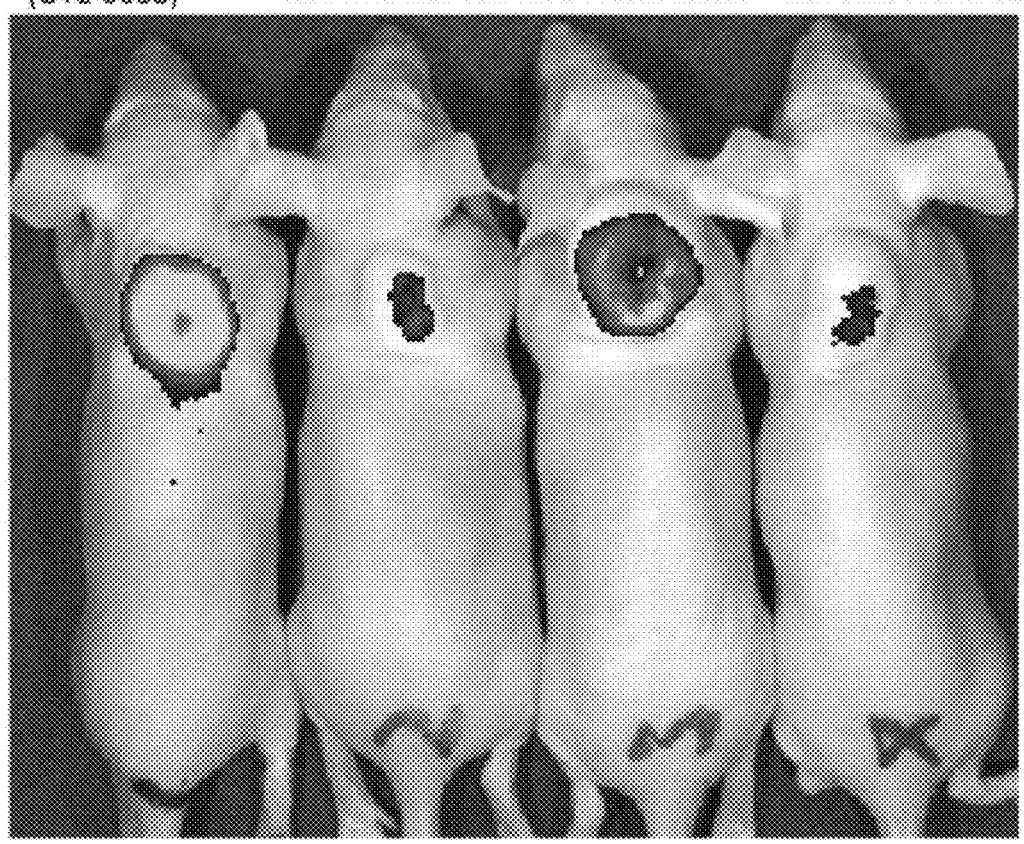
FIG. 12A shows body fluorescent images.
Figure 12B:
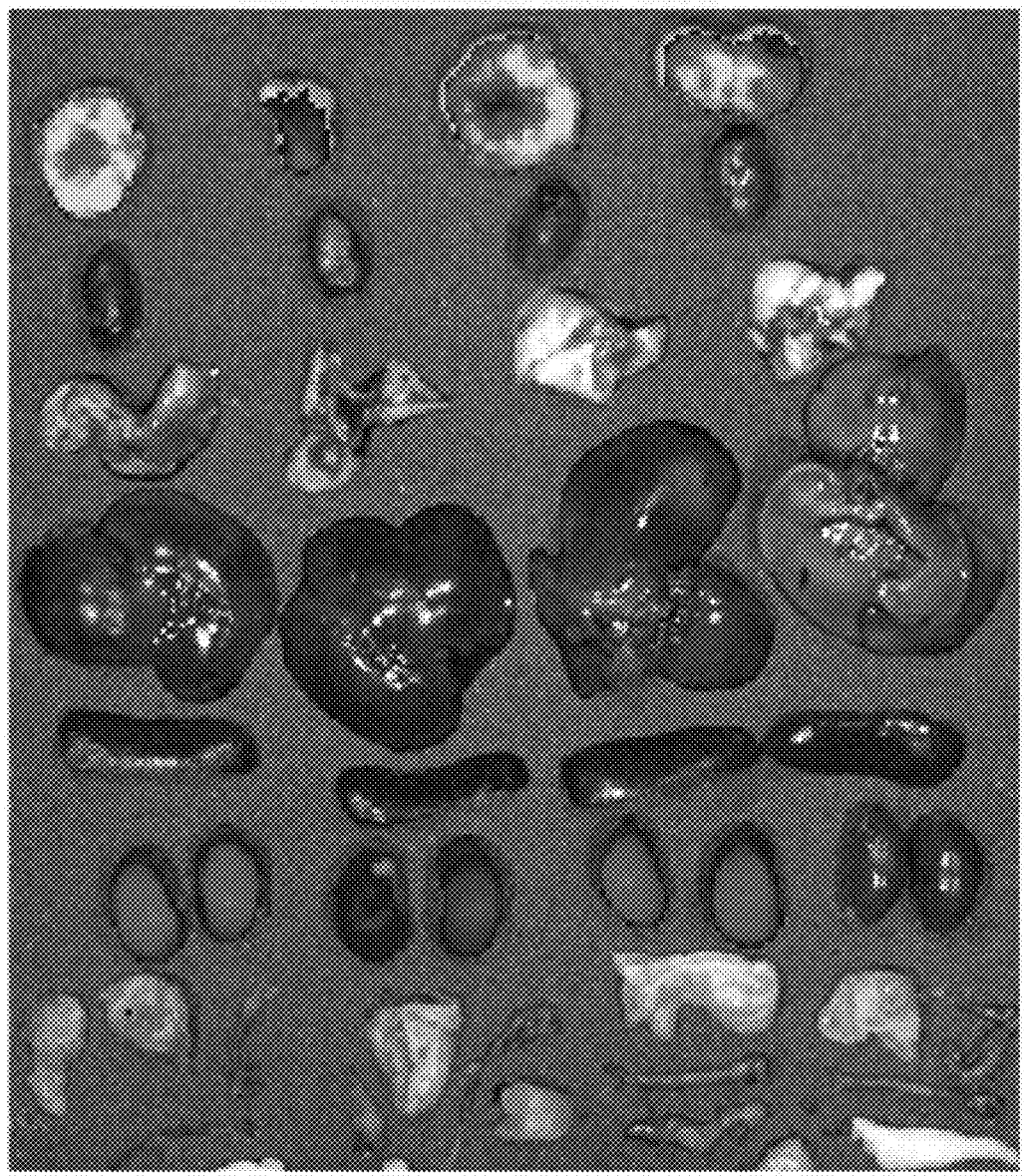
FIG. 12B shows ex vivo tissue biodistribution.
Figure 12C:
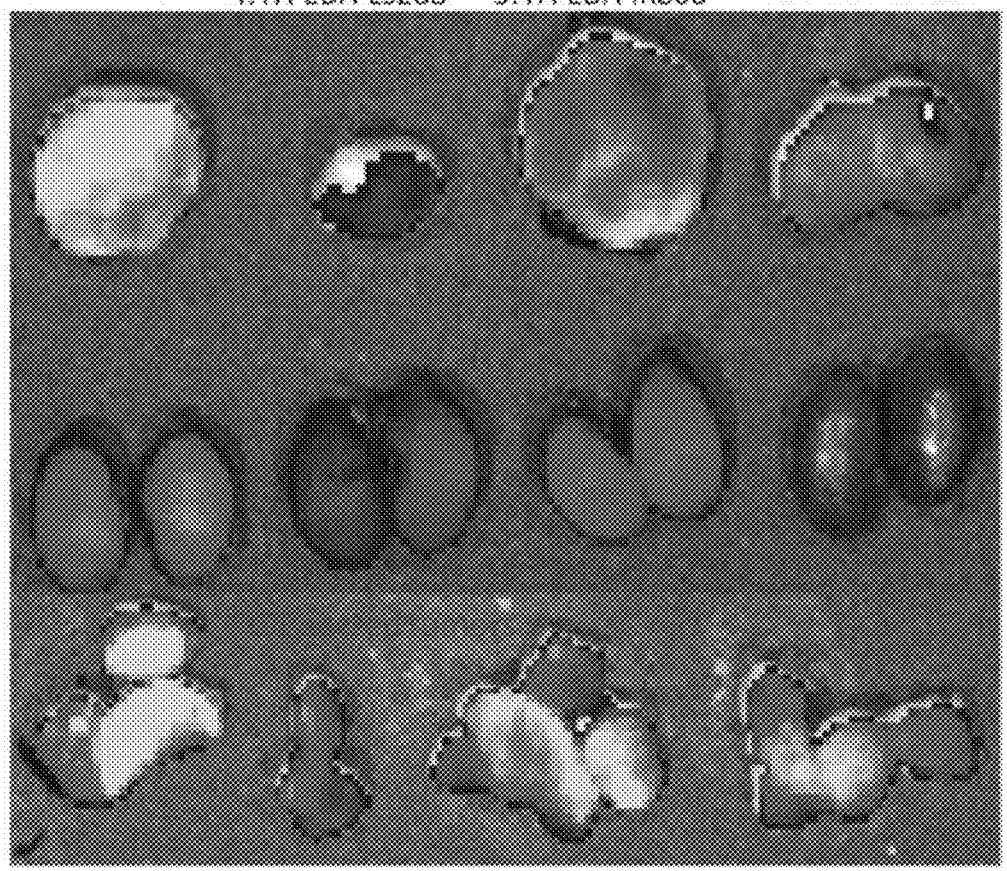
FIG. 12C shows tumor and kidney images 2 h after administering Pte-Tyr-S0456 and $2^{nd}$ generation folate-NIR conjugates (10 nmol) to nude mice. Dissected (sliced) tumors showed homogeneous uptake of the targeted imaging agents in the tumors.
Figure 13:
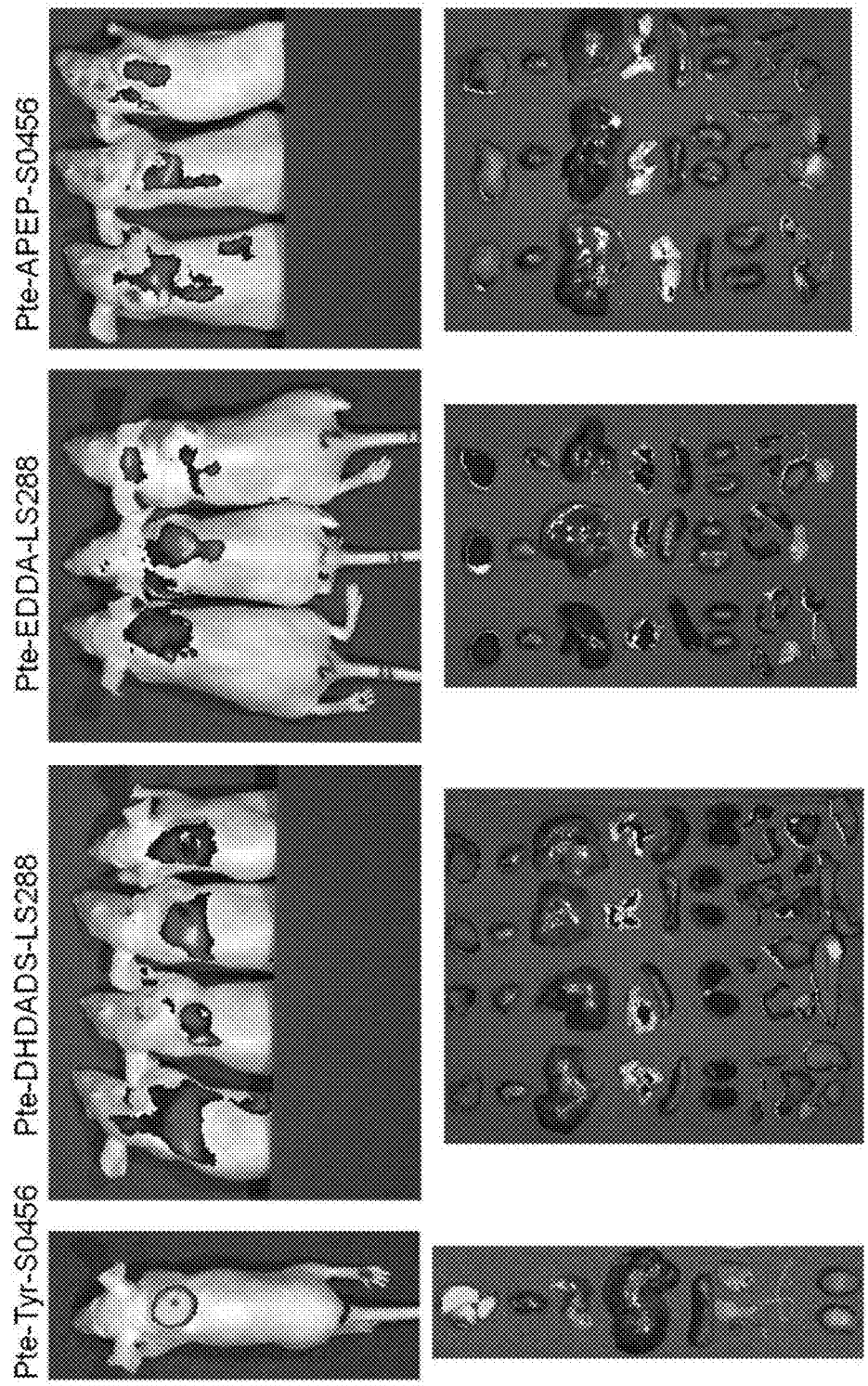
FIG. 13 shows comparisons of tumor accumulation and tumor specificity of Pte-Tyr-S0456 with other pteroyl-NIR dye conjugate after administering 10 nmol of each conjugates to mice bearing folate receptor positive tumor xenografts.

To establish the in vivo specificity, Pte-Tyr-50456 was administered to mice bearing folate receptor positive tumor xenografts on their shoulders. In vivo whole body imaging studies demonstrated that Pte-Tyr-50456 is mainly accumulated in the folate receptor positive tumors and no fluorescence was observed in other tissues (FIG. 11A). Ex vivo tissue biodistribution studies indicated that Pte-Tyr-50456 accumulated predominantly in the folate receptor positive tumors with no substantial fluorescence activity in other organs except the kidneys (FIGS. 11B, and 12 B). Significant uptake in kidneys was anticipated, since the apical membrane of the proximal tubule of the kidney has been known to express high levels of FR. Head-to-head comparison study of Pte-Tyr-50456 with folate-IR800CW, folate-LS288, and folate-ZW800 demonstrated that Pte-Tyr-50456 is competitive, in terms of fluorescent brightness, to all folate-NIR conjugates (FIGS. 12 A & B). Moreover, fluorescence imaged of sliced (dissected) tumors suggested that both Pte-Tyr-50456 and all folate-NIR conjugates were accumulated homogeneously in all tumor cells even that are buried inside the tumor (FIG. 12C).

Example 5

In Vitro Pharmacology Studies of Folate- and Pteroyl-NIR Dyes

Material and Methods:

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

KB cells that overexpress FR-α were seeded in 24-well (100,000 cells/well) Falcon plates (BD Biosciences, CA) and allowed to form monolayers over a period of 12 h. Spent medium in each well was combined with 10 nM of [$^3$H]-folic acid (tritiated folic acid) in the presence of increasing concentration (0.1 nM-1 μM) of the test article or folic acid (Sigma-Aldrich, MO) in fresh medium (0.5 mL). After incubating for 1 h at 37° C., cells were rinsed with PBS (3×0.5 mL, Gibco, NY) to remove any unbound radioactive materials. After adding 0.25 M sodium hydroxide (0.5 mL) and incubating for 12 h at 4° C., cells were transferred into individual scintillation vials containing Ecolite scintillation cocktail (3.0 mL, MP Biomedicals, OH) and counted in a liquid scintillation analyzer (Packard). The relative binding affinities were calculated using a plot of % cell bound radioactivity versus the log concentration of the test article using GraphPad Prism 4.

Results:

The dissociation constants ($K_D$) derived from the studies was calculated to be 30.7 nM, 19.3 Nm, 23.3 nM, 30.6 nM, 50.1 nM, 22.8 nM, 30.5 nM, 39.7 nM, 49.6 nM, 30.5 nM, and 8 nM for compounds OTL-001-OTL-0010 and folic acid respectively. Relative binding affinities were calculated to be 0.270, 0.430, 0.356, 0.271, 0.166, 0.364, 0.272, 0.209, 0.167, 0.272 and 1 for OTL-0001-OTL-0010 and folic acid respectively. All the test articles competed quantitatively with [$^3$H]-folic acid. Relative binding affinity is defined as the molar ratio of the compound required to displace 50% of [$^3$H]-folic acid bound to folate receptor on cells; relative affinity of folic acid=1; relative affinity <1 indicates weaker affinity for folate receptor; relative affinity >1 indicates stronger binding to folate receptor.

Conclusion:

All the compounds have a affinity for folate receptor and they compare moderately well with the binding affinity of folic acid. All the compounds competed well with [$^3$H]-folic acid indicating that folate receptor constitutes the sole binding site on cancer cells and they are highly specific for folate receptor.

Example 6

In Vitro Pharmacology Studies of OTL-0038 and OTL-0039 (D-isomer of OTL-0038)

Two ligand-NIR conjugates were developed and designated OTL-0038 and OTL-0039. OTL-0038 compound refers to PTE-L-Tyr-S0456, where pteroyl, the ligand is conjugated to L-tyrosine, which is linked to S0456. OTL-0039 is the D-isomer of OTL-0038. The binding affinity and binding specificity of both compounds for folate receptors were examined in comparison to folic acid, the conjugate ligand for folate receptors.

A. Material and Methods

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

KB cells that overexpress FR-a were seeded in 24-well (100,000 cells/well) Falcon plates (BD Biosciences, CA) and allowed to form monolayers over a period of 12 hours. Spent medium in each well was combined with 10 nM of [$^3$H]-folic acid (tritiated folic acid) in the presence of increasing concentration (0.1 nM-1 μM) of the OTL-0039 (D-isomer) and OTL-0038 (L-isomer), or folic acid (Sigma-Aldrich, MO) in fresh medium (0.5 mL). After incubating for 1 hour at 37° C., cells were rinsed with PBS (3×0.5 mL, Gibco, NY) to remove any unbound radioactive materials. After adding 0.25 M sodium hydroxide (0.5 mL) and incubating for 12 hours at 4° C., cells were transferred into individual scintillation vials containing Ecolite scintillation cocktail (3.0 mL, MP Biomedicals, OH) and counted in a liquid scintillation analyzer (Packard). The relative binding affinities were calculated using a plot of % cell bound radioactivity versus the log concentration of the test article using GraphPad Prism 4.

B. Results

The dissociation constants ($K_D$) derived from the studies was calculated to be 81.8 nM, 10.4 nM, and 7.4 nM for OTL-0039, OTL-0038, or folic acid respectively. Relative binding affinities were calculated to be 0.09, 0.71, and 1 for OTL-0039, OTL-0038, and folic acid respectively. All three test articles competed quantitatively with [$^3$H]-folic acid.

Relative binding affinity is defined as the molar ratio of the compound required to displace 50% of [$^3$H]-folic acid bound to folate receptor on cells; relative affinity of folic acid=1; relative affinity <1 indicates weaker affinity for folate receptor; relative affinity >1 indicates stronger binding to folate receptor.

C. Conclusion

OTL-0038 has affinity for folate receptor and it compares well with the binding affinity of folic acid (10.4 nM Vs 7.4 nM). On the other hand, OTL-0039 has lower affinity for folate receptor when compared to folic acid and OTL-0038. OTL-0038 competed well with [$^3$H]-folic acid indicating that folate receptor constitutes the sole OTL-0038 binding site on cancer cells and it is highly specific for folate receptor.

Example 7

Whole Body Imaging and Biodistribution of OTL-0038 and OTL-0039 (D-isomer of OTL-0038) in Mice Bearing folate Receptor—positive Tumor Xenografts The folate receptor positive tumor uptake of OTL-0038 (PTE-L-Tyr-S0456) and OTL-0039 (PTE-D-Tyr-S0456) was examined to determine how well both compounds were taken up by target receptors on tumors. The tissue biodistribution of the compounds were also examined. Both properties were examined in mice two and a half hours following intravenous administration of the compounds.

A. Material and Methods

Cell Culturing and Animal Preparation

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude (nu/nu) mice (5 weeks old, 18-20 g) were purchased from Harlan Laboratories (Indianapolis, Ind.) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 hour light-dark cycle for the duration of the study. Mice were identified individually by ear punch. All animal procedures were approved by Purdue Animal Care and Use Committee. Animal care and studies were performed according to national and international guidelines for the humane treatment of animals.
Whole Body Imaging Seven-week-old female nu/nu mice were inoculated subcutaneously with KB cells ($1.0\times10^6$/mouse in folate free RPMI1640 medium) on the shoulder. Growth of the tumors was measured in perpendicular directions every 2 days using a caliper (body weights were monitored on the same schedule), and the volumes of the tumors were calculated as $0.5\times L\times W^2$ (L=longest axis and W=axis perpendicular to L in millimeters). Once tumors reached between 400 and 500 $mm^3$ in volume, animals (5 mice/group) were intravenously injected with 10 nmol of OTL-0038 or OTL-0039 in phosphate buffered saline (100 μL). After 2.5 hours, animals were euthanized by $CO_2$ asphyxiation. Whole body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: ICG(indocyanine green); epi illumination; binning: 4 (M), FOV=12.5; f-stop=2; acquisition time=1 s.
Tissue Biodistribution Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:—lamp level: medium; excitation: 745 nm; emission: ICG; epi illumination; binning: 4 (M), FOV=12.5; f-stop=2; acquisition time=1 s.
B. Results
Whole Body Imaging As seen in the FIG. 14, OTL-0038 accumulated predominantly in the folate receptor positive tumors, with no substantial fluorescence activity in the other tissues.
Tissue Biodistribution Analysis of tissue biodistribution was performed on the same animals that were subjected to whole body imaging by euthanizing each mouse, removing their organs and imaging using IVIS imager. As seen in the FIG. 15, the highest fluorescence intensity was observed in FR-positive tumors with no accumulation in the other tissues except the kidneys. Uptake of OTL-0038 in the kidneys was anticipated, since the apical membrane of the proximal tubule of the kidney has been known to express high levels of folate receptor. Moreover, it is possible that the probes are excreted through the kidneys due to their low molecular weights and half-life (most of the folate conjugates have <30 min half-life).
C. Conclusion OTL-0038 mainly accumulated in folate receptor positive tumor xenografts and kidneys. All the other normal tissues displayed minimal levels or no uptake, resulting in excellent tumor-to-normal tissue fluorescence ratios.

Example 8

Comparative Analysis of OTL-0038 (L-Isomer) with Folate Derived Near IR Agents

The whole body imaging and tissue biodistribution of OTL-0038 was compared to folate-LS288, folate-IR800, and folate-ZW800. These compounds were conjugated to folate and commercially available near-infrared dyes, LS288, IR800, and ZW800.
A. Material and Methods
Cell Culture and Mouse Preparation KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Figures 15, 15A, 15B:
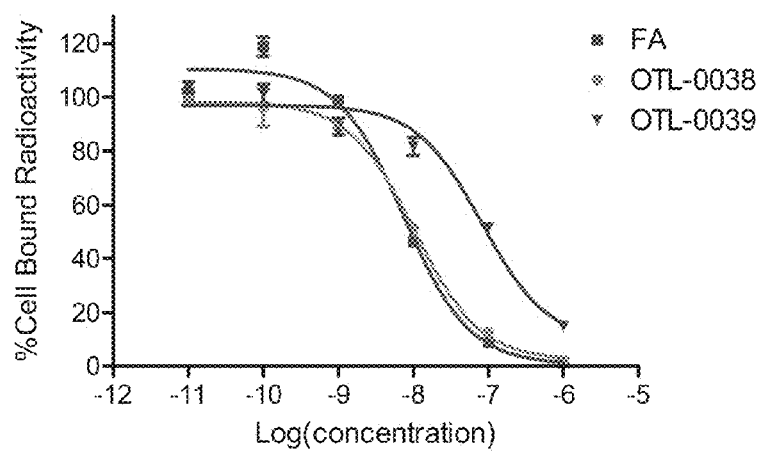
FIG. 15 depicts the relative binding affinity of OTL-0038, OTL-0039 (D-Isomer of OTL-0038), and folic acid for folate receptors.
FIG. 15A is a plot which depicts the binding curve of each compound for folate receptors.
FIG. 15B is a table illustrating the binding affinity and relative binding affinity of all three compounds.
Figure 16A:
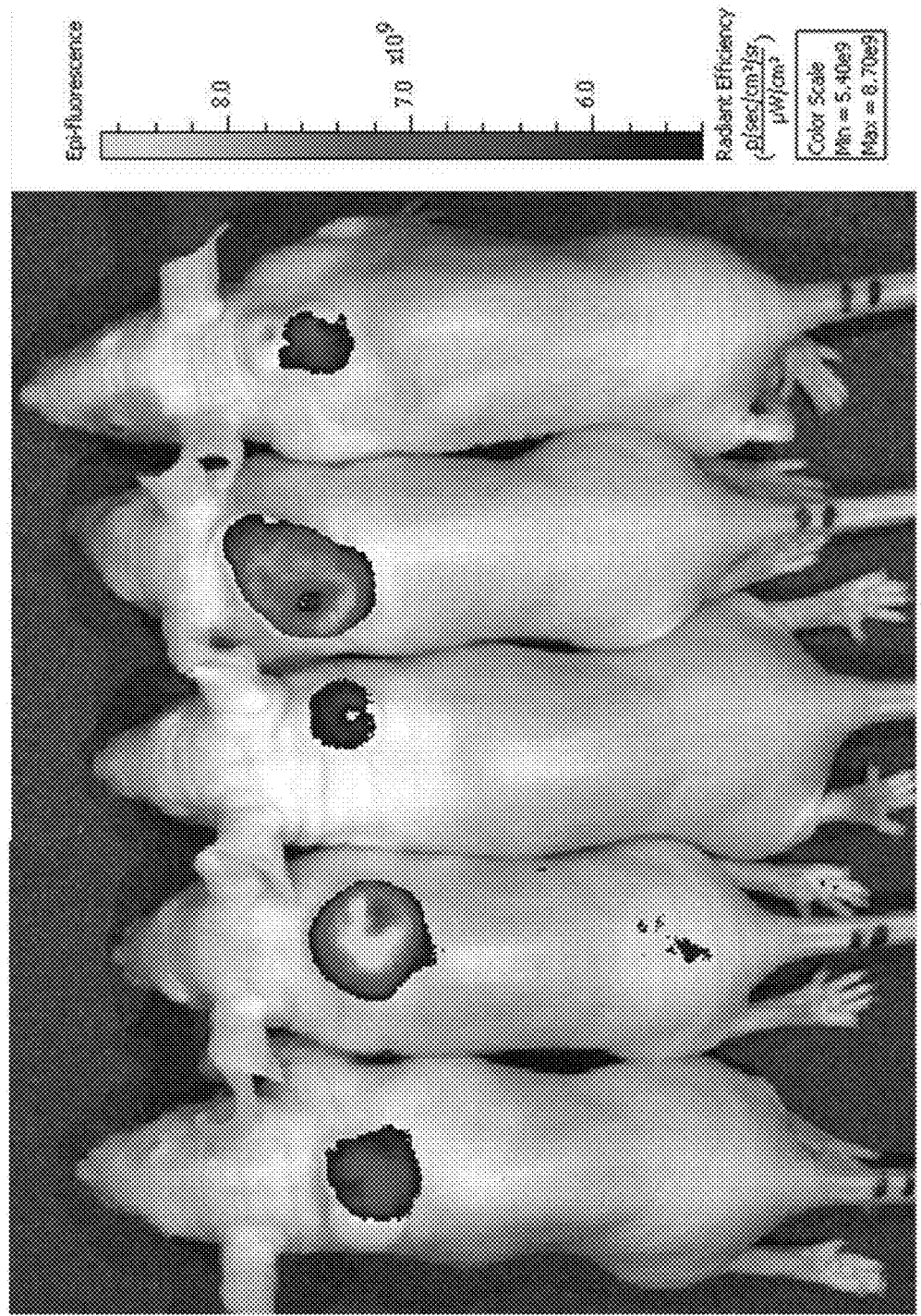
FIG. 16A depicts the whole body fluorescence image of nude mice with KB tumor xenografts injected with OTL-0039. Mice were intravenously injected with 10 nmol of OTL-0039 in phosphate buffered saline (100 µL). After 2.5 hours, animals were euthanized by $CO_2$ asphyxiation. Whole body imaging experiments were then performed using a Caliper IVIS Lumina II Imaging Station with Living Image 4.0 software.
Figure 16B:
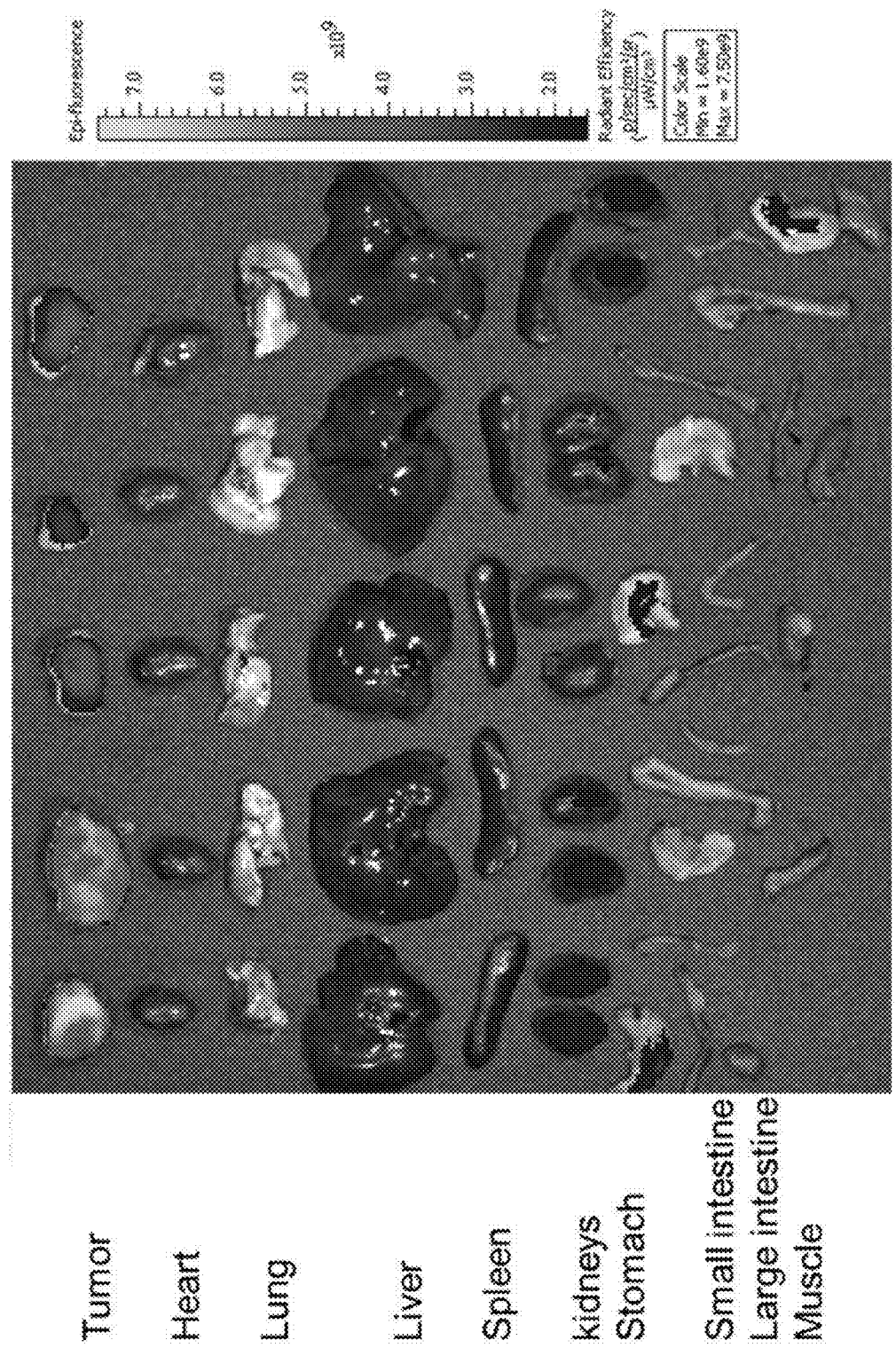
FIG. 16B illustrates tissue biodistribution of mice injected with OTL-0039 in FIG. 5A, 2.5 hours following injection of compound. Following whole body imaging animals were dissected, and select tissues (heart, lung, liver, spleen, kidneys, stomach, small intestine, large intestine, muscle, skin, and tumor) were analyzed for fluorescence activity using IVIS imager as before.
Figure 18:
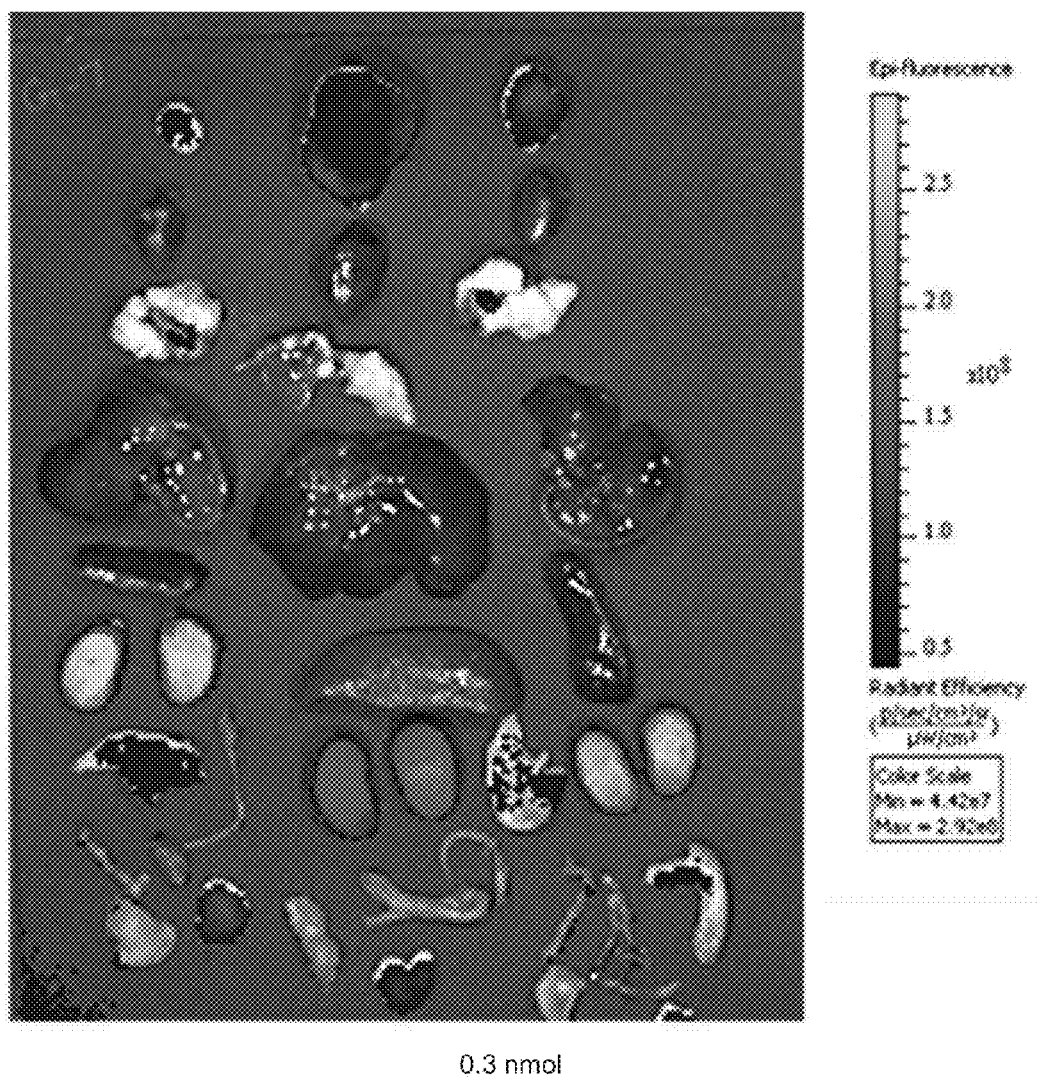
FIG. 18 illustrates the tissue biodistribution of mice injected with increasing amounts of OTL-0038. The compound concentrations ranging from 0.3-90 nmol was administered to mice intravenously. Data analysis of biodistribution was examined 2.5 hours post injection.
Figure 19:
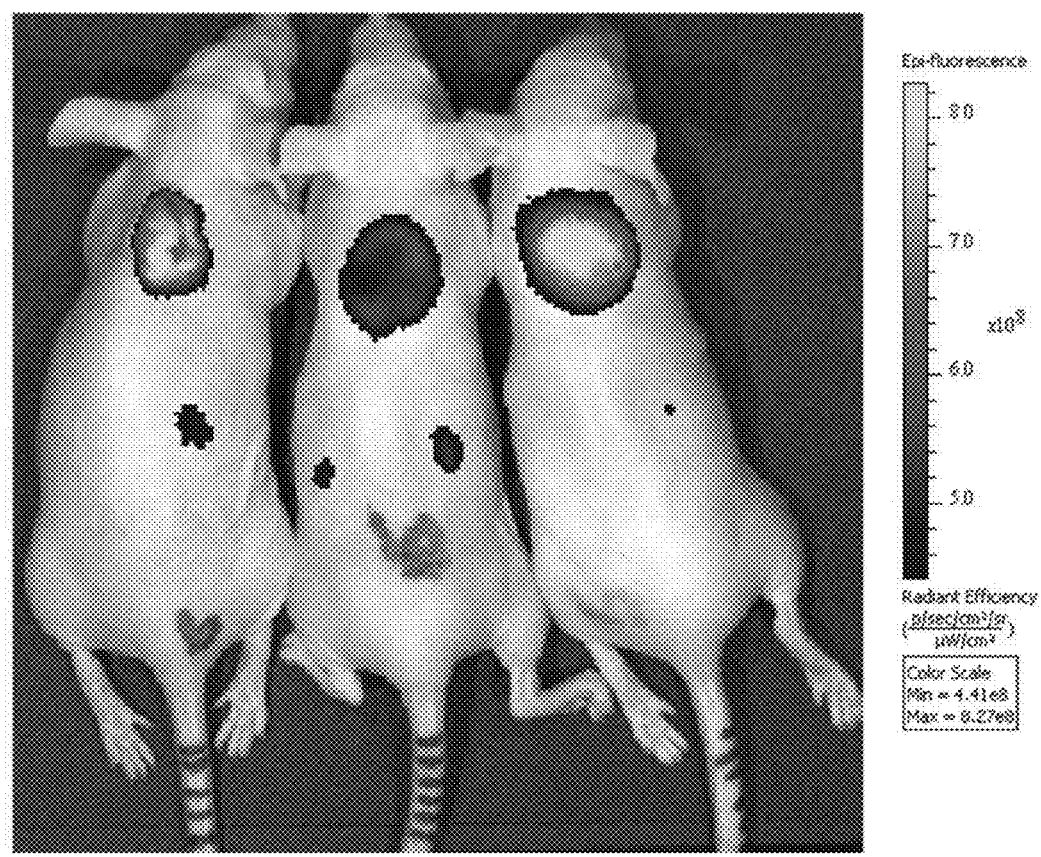
FIG. 19 illustrates the whole body fluorescence imaging of nude mice with KB tumor xenografts injected with 1 nmol of OTL-0038. This demonstrates that we need very low concentration of OTL-0038 to image tumor due to its high affinity for FR and higher brightness of the dye. After 2.5 hours, animals were euthanized by $CO_2$ asphyxiation. Whole body imaging experiments were then performed using a Caliper IVIS Lumina II Imaging Station with Living Image 4.0 software.
Figure 20A:
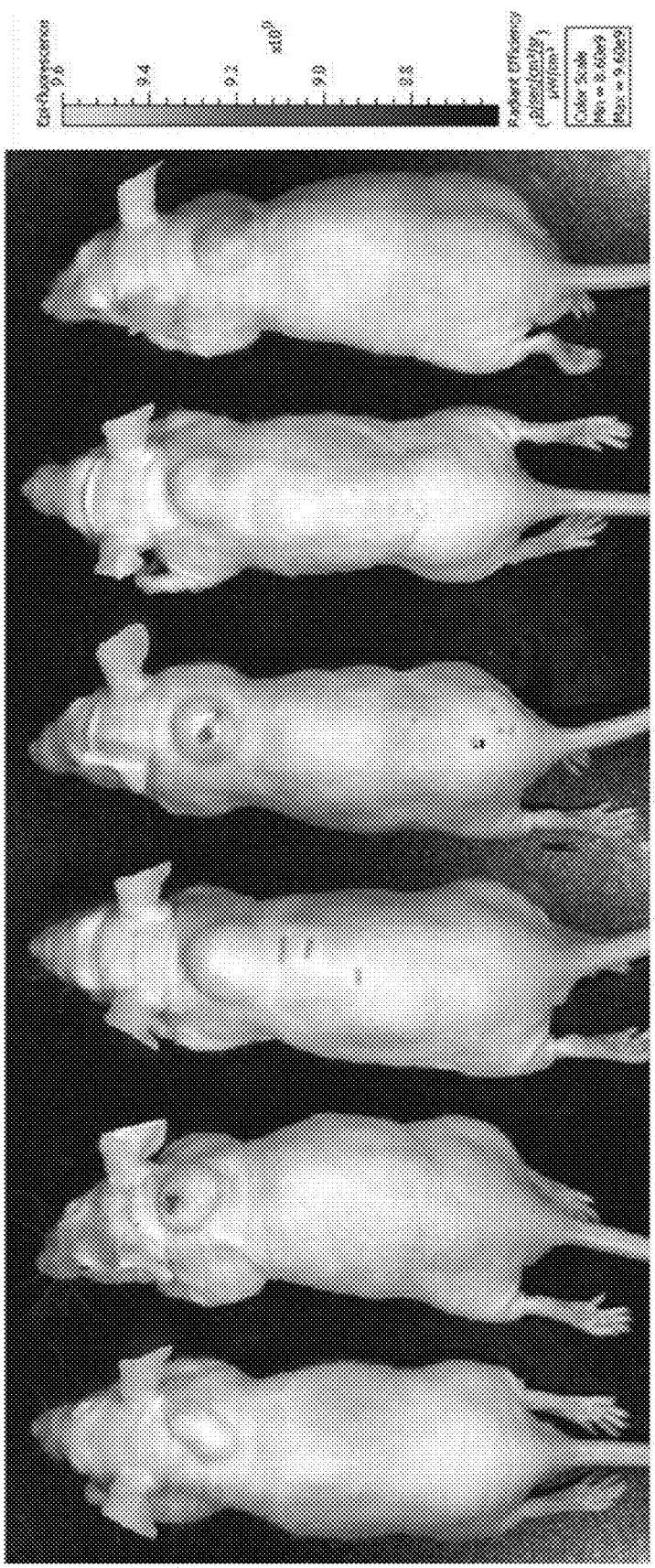
FIG. 20A depicts the whole body fluorescence image of mice bearing tumor xenografts negative for folate receptors. Whole body imaging was performed 2.5 hours after administration of 10 nmol of OTL-0038.
Figure 20B:
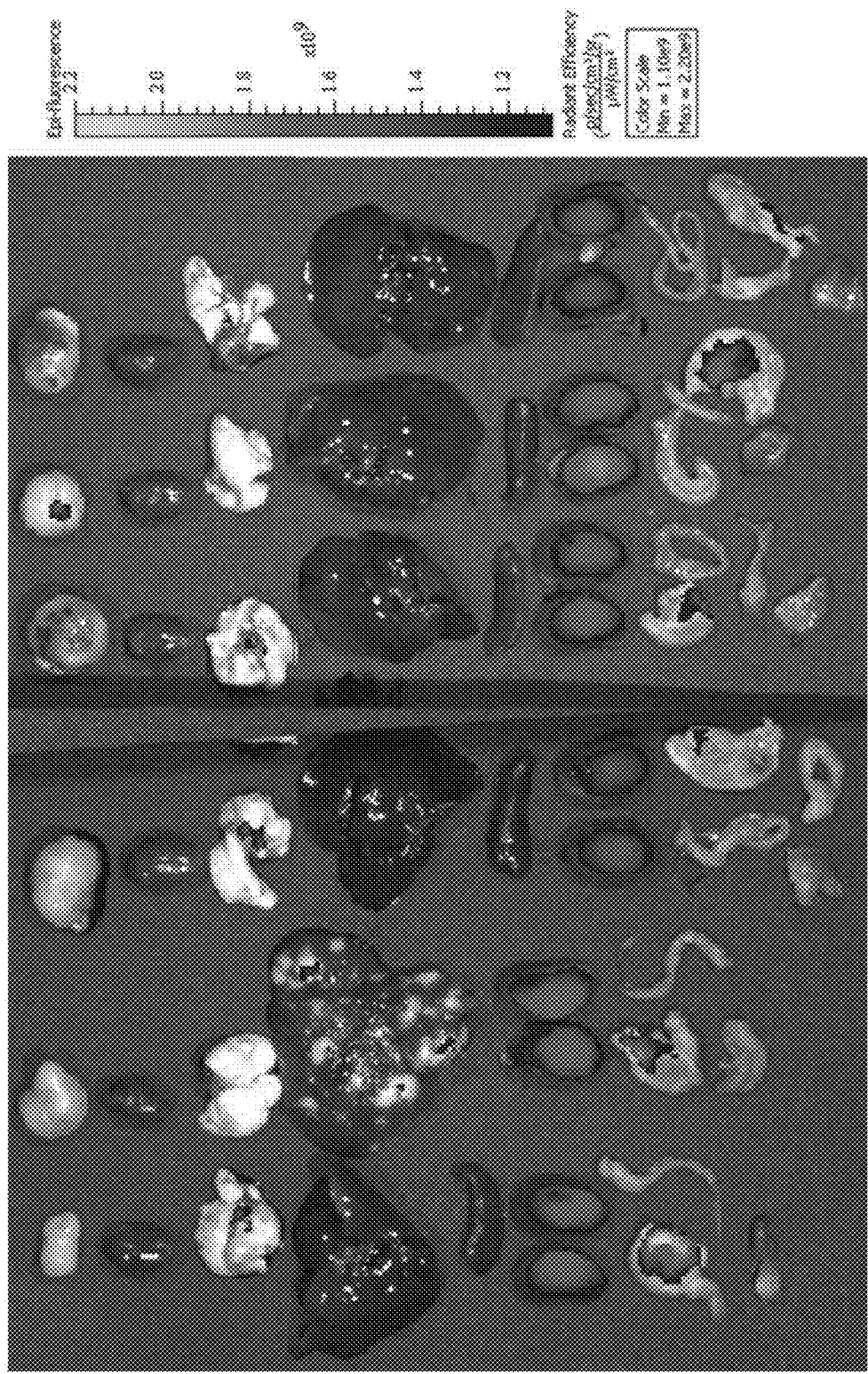
FIG. 20B illustrates invasive tumor and kidney uptake of OTL-0038, by folate receptor—negative tumor xenografts and folate receptor—positive kidneys. Data analysis was performed 2.5 hours post injection.
Figure 21:
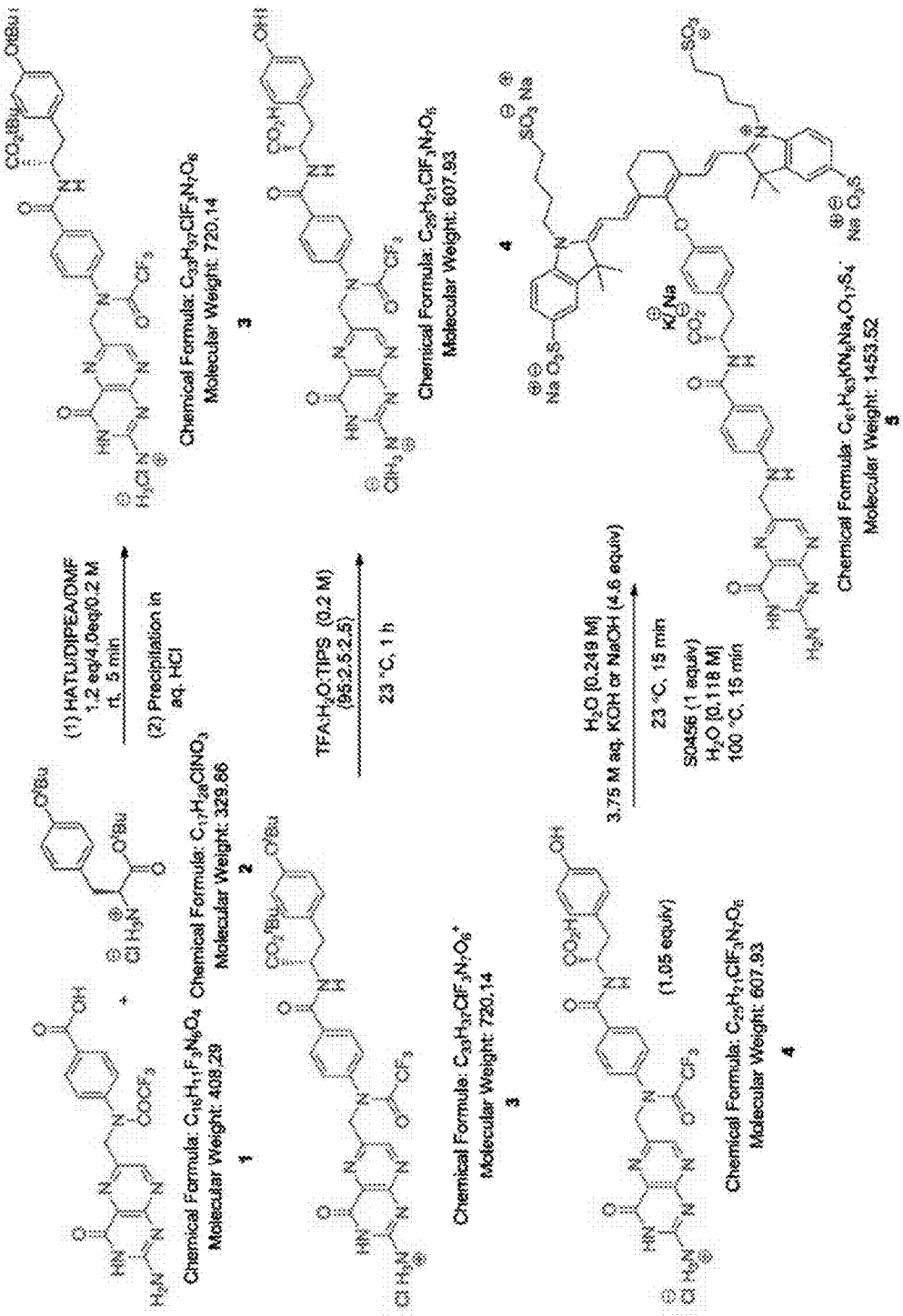
FIG. 21 depicts a three step reaction schematic for solution phase synthesis of imaging compounds.

Athymic female nude mice (5 weeks old, 18-20 g) were purchased from Harlan Laboratories (Indianapolis, Ind.) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 hour light-dark cycle for the duration of the study. Mice were identified individually by ear punch. All animal procedures were approved by Purdue Animal Care and Use Committee. Animal care and studies were performed according to national and international guidelines for the humane treatment of animals.
Whole Body Imaging Seven-week-old female nu/nu mice were inoculated subcutaneously with KB cells ($1.0\times10^6$/mouse in folate free RPMI1640 medium) on the shoulder. Growth of the tumors was measured in perpendicular directions every 2 days using a caliper (body weights were monitored on the same schedule), and the volumes of the tumors were calculated as $0.5\times L\times W^2$ (L=longest axis and W=axis perpendicular to L in millimeters). Once tumors reached between 400 and 500 $mm^3$ in volume, animals (2 mice/group) were intravenously injected with 10 nmol of test article (OTL-0038, folate-LS288, folate-IR800, folate-ZW800) in phosphate buffered saline (100 μL). After 2.5 h, animals were euthanized by $CO_2$ asphyxiation. Whole body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: ICG (indocyanine green); epi illumination; binning: 4 (M), FOV=12.5; f-stop=2; acquisition time=1 s.
Tissue Biodistribution Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:—lamp level: medium; excitation: 745 nm; emission: ICG; epi illumination; binning: 4 (M), FOV=12.5; f-stop=2; acquisition time=1 s.
B. Results
Whole Body Imaging As seen in the FIG. 14, OTL-0038 (L-isomer), folate-LS288, folate-IR800, folate-ZW800 accumulated predominantly in the folate receptor positive tumors, with no substantial fluorescence activity in the other tissues. Moreover, direct comparison demonstrated that tumor fluorescence intensity OTL-0038 injected mice were brighter (higher) than the mice treated with the other folate-conjugated near IR dyes (FIG. 15).
Tissue Biodistribution Analysis of tissue biodistribution was performed on the same animals that were subjected to whole body imaging by euthanizing each mouse, removing their organs and imaging them using an IVIS imager. As seen in the FIG. 16, the highest fluorescence intensity was observed in FR-positive tumors and the kidneys. The kidney uptake was anticipated since the apical membrane of the proximal tubule of the kidney has been known to express high levels of folate receptor. Moreover, it's possible that the probes are excreted through the kidneys due to their low molecular weights and half-life (most of the folate conjugates have <30 min half-life).
C. Conclusion OTL-0038 has beneficial aspects relative to folate-LS288, folate-IR800, and folate-ZW800 in tumor accumulated fluorescence intensity. OTL-0038 may be brighter than other commercially available near IR dyes such as LS288, IR800, and ZW800.

Example 9

Dose Escalating Studies of OTL-0038 in Mice Bearing Folate Receptor Positive Tumor Xenografts Dosage range experiments were performed to determine the lowest dose of OTL-0038 that can be administered to obtain best tumor-to-background ratio. In addition, experiments were performed to determine the highest dose of OTL-0038 that can be administered to obtain best tumor (targeted)-to-non-targeted tissue ratio.

A. Material and Methods

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude (nu/nu) mice (5 weeks old, 18-20 g) were purchased from Harlan Laboratories (Indianapolis, Ind.) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 hours light-dark cycle for the duration of the study. Mice were identified individually by ear punch. All animal procedures were approved by Purdue Animal Care and Use Committee. Animal care and studies were performed according to national and international guidelines for the humane treatment of animals.

Seven-week-old female nu/nu mice were inoculated subcutaneously with KB cells ($1.0 \times 10^6$/mouse in folate free RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm$^3$ in volume, animals (3 mice/group) were intravenously injected with increasing concentration of OTL-0038 (0.3 nmol, 1 nmol, 3 nmol, 10 nmol, 30 nmol, 60 nmol, 90 nmol) in phosphate buffered saline (100 µL). After 2.5 h, animals were euthanized by $CO_2$ asphyxiation. Tissue biodistribution studies were performed using a Caliper IVIS Lumina II Imaging Station with Living Image 4.0 software (PerkinElmer Inc, MA). Settings for imaging:—lamp level: medium; excitation: 745 nm; emission: ICG(indocyanine green); epi illumination; binning: 4 (M), FOV=12.5; f-stop=2; acquisition time=1 s.

Whole body images (intact tumor) were taken 2.5 hours after injecting 1 nmol of OTL-0038 using a Caliper IVIS Lumina II Imaging Station with Living Image 4.0 software (PerkinElmer Inc, MA). Settings for imaging:—lamp level: medium; excitation: 745 nm; emission: ICG; epi illumination; binning: 4 (M), FOV=12.5; f-stop=2; acquisition time=1 s.

B. Results

Figure 14:
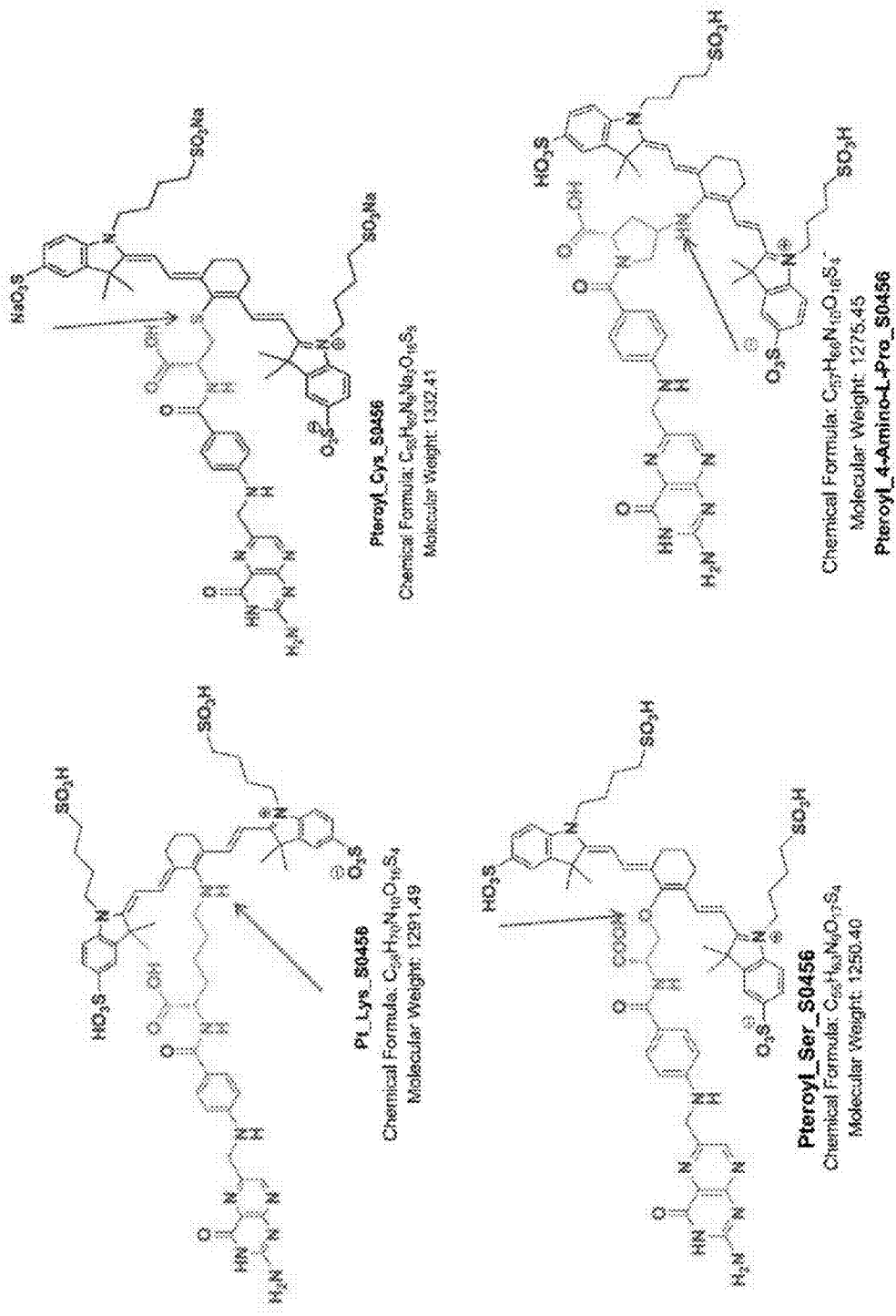
FIG. 14 depicts the structure of four compounds conjugated with an amino acid linking group including Pte-Lys-S0456, Pteroyl-Cys-S0456, Pte-Ser-S0456, and Pte-4-amino-L-Pro-S0456.

As shown in the Table 1 and FIG. 14, all the doses had higher tumor uptake in the folate receptor positive tumors except 0.3 nmol dose. On the other hand, higher kidney uptake was also observed for dose range 0.3-10 nmol and less kidney uptake (relative to tumor uptake) was observed for dose range 30-90 nmol. Moreover, higher non-specific uptake was observed at 60 and 90 nmol doses.

C. Conclusion

Figure 22:
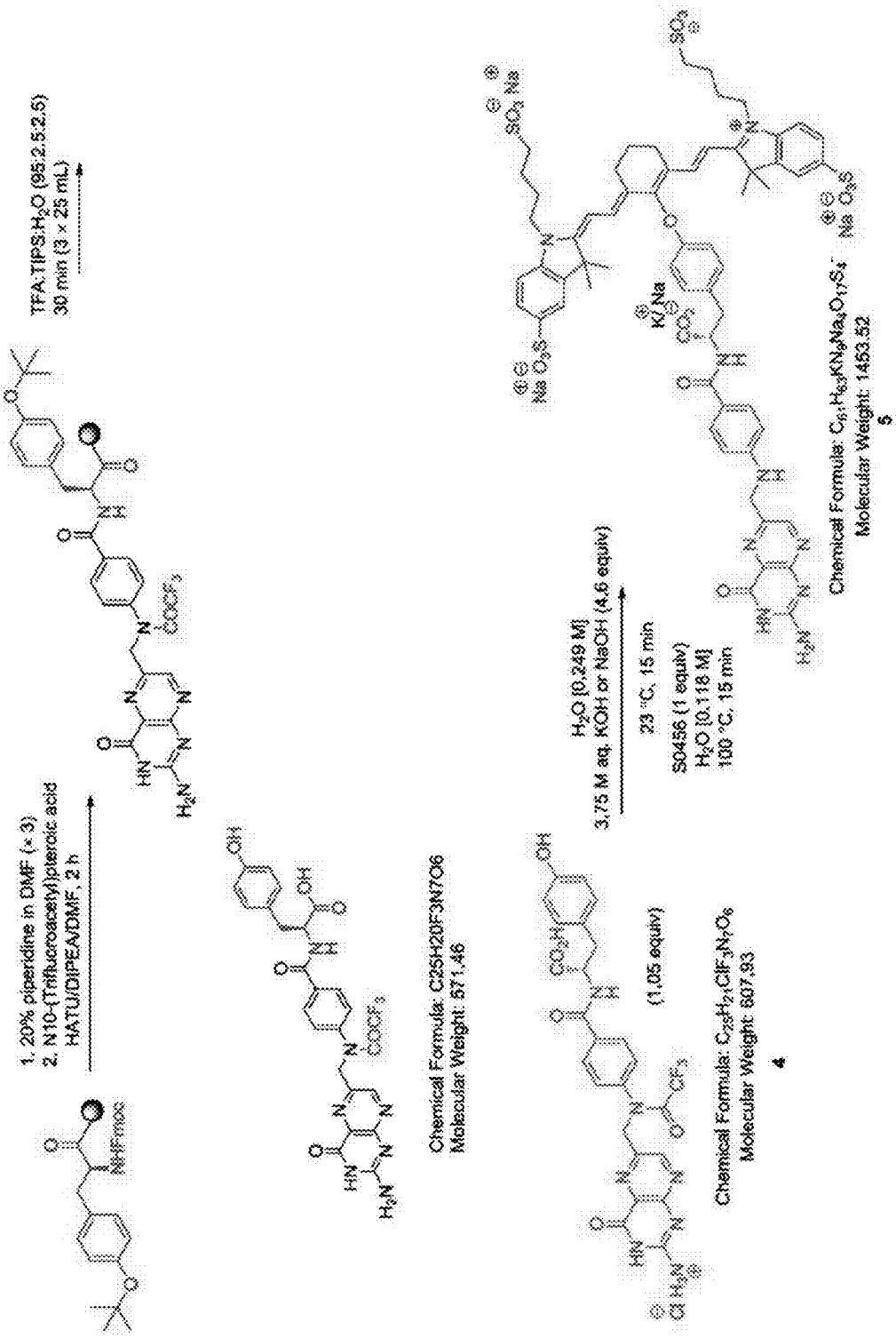
FIG. 22 depicts a two step reaction schematic for solid phase synthesis of imaging compounds.
Figure 23A:
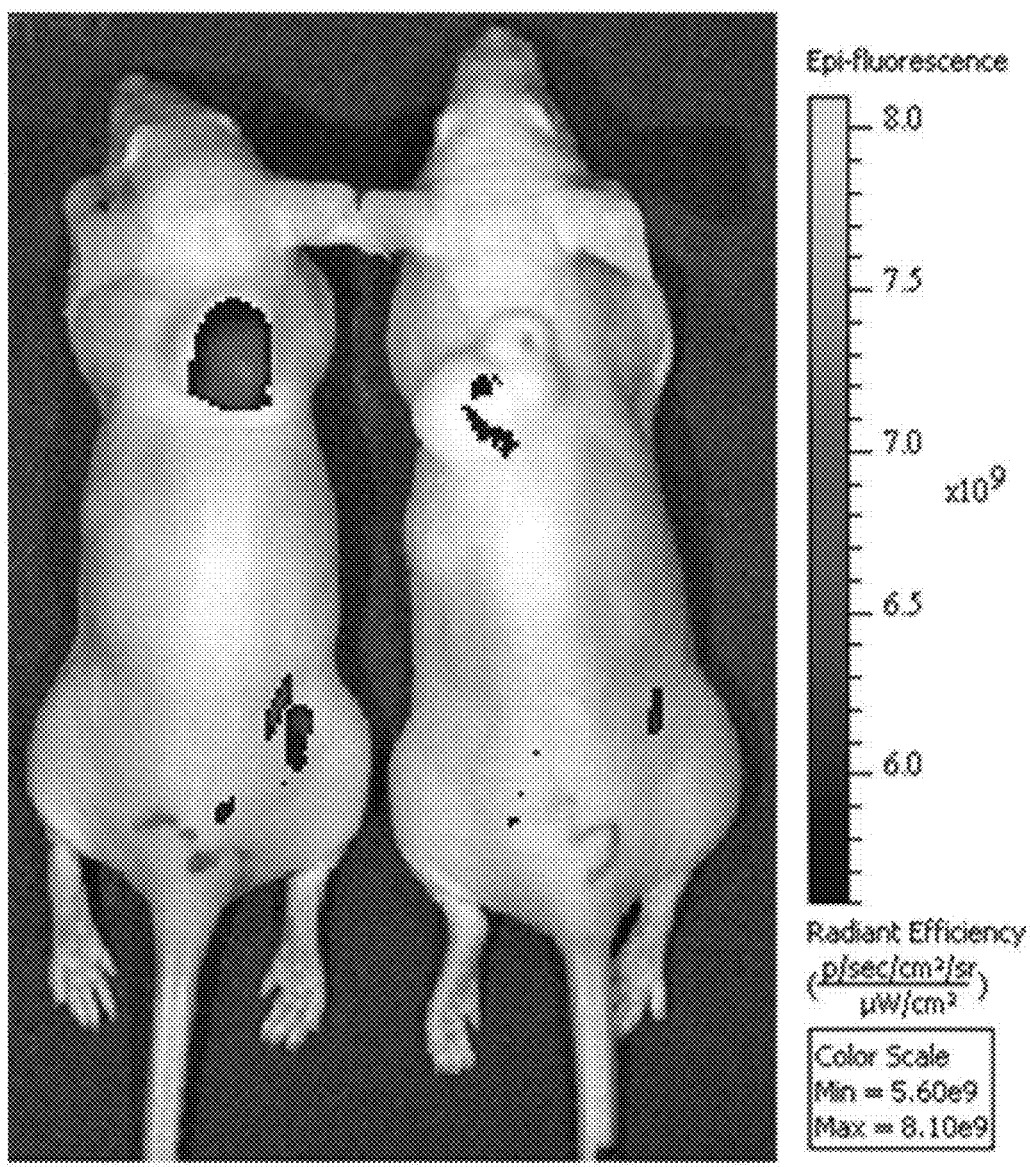
FIG. 23A presents whole-body fluorescence images of mice injected with 10 nmol of Pte-Tyrosine Analogues-S0456 2 hours post injection.
Figure 23B:
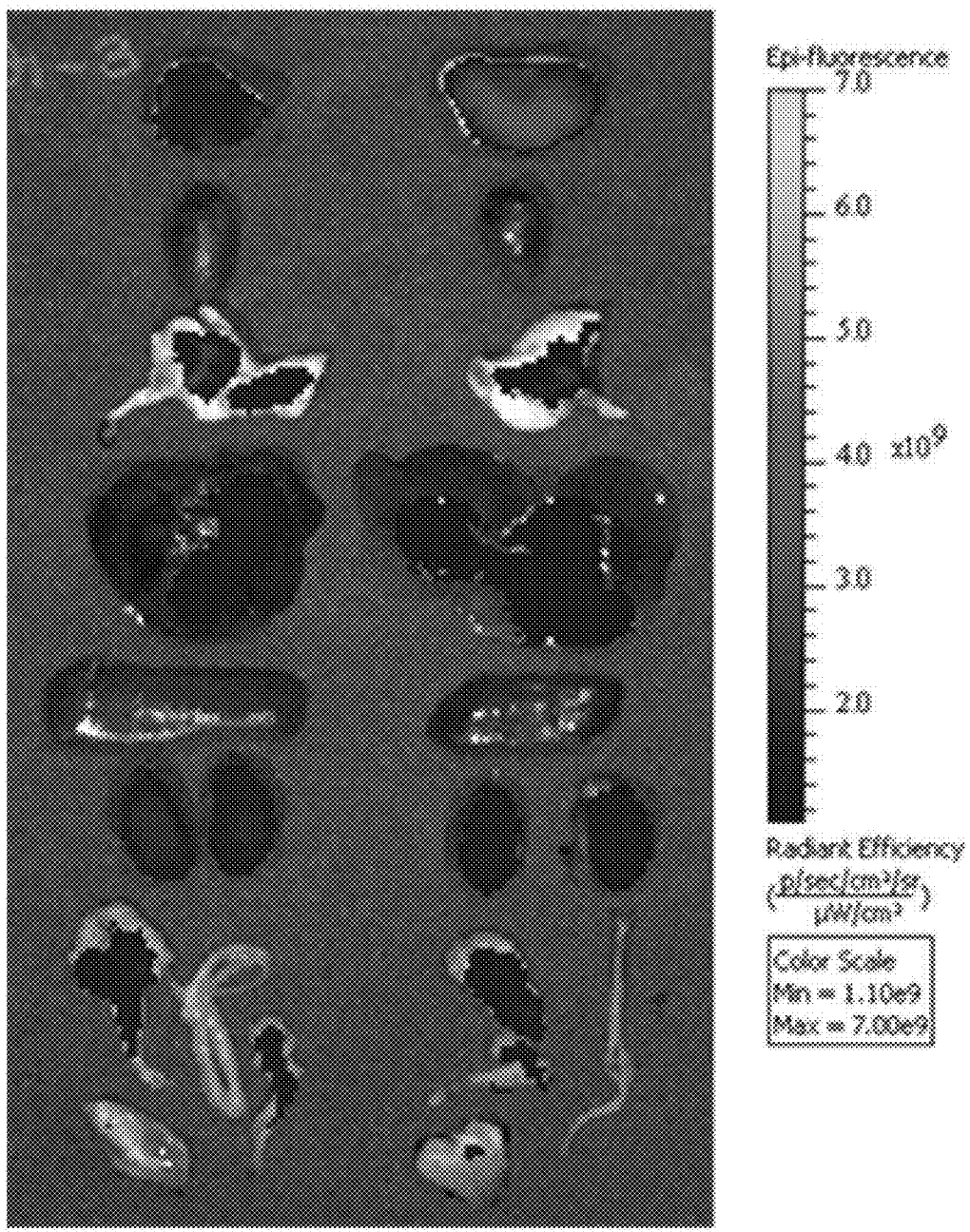
FIG. 23B presents tissue biodistribution of Pte-Tyrosine Analogues-S0456 2 hours post injection.
Figure 24:
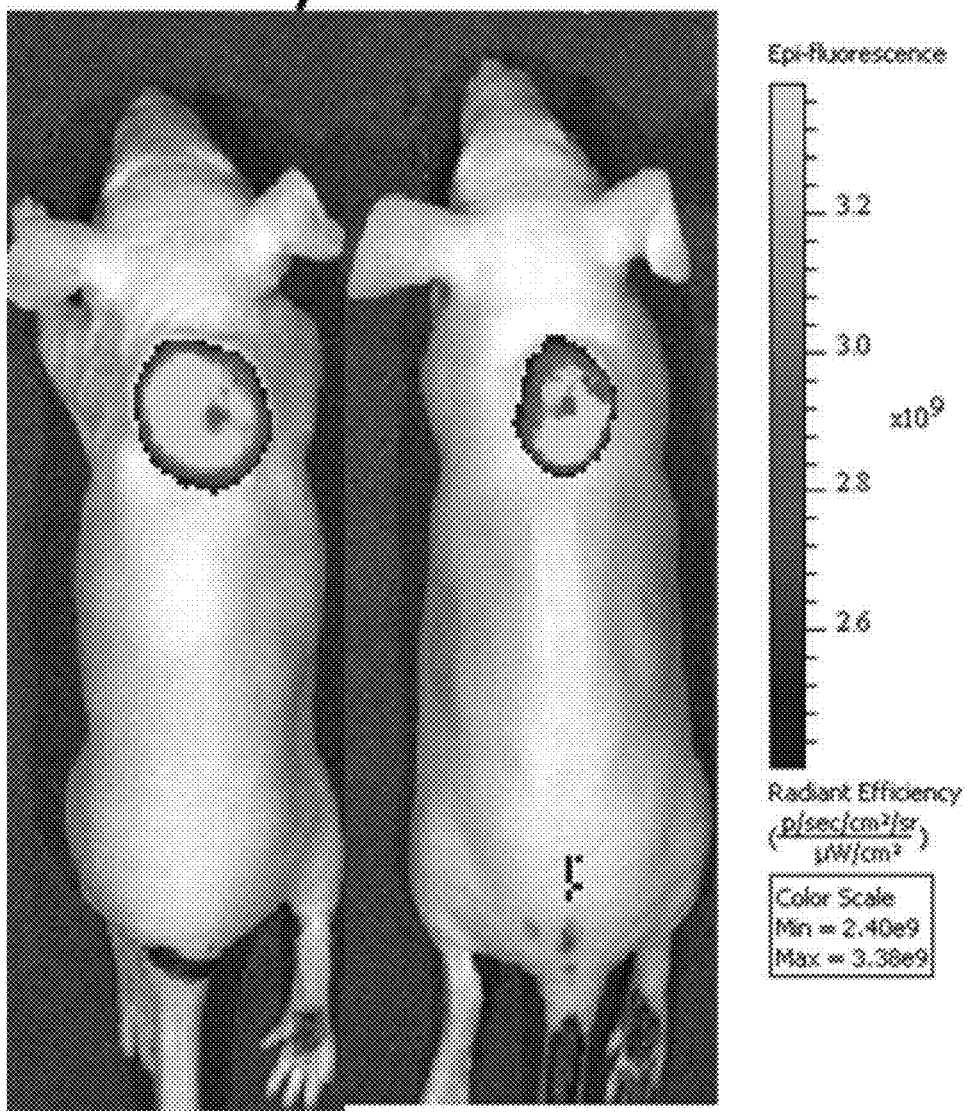
FIG. 24 demonstrates whole-body fluorescence images of mice injected with 10 nmol of OTL-0038 (Pte-Tyr-S0456), OTL-0053 (Pteroyl-Lys-S0456), and OTL-0054 (Pteroyl-Cys-S0456) 2 hours post injection. Excitation: 745 nm. Emission: 830 nm.
Figure 26:
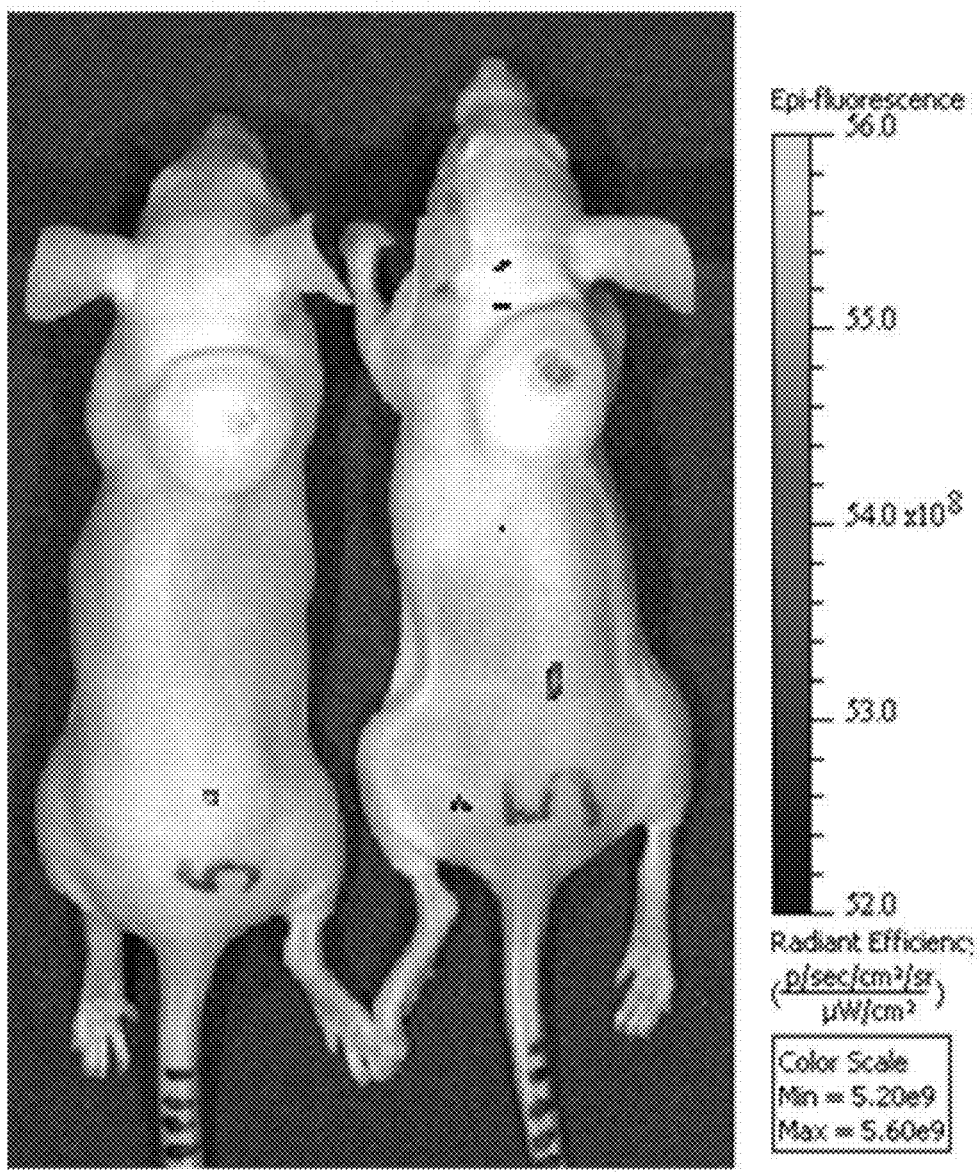
FIG. 26 depicts whole-body and half-body fluorescence images of mice injected with 10 nmol of OTL-0051 (Pteroyl-Tyr-IRD28), and OTL-0052 (Pteroyl-Tyr-Kodak) 2 hours post injection.
Figure 27:
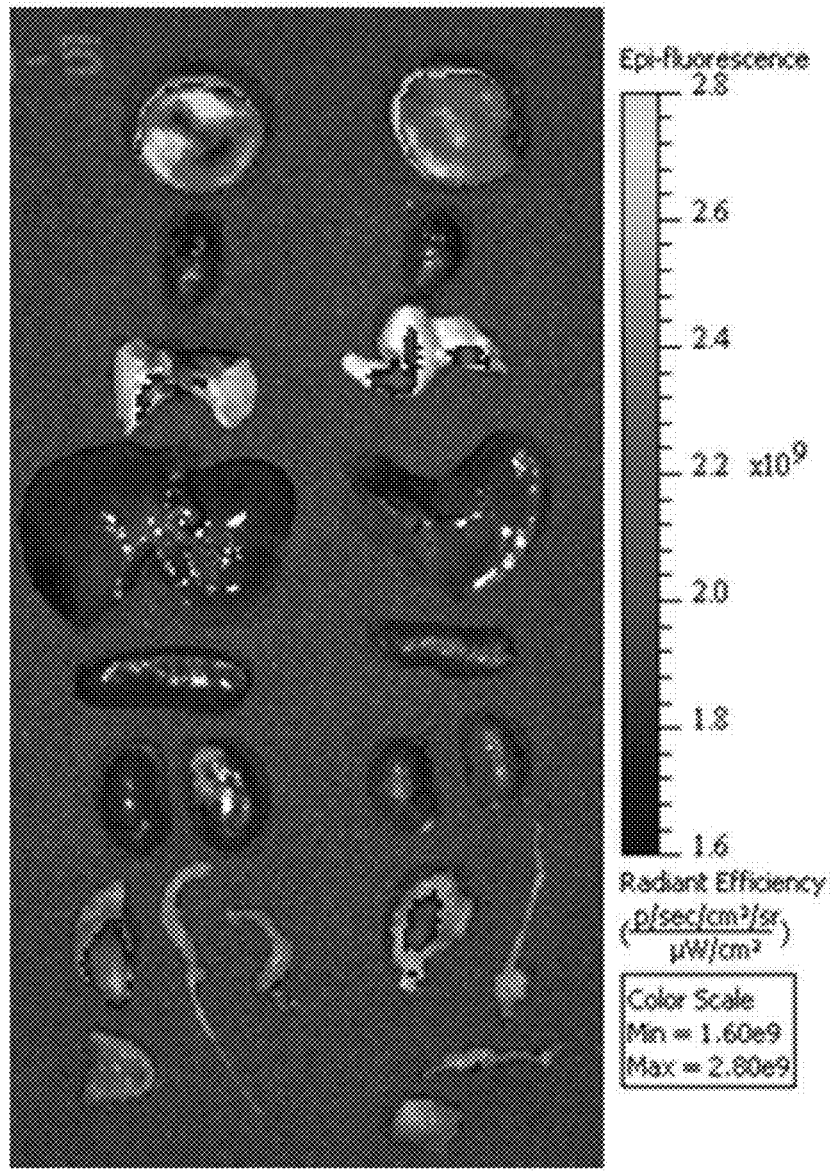
FIG. 27 depicts tissue biodistribution of OTL-0051 (Pteroyl-Tyr-IRD28), and OTL-0052 (Pteroyl-Tyr-Kodak) 2 hours post injection.

Observed lower uptake in folate receptor-positive tumors (weak fluorescence intensity) at 0.3 nmol dose may be due to incomplete saturation of folate receptors on the tumor cells. On the other hand, observed higher fluorescence intensity in the kidneys may be due to the clearance of the probe through the kidneys. Moreover, the apical membrane of the proximal tubule of the kidney has been known to express high levels of folate receptor. Dose range between 1.0-30.0 nmol showed tumor uptake and excellent tumor-to-normal tissue ratio (signal-to-background ratio). Higher kidney uptake may be due to the clearance of the probe through the kidneys (except 30 nmol dose) and expression of folate receptor on kidneys. Dose level 60.0 nmol and beyond shows higher non-specific uptake. However, these still have high tumor uptake and less kidney uptake (including 30 nmol dose). Less kidney uptake may be due to the alternative clearance of the probe through liver and gut. Therefore, OTL-0038 may be forming aggregates at this higher concentration. We can conclude that 1.0 nmol is the lowest dose to administer to obtain good tumor-to-background ratio while maintaining the non-invasive aspect for tumor imaging (FIG. 22) and 30 nmol as the highest dose to administer to obtain best tumor-to-background ratio.

Example 10

Whole Body Imaging and Biodistribution of OTL-0038 in Mice Bearing Folate Receptor—Negative Tumor Xenografts Whole body imaging and tissue biodistribution was performed to determine the in vivo specificity of OTL-0038 for folate receptors. Experiments used mice harboring a tumor that is negative for folate receptors to characterize the specificity of OTL-038 compound for folate receptors.

A. Material and Methods

Cell Culture and Mouse Preparation

A549 cells (a alveolar basal epithelial carcinoma cell line) were obtained from American type culture collection (Rockville, Md.) and grown as a monolayer using 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude (nu/nu) mice (6 weeks old, 18-20 g) were purchased from Harlan Laboratories (Indianapolis, Ind.) and maintained on normal diet (Teklad, WI). Animals were housed 5/cage in a barrier, pathogen-free cloaked rack. Autoclaved tap water and food were given as needed. The animals were housed in a sterile environment on a standard 12 hours light-dark cycle for the duration of the study. Mice were identified individually by ear punch. All animal procedures were approved by Purdue Animal Care and Use Committee. Animal care and studies were performed according to national and international guidelines for the humane treatment of animals.

Whole Body Imaging

Seven-week-old female nu/nu mice were inoculated subcutaneously with A549 cells ($1.0 \times 10^6$/mouse in RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm³ in volume, animals (6 mice/group) were intravenously injected with 10 nmol of OTL-0038 in phosphate buffered saline (100 µL). After 2.5 h, animals were sacrificed by $CO_2$ asphyxiation. Whole body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: ICG (indocyanine green); epi illumination; binning: 4 (M), FOV=12.5; f-stop=2; acquisition time=1 s.

Tissue Biodistribution

Following whole body imaging, animals were dissected and selected tissues (heart, lung, liver, spleen, kidneys, stomach, small intestine, large intestine, muscle, skin, tumor) were analyzed for fluorescence activity using IVIS imager as before. Settings for imaging:—lamp level: medium; excitation: 745 nm; emission: ICG; epi illumination; binning: 4 (M), FOV=12.5; f-stop=2; acquisition time=1 s.

B. Results

Whole Body Imaging

As seen in the FIG. 14, OTL-0038 did not accumulated in the folate receptor negative tumors and there was no substantial fluorescence activity in the other tissues except kidneys.

Invasive Tumor and Kidney Uptake

Analysis of tumor and kidney accumulation was performed on the same animals that were subjected whole body imaging by euthanizing each mouse, removing their organs and imaging using IVIS imager. As we anticipated, no fluorescence was observed in folate receptor negative tumors there was high kidney uptake. Since the apical membrane of the proximal tubule of the kidney has been known to express high levels of FR, kidney uptake is expected. Moreover, it's possible that the probes are excreted through the kidneys due to their low molecular weights and half-life (most of the folate conjugates have <30 min half-life).

C. Conclusion

OTL-0038 is highly specific for folate receptor.

Example 11

Evaluation of Toxicity OTL-0038 and OTL-0039 (D-Isomer of OTL-0038) in Healthy nude Mice The in-vivo toxicity of OTL-0038 and OTL-0039 was characterized in healthy mice. Mice were administered by 1 nmol or 1000× of the clinical dose of each compound to examine toxicity of the compounds.

A. Material and Methods

Athymic female nude (nu/nu) mice (6 weeks old, 18-20 g) were purchased from Harlan Laboratories (Indianapolis, Ind.) and maintained on normal diet (Teklad, WI). Animals were housed 5/cage in a barrier, pathogen-free cloaked rack. Autoclaved tap water and food were given as needed. The animals were housed in a sterile environment on a standard 12 hours light-dark cycle for the duration of the study. Mice were identified individually by ear punch. All animal procedures were approved by Purdue Animal Care and Use Committee. Animal care and studies were performed according to national and international guidelines for the humane treatment of animals.

Seven-week-old healthy female nude mice (5 mice/group) were administered with 1 µmol of freshly prepared OTL-0038 or OTL-0039 dissolved in 100 µL of phosphate buffered saline via tail vein injection on day zero. Body weights and clinical observations were monitored prior to dosing and daily thereafter from day zero to 7. Any animals with a body weight loss of 20% or more over two consecutive days would be euthanized, but this was not necessary. The animals were euthanized by $CO_2$ asphyxiation on day 7 and selected tissues (brain, heart, lung, liver, spleen, kidney, stomach, small intestine, large intestine, muscle, skin) were collected into vials containing 4% formalin. Formalin fixed tissues were sectioned into 10 µm thick sections and mounted onto Superfrost Plus™ slides (Fisher Scientific, Pittsburgh Pa.). After staining the slides with H&E, immunohistochemistry (1HC) analysis of the tissues was conducted to determine to the toxicity of OTL-0038 and OTL-0039.

B. Results

Immediately after the injection of OTL-0038 or OTL-0039, the skin of the animals became green. However, the green color disappeared within 24 hours. The animals were active after administration of the test articles and behaved normally throughout the study. As seen in FIG. 14, the body weights over the course of the study remained stable. According to IHC data (FIG. 15), there were no lesions identified in any tissues.

C. Conclusion

1 µmol (1000× clinical dose) of OTL-0038 or OTL-0039 is not toxic to animals suggesting that OTL-0038 (1 nmol) and OTL-0039 (1 nmol) will not be toxic to human in the clinic.

Example 12

In Vitro Pharmacological Studies of Pte-Tyrosine Analogues-S0456 (Modified OTL-0038 Analogues)

Test Articles: OTL-0040 (Pte-Tyr-$^{13}$C—S0456), OTL-0042 (Pte-Tyr-$^{2}$H(Deuterated)-S0456), OTL-0043 [Pte-Tyr-(OBn)-S0456], OTL-0044 [Pte-N(Me)-Tyr-S0456], OTL-0045 [Pte-NHNH-Tyr-(OAc)—S0456], OTL-0046 (Pte-homo-Tyr-S0456), OTL-0047 (Pte-β-homo-Tyr-S0456), OTL-0049 (Pte-Tyramine-S0456)

Material and Methods:

KB cells (a human nasopharyngeal cell line) were obtained from American type culture collection (Rockville, Md.) and grown as a monolayer using folate-free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

KB cells that overexpress FR-a were seeded in 24-well (100,000 cells/well) Falcon plates (BD Biosciences, CA) and allowed to form monolayers over a period of 12 h. Spent medium in each well was combined with 10 nM of [$^{3}$H]-folic acid (tritiated folic acid) in the presence of increasing concentration (0.1 nM-1 µM) of the test article or folic acid (Sigma-Aldrich, MO) in fresh medium (0.5 mL). After incubating for 1 h at 37° C., cells were rinsed with PBS (3×0.5 mL, Gibco, NY) to remove any unbound radioactive materials. After adding 0.25 M sodium hydroxide (0.5 mL) and incubating for 12 h at 4° C., cells were transferred into individual scintillation vials containing Ecolite scintillation cocktail (3.0 mL, MP Biomedicals, OH) and counted in a liquid scintillation analyzer (Packard). The relative binding affinities were calculated using a plot of % cell bound radioactivity versus the log concentration of the test article using GraphPad Prism 4.

Results:

The dissociation constants ($K_D$) derived from the studies was calculated to be 27.6 nM, 61.7 nM, 14.8 nM, 13.8 nM, 12.8 nM, 30.2 and 8 nM for compounds OTL-0040, OTL-0042-OTL-0047, OTL-0049 and folic acid respectively.

Relative binding affinities were calculated to be 0.290, 0.130, 0.177, 0.580, 0.625, 0.265 and 1 for OTL-0040, OTL-0042-OTL-0047, OTL-0049 and folic acid respectively. All the test articles competed quantitatively with [$^3$H]-folic acid.

Conclusion:

All the compounds have an affinity for folate receptor except OTL-0044 and OTL-0045 and they compare moderately well with the binding affinity of folic acid. All the compounds competed well with [$^3$H]-folic acid indicating that folate receptor constitutes the sole binding site on cancer cells and they are highly specific for folate receptor.

Example 13

Whole-Body Imaging and Biodistribution of Pte-Tyrosine Analogues-S0456

Test Articles: OTL-0043 [Pte-Tyr-(OBn)-S0456], OTL-0044 [Pte-N(Me)-Tyr-S0456], OTL-0045 [Pte-NHNH-Tyr-(OAc)—S0456], OTL-0046 (Pte-homo-Tyr-S0456), OTL-0047 (Pte-β-homo-Tyr-S0456), OTL-0049 (Pte-Tyramine-S0456)

Material and Methods:

KB cells (a human nasopharyngeal cell line) were obtained from American type culture collection (Rockville, Md.) and grown as a monolayer using folate-free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude mice (5 weeks old, 18-20 g) were purchased from Harlan (IN) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 h light-dark cycle for the duration of the study. Mice were identified individually by ear punch. All animal procedures were approved by Purdue Animal Care and Use Committee. Animal care and studies were performed according to national and international guidelines for the humane treatment of animals.

Whole-Body Imaging:

Seven-week-old female nu/nu mice were inoculated subcutaneously with KB cells (1.0×10$^6$/mouse in folate-free RPMI1640 medium) on the shoulder. Growth of the tumors was measured in perpendicular directions every 2 days using a caliper (body weights were monitored on the same schedule), and the volumes of the tumors were calculated as 0.5× L×W$^2$ (L=longest axis and W=axis perpendicular to L in millimeters). Once tumors reached between 400 and 500 mm$^3$ in volume, animals (2-3 mice/group) were intravenously injected with 10 nmol of test article in phosphate buffered saline (100 µL). After 2 hours, animals were euthanized by CO$_2$ asphyxiation. Whole-body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: ICG (830 nm); epi illumination; binning: 4 (M), FOV=12.5; f-stop=2; acquisition time=1 s.

Tissue Biodistribution:

Following whole-body imaging, animals were dissected and selected tissues (heart, lung, liver, spleen, kidneys, stomach, small intestine, large intestine, muscle, skin, and tumor) were analyzed for fluorescence activity using IVIS imager as before. Settings for imaging:—lamp level: medium; excitation: 745 nm; emission:ICG (830 nm); epi illumination; binning: 4 (M), FOV=12.5; f-stop=2; acquisition time=1 s.

Results:

Whole-Body Imaging:

As seen in the FIG. 28A, OTL-0044, OTL-0046, and OTL-0047 accumulated predominantly in the folate receptor-positive tumors, with no substantial fluorescence activity in the other tissues.

Tissue Biodistribution:

Analysis of tissue biodistribution was performed on animals under the same conditions by euthanizing each mouse, removing their organs and imaging them using an IVIS imager. As seen in the FIG. 28B, the highest fluorescence intensity was observed in FR-positive tumors and the kidneys. The kidney uptake was anticipated since the apical membrane of the proximal tubule of the kidney has been known to express high levels of folate receptor. Moreover, it's possible that the probes are excreted through the kidneys due to their low molecular weights and half-life (most of the folate conjugates have <30 min half-life).

Conclusion:

While in vivo biodistribution demonstrated all the compounds accumulated in the tumors and kidneys, whole-body distribution demonstrated that OTL-0044, OTL-0046, and OTL-0047 mainly accumulated in the tumors indicating a requirement of alpha carboxylic acid for specificity and affinity.

Example 14

In Vitro Pharmacology Studies of OTL-0050 (Pteroyl-Tyr-50122), OTL-0051 (Pteroyl-Tyr-IRD28), and OTL-0052 (Pteroyl-Tyr-Kodak)

Material and Methods:

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

KB cells that overexpress FR-a were seeded in 24-well (100,000 cells/well) Falcon plates (BD Biosciences, CA) and allowed to form monolayers over a period of 12 h. Spent medium in each well was combined with 10 nM of [$^3$H]-folic acid (tritiated folic acid) in the presence of increasing concentration (0.1 nM-1 µM) of the test article or folic acid (Sigma-Aldrich, MO) in fresh medium (0.5 mL). After incubating for 1 h at 37° C., cells were rinsed with PBS (3×0.5 mL, Gibco, NY) to remove any unbound radioactive materials. After adding 0.25 M sodium hydroxide (0.5 mL) and incubating for 12 h at 4° C., cells were transferred into individual scintillation vials containing Ecolite scintillation cocktail (3.0 mL, MP Biomedicals, OH) and counted in a liquid scintillation analyzer (Packard). The relative binding affinities were calculated using a plot of % cell bound radioactivity versus the log concentration of the test article using GraphPad Prism 4.

Results:

The dissociation constants ($K_D$) derived from the studies was calculated to be 29.3 nM, 13.8 nM, 15.3 nM, and 7.4 nM for compounds OTL-050-OTL-0052 and folic acid respectively. Relative binding affinities were calculated to be 0.25, 0.54, 0.48 and 1 for OTL-0050-OTL-0052 and folic acid respectively. All the test articles competed quantitatively with [$^3$H]-folic acid.

Conclusion:

OTL-0050, OTL-0051, and OTL-0052 each have an affinity for folate receptor and the compounds compare moderately well with the binding affinity of folic acid. All the compounds competed well with [$^3$H]-folic acid indicating that folate receptor constitutes the sole binding site on cancer cells and they are highly specific for folate receptor.

Example 15

In Vitro Pharmacology Studies of Pteroyl-non Amino Acid-NIR Dye Conjugates

Material and Methods:

KB cells (a human nasopharyngeal cell line) were obtained from American type culture collection (Rockville, Md.) and grown as a monolayer using folate free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

KB cells that overexpress FR-α were seeded in 24-well (100,000 cells/well) Falcon plates (BD Biosciences, CA) and allowed to form monolayers over a period of 12 h. Spent medium in each well was combined with 10 nM of [$^3$H]-folic acid (tritiated folic acid) in the presence of increasing concentration (0.1 nM-1 µM) of the test article or folic acid (Sigma-Aldrich, MO) in fresh medium (0.5 mL). After incubating for 1 h at 37° C., cells were rinsed with PBS (3×0.5 mL, Gibco, NY) to remove any unbound radioactive materials. After adding 0.25 M sodium hydroxide (0.5 mL) and incubating for 12 h at 4° C., cells were transferred into individual scintillation vials containing Ecolite scintillation cocktail (3.0 mL, MP Biomedicals, OH) and counted in a liquid scintillation analyzer (Packard). The relative binding affinities were calculated using a plot of % cell bound radioactivity versus the log concentration of the test article using GraphPad Prism 4.

Results:

The dissociation constants ($K_D$) derived from the studies was calculated to be 95.2 nM, 121.3 nM, 90.2 nM, 250.5 nM, 225.8 nM, 41.7 nM for compounds OTL-0056 (Pteroyl-DAP-S0456), OTL-0057 (Pteroyl-BAMB-50456), OTL-0058 (Pteroyl-AMHMB-50456), OTL-0059 (Pteroyl-DHDADS-50456), OTL-0060 (Pteroyl-DADS-50456), OTL-0061 (Pteroyl-4APEP-50456) and folic acid respectively. Relative binding affinities were calculated to be 0.078, 0.061, 0.082, 0.029, 0.033, 0.171 and 1 for OTL-0056-OTL-0061 and folic acid respectively. All the test articles competed quantitatively with [$^3$H]-folic acid.

Conclusion:

Compounds OTL-0056-OTL-0061 each have an affinity for folate receptor and they compare moderately well with the binding affinity of folic acid. All the compounds competed well with [$^3$H]-folic acid indicating that folate receptor constitutes the sole binding site on cancer cells and they are highly specific for folate receptor.

Example 16

In Vitro Pharmacological Studies of Pteroyl-non Amino Acid-NIR Dye Conjugates

Material and Methods:

KB cells (a human nasopharyngeal cell line) were obtained from American type culture collection (Rockville, Md.) and grown as a monolayer using folate-free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

KB cells that overexpress FR-a were seeded in 24-well (100,000 cells/well) Falcon plates (BD Biosciences, CA) and allowed to form monolayers over a period of 12 h. Spent medium in each well was combined with 10 nM of [$^3$H]-folic acid (tritiated folic acid) in the presence of increasing concentration (0.1 nM-1 µM) of the test article or folic acid (Sigma-Aldrich, MO) in fresh medium (0.5 mL). After incubating for 1 h at 37° C., cells were rinsed with PBS (3×0.5 mL, Gibco, NY) to remove any unbound radioactive materials. After adding 0.25 M sodium hydroxide (0.5 mL) and incubating for 12 h at 4° C., cells were transferred into individual scintillation vials containing Ecolite scintillation cocktail (3.0 mL, MP Biomedicals, OH) and counted in a liquid scintillation analyzer (Packard). The relative binding affinities were calculated using a plot of % cell bound radioactivity versus the log concentration of the test article using GraphPad Prism 4.

Results:

The dissociation constants ($K_D$) derived from the studies were calculated and found to be 95.2 nM, 121.3 nM, 90.2 nM, 250.5 nM, 225.8 nM, 41.7 nM and 7.4 nM for compounds OTL-0056-OTL-0061 and folic acid respectively. Relative binding affinities were calculated and found to be 0.078, 0.061, 0.082, 0.029, 0.033, 0.171 and 1 for OTL-0056 (Pte-DAP-S0456), OTL-0057 (Pte-BAMB-S0456), OTL-0058 (Pteroyl-AMHMB-S0456), OTL-0059 (Pte-DHDADS-S0456), OTL-0060 (Pte-DADS-S0456), OTL-0061 (Pte-4APEP-S0456) and folic acid respectively. All the test articles competed quantitatively with [$^3$H]-folic acid.

Conclusion: All the compounds have a weak affinity for folate receptor. All the compounds competed with [$^3$H]-folic acid indicating that folate receptor constitutes the sole binding site on cancer cells and they are highly specific for folate receptor.

Example 17

Whole-Body Imaging and Biodistribution of Pteroyl-Amino Acid-NIR Dye Conjugates

Test Articles: OTL-0038 (Pte-Tyr-S0456), OTL-0053 (Pteroyl-Lys-S0456), and OTL-0054 (Pteroyl-Cys-S0456)

Material and Methods:

KB cells (a human nasopharyngeal cell line) were obtained from American type culture collection (Rockville, Md.) and grown as a monolayer using folate-free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude mice (5 weeks old, 18-20 g) were purchased from Harlan (IN) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 h light-dark cycle for the duration of the study. Mice were identified individually by ear punch. All animal procedures were approved by Purdue Animal Care and Use Committee. Animal care and studies were performed according to national and international guidelines for the humane treatment of animals.

Whole-Body Imaging:

Seven-week-old female nu/nu mice were inoculated subcutaneously with KB cells ($1.0 \times 10^6$/mouse in folate-free RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm³ in volume, animals (2-3 mice/group) were intravenously injected with 10 nmol of test article in phosphate buffered saline (100 µL). After 2 hours, animals were euthanized by $CO_2$ asphyxiation. Whole-body (intact tumor) images were then taken using a Caliper IVIS Lumina II Imaging Station with Living Image 4.0 software (PerkinElmer Inc, MA). Settings for imaging:—lamp level: medium; excitation: 745 nm; emission: ICG (830 nm); epi illumination; binning: 4 (M), FOV=12.5; f-stop=2; acquisition time=1 s. In the case of Pte-Lys-S0456, excitation: 745 nm, 710 nm, 675 nm, 640 nm, 605 nm; emission: ICG and rest of the parameters are same.

Tissue Biodistribution:

Following whole-body imaging, animals were dissected and selected tissues (heart, lung, liver, spleen, kidneys, stomach, small intestine, large intestine, muscle, skin, and tumor) were analyzed for fluorescence activity using IVIS imager as before. Settings for imaging:—lamp level: medium; excitation: 745 nm; emission:ICG (830 nm); epi illumination; binning: 4 (M), FOV=12.5; f-stop=2; acquisition time=1 s.

Results:

Whole-Body Imaging:

As seen in the FIG. 29, OTL-0038 (Pte-Tyr-S0456) and OTL-0054 (Pte-Cys-S0456) accumulated predominantly in the folate receptor-positive tumors, with no substantial fluorescence activity in the other tissues. Moreover, direct comparison demonstrated that tumor fluorescence intensity of OTL-0038 injected mice were brighter than the mice treated with the other conjugates. On the other hand, Pte-Lys-S0456 had bright tumor fluorescence when excited at 605-675 nm wave lengths and emitted at ICG (830 nm) with only a moderate brightness when excited at 710-745 nm and emitted at ICG, as seen in FIG. 30 (same parameters used with the other conjugates).

Tissue Biodistribution:

Analysis of tissue biodistribution was performed on animals under the same conditions by euthanizing each mouse, removing their organs and imaging them using an IVIS imager. As seen in the FIG. 31, the highest fluorescence intensity was observed in FR-positive tumors and the kidneys. The kidney uptake was anticipated since the apical membrane of the proximal tubule of the kidney has been known to express high levels of folate receptor. Moreover, it's possible that the probes are excreted through the kidneys due to their low molecular weights and half-life (most of the folate conjugates have <30 min half-life).

Conclusion:

The brightness and specificity of the conjugates listed from best to worst are as follows at Ex=745 nm and Em=ICG: Pte-Tyr-S0456, Pte-Cys-S0456, and Pte-Lys-S0456. Pte-Lys-S0456 all showed a longer Stoke's shift, indicating that we can excite at 605 nm and emit at ICG (830 nm) to observe a bright tumor fluorescence.

Example 18

Whole-Body Imaging and Biodistribution of Pte-Tyr-Kodak Derivatives [OTL-0051 (Pteroyl-Tyr-IRD28), and OTL-0052 (Pteroyl-Tyr-Kodak)]

Test Articles: OTL-0051 (Pteroyl-Tyr-IRD28), and OTL-0052 (Pteroyl-Tyr-Kodak)

Material and Methods:

KB cells (a human nasopharyngeal cell line) were obtained from American type culture collection (Rockville, Md.) and grown as a monolayer using folate-free 1640 RPMI medium containing (Gibco, NY) 10% heat-inactivated fetal bovine serum (Atlanta Biological, GA) and 1% penicillin streptomycin (Gibco, NY) in a 5% carbon dioxide: 95% air-humidified atmosphere at 37° C. for at least six passages before they were used for the assays.

Athymic female nude mice (5 weeks old, 18-20 g) were purchased from Harlan (IN) and maintained on gamma-irradiated folate-deficient special diet (Teklad, WI) for at least 2 weeks before the start of the study. Animals were housed 5/cage in a barrier, pathogen-free cloaked rack. Autoclaved tap water and food were given as needed. The animals were housed in a sterile environment on a standard 12 h light-dark cycle for the duration of the study. Mice were identified individually by ear punch. All animal procedures were approved by Purdue Animal Care and Use Committee. Animal care and studies were performed according to national and international guidelines for the humane treatment of animals.

Whole-Body Imaging:

Seven-week-old female nu/nu mice were inoculated subcutaneously with KB cells ($1.0 \times 10^6$/mouse in folate free RPMI1640 medium) on the shoulder. Growth of the tumors was measured in perpendicular directions every 2 days using a caliper (body weights were monitored on the same schedule), and the volumes of the tumors were calculated as $0.5 \times L \times W^2$ (L=longest axis and W=axis perpendicular to L in millimeters). Once tumors reached between 400 and 500 mm³ in volume, animals (2-3 mice/group) were intravenously injected with 10 nmol of test article in phosphate buffered saline (100 µL). After 2 hours, animals were euthanized by $CO_2$ asphyxiation. Whole-body imaging (intact tumor) experiments were then performed using a Caliper IVIS Lumina II Imaging Station with Living Image 4.0 software (PerkinElmer Inc, MA). Settings for imaging:—lamp level: medium; excitation: 745 nm; emission: ICG (830 nm); epi illumination; binning: 4 (M), FOV=12.5; f-stop=2; acquisition time=1 s. In the case of Pte-Lys-S0456, excitation: 745 nm, 710 nm, 675 nm, 640 nm, 605 nm; emission: ICG (830 nm) and rest of the parameters are same.

Tissue Biodistribution:

Following whole-body imaging, animals were dissected and selected tissues (heart, lung, liver, spleen, kidneys, stomach, small intestine, large intestine, muscle, skin, and tumor) were analyzed for fluorescence activity using IVIS imager as before. Settings for imaging:—lamp level: medium; excitation: 745 nm; emission:ICG (830 nm); epi illumination; binning: 4 (M), FOV=12.5; f-stop=2; acquisition time=1 s.

Results:

Whole-Body Imaging:

As seen in the FIG. 32, OTL-0051 (Pteroyl-Tyr-IRD28), and OTL-0052 (Pteroyl-Tyr-Kodak) accumulated moderately well in the folate receptor-positive tumors, with no substantial fluorescence activity in the other tissues. While the Kodak dye excited at 800 nM, IVIS image system does not have filter to excite at 800 nM. Therefore, the low observed fluorescence uptake in the tumors may be due to the use of a poor excitation wavelength.

Tissue Biodistribution:

Analysis of tissue biodistribution was performed on animals under the same conditions by euthanizing each mouse, removing their organs and imaging them using an IVIS imager. As seen in the FIG. 33, the highest fluorescence intensity was observed in FR-positive tumors. We also observed uptake in the lungs. Although we anticipated having kidney uptake (since the apical membrane of the proximal tubule of the kidney has been known to express high levels of folate receptor), the kidney uptake was low.

Conclusion:

Tissue biodistribution studies demonstrated that OTL-0051 (Pteroyl-Tyr-IRD28), and OTL-0052 (Pteroyl-Tyr-Kodak) conjugates uptake in the folate receptor positive tumors.

The invention claimed is:

1. A compound having the formula:

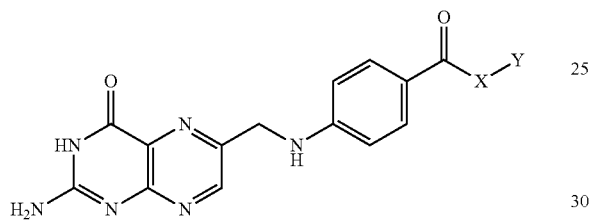

or a pharmaceutically acceptable salt thereof,
or isotopes thereof,
wherein:
X is a single amino acid or a single amino acid derivative thereof, wherein the single amino acid or single amino acid derivative contains an —OH, —NH$_2$, or —SH functional group, and
Y is a dye that has a fluorescence excitation and emission spectra in the near infra red range, wherein Y is represented by the formula:

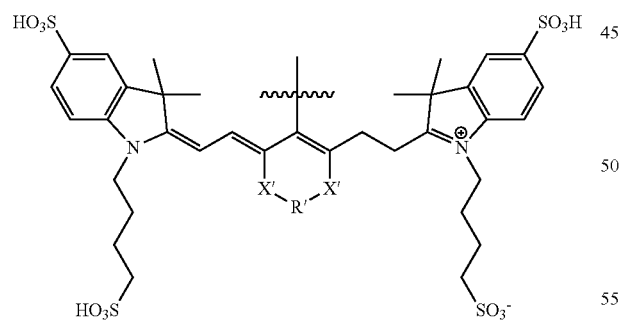

wherein, X' is independently selected from the group consisting of O, S, N and C, and R' is independently selected from the group consisting of CH$_2$ and CH$_2$CH$_2$, and the compound maintains or enhances the fluorescence of the dye, Y.

2. The compound of claim 1 wherein the amino acid is selected from the group consisting of tyrosine, cysteine, lysine, serine or a derivative thereof.

3. The compound of claim 1 wherein the amino acid is tyrosine, wherein the aromatic ring of tyrosine comprises a carbon isotope and/or a hydrogen isotope.

4. The compound of claim 1 wherein the amino acid derivative is a derivative of tyrosine selected from the group consisting of:

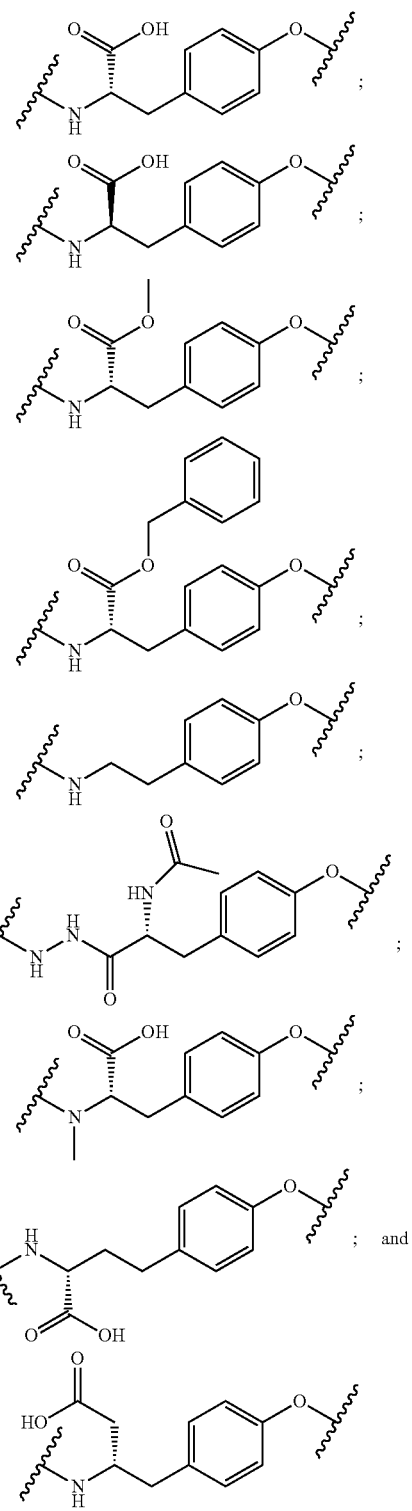

or racemic mixtures thereof.

5. The compound of claim 1 wherein the amino acid is cysteine or a derivative of cysteine.

6. A compound of claim 1, wherein the compound has the formula:

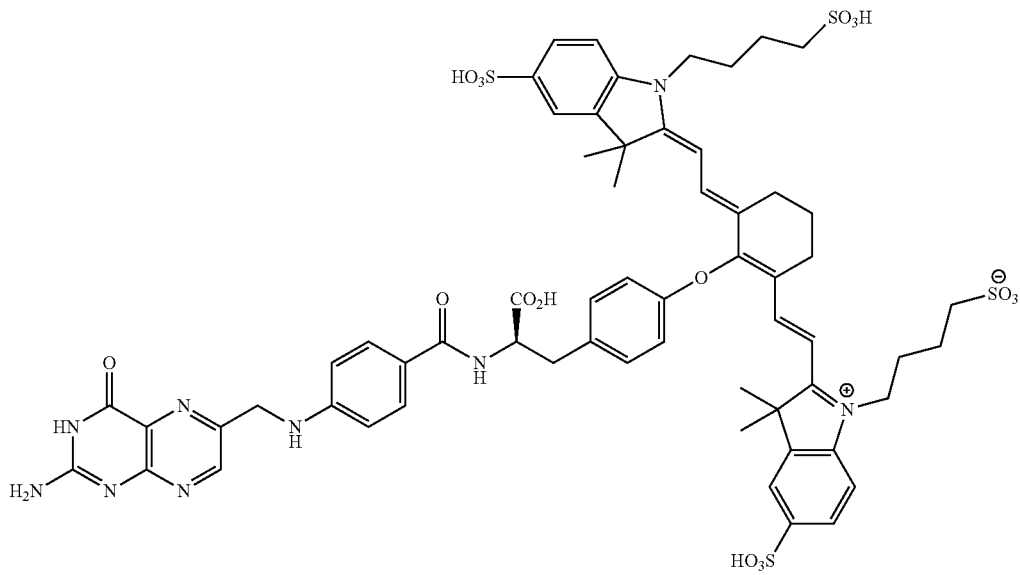

or is a potassium, sodium, or ammonium salt thereof.

7. The compound of claim 1, wherein the compound has the formula:

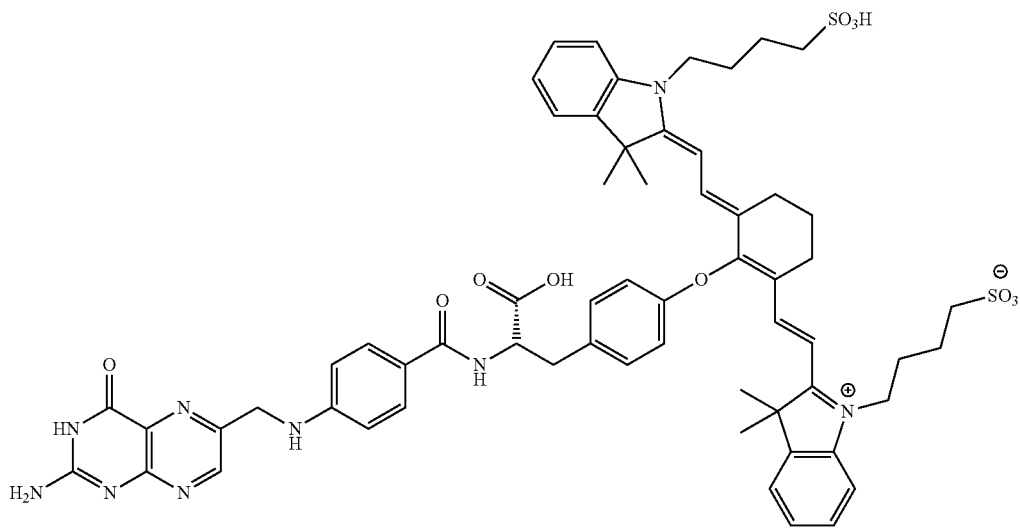

or a pharmaceutically acceptable salt thereof.

8. The compound of claim 1, wherein the compound has an absorption and emission maxima between about 600 nm and 800 nm.

9. The compound of claim 1, wherein the compound is made to fluoresce after distribution thereof in the tissue cells.

10. The compound of claim 1 wherein the compound is highly selective for targeting to a tumor cell.

11. A composition comprising a compound of claim 1 and a pharmaceutically acceptable carrier, excipient or diluent.

12. A method of identifying a target cell type in a biological sample comprising a) contacting the biological sample with a compound of claim 1 for a time and under conditions that allow for binding of the compound to at least one cell of the target cell type; and b) optically detecting the presence or absence of the compound of in the biological sample, wherein presence of the compound in detecting step b) indicates that the target cell type is present in the biological sample.

13. The method of claim 12 wherein the tissue is a tumor or a lymph node.

14. A method of performing image guided surgery on a subject comprising:

a) administering a composition comprising the compound of claim 1 under conditions and for a time sufficient for the compound to accumulate at a given surgical site;

b) illuminating the compound to visualize the compound using infrared light; and c) performing surgical resection of the areas that fluoresce upon excitation by the infrared light.

15. The method of claim 14, wherein the illuminating and detecting steps are performed using an endoscope, catheter, tomographic system, hand-held optical imaging system, surgical goggles, or intra-operative microscope.

16. The method of claim 14, wherein the wherein the disease is selected from the group consisting of cancer, cardiovascular diseases, neurodegenerative diseases, immunologic diseases, autoimmune diseases, respiratory diseases, metabolic diseases, inherited diseases, infectious diseases, bone diseases, and environmental diseases.

17. The method of claim 14, wherein the infrared light wavelength is within a range from about 650 to 900 nanometers.

18. A method of diagnosing a disease in a subject comprising:

a) administering to a subject in need of diagnosis an amount of a compound of claim 1 for a time and under conditions that allow for binding of the compound to at least one cell of the target cell type;

b) measuring the signal from the compound of claim 1 present in the biological sample;

c) comparing the signal measured in b) with at least one control data set, wherein the at least one control data set comprises signals from the compound of claim 1 contacted with a biological sample that does not comprise the target cell type; and d) providing a diagnosis of disease wherein the comparison in step c) indicates the presence of the disease.

19. The compound of claim 1, wherein the compound has a formula selected from the group consisting of:

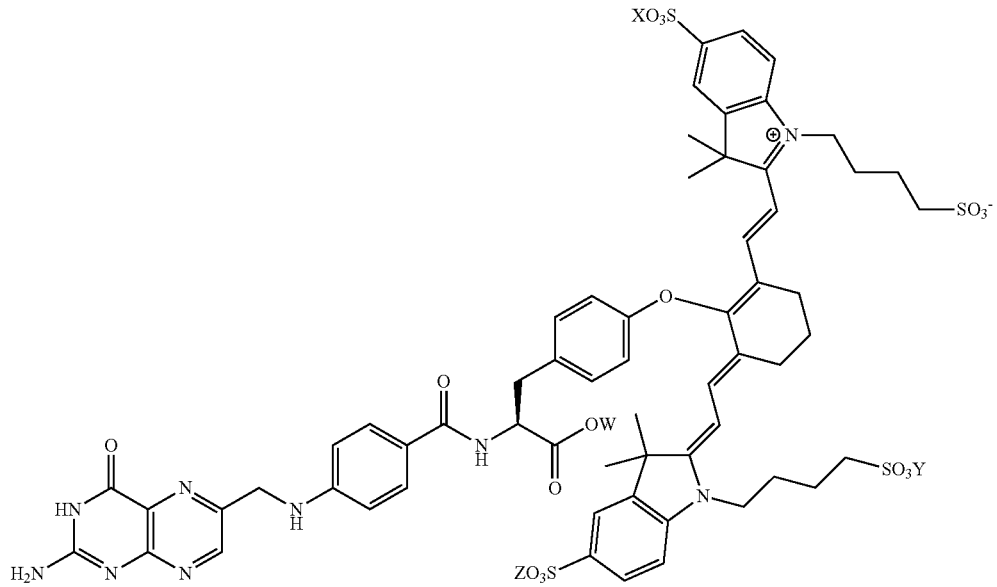

wherein W, X, Y, or Z is H, Na, or $NH_4^+$,

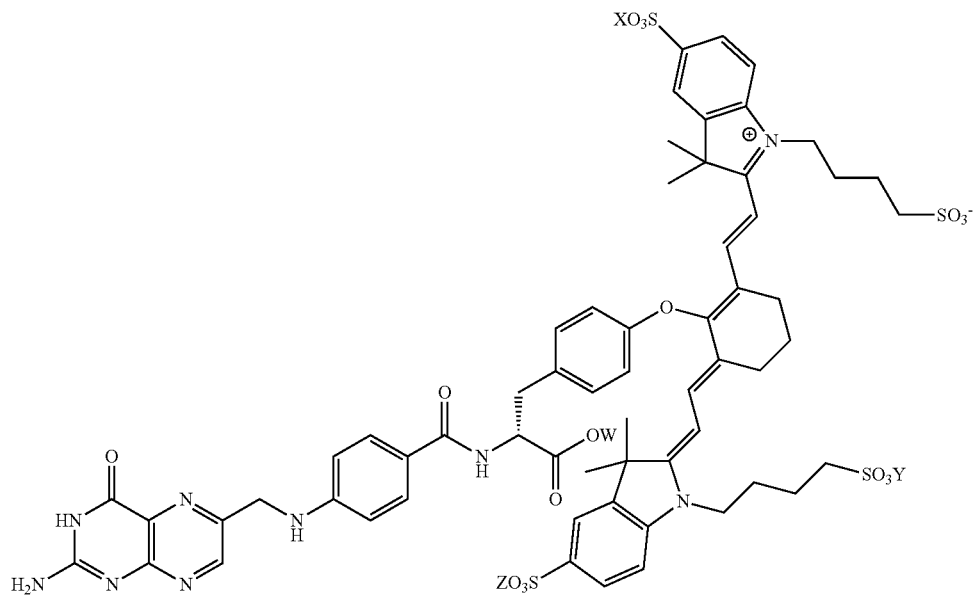

wherein W, X, Y, or Z is H, Na, or $NH_4^+$,

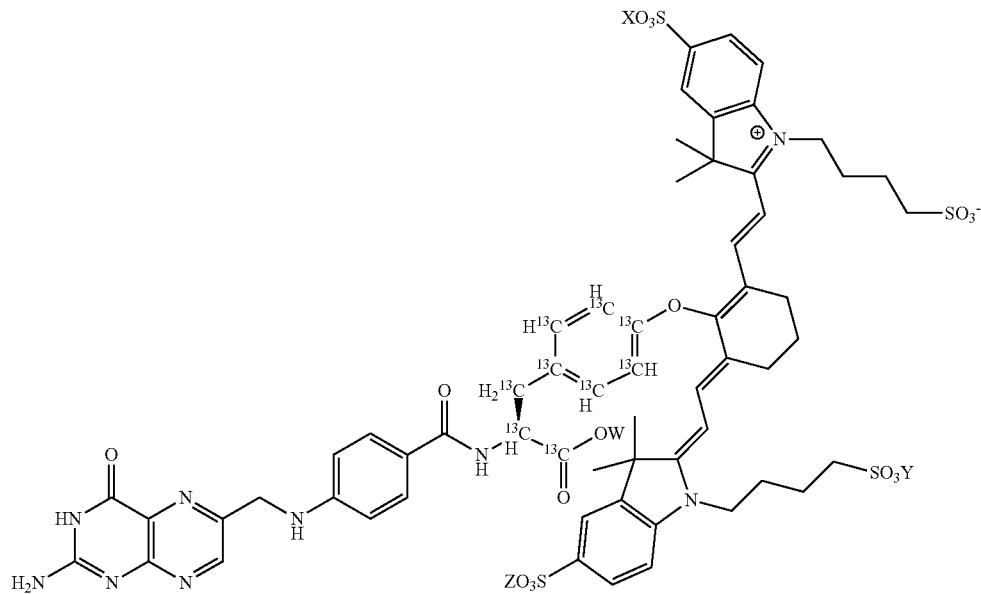
wherein W, X, Y, or Z is H, Na, or $NH_4^+$,
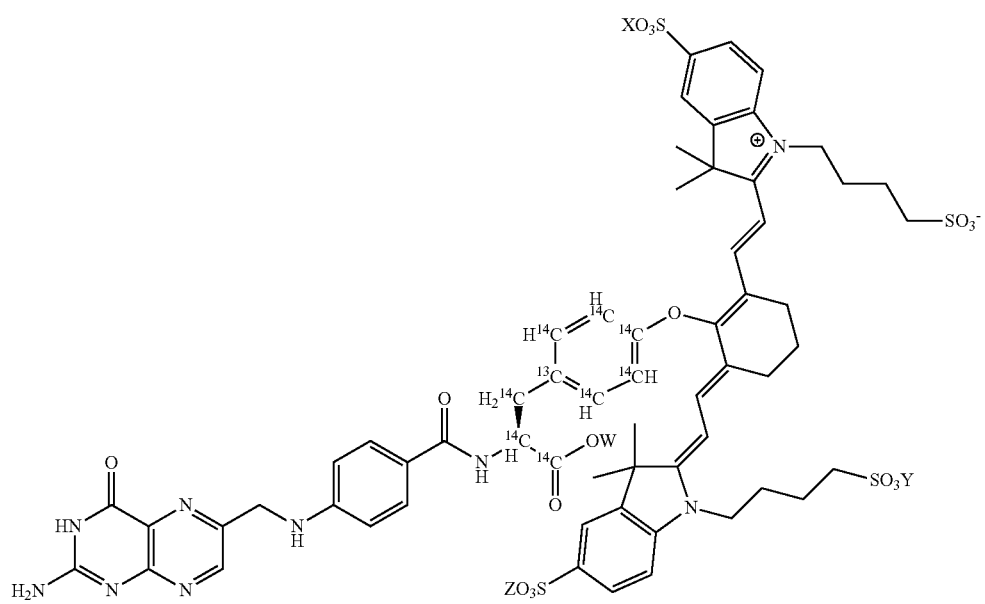
wherein W, X, Y, or Z is H, Na, or $NH_4^+$,

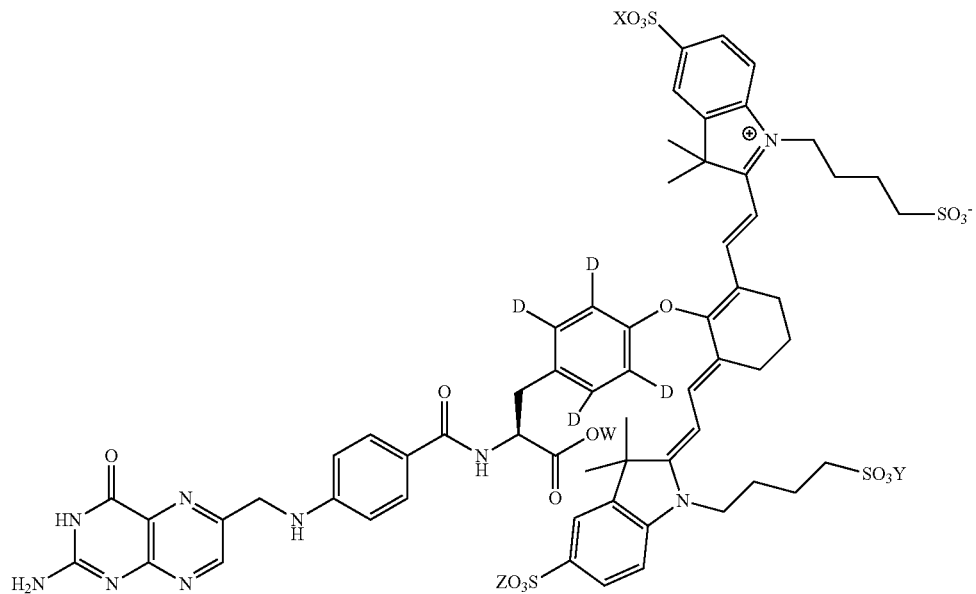
wherein W, X, Y, or Z is H, Na, or $NH_4^+$,
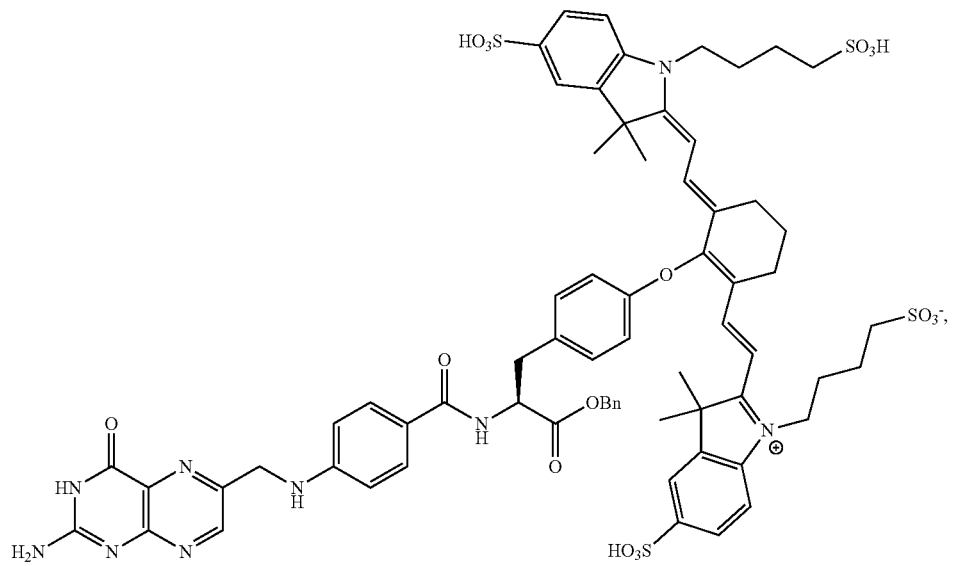

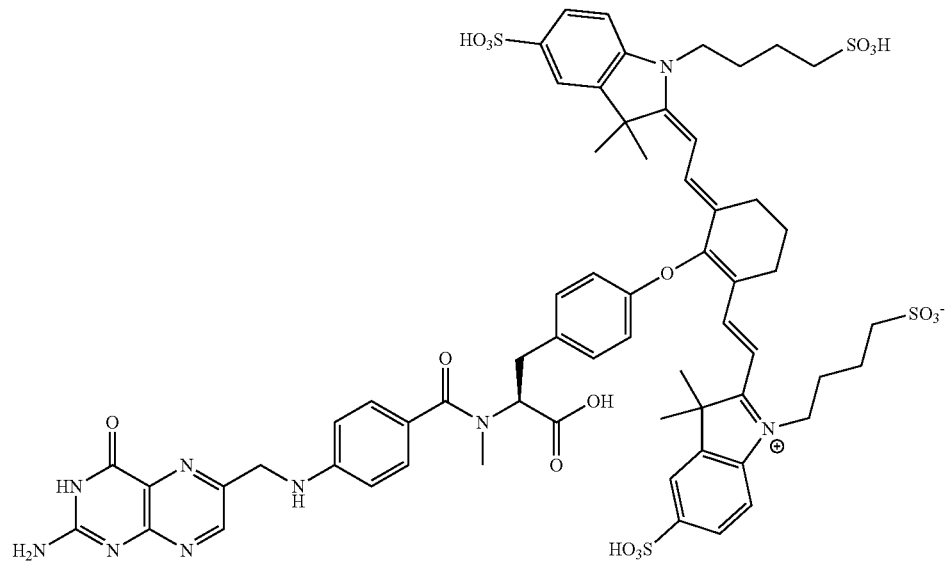
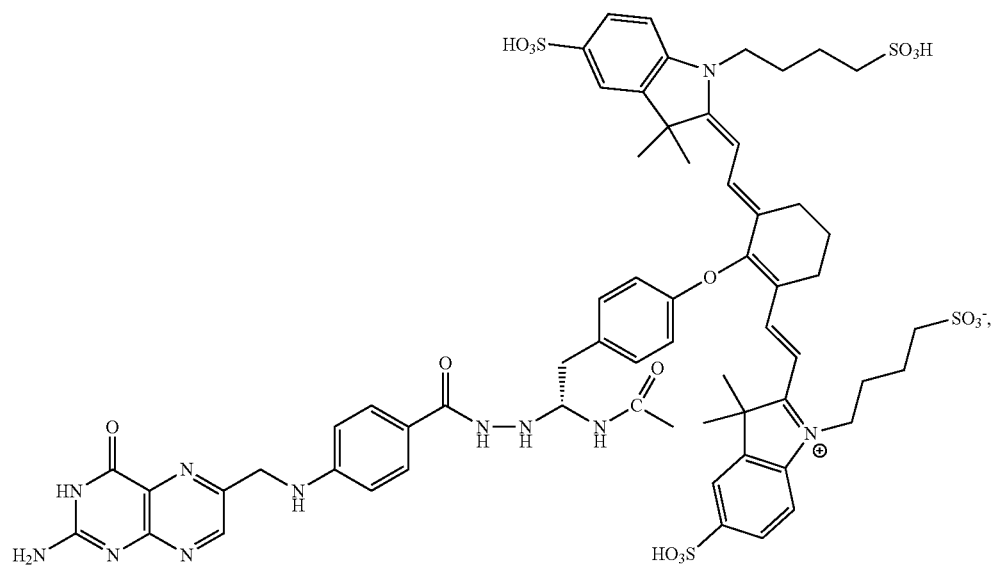

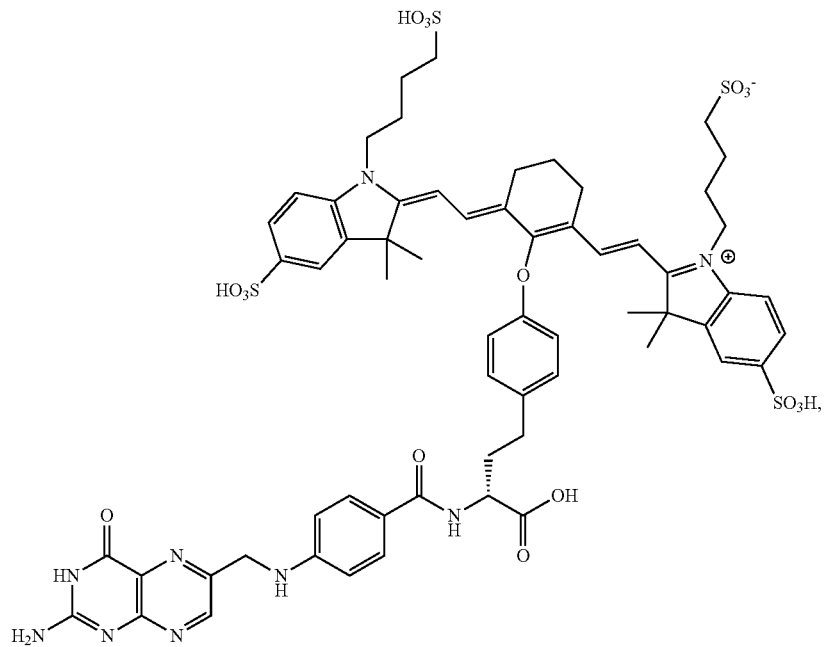
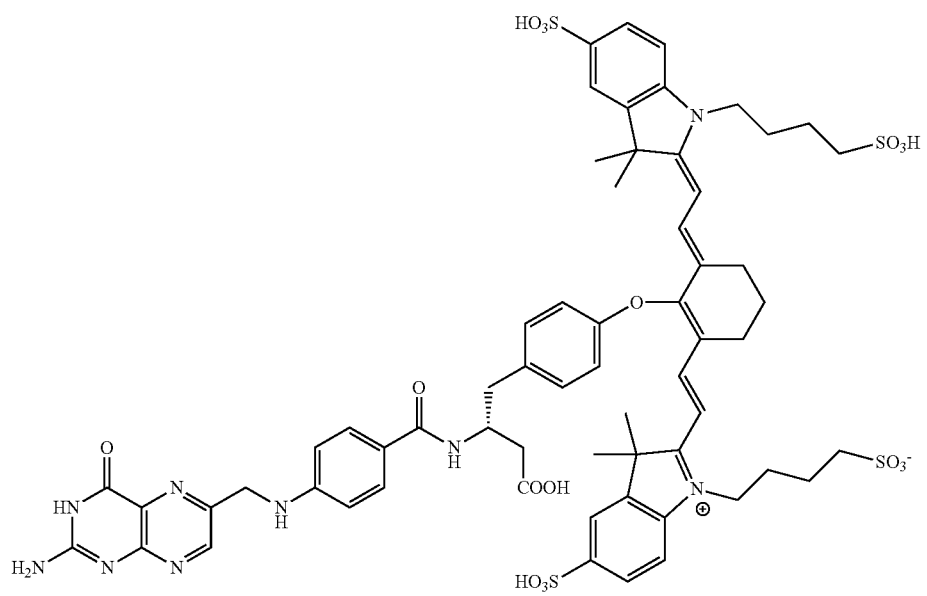
wherein tyrosine is beta homo,

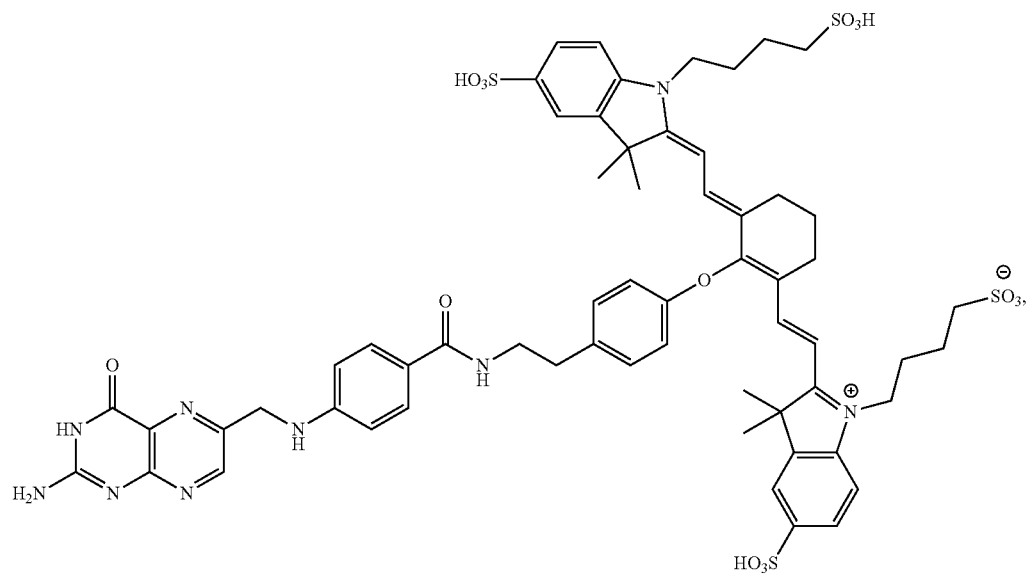
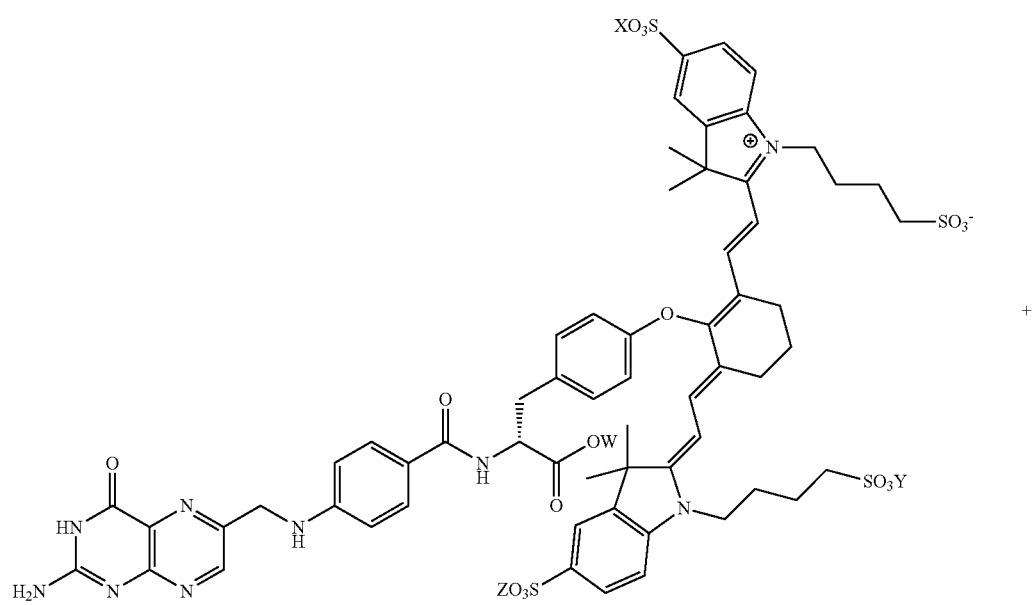

-continued
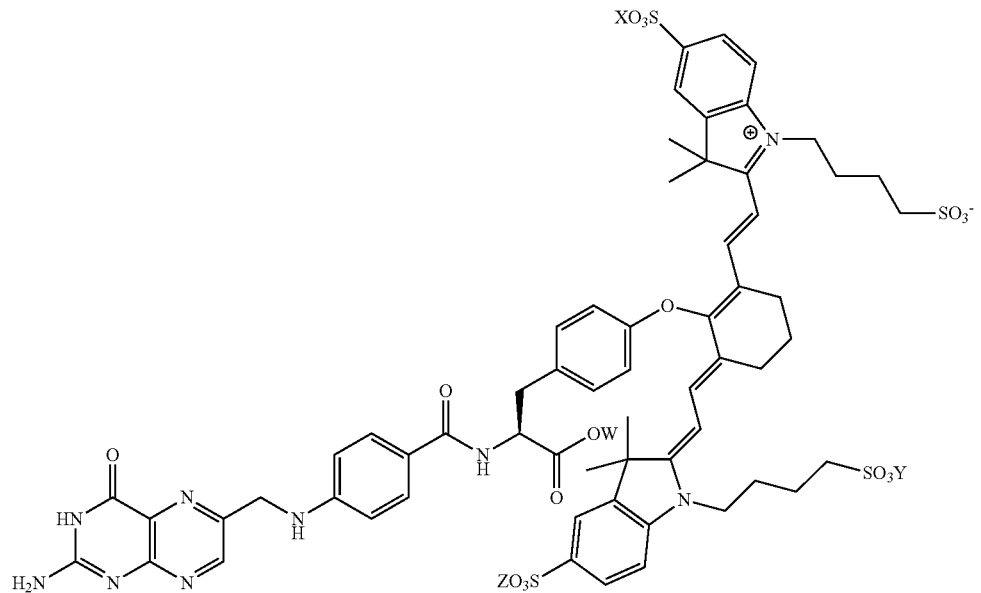
wherein W, X, Y, or Z is H, Na, or $NH_4^+$,
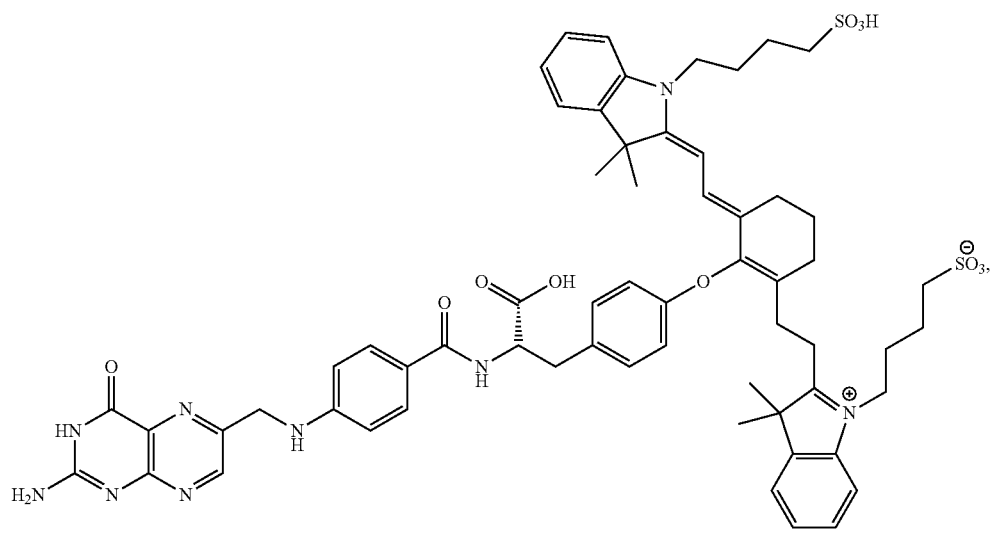

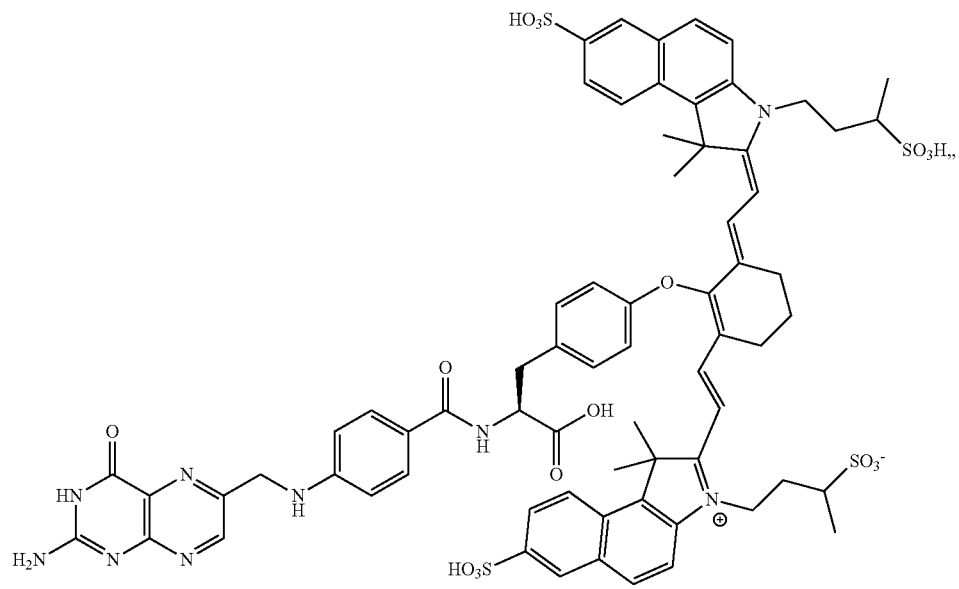
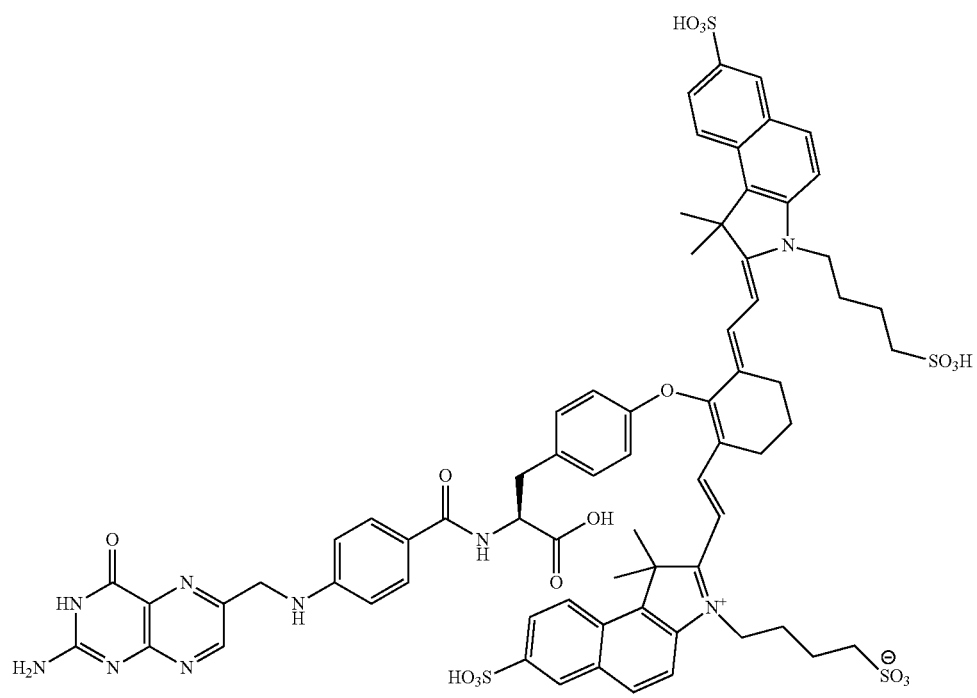

-continued
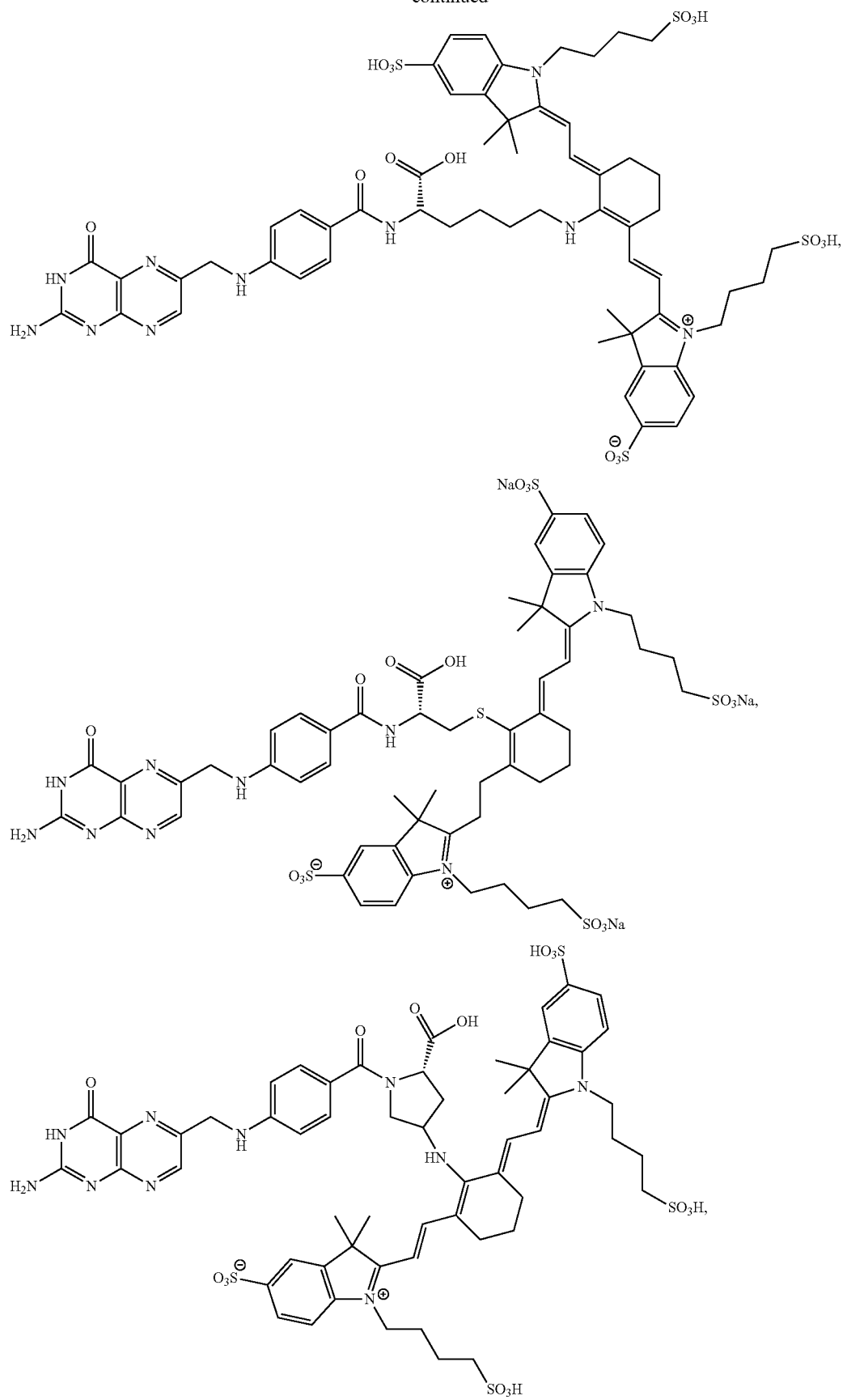

-continued
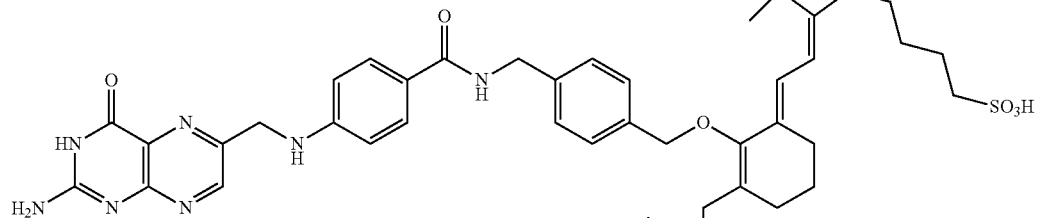
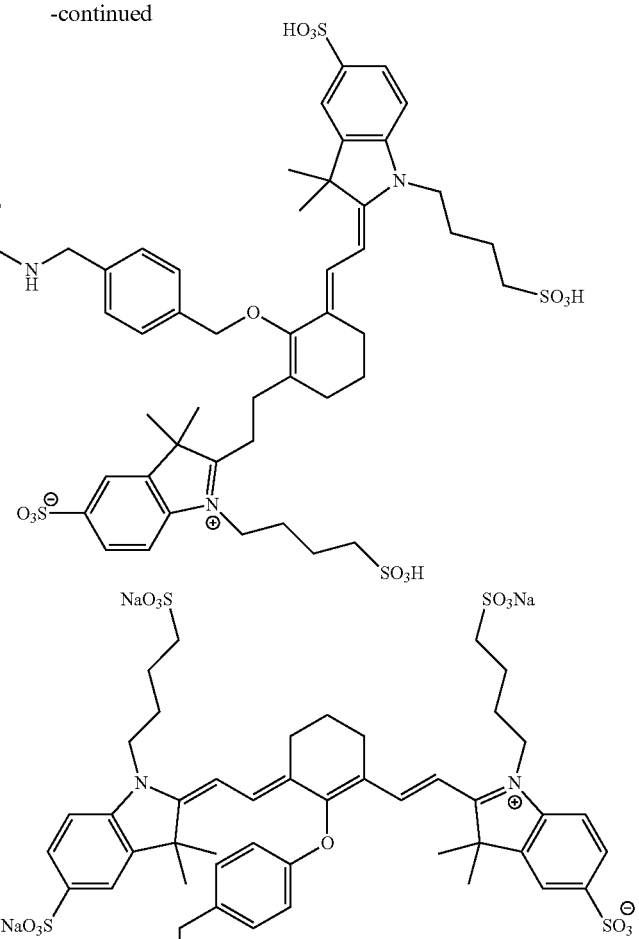
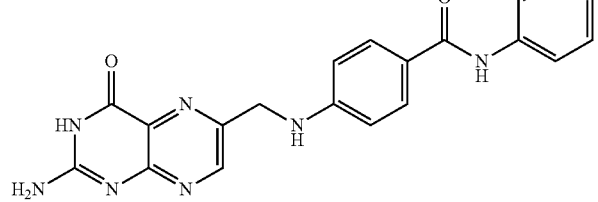
and a pharmaceutically acceptable salt thereof.
* * * * *

UNITED STATES PATENT AND TRADEMARK OFFICE
CERTIFICATE OF CORRECTION

PATENT NO. : 9,061,057 B2  
APPLICATION NO. : 14/207130  
DATED : June 23, 2015  
INVENTOR(S) : Kularatne et al.

Page 1 of 1

It is certified that error appears in the above-identified patent and that said Letters Patent is hereby corrected as shown below:

In the Claims

In Column 85, the formula at Lines 44-56 reading

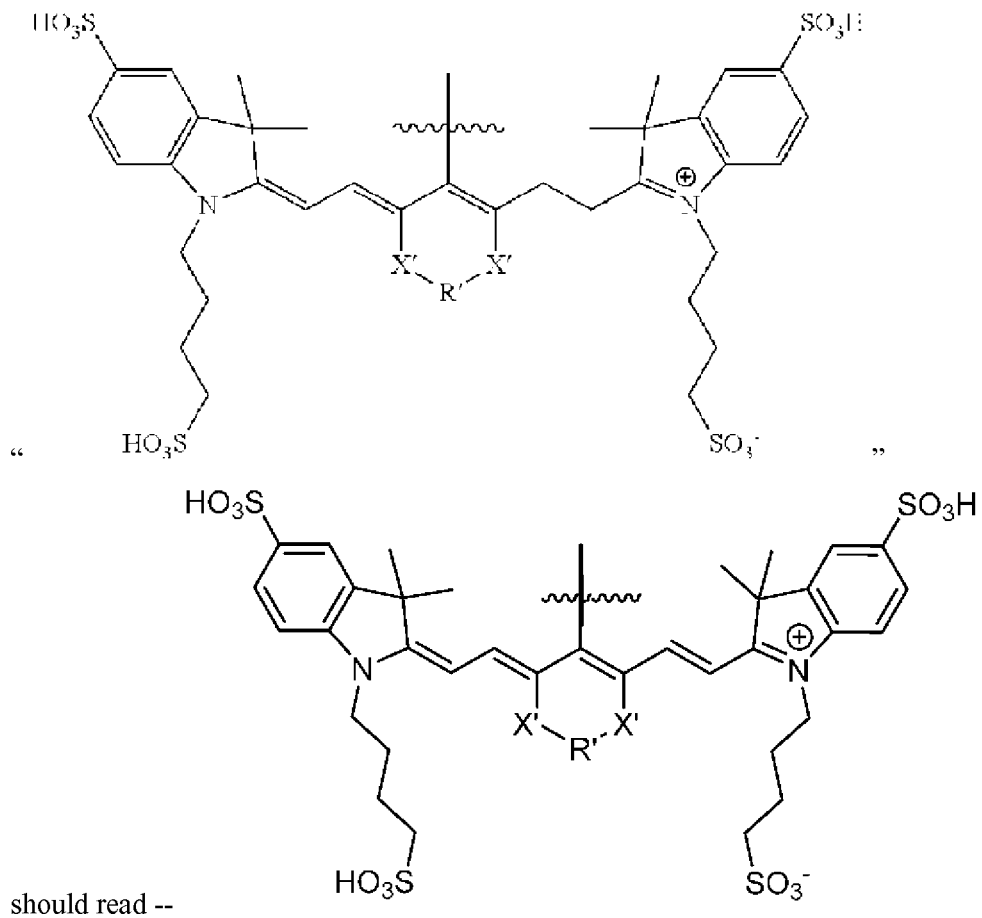

should read -- --

Signed and Sealed this  
Seventh Day of November, 2017

Joseph Matal  
*Performing the Functions and Duties of the*  
*Under Secretary of Commerce for Intellectual Property and*  
*Director of the United States Patent and Trademark Office*

UNITED STATES PATENT AND TRADEMARK OFFICE
CERTIFICATE OF CORRECTION

PATENT NO. : 9,061,057 B2
APPLICATION NO. : 14/207130
DATED : June 23, 2015
INVENTOR(S) : Sumith A. Kularatne et al.

Page 1 of 3

It is certified that error appears in the above-identified patent and that said Letters Patent is hereby corrected as shown below:

In the Claims

Column 85, Line 59, Claim 1, delete "and C" and insert --C, and $CH_2$--
Column 87, Lines 35-57, Claim 7, the structure reading

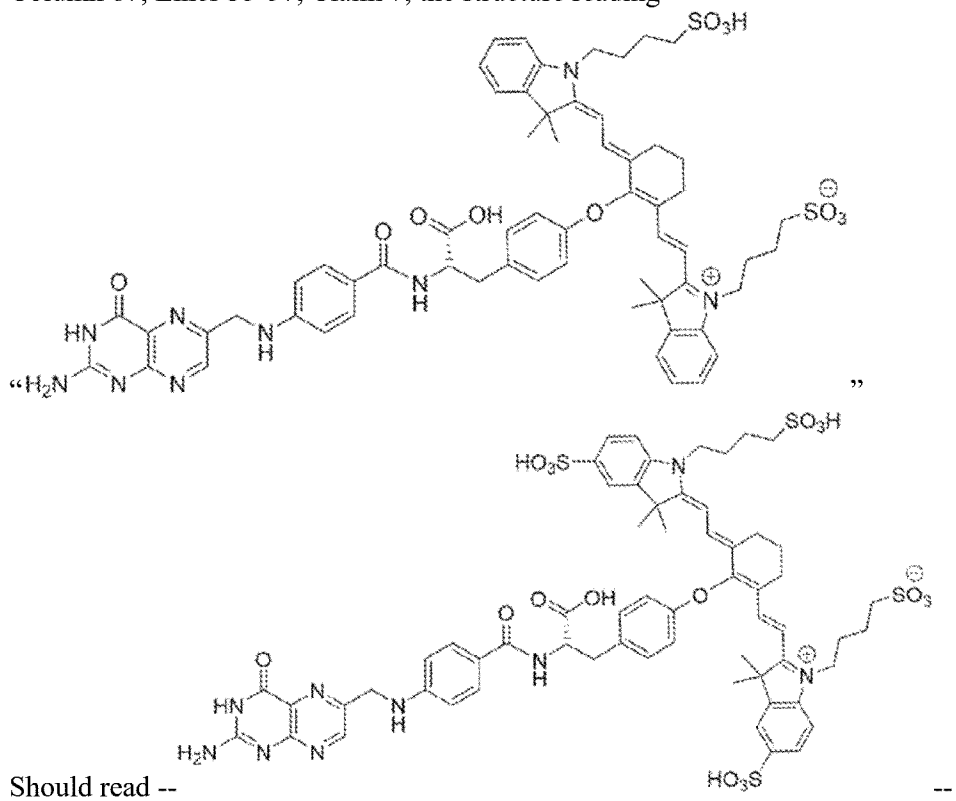

Should read -- --

Signed and Sealed this
Fifteenth Day of July, 2025

Coke Morgan Stewart
*Acting Director of the United States Patent and Trademark Office*

CERTIFICATE OF CORRECTION (continued)
U.S. Pat. No. 9,061,057 B2

Page 2 of 3

Column 90, Claim 19, the first structure reading

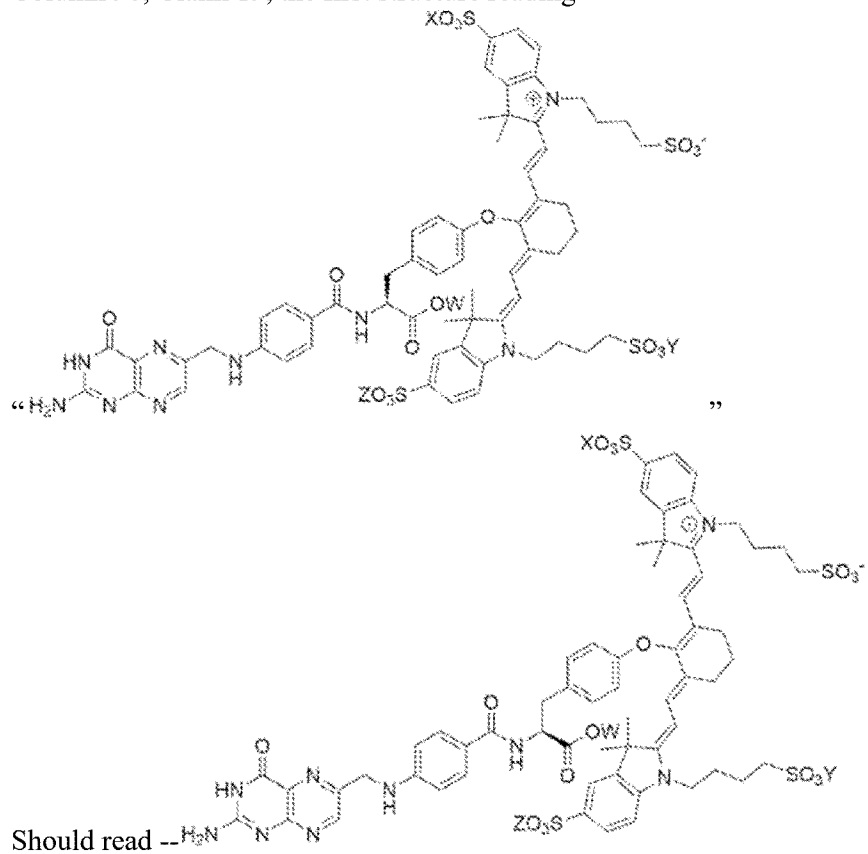

Should read --

Column 90, Claim 19, the second structure reading

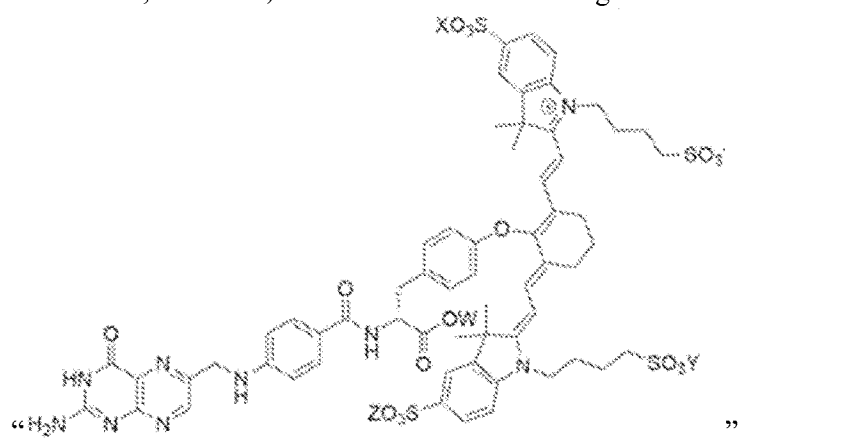

CERTIFICATE OF CORRECTION (continued)
U.S. Pat. No. 9,061,057 B2

Should read -- 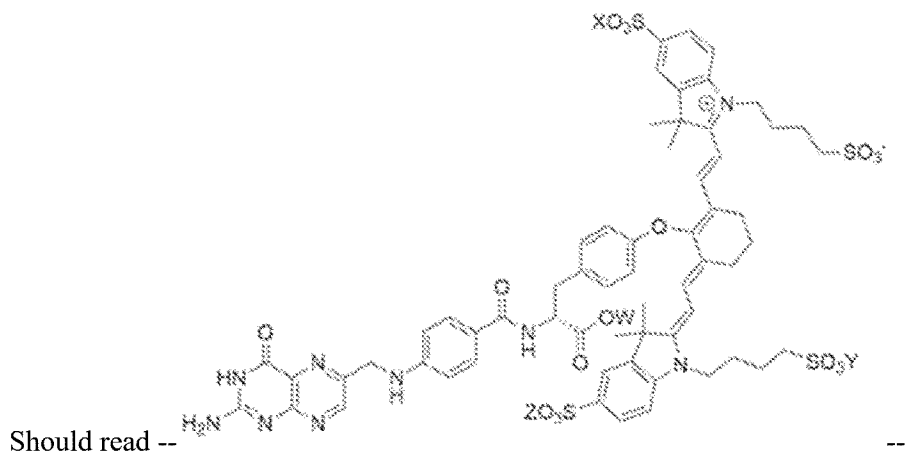 --